(12) United States Patent
Khakpour et al.

(10) Patent No.: US 10,363,120 B2
(45) Date of Patent: Jul. 30, 2019

(54) APPARATUS AND METHODS FOR CLEANING TEETH AND ROOT CANALS

(71) Applicant: SONENDO, INC., Laguna Hills, CA (US)

(72) Inventors: Mehrzad Khakpour, Laguna Hills, CA (US); Bjarne Bergheim, Mission Viejo, CA (US); Ryan Evans, Irvine, CA (US)

(73) Assignee: SONENDO, INC., Laguna Hills, CA (US)

( * ) Notice: Subject to any disclaimer, the term of this patent is extended or adjusted under 35 U.S.C. 154(b) by 532 days.

(21) Appl. No.: 14/699,878

(22) Filed: Apr. 29, 2015

(65) Prior Publication Data
US 2016/0095679 A1    Apr. 7, 2016

Related U.S. Application Data

(63) Continuation-in-part of application No. 14/137,937, filed on Dec. 20, 2013.
(Continued)

(51) Int. Cl.
*A61C 5/40* (2017.01)
*A61C 17/02* (2006.01)
*A61C 17/20* (2006.01)

(52) U.S. Cl.
CPC ............ *A61C 17/0202* (2013.01); *A61C 5/40* (2017.02); *A61C 17/02* (2013.01); *A61C 17/0208* (2013.01); *A61C 17/20* (2013.01)

(58) Field of Classification Search
CPC ......... A61C 5/02; A61C 5/04; A61C 17/0208; A61C 17/0202; A61H 9/0028; A61H 9/0078; A61H 2205/10
(Continued)

(56) References Cited

U.S. PATENT DOCUMENTS

| 1,500,107 A | 7/1924 | Chandler |
| 2,108,558 A | 2/1938 | Jackman |

(Continued)

FOREIGN PATENT DOCUMENTS

| AU | 2012-202315 A1 | 4/2012 |
| AU | 2007140780 | 5/2014 |

(Continued)

OTHER PUBLICATIONS

Alomairy, Evaluating two techniques on removal of fractured rotary nickel-titanium endodontic instruments from root canals: an in vitro study. J Endod 2009;35:559-62.
(Continued)

*Primary Examiner* — Wade Miles
*Assistant Examiner* — Matthew P Saunders
(74) *Attorney, Agent, or Firm* — Knobbe, Martens, Olson & Bear LLP

(57) ABSTRACT

Various systems, method, and compositions for treating a tooth are disclosed herein. For example, an apparatus for treating a tooth is disclosed. The apparatus can include a chamber having an access port which places the chamber in fluid communication with a treatment region of the tooth when the chamber is coupled to tooth. A fluid motion generator can be coupled to the chamber. The fluid motion generator can be configured to direct fluid across the access port to generate fluid motion in the chamber. In various embodiments, fluid motion (e.g., vortices, swirl, etc.) can be induced at or near treatment regions of the tooth, such as a root canal or carious region.

28 Claims, 47 Drawing Sheets

Related U.S. Application Data

(60) Provisional application No. 62/017,208, filed on Jun. 25, 2014, provisional application No. 61/986,016, filed on Apr. 29, 2014, provisional application No. 61/907,345, filed on Nov. 21, 2013, provisional application No. 61/740,351, filed on Dec. 20, 2012.

(58) Field of Classification Search
USPC .............................. 433/81, 88; 601/162, 163
See application file for complete search history.

(56) References Cited

U.S. PATENT DOCUMENTS

| | | |
|---|---|---|
| 3,023,306 A | 2/1962 | Kester |
| 3,401,690 A | 9/1968 | Martin |
| 3,460,255 A | 8/1969 | Hutson |
| 3,514,328 A | 5/1970 | Malin |
| 3,521,359 A | 7/1970 | Harris |
| 3,522,801 A | 8/1970 | Seymour |
| 3,547,110 A | 12/1970 | Balamuth |
| 3,561,433 A | 2/1971 | Kovach |
| 3,590,813 A | 7/1971 | Roszyk |
| 3,624,907 A | 12/1971 | Brass et al. |
| 3,703,170 A | 11/1972 | Ryckman, Jr. |
| 3,756,225 A | 9/1973 | Moret et al. |
| 3,828,770 A | 8/1974 | Kuris et al. |
| 3,921,296 A | 11/1975 | Harris |
| 3,930,505 A | 1/1976 | Wallach |
| 3,962,790 A | 6/1976 | Riitano et al. |
| 4,021,921 A * | 5/1977 | Detaille ............ A61C 17/0208 433/81 |
| 4,060,600 A | 11/1977 | Vit |
| 4,215,476 A | 8/1980 | Armstrong |
| 4,247,288 A | 1/1981 | Yoshii et al. |
| 4,274,555 A | 6/1981 | Sneider |
| 4,276,880 A | 7/1981 | Malmin |
| 4,293,188 A | 10/1981 | McMahon |
| 4,376,835 A | 3/1983 | Schmitt et al. |
| 4,386,911 A | 6/1983 | Maloney et al. |
| 4,424,036 A | 1/1984 | Lokken |
| 4,474,251 A | 2/1984 | Johnson, Jr. |
| 4,462,803 A | 7/1984 | Landgraff et al. |
| 4,492,575 A | 1/1985 | Mabille |
| 4,534,542 A | 8/1985 | Russo |
| 4,539,987 A | 9/1985 | Nath et al. |
| 4,608,017 A | 8/1986 | Sadohara |
| 4,659,218 A | 4/1987 | de Lasa et al. |
| 4,661,070 A | 4/1987 | Friedman |
| 4,671,259 A * | 6/1987 | Kirchner ............ A61C 17/0202 433/80 |
| 4,676,586 A | 6/1987 | Jones et al. |
| 4,676,749 A | 6/1987 | Mabille |
| 4,684,781 A | 8/1987 | Frish et al. |
| 4,732,193 A | 3/1988 | Gibbs |
| 4,789,335 A | 12/1988 | Geller et al. |
| 4,872,837 A | 10/1989 | Issalene et al. |
| 4,941,459 A | 7/1990 | Mathur |
| 4,957,436 A | 9/1990 | Ryder |
| 4,973,246 A | 11/1990 | Black et al. |
| 4,985,027 A | 1/1991 | Dressel |
| 4,993,947 A | 2/1991 | Grosrey |
| 5,013,300 A | 5/1991 | Williams |
| 5,029,576 A | 7/1991 | Evans, Sr. |
| 5,037,431 A | 8/1991 | Summers et al. |
| 5,046,950 A | 9/1991 | Favonio |
| 5,055,048 A | 10/1991 | Vassiliadis et al. |
| 5,066,232 A | 11/1991 | Negri et al. |
| 5,094,256 A | 3/1992 | Barth |
| 5,112,224 A | 5/1992 | Shirota |
| 5,116,227 A | 5/1992 | Levy |
| 5,173,049 A | 12/1992 | Levy |
| 5,173,050 A | 12/1992 | Dillon |
| 5,188,532 A | 2/1993 | Levy |
| 5,188,634 A | 2/1993 | Hussein et al. |
| 5,194,723 A | 3/1993 | Cates et al. |
| 5,195,952 A | 3/1993 | Solnit et al. |
| 5,224,942 A | 7/1993 | Beuchat et al. |
| 5,267,856 A | 12/1993 | Wolbarsht et al. |
| 5,267,995 A | 12/1993 | Doiron et al. |
| 5,269,777 A | 12/1993 | Doiron et al. |
| 5,292,253 A | 3/1994 | Levy |
| 5,295,828 A | 3/1994 | Grosrey |
| 5,307,839 A | 5/1994 | Loebker et al. |
| 5,322,504 A | 6/1994 | Doherty et al. |
| 5,324,200 A | 6/1994 | Vassiliadis et al. |
| 5,326,263 A | 7/1994 | Weissman |
| 5,334,019 A | 8/1994 | Goldsmith et al. |
| 5,380,201 A | 1/1995 | Kawata |
| 5,387,376 A | 2/1995 | Gasser |
| D356,866 S | 3/1995 | Meller |
| 5,399,089 A | 3/1995 | Eichman et al. |
| 5,428,699 A | 6/1995 | Pon |
| 5,435,724 A | 7/1995 | Goodman et al. |
| 5,474,451 A | 12/1995 | Dalrymple et al. |
| 5,490,779 A | 2/1996 | Malmin |
| 5,503,559 A | 4/1996 | Vari |
| 5,540,587 A | 7/1996 | Malmin |
| 5,547,376 A | 8/1996 | Harrel |
| 5,554,896 A | 9/1996 | Hogan |
| 5,562,692 A | 10/1996 | Bair |
| 5,564,929 A | 10/1996 | Alpert |
| 5,570,182 A | 10/1996 | Nathel et al. |
| 5,591,184 A | 1/1997 | McDonnell et al. |
| 5,601,430 A | 2/1997 | Kutsch et al. |
| 5,620,414 A | 4/1997 | Campbell, Jr. |
| 5,639,239 A | 6/1997 | Earle |
| 5,642,997 A | 7/1997 | Gregg et al. |
| 5,643,299 A | 7/1997 | Bair |
| 5,660,817 A | 8/1997 | Masterman et al. |
| 5,662,501 A | 9/1997 | Levy |
| 5,674,226 A | 10/1997 | Doherty et al. |
| 5,688,486 A | 11/1997 | Watson et al. |
| 5,720,894 A | 2/1998 | Neev et al. |
| 5,730,727 A | 3/1998 | Russo |
| 5,735,815 A | 4/1998 | Bair |
| 5,740,291 A | 4/1998 | De Lasa et al. |
| 5,755,752 A | 5/1998 | Segal |
| 5,759,159 A | 6/1998 | Masreliez |
| 5,762,501 A | 6/1998 | Levy |
| 5,795,153 A | 8/1998 | Rechmann |
| 5,797,745 A | 8/1998 | Ruddle |
| 5,810,037 A | 9/1998 | Sasaki et al. |
| 5,816,807 A | 10/1998 | Matsutani et al. |
| 5,820,373 A | 10/1998 | Okano et al. |
| 5,825,958 A | 10/1998 | Gollihar et al. |
| 5,839,896 A | 11/1998 | Hickok et al. |
| 5,842,863 A | 12/1998 | Bruns et al. |
| 5,846,080 A | 12/1998 | Schneider |
| 5,853,384 A | 12/1998 | Bair |
| 5,865,790 A | 2/1999 | Bair |
| 5,868,570 A | 2/1999 | Hickok et al. |
| 5,874,677 A | 2/1999 | Bab et al. |
| 5,879,160 A | 3/1999 | Ruddle |
| 5,897,314 A | 4/1999 | Hack et al. |
| 5,915,965 A | 6/1999 | Ohlsson et al. |
| 5,921,775 A | 7/1999 | Buchanan |
| 5,968,039 A | 10/1999 | Deutsch |
| 5,975,897 A | 11/1999 | Propp et al. |
| 5,989,023 A | 11/1999 | Summer et al. |
| 6,004,319 A | 12/1999 | Goble et al. |
| 6,019,605 A | 2/2000 | Myers |
| 6,053,735 A | 4/2000 | Buchanan |
| 6,079,979 A | 7/2000 | Riitano |
| 6,122,300 A | 9/2000 | Freiberg et al. |
| 6,129,721 A | 10/2000 | Kataoka et al. |
| 6,139,319 A | 10/2000 | Sauer et al. |
| 6,143,011 A | 11/2000 | Hood et al. |
| D435,651 S * | 12/2000 | Hartwein ..................... D24/111 |
| 6,159,006 A | 12/2000 | Cook et al. |
| 6,162,052 A | 12/2000 | Kokubu |
| 6,162,177 A | 12/2000 | Bab et al. |
| 6,162,202 A | 12/2000 | Sicurelli et al. |
| 6,164,966 A | 12/2000 | Turdiu et al. |
| 6,179,617 B1 | 1/2001 | Ruddle |

(56) References Cited

U.S. PATENT DOCUMENTS

| | | |
|---|---|---|
| 6,190,318 B1 | 2/2001 | Bab et al. |
| 6,221,031 B1 | 4/2001 | Heraud |
| 6,224,378 B1 | 5/2001 | Valdes et al. |
| 6,227,855 B1 | 5/2001 | Hickok et al. |
| 6,245,032 B1 | 6/2001 | Sauer et al. |
| 6,282,013 B1 | 8/2001 | Ostler et al. |
| 6,288,499 B1 | 9/2001 | Rizoiu et al. |
| 6,290,502 B1 | 9/2001 | Hugo |
| 6,312,440 B1 | 11/2001 | Hood et al. |
| 6,315,557 B1 | 11/2001 | Messick |
| 6,343,929 B1 | 2/2002 | Fischer |
| 6,386,871 B1 | 5/2002 | Rossell |
| 6,390,815 B1 | 5/2002 | Pond |
| 6,428,319 B1 | 8/2002 | Lopez et al. |
| 6,440,103 B1 | 8/2002 | Hood et al. |
| 6,454,566 B1 | 9/2002 | Lynch et al. |
| 6,464,498 B1 | 10/2002 | Pond |
| 6,485,304 B2 | 11/2002 | Beerstecher et al. |
| 6,497,572 B2 | 12/2002 | Hood et al. |
| 6,511,493 B1 | 1/2003 | Moutafis et al. |
| 6,514,077 B1 | 2/2003 | Wilk |
| 6,527,766 B1 | 3/2003 | Bair |
| 6,538,739 B1 | 3/2003 | Visuri et al. |
| 6,562,050 B1 | 5/2003 | Owen |
| 6,572,709 B1 | 6/2003 | Kaneda et al. |
| 6,602,074 B1 | 8/2003 | Suh et al. |
| 6,616,447 B1 | 9/2003 | Rizoiu et al. |
| 6,638,219 B1 | 10/2003 | Asch et al. |
| 6,641,394 B2 | 11/2003 | Garman |
| 6,663,386 B1 | 12/2003 | Moelsgaard |
| 6,676,409 B2 | 1/2004 | Grant |
| 6,783,364 B1 | 8/2004 | Juan |
| 6,817,862 B2 | 11/2004 | Hickok |
| 6,821,272 B2 | 11/2004 | Rizoiu et al. |
| D499,486 S | 12/2004 | Kuhn et al. |
| 6,827,766 B2 | 12/2004 | Carnes et al. |
| 6,881,061 B2 | 4/2005 | Fisher |
| 6,910,887 B2 | 6/2005 | Van Den Houdt |
| 6,948,935 B2 | 9/2005 | Nusstein |
| 6,971,878 B2 | 12/2005 | Pond |
| 6,976,844 B2 | 12/2005 | Hickok et al. |
| 6,981,869 B2 | 1/2006 | Ruddle |
| 6,997,714 B1 | 2/2006 | Schoeffel |
| 7,011,521 B2 | 3/2006 | Sierro et al. |
| 7,011,644 B1 | 3/2006 | Andrew et al. |
| 7,014,465 B1 | 3/2006 | Marais |
| 7,044,737 B2 | 5/2006 | Fu |
| 7,090,497 B1 | 8/2006 | Harris |
| 7,108,693 B2 | 9/2006 | Rizoiu et al. |
| 7,115,100 B2 | 10/2006 | McRury et al. |
| 7,147,468 B2 | 12/2006 | Snyder et al. |
| 7,163,400 B2 | 1/2007 | Cozean et al. |
| 7,238,342 B2 | 7/2007 | Torabinejad et al. |
| 7,261,561 B2 | 8/2007 | Ruddle et al. |
| 7,269,306 B1 | 9/2007 | Koeneman et al. |
| 7,270,544 B2 | 9/2007 | Schemmer et al. |
| 7,288,086 B1 | 10/2007 | Andriasyan |
| 7,296,318 B2 | 11/2007 | Mourad et al. |
| 7,306,459 B1 | 12/2007 | Williams et al. |
| 7,306,577 B2 | 12/2007 | Lemoine et al. |
| 7,326,054 B2 | 2/2008 | Todd et al. |
| 7,356,225 B2 | 4/2008 | Loebel |
| 7,384,419 B2 | 6/2008 | Jones et al. |
| 7,415,050 B2 | 8/2008 | Rizoiu et al. |
| 7,421,186 B2 | 9/2008 | Boutoussov et al. |
| 7,445,618 B2 | 11/2008 | Eggers et al. |
| 7,470,124 B2 | 12/2008 | Bornstein |
| 7,485,116 B2 | 2/2009 | Cao |
| 7,549,861 B2 | 6/2009 | Ruddle et al. |
| 7,620,290 B2 | 11/2009 | Rizoiu et al. |
| 7,621,745 B2 | 11/2009 | Bornstein |
| 7,630,420 B2 | 12/2009 | Boutoussov |
| 7,641,668 B2 | 1/2010 | Perry et al. |
| 7,670,141 B2 | 3/2010 | Thomas et al. |
| 7,695,469 B2 | 4/2010 | Boutoussov et al. |
| 7,696,466 B2 | 4/2010 | Rizoiu et al. |
| 7,702,196 B2 | 4/2010 | Boutoussov et al. |
| 7,748,979 B2 | 7/2010 | Nahlieli |
| 7,778,306 B2 | 8/2010 | Marincek et al. |
| 7,815,630 B2 | 10/2010 | Rizoiu et al. |
| 7,817,687 B2 | 10/2010 | Rizoiu et al. |
| 7,833,016 B2 | 11/2010 | Gharib et al. |
| 7,845,944 B2 | 12/2010 | DiGasbarro |
| 7,867,224 B2 | 1/2011 | Lukac et al. |
| 7,901,373 B2 | 3/2011 | Tavger |
| 7,909,817 B2 | 3/2011 | Griffin et al. |
| 7,916,282 B2 | 3/2011 | Duineveld et al. |
| 7,959,441 B2 | 6/2011 | Glover et al. |
| 7,970,027 B2 | 6/2011 | Rizoiu et al. |
| 7,970,030 B2 | 6/2011 | Rizoiu et al. |
| 7,980,854 B2 | 7/2011 | Glover et al. |
| 7,980,923 B2 | 7/2011 | Olmo et al. |
| 8,002,544 B2 | 8/2011 | Rizoiu et al. |
| 8,011,923 B2 | 9/2011 | Lukac et al. |
| 8,033,825 B2 | 10/2011 | Rizoiu et al. |
| 8,047,841 B2 | 11/2011 | Jefferies |
| 8,128,401 B2 | 3/2012 | Ruddle et al. |
| 8,152,797 B2 | 4/2012 | Boutoussov et al. |
| 8,204,612 B2 | 6/2012 | Feine et al. |
| 8,295,025 B2 | 10/2012 | Edel et al. |
| 8,298,215 B2 | 10/2012 | Zinn |
| 8,317,514 B2 | 11/2012 | Weill |
| 8,322,910 B2 | 12/2012 | Gansmuller et al. |
| 8,328,552 B2 | 12/2012 | Ruddle |
| 8,388,345 B2 | 3/2013 | Ruddle |
| 8,419,719 B2 | 4/2013 | Rizoiu et al. |
| 8,439,676 B2 | 5/2013 | Florman |
| 8,506,293 B2 | 8/2013 | Pond |
| D699,180 S | 2/2014 | Sweere et al. |
| 8,672,678 B2 | 3/2014 | Gramann et al. |
| 8,684,956 B2 | 4/2014 | McDonough et al. |
| 8,709,057 B2 | 4/2014 | Tettamanti et al. |
| 8,740,957 B2 | 6/2014 | Masotti |
| 8,747,005 B2 | 6/2014 | Kemp et al. |
| 8,753,121 B2 | 6/2014 | Gharib et al. |
| 8,758,010 B2 | 6/2014 | Yamanaka et al. |
| 8,801,316 B1 | 8/2014 | Abedini |
| 8,834,457 B2 | 9/2014 | Cao |
| 8,977,085 B2 | 3/2015 | Walsh et al. |
| D726,324 S | 4/2015 | Duncan et al. |
| 9,022,959 B2 | 5/2015 | Fusi, II et al. |
| 9,022,961 B2 | 5/2015 | Fougere et al. |
| 9,025,625 B2 | 5/2015 | Skrabelj et al. |
| 9,050,157 B2 | 6/2015 | Boyd et al. |
| 9,101,377 B2 | 8/2015 | Boutoussov et al. |
| 9,186,222 B2 | 11/2015 | Marincek et al. |
| D745,966 S | 12/2015 | Piorek et al. |
| 9,216,073 B2 | 12/2015 | McDonough et al. |
| 9,308,326 B2 | 4/2016 | Hunter et al. |
| 9,333,060 B2 | 5/2016 | Hunter |
| 9,341,184 B2 | 5/2016 | Dion et al. |
| 9,492,244 B2 | 11/2016 | Bergheim et al. |
| 9,504,536 B2 | 11/2016 | Bergheim et al. |
| 9,572,632 B2 | 2/2017 | Lukac et al. |
| 9,579,174 B2 | 2/2017 | Yamamoto et al. |
| 9,610,125 B2 | 4/2017 | Kazic et al. |
| 9,700,382 B2 | 7/2017 | Pond et al. |
| 9,700,384 B2 | 7/2017 | Yamamoto et al. |
| 9,713,511 B2 * | 7/2017 | Lifshitz .............. A61C 5/40 |
| 9,788,899 B2 | 10/2017 | Sivriver et al. |
| 9,820,827 B2 | 11/2017 | Feine et al. |
| 9,820,834 B2 | 11/2017 | Maxwell et al. |
| 9,872,748 B2 | 1/2018 | Schoeffel |
| 9,877,801 B2 | 1/2018 | Khakpour et al. |
| 9,931,187 B2 | 4/2018 | Fregoso et al. |
| 9,987,200 B2 | 6/2018 | Kishen |
| 10,010,388 B2 | 7/2018 | Gharib et al. |
| 10,016,263 B2 | 7/2018 | Gharib et al. |
| 10,039,625 B2 | 8/2018 | Gharib et al. |
| 2001/0041324 A1 | 11/2001 | Riitano |
| 2002/0012897 A1 | 1/2002 | Tingley et al. |
| 2002/0072032 A1 | 6/2002 | Senn et al. |
| 2002/0086264 A1 | 7/2002 | Okawa et al. |
| 2002/0090594 A1 | 7/2002 | Riitano et al. |

(56) References Cited

U.S. PATENT DOCUMENTS

| | | |
|---|---|---|
| 2002/0108614 A1 | 8/2002 | Schultz |
| 2002/0183728 A1 | 12/2002 | Rosenberg et al. |
| 2003/0013064 A1 | 1/2003 | Zirkel |
| 2003/0096213 A1 | 5/2003 | Hickok et al. |
| 2003/0121532 A1 | 7/2003 | Coughlin et al. |
| 2003/0191429 A1 | 10/2003 | Andrew et al. |
| 2003/0207231 A1 | 11/2003 | Nance |
| 2003/0207232 A1 | 11/2003 | Todd et al. |
| 2003/0236517 A1 | 12/2003 | Appling |
| 2004/0038170 A1 | 2/2004 | Hiszowicz et al. |
| 2004/0048226 A1 | 3/2004 | Garman |
| 2004/0063074 A1 | 4/2004 | Fisher |
| 2004/0072122 A1 | 4/2004 | Hegemann |
| 2004/0073374 A1 | 4/2004 | Lockhart et al. |
| 2004/0101809 A1 | 5/2004 | Weiss et al. |
| 2004/0126732 A1 | 7/2004 | Nusstein |
| 2004/0127892 A1 | 7/2004 | Harris |
| 2004/0193236 A1 | 9/2004 | Altshuler |
| 2004/0210276 A1 | 10/2004 | Altshuler et al. |
| 2004/0224288 A1 | 11/2004 | Bornstein |
| 2004/0259053 A1 | 12/2004 | Bekov et al. |
| 2005/0064371 A1 | 3/2005 | Soukos et al. |
| 2005/0096529 A1 | 5/2005 | Cooper et al. |
| 2005/0136375 A1 | 6/2005 | Sicurelli, Jr. et al. |
| 2005/0155622 A1 | 7/2005 | Leis |
| 2005/0170312 A1* | 8/2005 | Pond ................ A61C 5/40 433/81 |
| 2005/0199261 A1 | 9/2005 | Vanhauwemeiren et al. |
| 2005/0271531 A1 | 12/2005 | Brown et al. |
| 2005/0277898 A1 | 12/2005 | Dimalanta et al. |
| 2005/0281530 A1 | 12/2005 | Rizoiu et al. |
| 2006/0019220 A1 | 1/2006 | Loebel et al. |
| 2006/0021642 A1 | 2/2006 | Sliwa et al. |
| 2006/0036172 A1 | 2/2006 | Abe |
| 2006/0064037 A1 | 3/2006 | Shalon et al. |
| 2006/0110710 A1 | 5/2006 | Schemmer et al. |
| 2006/0184071 A1 | 8/2006 | Klopotek |
| 2006/0189965 A1 | 8/2006 | Litvak et al. |
| 2006/0234182 A1 | 10/2006 | Ruddle et al. |
| 2006/0234183 A1 | 10/2006 | Ruddle et al. |
| 2006/0240386 A1 | 10/2006 | Yaniv et al. |
| 2006/0246395 A1 | 11/2006 | Pond |
| 2006/0257819 A1 | 11/2006 | Johnson |
| 2006/0264808 A1 | 11/2006 | Staid et al. |
| 2007/0009449 A1 | 1/2007 | Kanca |
| 2007/0016177 A1 | 1/2007 | Vaynberg et al. |
| 2007/0016178 A1 | 1/2007 | Vaynberg et al. |
| 2007/0020576 A1 | 1/2007 | Osborn et al. |
| 2007/0042316 A1 | 2/2007 | Pichat et al. |
| 2007/0049911 A1 | 3/2007 | Brown |
| 2007/0072153 A1 | 3/2007 | Gross et al. |
| 2007/0083120 A1 | 4/2007 | Cain et al. |
| 2007/0148615 A1 | 6/2007 | Pond |
| 2007/0175502 A1 | 8/2007 | Sliwa |
| 2007/0179486 A1 | 8/2007 | Welch et al. |
| 2007/0265605 A1 | 11/2007 | Vaynberg et al. |
| 2007/0287125 A1 | 12/2007 | Weill |
| 2008/0014545 A1 | 1/2008 | Schippers |
| 2008/0032259 A1* | 2/2008 | Schoeffel ........... A61C 17/0208 433/81 |
| 2008/0044789 A1 | 2/2008 | Johnson |
| 2008/0050702 A1 | 2/2008 | Glover et al. |
| 2008/0070195 A1 | 3/2008 | DiVito et al. |
| 2008/0085490 A1 | 4/2008 | Jabri |
| 2008/0138761 A1 | 6/2008 | Pond |
| 2008/0138772 A1 | 6/2008 | Bornstein |
| 2008/0155770 A1 | 7/2008 | Grez |
| 2008/0159345 A1 | 7/2008 | Bornstein |
| 2008/0160479 A1 | 7/2008 | Ruddle et al. |
| 2008/0160480 A1 | 7/2008 | Ruddle et al. |
| 2008/0188848 A1 | 8/2008 | Deutmeyer et al. |
| 2008/0199831 A1 | 8/2008 | Teichert et al. |
| 2008/0255498 A1 | 10/2008 | Houle |
| 2008/0285600 A1 | 11/2008 | Marincek et al. |
| 2008/0311540 A1 | 12/2008 | Gottenbos et al. |
| 2009/0004621 A1 | 1/2009 | Quan et al. |
| 2009/0011380 A1 | 1/2009 | Wang |
| 2009/0042171 A1 | 2/2009 | Rizoiu et al. |
| 2009/0047624 A1 | 2/2009 | Tsai |
| 2009/0047634 A1 | 2/2009 | Calvert |
| 2009/0054881 A1 | 2/2009 | Krespi |
| 2009/0059994 A1 | 3/2009 | Nemes et al. |
| 2009/0111068 A1 | 4/2009 | Martinez |
| 2009/0111069 A1 | 4/2009 | Wagner |
| 2009/0130622 A1 | 5/2009 | Bollinger et al. |
| 2009/0208898 A1 | 8/2009 | Kaplan |
| 2009/0211042 A1 | 8/2009 | Bock |
| 2009/0220908 A1 | 9/2009 | Divito et al. |
| 2009/0227185 A1 | 9/2009 | Summers et al. |
| 2009/0263759 A1 | 10/2009 | Van Herpern |
| 2010/0042040 A1 | 2/2010 | Arentz |
| 2010/0047734 A1 | 2/2010 | Harris et al. |
| 2010/0143861 A1 | 6/2010 | Gharib |
| 2010/0152634 A1* | 6/2010 | Dove ................. A61C 17/0202 601/162 |
| 2010/0160838 A1 | 6/2010 | Krespi |
| 2010/0160904 A1 | 6/2010 | McMillan et al. |
| 2010/0209867 A1 | 8/2010 | Becker et al. |
| 2010/0229316 A1 | 9/2010 | Hohlbein et al. |
| 2010/0273125 A1 | 10/2010 | Janssen et al. |
| 2010/0279250 A1 | 11/2010 | Pond et al. |
| 2010/0330539 A1 | 12/2010 | Glover et al. |
| 2011/0027746 A1 | 2/2011 | McDonough et al. |
| 2011/0070552 A1 | 3/2011 | Bornstein |
| 2011/0072605 A1 | 3/2011 | Steur |
| 2011/0087605 A1 | 4/2011 | Pond |
| 2011/0111365 A1 | 5/2011 | Gharib et al. |
| 2011/0117517 A1* | 5/2011 | Bergheim ................ A61C 5/02 433/81 |
| 2011/0143310 A1 | 6/2011 | Hunter |
| 2011/0198370 A1 | 8/2011 | Ho |
| 2011/0229845 A1 | 9/2011 | Chen |
| 2011/0256503 A1 | 10/2011 | Fraser |
| 2011/0269099 A1 | 11/2011 | Glover et al. |
| 2011/0270241 A1 | 11/2011 | Boutoussov |
| 2012/0135373 A1 | 5/2012 | Cheng et al. |
| 2012/0141953 A1 | 6/2012 | Mueller |
| 2012/0237893 A1* | 9/2012 | Bergheim ................ A61C 5/02 433/81 |
| 2012/0276497 A1 | 11/2012 | Gharib |
| 2012/0282570 A1 | 11/2012 | Mueller |
| 2012/0021375 A1 | 12/2012 | Binner et al. |
| 2013/0040267 A1* | 2/2013 | Bergheim ................ A61C 3/03 433/216 |
| 2013/0084544 A1 | 4/2013 | Boutoussov et al. |
| 2013/0084545 A1 | 4/2013 | Netchitailo et al. |
| 2013/0085486 A1 | 4/2013 | Boutoussov et al. |
| 2013/0131656 A1 | 5/2013 | Marincek et al. |
| 2013/0143180 A1 | 6/2013 | Glover et al. |
| 2013/0177865 A1 | 7/2013 | Ostler |
| 2013/0190738 A1 | 7/2013 | Lukac et al. |
| 2013/0216980 A1 | 8/2013 | Boronkay et al. |
| 2013/0236857 A1 | 9/2013 | Boutoussov et al. |
| 2013/0288195 A1 | 10/2013 | Mueller |
| 2013/0296910 A1 | 11/2013 | Deng |
| 2013/0330684 A1 | 12/2013 | Dillon et al. |
| 2013/0337404 A1 | 12/2013 | Feine |
| 2014/0032183 A1 | 1/2014 | Fisker et al. |
| 2014/0080090 A1* | 3/2014 | Laufer .................... A61C 3/025 433/88 |
| 2014/0087333 A1 | 3/2014 | DiVito et al. |
| 2014/0099597 A1* | 4/2014 | Bergheim .............. A61C 17/02 433/80 |
| 2014/0113243 A1 | 4/2014 | Boutoussov et al. |
| 2014/0124969 A1 | 5/2014 | Blaisdell et al. |
| 2014/0127641 A1 | 5/2014 | Hilscher et al. |
| 2014/0170588 A1 | 6/2014 | Miller et al. |
| 2014/0205965 A1 | 7/2014 | Boutoussov et al. |
| 2014/0220505 A1 | 8/2014 | Khakpour |
| 2014/0220511 A1 | 8/2014 | DiVito et al. |
| 2014/0242551 A1 | 8/2014 | Downs |
| 2014/0261534 A1 | 9/2014 | Schepis |
| 2014/0272782 A1 | 9/2014 | Luettgen et al. |
| 2014/0342303 A1 | 11/2014 | Altshuler et al. |

(56) References Cited

U.S. PATENT DOCUMENTS

| | | |
|---|---|---|
| 2014/0349246 A1 | 11/2014 | Johnson et al. |
| 2015/0010878 A1 | 1/2015 | Seibel et al. |
| 2015/0010882 A1 | 1/2015 | Bergheim |
| 2015/0017599 A1 | 1/2015 | Marincek et al. |
| 2015/0044631 A1* | 2/2015 | Lifshitz .................. A61C 5/02 433/81 |
| 2015/0044632 A1 | 2/2015 | Bergheim et al. |
| 2015/0056567 A1 | 2/2015 | Fregoso et al. |
| 2015/0056570 A1 | 2/2015 | Kansal |
| 2015/0125811 A1 | 5/2015 | Lifshitz et al. |
| 2015/0132712 A1 | 5/2015 | Gharib |
| 2015/0140503 A1 | 5/2015 | Bergheim et al. |
| 2015/0147715 A1 | 5/2015 | Breysse |
| 2015/0147717 A1 | 5/2015 | Taylor et al. |
| 2015/0147718 A1 | 5/2015 | Khakpour |
| 2015/0150650 A1 | 6/2015 | Netchitailo et al. |
| 2015/0173850 A1 | 6/2015 | Garrigues et al. |
| 2015/0173852 A1 | 6/2015 | Khakpour |
| 2015/0190597 A1 | 7/2015 | Zachar et al. |
| 2015/0216597 A1 | 8/2015 | Boutoussov et al. |
| 2015/0230865 A1 | 8/2015 | Sivriver et al. |
| 2015/0268803 A1 | 9/2015 | Patton et al. |
| 2015/0277738 A1 | 10/2015 | Boutoussov et al. |
| 2015/0283277 A1 | 10/2015 | Schafer et al. |
| 2015/0327964 A1 | 11/2015 | Bock |
| 2015/0335410 A1 | 11/2015 | Zhao |
| 2015/0366634 A1 | 12/2015 | Gharib |
| 2015/0367142 A1 | 12/2015 | Kazic et al. |
| 2015/0374471 A1 | 12/2015 | Stangel et al. |
| 2016/0022392 A1 | 1/2016 | Chang et al. |
| 2016/0067149 A1 | 3/2016 | Kishen |
| 2016/0100921 A1 | 4/2016 | Ungar |
| 2016/0113733 A1 | 4/2016 | Pond et al. |
| 2016/0128815 A1 | 5/2016 | Birdee et al. |
| 2016/0135581 A1 | 5/2016 | Pai |
| 2016/0149370 A1 | 5/2016 | Marincek et al. |
| 2016/0149372 A1 | 5/2016 | Marincek et al. |
| 2016/0324600 A1 | 11/2016 | Gharib |
| 2016/0367346 A1 | 12/2016 | Gharib |
| 2017/0027646 A1 | 2/2017 | DiVito et al. |
| 2017/0036253 A1 | 2/2017 | Lukac et al. |
| 2017/0056143 A1 | 3/2017 | Hyun |
| 2017/0196658 A1 | 7/2017 | Schoeffel |
| 2017/0216579 A1 | 8/2017 | Becker et al. |
| 2017/0273758 A1 | 9/2017 | Bergheim |
| 2017/0281305 A1 | 10/2017 | Bergheim |
| 2017/0281312 A1 | 10/2017 | Khakpour |
| 2017/0300220 A1 | 10/2017 | Boutoussov et al. |
| 2017/0325889 A1 | 11/2017 | DiVito et al. |
| 2018/0116761 A1 | 5/2018 | Bergheim |
| 2018/0214247 A1 | 8/2018 | Sharma et al. |

FOREIGN PATENT DOCUMENTS

| | | |
|---|---|---|
| AU | 2011316839 | 8/2015 |
| CN | 102724929 | 10/2012 |
| CN | 103027762 A | 4/2013 |
| CN | 103347462 | 10/2013 |
| CN | 104470464 A | 3/2015 |
| DE | 37 08 801 A1 | 9/1988 |
| DE | 102 48 336 | 5/2004 |
| DE | 103 31 583 | 7/2004 |
| EP | 0 261 466 | 3/1988 |
| EP | 1 214 916 | 6/2002 |
| EP | 0 902 654 | 8/2004 |
| EP | 2 498 713 | 9/2012 |
| EP | 2 821 027 | 1/2015 |
| EP | 2 836 156 | 2/2015 |
| EP | 2 836 157 | 2/2015 |
| EP | 2 934 364 | 10/2015 |
| EP | 2 951 019 | 12/2015 |
| EP | 2 959 861 | 12/2015 |
| EP | 3 013 277 | 5/2016 |
| EP | 3 231 385 | 10/2017 |
| FR | 1 225 547 | 7/1960 |
| FR | 2 831 050 | 10/2001 |
| GB | 917 633 | 2/1963 |
| HK | 1 188 108 A | 4/2014 |
| JP | 51-064791 A | 4/1976 |
| JP | 09-276292 | 10/1997 |
| JP | 10-33548 | 2/1998 |
| JP | 11-113927 A | 4/1999 |
| JP | 11-244303 A | 9/1999 |
| JP | 2000-254153 A | 9/2000 |
| JP | 2002-191619 | 7/2002 |
| JP | 2002-209911 | 7/2002 |
| JP | 2004-313659 | 11/2003 |
| JP | 3535685 B2 | 6/2004 |
| JP | 2004-261288 | 9/2004 |
| JP | 2004-267756 | 9/2004 |
| JP | 2005-095374 | 4/2005 |
| JP | 2007-533333 | 11/2007 |
| JP | 2008-93080 | 4/2008 |
| JP | 2008-132099 | 6/2008 |
| JP | 2009-114953 | 5/2009 |
| JP | 2013-510688 | 3/2013 |
| JP | 2013-544120 | 12/2013 |
| JP | 2015-510829 | 4/2015 |
| KR | 10-2008-0105713 A | 12/2008 |
| KR | 10-2012-0084897 A | 7/2012 |
| KR | 10-2013-0022553 A | 3/2013 |
| KR | 10-2013-0141103 A | 12/2013 |
| KR | 2004-72508 Y1 | 5/2014 |
| RU | 2326611 C1 | 12/2011 |
| TW | M 336 027 U | 7/2008 |
| WO | WO 1992/004871 | 4/1992 |
| WO | WO 1992/12685 | 8/1992 |
| WO | WO 1998/025536 | 6/1995 |
| WO | WO 1995/035069 | 12/1995 |
| WO | WO 1996/12447 | 5/1996 |
| WO | WO 1997/021420 | 6/1997 |
| WO | WO 1998/023219 | 6/1998 |
| WO | WO 2000/045731 | 8/2000 |
| WO | WO 2000/74587 | 12/2000 |
| WO | WO 2001/026577 | 4/2001 |
| WO | WO 2001/93773 | 12/2001 |
| WO | WO 2002/078644 | 10/2002 |
| WO | WO 2003/086223 | 10/2003 |
| WO | WO 2004/034923 | 4/2004 |
| WO | WO 2004/082501 | 9/2004 |
| WO | WO 2005/007008 | 1/2005 |
| WO | WO 2005/032393 | 4/2005 |
| WO | WO 2005/034790 | 4/2005 |
| WO | WO 2005/102033 | 11/2005 |
| WO | WO 2006/082101 | 8/2006 |
| WO | WO 2007/007335 | 1/2007 |
| WO | WO 2007/007336 | 1/2007 |
| WO | WO 2007/124038 | 11/2007 |
| WO | WO 2008/024442 | 2/2008 |
| WO | WO 2008/092125 | 7/2008 |
| WO | WO 2008/120018 | 10/2008 |
| WO | WO 2009/036963 | 3/2009 |
| WO | WO 2009/047670 | 4/2009 |
| WO | WO 2009/064947 | 5/2009 |
| WO | WO 2009/137815 | 11/2009 |
| WO | WO 2010/007257 | 1/2010 |
| WO | WO 2010/099538 | 9/2010 |
| WO | WO 2011/060327 | 5/2011 |
| WO | WO 2011/077291 | 6/2011 |
| WO | WO 2011/136798 | 11/2011 |
| WO | WO 2012/054905 | 4/2012 |
| WO | WO 2012/074918 | 6/2012 |
| WO | WO 2013/15700 | 1/2013 |
| WO | WO 2013/061251 | 5/2013 |
| WO | WO 2013/142385 | 9/2013 |
| WO | WO 2013/155492 | 10/2013 |
| WO | WO 2013/160888 | 10/2013 |
| WO | WO 2014/100751 | 6/2014 |
| WO | WO 2014/121293 | 8/2014 |
| WO | WO 2015/168329 | 11/2015 |
| WO | WO 2016/005221 | 1/2016 |

(56) References Cited

FOREIGN PATENT DOCUMENTS

| WO | WO 2017/162705 | 9/2017 |
|----|----------------|--------|
| WO | WO 2017/162706 | 9/2017 |
| WO | WO 2018/075652 | 4/2018 |

OTHER PUBLICATIONS

Bahia, et al.: Physical and mechanical characterization and the influence of cyclic loading on the behaviour of nickel-titanium wires employed in the manufacture of rotary endodontic instruments. Int Endod. J. 2005;38:795-801.

Charara, et al.: "Assessment of apical extrusion during root canal procedure with the novel GentleWave system in a simulated apical environment," J Endod 2015. In Press.

Crump et al., "Relationship of broken root canal instruments to endodontic case prognosis: a clinical investigation," J Am Dent Assoc 1970;80:1341-7.

D'Arcangelo, et al.: "Broken instrument removal—two cases," J Endod 2000;26:368-70.

Esen, et al.: "Apical microleakage of root-end cavities prepared by $CO_2$ laser," J Endod 2004;30:662-4.

Feldman, et al.: "Retrieving broken endodontic instruments," J Am Dent Assoc. 1974:88:588-91.

Fors, et al.: "A method for the removal of broken endodontic instruments from root canals," J Endod 1983;9:156-9.

Gencoglu, et al.: Comparison of the different techniques to remove fractured endodontic instruments from root canal systems. Eur J Dent 2009;3:90-5.

Haapasalo, et al.: "Tissue dissolution by a novel multisonic ultracleaning system and sodium hypochlorite," J Endod 2014;40:1178-81.

Haikel, et al.: Dynamic and cyclic fatigue of engine-driven rotary nickel-titanium endodontic instruments. J Endod 1999;25:434-40.

Haikel, et al.: Dynamic fracture of hybrid endodontic hand instruments compared with traditional files. J Endod 1991;17:217-20.

Hulsmann, et al.: Influence of several factors on the success or failure of removal of fractured instruments from the root canal. Endod Dent Traumatol 199;15:252-8.

Hulsmann: "Methods for removing metal obstructions from the root canal," Endod Dent Traumatol 1993;9:223-37.

Iqbal, et al.: "A comparison of three methods for preparing centered platforms around separated instruments in curved canals," J Endod 2006;32:48-51.

Ma, et al.: "In vitro study of calcium hydroxide removal from mandibular molar root canals," J Endod 2015;41:553-8.

Madarati, et al.: "Efficiency of a newly designed ultrasonic unit and tips in reducing temperature rise on root surface during the removal of fractured files," J Endod 2009;35:896-9.

Madarati, et al.: "Management of intracanal separated instruments," J Endod 2013;39:569-81.

Madarati, et al.: "Qualtrough AJ. Factors contributing to the separation of endodontic files," Br Dent J 2008;204:241-5.

Molina, et al.: "Histological evaluation of root canal debridement of human molars using the GentleWaveTM system," J Endod 2015;41:1702-5.

Nevares, et al.: "Success rates for removing or bypassing fractured instruments: a prospective clinical study," J Endod 2012;38:442-4.

Roth, et al.: "A study of the strength of endodonitc files: potential for torsional breakage and relative flexibility," J Endod 1983; 9:228-32.

Ruddle, "Nonsurgical retreatment," J Endod 2004;30:827-45.

Schneider, et al.: "A comparison of canal preparations in straight and curved root canals," Oral Surg Oral Med Oral Pathol 1971;32:271-5.

Schneider, et al.: "NIH Image to ImageJ: 25 years of image analysis," Nat Methods 2012;9:671-5.

Shen, et al.: "Factors associated with the removal of fractured NiTi instruments from root canal systems," Oral Surg Oral Med Oral Pathol Oral Radiol Endod 2004;98:605-10.

Skyttner, "Endodontic instrument separations: evaluation of a patient cases series with separated endodontic instruments and factors related to the treatment regarding separated instruments [thesis]," Stockholm: Karolinska Institutet; 2007.

Souter, et al.: "Complications associated with fractured file removal using an ultrasonic technique," J Endod 2005;31:450-2.

Suter, et al.: "Probability of removing fractured instruments from root canals," Int Endod J 2005;38:112-23.

Terauchi, et al.: "Evaluation of the efficiency of a new file removal system in comparison with two conventional systems," J. Endod 2007;33:585-8.

Ward Jr.: "The use of an ultrasonic technique to remove a fractured rotary nickel-titanium instrument from the apical third of a curved root canal," Aust Endod J 2003;29:25-30.

Yoldas, et al.: "Perforation risks associated with the use of Masserann endodontic kit drills in mandibular molars," Oral Surg Oral Med Oral Pathol Oral Radiol Endod 2004;97:513-7.

Yu et al.: "Study on removal effects of filling materials and broken files from root canals using pulsed Nd:YAG laser," J Clin Laser Med Surg 2000;18:23-8.

Adachi et al; Jet Structure Analyses on High-Speed Submerged Water Jets through Cavitation 110 Noises; pp. 568-574; The Japan Society of Mechanical Engineers International Journal—Series B, vol. 39, No. 3; Nov. 1996.

Al-Jadaa et al; Acoustic Hypochlorite Activation in Simulated Curved Canals; pp. 1408-1411; Journal of Endodontics, vol. 35, No. 10; Oct. 2009.

Anand et al; Prevention of Nozzle Wear in High-Speed Slurry Jets Using Porous Lubricated Nozzles; pp. 1-13; Department of Mechanical Engineering, The Johns Hopkins University, Oct. 2000.

Anantharamaiah et al; A simple expression for predicting the inlet roundness of micro-nozzles; pp. N31-N39; Journal of Micromechanics and Microengineering, vol. 17; Mar. 21, 2007.

Anantharamaiah et al; A study on flow through hydroentangling nozzles and their degradation; pp. 4582-4594; Chemical Engineering Science, vol. 61; May 2006.

Anantharamaiah et al; Numerical Simulation of the Formation of Constricted Waterjets in Hydroentangling Nozzles Effects of Nozzle Geometry; pp. 31-238; Chemical Engineering Research and Design, vol. 84; Mar. 2006.

Attin et al; Clinical evaluation of the cleansing properties of the nonistrumental technique for cleaning root canals; pp. 929-933; International Endodontic Journal, vol. 35, Issue 11; Nov. 2002.

Batchelor et al; Analysis of the stability of axisymmetric jets; pp. 529-551; Journal of Fluid Mechanics, vol. 14; Dec. 1962.

Begenir et al; Effect of Nozzle Geometry on Hydroentangling Water Jets: Experimental Observations; pp. 178-184; Textile Research Journal, vol. 74; Feb. 2004.

Begenir, Asli; The Role of Orifice Design in Hydroentanglement; Thesis submitted to North Carolina State University; dated Dec. 2002, in 107 pages.

Borkent et al; Is there gas entrapped on submerged silicon wafers? Visualizing nano-scale bubbles with cavitation; pp. 225-228; Solid State Phenomena, vol. 134 (2008); available online Nov. 2007.

Bremond et al; Cavitation on surfaces; pp. S3603-S3608; Journal of Physics: Condensed Matter, vol. 17; Oct. 28, 2005.

Brennen, Christopher E.; Fission of collapsing cavitation bubbles; pp. 153-166; Journal of Fluid Mechanics, vol. 472; Dec. 2002.

Chang et al; Effects of Inlet Surface Roughness, Texture, and Nozzle Material on Cavitation; pp. 299-317; Atomization and Sprays, vol. 16 (2006).

Culjat et al., "B-Scan Imaging of Human Teeth Using Ultrasound," Apr. 2003, in 4 pages.

Didenkulov et al; Nonlinear Acoustic Diagnostics of Scatterer Spatial Distribution in a Cavitation Jet; Nov. 19-23, 2001, pp. 276-278, XI Session of the Russion Acoustical Society.

Dumouchel, Christophe; On the experimental investigation on primary atomization of liquid streams; pp. 371-422; Experimental Fluids, vol. 45; Jun. 22, 2008.

Eddingfield et al; Mathematical Modeling of High Velocity Water Jets; pp. 25-39; Proceedings of 1st U.S. Water Jet Conference; 1981.

(56) References Cited

OTHER PUBLICATIONS

EMS Electro Medical Systems, "Cleaning", in 2 pages, dated 2005, downloaded from http://www.ems-dent.com/en/endodontics cleaning. htm.
ESI Endo Soft Instruments, EMS Electro Medical Systems, Brochure in 2 pages, downloaded from www.emsdent.com, dated Jan. 2004.
European Extended Search Report re EP Application No. 09743801. 4, dated Jun. 4, 2012.
European Extended Search Report re EP Application No. 14187012. 1, dated Mar. 3, 2015, in 10 pages.
European Extended Search Report, dated Sep. 22, 2011, for EP Application No. 07755777.5, in 7 pages.
European Extended Search Report, re EP Application No. 08728345. 3, dated Mar. 3, 2014.
European Extended Search Report, re EP Application No. 10830829. 7, dated Oct. 21, 2015.
European Extended Search Report, re EP Application No. 13775073. 3, dated Nov. 3, 2015.
Feng et al; Enhancement of ultrasonic cavitation yield by multi-frequency sonication; pp. 231-236; Ultrasonics Sonochemistry, vol. 9; Oct. 2002.
Flint, E. B., et al., "The Temperature of Cavitation", Science, vol. 253, Sep. 20, 1991, pp. 1397-1399.
Foldyna et al; Acoustic wave propagation in high-pressure system; ppe1457-e1460; Ultrasonics vol. 44 (Supplement 1); Jun. 8, 2006.
Fuchs, "Ultrasonic Cleaning: Fundamental Theory and Application," Blackstone-Ney Ultrasonics, Jamestown, NY, May 2002.
G.E. Reisman and C.E. Brennen, "Pressure Pulses Generated by Cloud Cavitation", FED—vol. 236, 1996 Fluids Engineering Division Conference, vol. 1, pp. 319-328, ASME 1996.
G.E. Reisman, Y.-C. Wang and C.E. Brennen, "Observations of shock waves in cloud cavitation", J. Fluid Mech. (1998), vol. 355, pp. 255-283.
Ghassemieh et al; Effect of Nozzle Geometry on the Flow Characteristics of Hydroentangling Jets; pp. 444-450; Textile Research Journal, vol. 73; May 2003.
Ghassemieh et al; The effect of nozzle geometry on the flow characteristics of small water jets; pp. 1739-1753; Proceedings of the Institute of Mechanical Engineers, Part C: Mechanical Engineering Science, vol. 12, Sep. 2006.
Hahn et al; Acoustic resonances in the bubble plume formed by a plunging water jet; pp. 1751-1782; Proceedings of the Royal Society of London A, vol. 459; May 16, 2003.
Hashish, Mohamed; Experimental Studies of Cutting with Abrasive Waterjets; pp. 402-416; Proceedings of 2nd American Water Jet Conference; 1983.
Herbert et al; Cavitation pressure in water; pp. 041603-1 to 041603-22; Physical Review E, vol. 74; Oct. 2006.
Hiroyasu, Hiro; Spray Breakup Mechanism from the Hole-Type Nozzle and its Applications; pp. 511-527; Atomization and Sprays, vol. 10 (2000).
Hmud R. et al. "Cavitational Effects in Aqueous Endodontic Irrigants Generated by Near-Infrared Lasers", Journal of Endodontics, vol. 36, Issue 2, Feb. 2010, available online Dec. 4, 2009, in 4 pages.
Hoque et al; Air entrainment and associated energy dissipation in steady and unsteady plunging jets at free surface; pp. 37-45; Applied Ocean Research, vol. 30; May 2008.
Hydrocision Products: SpineJet Hydrosurgery; system webpage in 2 pages, copyright 2010, downloaded from http://www.hydrocision.com on Apr. 22, 2010.
Hydrocision SpineJet XL HydroSurgery System; Brochure in 2 pages, copyright 2004-2006, downloaded from http://www.hydrocision.com on Apr. 22, 2010.
International Preliminary Report and Written Opinion dated Nov. 9, 2010 for International Appl. No. PCT/US09/43386, in 6 pages.
International Preliminary Report on Patentability and Written Opinion, dated Oct. 14, 2014, re PCT Application No. PCT/US2013/036493, in 14 pages.
International Preliminary Report on Patentability dated Aug. 6, 2009, for International Appl. No. PCT/US08/52122, in 13 pages.
International Preliminary Report on Patentability dated Oct. 30, 2008, for International Appl. No. PCT/US07/09633, in 5 pages.
International Preliminary Report on Patentability re App. No. PCT/US2010/056620, dated May 15, 2012, in 10 pages.
International Preliminary Report on Patentability re PCT Application No. PCT/US2014/014732, dated Aug. 4, 2015.
International Preliminary Report on Patentability, re PCT Application No. PCT/US11/57401, dated Jan. 25, 2013 in 13 pages.
International Preliminary Report on Patentability, re PCT Application No. PCT/US2013/077286, dated Jun. 23, 2015.
International Preliminary Report on Patentability, re PCT Application No. PCT/US2014/036451, dated Nov. 3, 2015, 2015, in 11 pages.
International Search Report and Written Opinion dated Apr. 11, 2008, for International Appl. No. PCT/US07/09633, in 8 pages.
International Search Report and Written Opinion dated Aug. 8, 2008, for International Appl. No. PCT/US08/52122, in 18 pages.
International Search Report and Written Opinion dated Jul. 29, 2009, for International Appl. No. PCT/US09/43386, in 8 pages.
International Search Report and Written Opinion from International Application No. PCT/US2011/057401, dated Jan. 30, 2012, in 20 pages.
International Search Report and Written Opinion dated Jun. 28, 2013, re PCT Application No. PCT/US2013/036493, in 21 pages.
International Search Report and Written Opinion re App. No. PCT/US2010/056620, dated Jan. 12, 2011, in 17 pages.
International Search Report and Written Opinion re App. No. PCT/US2014/014732, dated Jul. 18, 2014.
International Search Report and Written Opinion, re PCT Application No. PCT/US 13/32635, dated Jun. 17, 2013 in 14 pages.
International Search Report and Written Opinion, re PCT Application No. PCT/US2013/077286, dated May 27, 2014.
International Search Report and Written Opinion, re PCT Application No. PCT/US2014/036451, dated Jan. 21, 2015, in 20 pages.
International Search Report and Written Opinion, re PCT Application No. PCT/US2014/044186, dated Jan. 21, 2015, in 19 pages.
International Search Report and Written Opinion, re PCT Application No. PCT/US2015/028360, dated Sep. 28, 2015.
Jackson et al; Nozzle Design for Coherent Water Jet Production; pp. 53-89; Proceeding of the 2nd US Water Jet Conference; May 1983.
Junge et al; Cell Detachment Method Using Shock-Wave-Induced Cavitation; pp. 1769-1776; Ultrasound in Medicine & Biology, vol. 29, No. 12; Dec. 2003.
Kalumuck et al; Development of High Erosivity Well Scale Cleaning Tools; pp. 1-36; Dynaflow, Inc.; Report 98012 conducted under Contract No. DE-FG07-981013684 for the US Dept. of Energy; Jul. 1999, in 36 pages.
Karasawa et al; Effect of Nozzle Configuration on the Atomization of a Steady Spray; pp. 411-426; Atomization and Sprays, vol. 2 (1992).
Kato, Hiroharu; Utilization of Cavitation for Environmental Protection—Killing Planktons and Dispersing Spilled Oil; pp. 1-8; in CAV2001: Fourth International Symposium on Caviation; California Institute of Technology, Pasadena, CA; dated Jun. 2001.
Lee et al; The efficacy of ultrasonic irrigation to remove artificially placed dentine debris from different-sized simulated plastic root canals; pp. 607-612; International Endodontic Journal, vol. 37; May 2004.
Li et al; Cavitation Resonance; pp. 031302-1 to 031302-7; Journal of Fluids Engineering, vol. 130; Mar. 2008.
Lienhard V et al; Velocity Coefficients for Free Jets From Sharp-Edged Orifices; pp. 13-17; Reprinted from Mar. 1984, vol. 106, Journal of Fluids Engineering.
Lin et al; Drop and Spray Formation from a Liquid Jet; pp. 85-105; Jan. 1998: vol. 30; Annual Review of Fluid Mechanics.
Linfield, Kevin William; A Study of the Discharge Coefficient of Jets From Angled Slots and Conical Orifices; Thesis submitted to Dept. of Aerospace Science and Engineering; University of Toronto; dated 2000; in 148 pages.

(56) References Cited

OTHER PUBLICATIONS

Lussi et al; A new non-instrumental technique for cleaning and filling root canals; pp. 1-6; International Endodontic Journal, vol. 28; Jan. 1995.
Lussi et al; A Novel Noninstrumented Technique for Cleansing the Root Canal System; pp. 549-553; Journal of Endodontics, vol. 19, No. 11; Nov. 1993.
Lussi et al; In vivo performance of the new non-instrumentation technology (NIT) for root canal obturation; pp. 352-358; International Endodontic Journal, vol. 35; Apr. 2002.
Maximum Dental Inc ., "Canal Clean Max", "Intra Canal Irrigation and Aspiration Device", and "SonicMax, Endo-Perio Sonic Handpiece", in 3 pages, downloaded from www.dentalmaximum.com on May 8, 2008.
Ohrn et al; Geometric Effects on Spray Cone Angle for Plain-Orifice Atomizers; pp. 253-268; Atomization and Sprays, vol. 1 (1991).
Ohrn et al; Geometrical Effects on Discharge Coefficients for Plain-Orifice Atomizers; pp. 137-153; Atomization and Sprays, vol. 1, No. 2 (1991).
Phinney, Ralph E.; The breakup of a turbulent liquid jet in a gaseous atmosphere; pp. 689-701; J. Fluid Mechanics, vol. 60, Part 4; Oct. 1973.
Piezon Master 600 Ultrasound a la carte, EMS Electro Medical Systems, EMS SA FA-319.EN ed. Mar. 2009; Brochure dated Mar. 2009, in 2 pages.
Quinn, W. R.; Experimental study of the near field and transition region of a free jet issuing from a sharp-edged elliptic orifice plate; pp. 583-614; European Journal of Mechanics—B/Fluids, vol. 26; Jul.-Aug. 2007; available online Dec. 2006.
Ramamurthi et al; Disintegration of Liquid Jets from Sharp-Edged Nozzles; pp. 551-564; Atomization and Sprays, vol. 4 (1994).
Reitz et al; Mechanism of atomization of a liquid jet; pp. 1730-1742; Physics Fluids, vol. 25, No. 10; Oct. 1982.
Sabeti, "Healing of apical periodontitis after endodontic treatment with and without obturation in dogs," Journal of Endodontics, Jul. 2006, pp. 628-633.
Sallam et al; Liquid breakup at the surface of turbulent round liquid jets in still gases; pp. 427-449; International Journal of Multiphase Flow, vol. 28; Mar. 2002.
Sawant et al; Effect of hydrodynamic cavitation on zooplankton: A tool for disinfection; pp. 320-328; Biochemical Engineering Journal, vol. 42, Issue 3; Dec. 2008.
Shi et al; Comparison-speed liquid jets; Experiments in Fluids, vol. 35; pp. 486-492; Oct. 7, 2003.
Sou et al; Effects of cavitation in a nozzle on liquid jet atomization; pp. 3575-3582; International Journal of Heat and Mass Transfer, vol. 50; Mar. 2007.
Soyama et al; High-Speed Observation of Ultrahigh-Speed Submerged Water Jets; pp. 411-416; Experimental Thermal and Fluid Science, vol. 12 1996).
Soyama, Hitoshi; High-Speed Observation of a Cavitating Jet in Air; Journal of Fluids Engineering, vol. 127; pp. 1095-1101; Nov. 2005.
Summers, David A; Considerations in the Comparison of Cavitating and Plain Water Jets; pp. 178-184; Rock Mechanics and Explosive Research Center, Rolla, Missouri, 1983.
Summers, David A; The Volume Factor in Cavitation Erosion; Proceedings of 6th International Conference on Erosion by Liquid and Solid Impact; University of Missouri-Rolla; Rolla, Missouri, 1983, in 12 pages.
Suslick, K. S., et al., "The Sonochemical Hot Spot", Journal of the American Chemical Society, vol. 108, No. 18, Sep. 3, 1986, pp. 5641-5642.
Suslick, K. S., et al., "Heterogeneous Sonocatalysis with Nickel Powder", Journal of the American Chemical Society, vol. 109, No. 11, May 27, 1987, pp. 3459-3461.
Tafreshi et al; Simulating Cavitation and Hydraulic Flip Inside Hydroentangling Nozzles; pp. 359-364; Textile Research Journal, vol. 74, Apr. 2004.
Tafreshi et al; Simulating the Flow Dynamics in Hydroentangling Nozzles: Effect of Cone Angle and Nozzle Aspect Ratio; pp. 700-704; Textile Research Journal, vol. 73; Aug. 2003.
Tafreshi et al; The effects of nozzle geometry on waterjet breakup at high Reynolds numbers; pp. 364-371; Experiments in Fluids, vol. 35; Sep. 2, 2003.
Zuo et al; An Attribution of Cavitation Resonance: Volumetric Oscillations of Cloud; pp. 152-158; Journal of Hydrodynamics, vol. 21; Apr. 2009.
U.S. Appl. No. 15/478,039, filed Apr. 3, 2017, Khakpour et al.
U.S. Appl. No. 15/499,757, filed Apr. 27, 2017, DiVito et al.
Ahmad et al., "Ultrasonic Debridement of Root Canals: Acoustic Cavitation and Its Relevance," Journal of Endontics, vol. 14, No. 10, pp. 486-493, Oct. 1988.
DiVito et al.: "Cleaning and debriding efficacy of new radial and stripped tips using an Erbium laser on human root canal dentin walls—an in vitro study: SEM observations," undated.
ADA American Dental Association, "Glossary of Dental Clinical and Administrative Terms," http://www.ada.org/en/publications/cdt/glossary-of-dental-clinical-and-administrative-ter, downloaded May 4, 2017, in 46 pages.
Lukac et al.: "Photoacoustic Endodontics Using the Novel SWEEPS Er:YAG Laser Modality," Journal of the Laser and Health Academy, vol. 2017, No. 1; www.laserlaserandhealth.com.
Schoop et al., "The Impact of an Erbium, Chromium: yttrium-scandium-gallium-garnet laser with radial-firing tips on endonic treatment," Lasers in Medical Science, Springer-Verlag, LO. vol. 24, No. 1 Nov. 20, 2007.
Stamos et al., "Retreatodontics and ultrasonics", Journal of Endodontics, vol. 14., No. 1, pp. 39-42, Jan. 1, 1988.
Stamos et al., "Use of ultrasonics in single-visit endodontic therapy," Journal of Endodontics, vol. 13, No. 5, pp. 246-249, May 1, 1987.
Zehnder, "Root Canal Irrigants", Journal of Endodontics, vol. 32, No. 5, pp. 389-398, May 2006.
U.S. Appl. No. 61/701,947, filed Sep. 17, 2012, Laufer.
U.S. Appl. No. 61/894,762, filed Oct. 23, 2013, Lifshitz et al.
U.S. Appl. No. 61/895,316, filed Oct. 24, 2013, Lifshitz et al.
Ebihara et al.: "Er:YAG laser modification of root canal dentine: Influence of pulse duration, repetitive irradiation and water spray," Lasers in Medical Science, 17(3), 198-207, Aug. 2002.
Nammour et al.: "External temperature during KTP-nd:YAG laser irradiation in root canals: An in vitro study," Lasers in Medical Science, 19(1), 27-32, Jul. 2004.
Ulrich Schoop et al.: "The use of the erbium, chromium:yttrium-scandium-gallium-garnet laser in endodontic treatment: The results of an in vitro study," The Journal of the American Dental Association: vol. 138, Issue 7, Jul. 2007, pp. 949-955.
Wohlemuth et al.: "Effectiveness of GentleWave System in Removing Separated Instruments," JOE, vol. 41, No. 11, Nov. 2015.
U.S. Appl. No. 15/881,570, filed Jan. 26, 2018, Khakpour et al.
European Extended Search Report, re EP Application No. 18195055.1, dated Mar. 13, 2019.

* cited by examiner

APPARATUS AND METHODS FOR CLEANING TEETH AND ROOT CANALS

CROSS-REFERENCE TO RELATED APPLICATIONS

This application is a continuation-in-part of U.S. patent application Ser. No. 14/137,937, filed Dec. 20, 2013, which claims priority to U.S. Provisional Patent Application No. 61/740,351, filed Dec. 20, 2012, and to U.S. Provisional Patent Application No. 61/907,345, filed Nov. 21, 2013, the contents of each of which are incorporated by reference herein in their entirety and for all purposes. This application also claims priority to U.S. Provisional Patent Application No. 61/986,016, filed Apr. 29, 2014, and to U.S. Provisional Patent Application No. 62/017,208, filed Jun. 25, 2014, the contents of each of which are incorporated by reference herein in their entirety and for all purposes.

BACKGROUND

Field of the Invention

The present disclosure relates generally to dentistry and endodontics and to apparatus, methods, and compositions for treating a tooth.

Description of the Related Art

In conventional dental and endodontic procedures, mechanical instruments such as drills, files, brushes, etc. are used to clean unhealthy material from a tooth. For example, dentists often use drills to mechanically break up carious regions (e.g., cavities) in a surface of the tooth. Such procedures are often painful for the patient and frequently do not remove all the diseased material. Furthermore, in conventional root canal treatments, an opening is drilled through the crown of a diseased tooth, and endodontic files are inserted into the root canal system to open the canal spaces and remove organic material therein. The root canal is then filled with solid matter such as gutta percha or a flowable obturation material, and the tooth is restored. However, this procedure will not remove all organic material from the canal spaces, which can lead to post-procedure complications such as infection. In addition, motion of the endodontic file and/or other sources of positive pressure may force organic material through an apical opening into periapical tissues. In some cases, an end of the endodontic file itself may pass through the apical opening. Such events may result in trauma to the soft tissue near the apical opening and lead to post-procedure complications. Accordingly, there is a continuing need for improved dental and endodontic treatments.

SUMMARY

Various non-limiting aspects of the present disclosure will now be provided to illustrate features of the disclosed apparatus, methods, and compositions. Examples of apparatus, methods, and compositions for endodontic treatments are provided.

In one embodiment, an apparatus for treating a tooth is disclosed. The apparatus can include a chamber having an access port which places the chamber in fluid communication with a treatment region of the tooth when the chamber is coupled to the tooth, the access port having a central axis. The apparatus can include a fluid motion generator being arranged to generate rotational fluid motion in the chamber. The apparatus can include a suction port communicating with the chamber on a side of the chamber opposite of the access port, and being disposed relative to the access port such that the central axis of the access port passes through the suction port.

In another embodiment, an apparatus for treating a tooth is disclosed. The apparatus can comprise a chamber having a distal portion defining an access port that places the chamber in fluid communication with a treatment region of the tooth when the chamber is coupled to the tooth, the access port having a central axis. The apparatus can comprise a fluid motion generator coupled to the chamber, the fluid motion generator configured to generate rotational fluid motion in the chamber. The distal portion can be sized and shaped to be inserted into an access opening of the tooth, the distal portion tapering distally towards the central axis.

In another embodiment, an apparatus for treating a tooth is disclosed. The apparatus can include a chamber having an access port which places the chamber in fluid communication with a treatment region of the tooth when the chamber is coupled to tooth, the access port comprising a central axis. The apparatus can include a fluid motion generator coupled to the chamber, the fluid motion generator configured to generate a swirling influent fluid path around the central axis. The apparatus can include a suction port configured to remove fluid from the treatment region and the chamber. The apparatus can be configured to draw outgoing fluid from the treatment region to the suction port in a path that flows inside the swirling influent fluid path with a suction force applied to the suction port.

In yet another embodiment, a method of treating a tooth is disclosed. The method can include applying a chamber to a treatment region of the tooth, the chamber having an access port which places the chamber in fluid communication with the treatment region, the access port comprising a central axis. The method can include swirling influent fluid along a fluid path around the central axis. The method can include drawing outgoing fluid from the treatment region to a suction port in a path that flows inside the swirling influent fluid path.

In one embodiment, an apparatus for treating a tooth is disclosed. The apparatus can comprise a chamber having an access port which places the chamber in fluid communication with a treatment region of the tooth when the chamber is coupled to tooth. The apparatus can include a fluid motion generator coupled to the chamber, the fluid motion generator configured to direct fluid across the access port to generate fluid motion in the chamber.

In another embodiment, an apparatus for treating a tooth is disclosed. The apparatus can comprise a chamber configured to couple to a tooth. A fluid motion generator can be disposed in the chamber and configured to generate a rotational motion of fluid in the chamber. When the chamber is coupled to the tooth, the fluid motion generator can be positioned outside the tooth.

In another embodiment, a method of treating a tooth is disclosed. The method can include positioning a fluid motion generator near an access opening of the tooth. The fluid motion generator can be activated to pass a stream of fluid across the access opening of the tooth. Fluid motion can be generated at a treatment region of the tooth.

In another embodiment, a method of treating a tooth is disclosed. The method can include coupling a chamber to the tooth. The chamber can have a fluid motion generator disposed therein. The fluid motion generator can be disposed outside the tooth. The fluid motion generator can be activated to generate a rotational motion of fluid in the chamber.

In another embodiment, an apparatus for treating a tooth is disclosed. The apparatus can include a chamber configured to couple to a tooth. The apparatus can include a fluid motion generator disposed in the chamber and configured to generate a rotational motion of fluid in the chamber.

In yet another embodiment, an apparatus for treating a tooth is disclosed. The apparatus can comprise a chamber configured to couple to the tooth. A plurality of fluid motion generators can be disposed in the chamber.

In another embodiment, a method for treating a tooth is disclosed. The method can include coupling a chamber to the tooth. The chamber can include a plurality of fluid motion generators disposed therein. The plurality of fluid motion generators can be activated to clean the tooth.

In another embodiment, a method for treating a tooth is disclosed. The method can include forming an access opening in the tooth. The method can include applying a tooth seal around a perimeter of the access opening, the tooth seal having a peripheral boundary. The method can include positioning a chamber within the peripheral boundary of the tooth seal to secure the chamber to the tooth seal.

For purposes of this summary, certain aspects, advantages, and novel features of certain disclosed inventions are summarized. It is to be understood that not necessarily all such advantages may be achieved in accordance with any particular embodiment of the invention. Thus, for example, those skilled in the art will recognize that the inventions disclosed herein may be embodied or carried out in a manner that achieves one advantage or group of advantages as taught herein without necessarily achieving other advantages as may be taught or suggested herein. Further, the foregoing is intended to summarize certain disclosed inventions and is not intended to limit the scope of the inventions disclosed herein.

BRIEF DESCRIPTION OF THE DRAWINGS

The foregoing and other features, aspects, and advantages of the embodiments of the apparatus and methods of cleaning teeth are described in detail below with reference to the drawings of various embodiments, which are intended to illustrate and not to limit the embodiments of the invention. The drawings comprise the following figures in which.

Throughout the drawings, reference numbers may be re-used to indicate a general correspondence between referenced elements. The drawings are provided to illustrate example embodiments described herein and are not intended to limit the scope of the disclosure.

DETAILED DESCRIPTION

The present disclosure describes apparatus, methods, and compositions for performing dental and/or endodontic procedures. Various embodiments disclosed herein can effectively and safely remove unhealthy material from a treatment region of a tooth, e.g., from within the tooth and/or from outside surfaces of the tooth. In particular, the embodiments disclosed herein can remove unhealthy materials, such as unhealthy organic matter, inorganic matter, pulp tissue, caries, stains, calculus, plaque, biofilm, bacteria, pus, decayed tooth matter, and food remnants from the treatment region without substantially damaging healthy dentin or enamel. For example, the disclosed apparatus, methods, and compositions advantageously may be used with root canal cleaning treatments, e.g., to efficiently remove unhealthy or undesirable materials such as organic and/or inorganic matter from a root canal system and/or to disinfect the root canal system. Organic material (or organic matter) includes organic substances typically found in healthy or diseased teeth or root canal systems such as, for example, soft tissue, pulp, blood vessels, nerves, connective tissue, cellular matter, pus, and microorganisms, whether living, inflamed, infected, diseased, necrotic, or decomposed. Inorganic matter includes calcified tissue and calcified structures, which are frequently present in the root canal system. In some embodiments, the root canal can be filled with an obturation material (e.g., a flowable obturation material that can be hardened into a solid or semi-solid state, gutta percha or other solid or semi-solid materials) after treatment of the root canal.

I. Overview of Various Disclosed Embodiments

A. System Overview

Figure 1A:
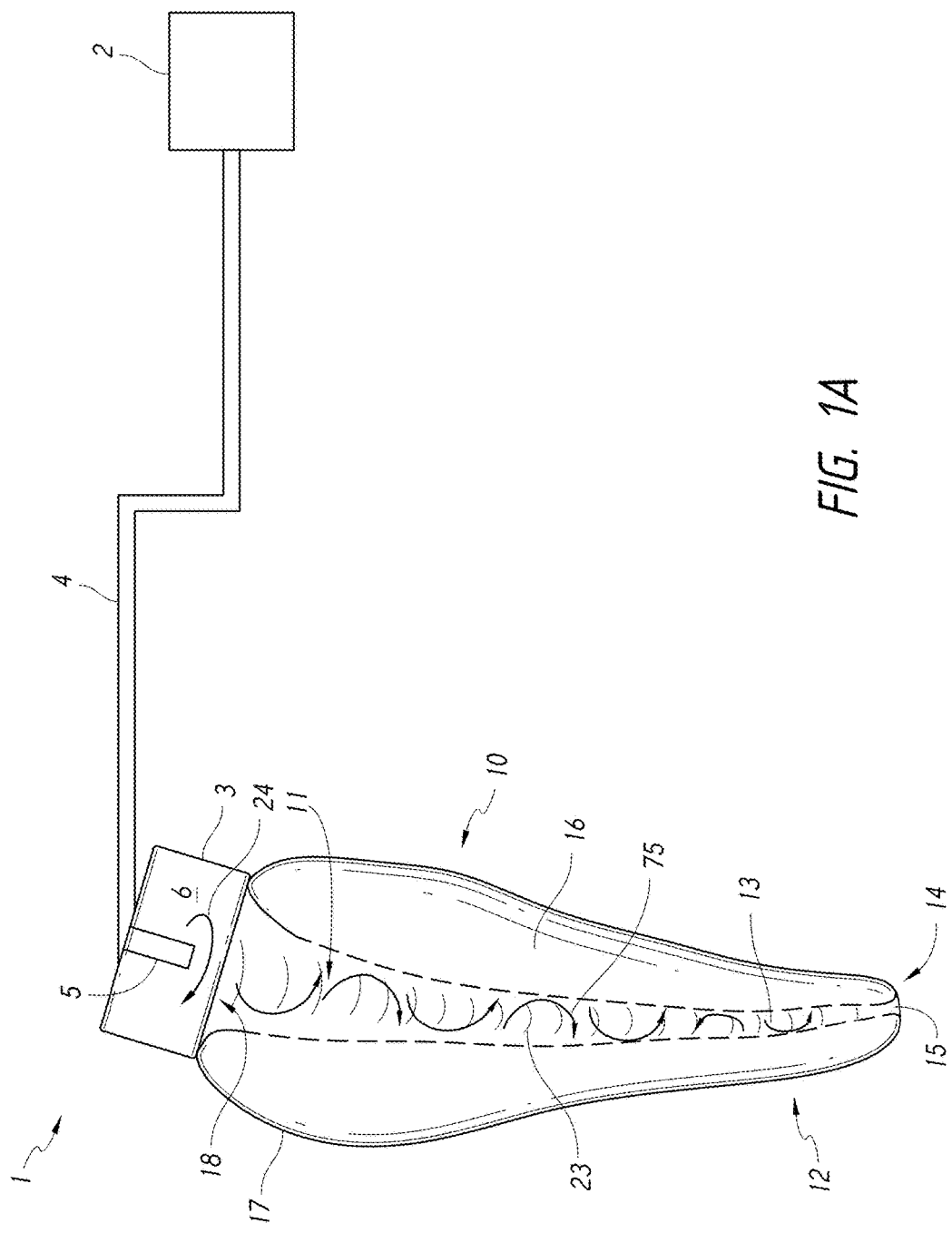
FIG. 1A is a schematic diagram of a system that includes components capable of removing unhealthy or undesirable materials from a root canal tooth.

FIG. 1A is a schematic diagram of a system 1 that includes components capable of removing unhealthy or undesirable materials from a tooth 10. The tooth 10 illustrated in FIG. 1A is a premolar tooth, e.g., a tooth located between canine and molar teeth in a mammal such as a human. The tooth 10 includes hard structural and protective layers, including a hard layer of dentin 16 and a very hard outer layer of enamel 17. A pulp cavity 11 is defined within the dentin 16. The pulp cavity 11 comprises one or more root canals 13 extending toward an apex 14 of each root 12. The pulp cavity 26 and root canal 13 contain dental pulp, which is a soft, vascular tissue comprising nerves, blood vessels, connective tissue, odontoblasts, and other tissue and cellular components. Blood vessels and nerves enter/exit the root canal 13 through a tiny opening, the apical foramen or apical opening 15, near a tip of the apex 14 of the root 12. It should be appreciated that, although the tooth 10 illustrated herein is a premolar, the embodiments disclosed herein can advantageously be used to treat any suitable type of tooth, including molars, canines, incisors, etc.

As illustrated in FIG. 1A, the system 1 can be used to remove unhealthy materials (such as organic and inorganic matter) from an interior of the tooth 10, e.g., from the root canal 13 of the tooth 10. For example, an endodontic access opening 18 can be formed in the tooth 10, e.g., on an occlusal surface, a buccal surface, or a lingual surface. The access opening 18 provides access to a portion of a pulp cavity 11 of the tooth 10. The system 1 can include a console 2, a pressure wave generator 5, and a coupling member 3 adapted to couple to the tooth 10. The coupling member 3 can define a chamber 6 configured to retain fluid therein. In some embodiments, the coupling member 3 can be held or pressed against the tooth by the clinician. In some embodiments, the coupling member 3 can be attached to the tooth, e.g., using an adhesive. One or more conduits 4 can electrically, mechanically, and/or fluidly connect the console 2 with the coupling member 3 and pressure wave generator 5. The console 2 can include a control system and various fluid management systems configured to operate the pressure wave generator 5 during a treatment procedure.

As explained herein, the system 1 can be used in cleaning procedures to clean substantially the entire root canal system. In other embodiments, such as obturation procedures, the system 1 can be used to fill substantially the entire root canal system with an obturation or filler material. For example, in various embodiments disclosed herein, the pressure wave generator 5 can generate pressure waves 23 of sufficient power and relatively low frequencies to produce fluid motion 24 in the chamber 6—such that the pressure wave generators 5 disclosed herein can act as a fluid motion generator—and can generate pressure waves of sufficient power and relatively higher frequencies to produce surface effect cavitation on a dental surface, either inside or outside the tooth. That is, for example, the pressure wave generators 5 disclosed herein can act as fluid motion generators to generate large-scale or bulk fluid motion 24 in or near the tooth 10, and can also generate smaller-scale fluid motion at higher frequencies. In some arrangements, the fluid motion 24 in the chamber 6 can generate induced fluid motion such as vortices 75, swirl 76 (see FIG. 2B), etc. in the tooth 10 and root canal 13 that can clean and/or fill the canal 13.

Figure 1B:
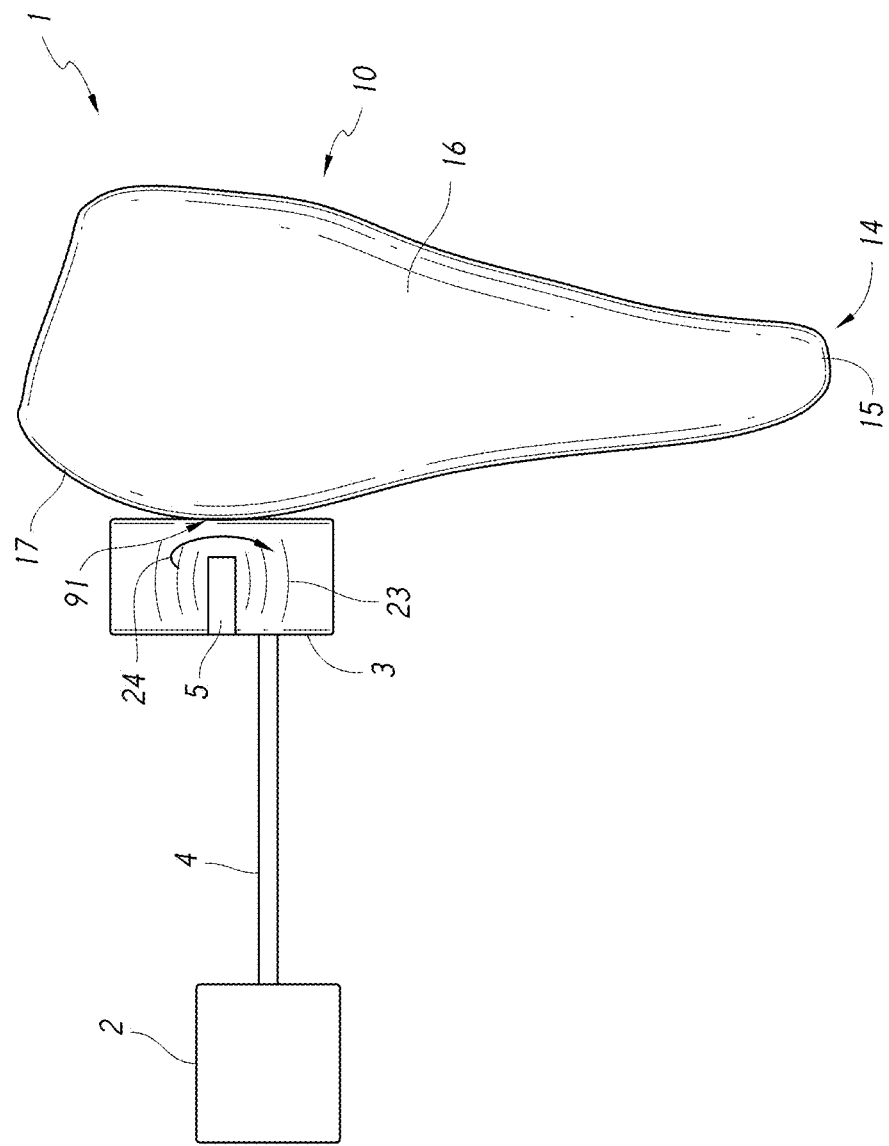
FIG. 1B is a schematic diagram of a system that includes components capable of removing unhealthy or undesirable material from a treatment region on an exterior surface of the tooth.

FIG. 1B is a schematic diagram of a system 1 that includes components capable of removing unhealthy or undesirable material from a treatment region 91 on an exterior surface of the tooth. For example, as in FIG. 1A, the system 1 can include a coupling member 3 and a pressure wave generator 5. The coupling member 3 can communicate with a console 2 by way of one or more conduits 4. Unlike the system 1 of FIG. 1A, however, the coupling member 3 is coupled to a treatment region 91 on an exterior surface of the tooth 10. For example, the system 1 of FIG. 1B can be activated to clean an exterior surface of the tooth 10, e.g., a carious region of the tooth 10. In other embodiments, the system 1 can be activated to fill a treated region on the exterior surface of the tooth 10. As with the embodiment of FIG. 1A, fluid motion 24 can be generated in the coupling member 3 and chamber, which can act to clean and/or fill the treatment region 91 of the tooth 10.

Figure 2A:
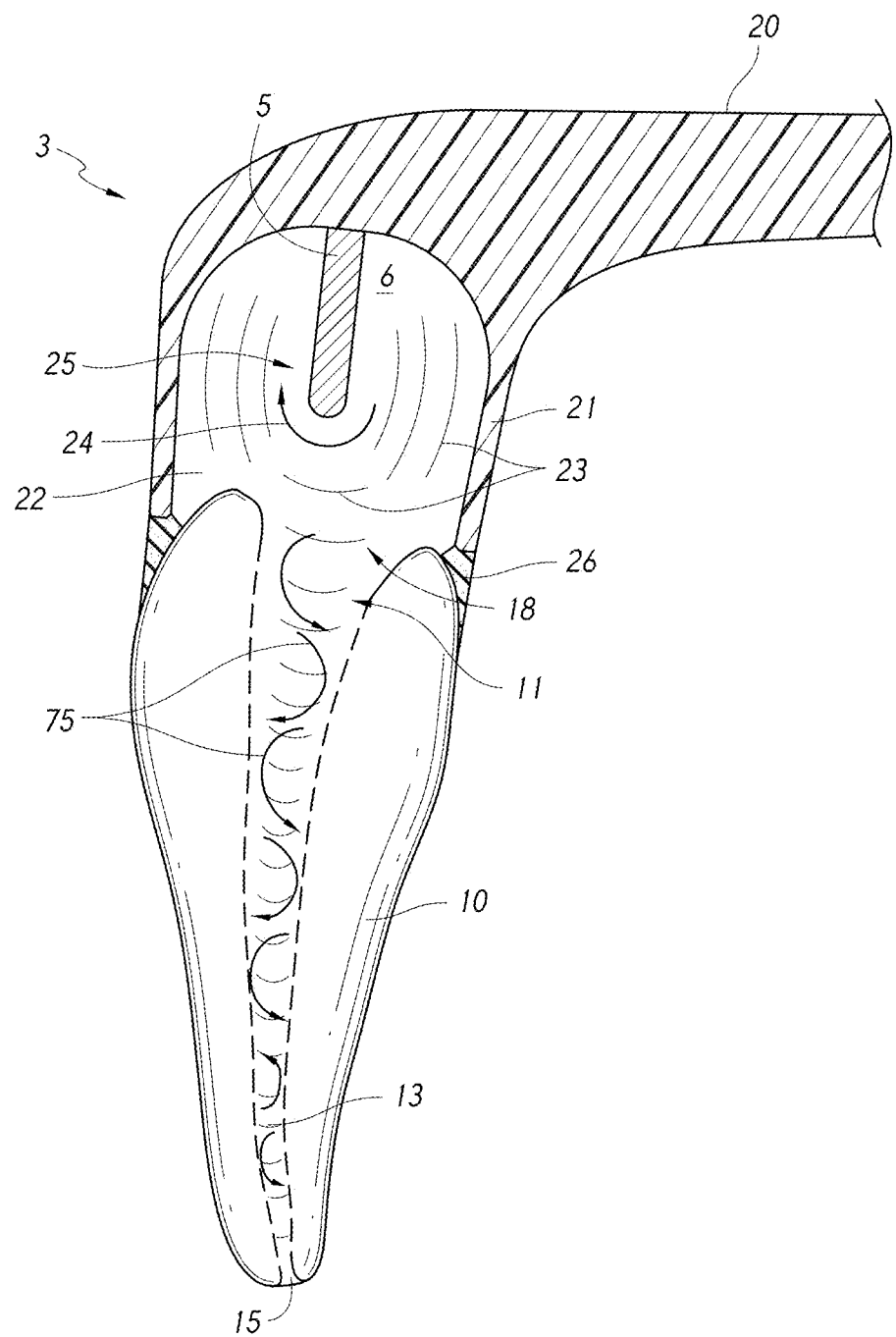
FIG. 2A is a schematic side cross-sectional view of a coupling member coupled to a tooth and a pressure wave generator having a distal end portion disposed in a chamber outside the tooth.

FIG. 2A is a schematic side cross-sectional view of a coupling member 3 coupled to a tooth 10 and a pressure wave generator 5 having a distal end portion 25 disposed in a chamber 6 outside the tooth 10. The coupling member 3 can be adapted to couple to the tooth 10 to provide a stable platform during the dental procedure. The coupling member 3 can define or include a chamber 6 configured to retain fluid 22. For example, the chamber 6 can be substantially filled with a fluid 22 to provide a propagation medium upon and/or through which the pressure wave generator 5 acts. The fluid 22 can be a treatment fluid in various cleaning treatments to substantially clean a treatment region of the tooth (such as in root canal treatments, treatments of carious regions, treatments of plaque and other unhealthy deposits). Alternatively, in obturation treatments, the fluid 22 can comprise a flowable obturation material having a flowable state that can be hardened into a solid state, and the pressure wave generator 5 can be activated to substantially fill or obturate the treatment region. The obturation material, once it fills the treatment region, can be hardened by a catalyst, be it heat, light, or chemical.

Moreover, the chamber 6 and coupling member 3 can prevent fluid 22 and/or waste materials from leaving the tooth 10. In various embodiments, the coupling member 3 can also be configured to regulate fluid pressure in the tooth 10 such that liquid can flow out from the chamber 6 if pressure rises above a predetermined threshold. In the embodiment of FIG. 2A, the coupling member 3 comprises a distal portion 21 of a handpiece 20 (see, e.g., FIG. 3B). For example, the distal portion 21 of the handpiece 20 can be shaped to define walls enclosing the chamber 6. In other embodiments, the coupling member 3 can be applied to the tooth 10 with a mechanical clasp or clamp, a dental adhesive, or by pressure applied by the patient by biting on the coupling member 3. In still other embodiments, a separate cap or fluid retainer can be removably coupled to the distal portion 21 of the handpiece 20.

During a dental treatment, a clinician can apply the coupling member 3 to the tooth 10. As illustrated in FIGS. 1A and 2A, for example, the clinician can apply the coupling member 3 over the access opening 18. The clinician can secure the coupling member 3 to the tooth 10 by way of a tooth seal 26. In some embodiments, one or more alignment features can be applied to align the coupling member 3 to the treatment region of the tooth 10 (see, e.g., FIGS. 8A-8C). In some embodiments, the coupling member 3 can be attached to the tooth 10 in a manner that permits the clinician to rotate or otherwise orient the coupling member 3 and pressure wave generator 5 at a desired orientation relative to the tooth 10 (see, e.g., FIG. 8B). In still other embodiments, the clinician can apply the coupling member 3 and pressure wave generator 5 to an exterior surface of the tooth 10. For example, the clinician can apply the coupling member 3 over a carious region formed near an outer surface of the tooth 10. In yet other embodiments, the clinician or a user can apply the coupling member 3 over an exterior surface of the tooth 10 to remove undesirable dental deposits, such as plaque, calculus, biofilms, etc.

Figure 2B:
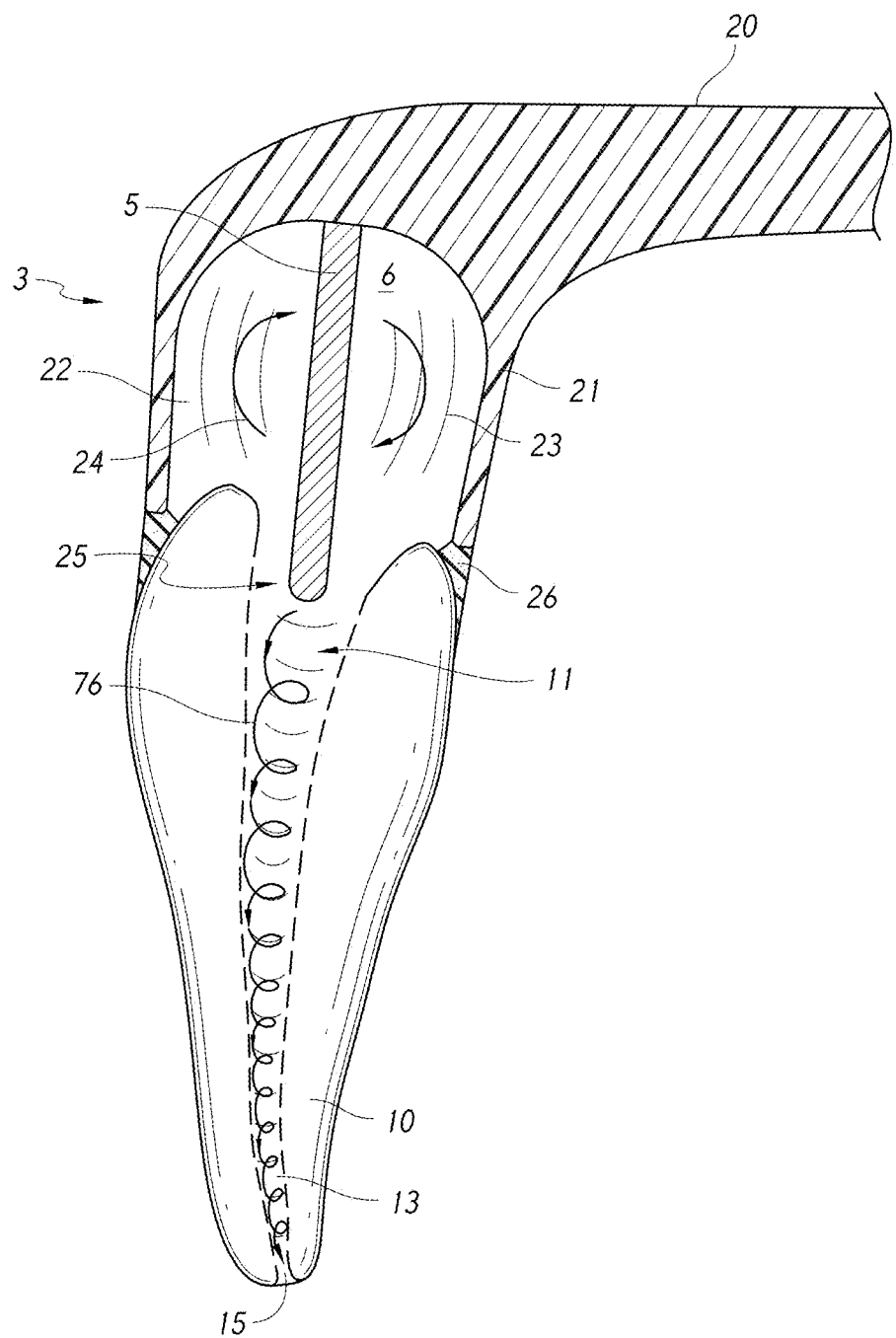
FIG. 2B is a schematic side cross-sectional view of a coupling member coupled to a tooth and a pressure wave generator having a distal end portion disposed inside the tooth.

The pressure wave generator 5 can be coupled with or integrally formed with the coupling member 3. In some embodiments, the pressure wave generator 5 can comprise an elongated member extending from the coupling member 3 through a portion of the chamber 6. As shown in FIGS. 1A and 2A, the distal end portion 25 of the pressure wave generator 5 can be disposed in the chamber 5 defined by the coupling member 3. As shown in FIG. 2A, the distal end portion 25 of the pressure wave generator 5 can be disposed outside the tooth 10, e.g., outside the pulp cavity 11. In other embodiments, the distal end portion 25 of the pressure wave generator 5 can extend into an interior space of the tooth 10, e.g., the pulp cavity 11. For example, FIG. 2B is a schematic side cross-sectional view of a coupling member 3 coupled to a tooth 10 and a pressure wave generator 5 having a distal end portion 25 disposed inside the tooth 10, e.g., inside a portion of the pulp cavity 11.

During cleaning procedures, the distal end portion 25 of the pressure wave generator 5 can be submerged in treatment fluid retained in the chamber 6 by the coupling member 3. The pressure wave generator 5 can be activated, and unhealthy materials (e.g., unhealthy organic matter, inorganic matter, pulp tissue, caries, stains, calculus, plaque, biofilm, bacteria, pus, decayed tooth matter, and food remnants) can be safely and efficiently removed from the tooth 10. For example, in the embodiments illustrated in FIGS. 1A-2B, diseased pulp and other undesirable materials can be removed from the pulp cavity 11 and root canal 13 of the tooth 10.

The pressure wave generator 5 can clean treatment regions of the tooth 10 that are remote from the pressure wave generator 5. For example, in root canal procedures, the pressure wave generator can clean substantially the entire root canal 13, including laterally-extending tubules and various small cracks and crevices that are formed in the tooth 10. Similarly, in other cleaning procedures, such as procedures that clean carious regions, plaque, other dental deposits, etc., the pressure wave generators 5 disclosed herein can clean substantially the entire treatment region of the tooth. The pressure wave generators 5 disclosed herein can therefore improve patient outcomes by removing unhealthy materials from the entire treatment region, which reduces the risk of infection or recurrences of unhealthy material at the treatment region.

In other embodiments, the pressure wave generator 5 can fill or obturate the treatment region of the tooth (e.g., a cleaned root canal space, a cleaned carious region on an exterior surface of the tooth, etc.) after cleaning. For example, in root canal procedures, the disclosed pressure wave generators 5 can substantially fill the entire root canal system, including the main canals, laterally-extending tubules, and various small cracks, spaces, crevices, etc. The improved obturation provided by the pressure wave generators 5 disclosed herein can improve patient outcomes by reducing the risk of infection from unobturated spaces in cleaned canals.

Various embodiments of the pressure wave generator 5 disclosed herein can clean and/or fill the tooth 10 by way of a combination of several different phenomena. For example, the pressure wave generator 5 can generate pressure waves 23 that propagate through the fluid 22 and inside the tooth 10, and the pressure wave generator 5 can also act as a fluid motion generator to generate a motion 24 of fluid 22 in the chamber 6.

The fluid motion 24 generated by the fluid motion generators disclosed herein (e.g., the pressure wave generators 5) can be induced by flowing the fluid across an access port of the chamber 6 and/or the coupling member 3. For example, the fluid 22 can be flowed across the access port in a direction substantially parallel to a plane of the access port and/or perpendicular to the central axis of the root canal 13. The fluid motion 24 described in each embodiment disclosed herein can comprise rotational or non-rotational flow patterns in the chamber 6. The fluid motion 24 can be laminar or turbulent. For example, in laminar fluid motions 24, larger or bulk fluid motion may be generated. In turbulent fluid motions 24, smaller fluid motions or perturbations can be generated. In some arrangements, a combination of laminar and turbulent flow may be generated. The fluid flow 24 in the chamber and the induced flow (e.g., vortices, swirl, etc.) in the tooth can be generated in a substantially continuous manner or can be intermittent or periodic. In some embodiments, the fluid motion 24 can comprise rotational motion, e.g., the fluid can rotate about an axis transverse to a central axis of the root canal 13 (see, e.g., FIG. 2A). In some arrangements, the fluid motion 24 can induce vortices 75 flowing about an axis substantially perpendicular to the central axis of the root canal 13 (see, e.g., FIG. 2A). In other embodiments, the fluid motion 24 can be generated about the central axis of the root canal 13 and can generate a swirl flow 76 that can propagate through the canal 13 (see, e.g., FIG. 2B). In still other embodiments, the fluid motion 24 can comprise planar fluid flow, e.g., fluid flow that comprises planar wavefronts. In some embodiments, the fluid motion 24 can comprise unsteady or chaotic flow.

As explained herein, the pressure waves 23 can enhance the chemical reactions produced between treatment fluids and the unhealthy material to enable the detachment of unhealthy materials from the tooth 10 in a safe and efficient manner. For example, the pressure wave generator 5 can be configured to induce acoustic cavitation throughout the tooth 10, which can assist in removing unhealthy materials from larger spaces in the tooth, such as the main root canal 13, as well as from extremely small spaces in the tooth 10, such as tubules and various cracks and crevices that may be formed in the tooth 10.

In tooth cleaning procedures, the motion 24 of the fluid 22 can also improve the cleaning of the tooth 10 by refreshing the chemical reactants used in the fluid 22, which can act to speed up the chemical reactions between the fluid 22 and the unhealthy materials in the tooth. Furthermore, the motion 24 of the fluid 22 can impart momentum in the tooth 10 that helps to dislodge the unhealthy or undesirable materials from the tooth 10 and to irrigate the dislodged materials out of the tooth 10. As explained herein, the motion 24 of the fluid 22 can also reduce apical pressures at or near the apical opening 15 of the tooth 10.

Accordingly, the pressure waves 23 and motion 24 generated by the systems disclosed herein can improve patient outcomes as compared with other treatments by cleaning unhealthy materials from both large and small spaces of the tooth, and by enhancing the chemical reactions between the fluid 22 and the unhealthy materials to be removed from the tooth 10. Furthermore, because the tooth 10 is cleaned without the use of a file, drill, brush, or other abrasive instrument, the systems and methods disclosed herein can clean the tooth with little or no discomfort to the patient. In addition, in obturation procedures, the embodiments disclosed herein can advantageously obturate or fill substantially the entire canal(s) and/or branch structures therefrom, as explained in greater detail below.

In various implementations, the pressure wave generator 5 comprises one or more embodiments of the various apparatus described herein. For example, the pressure wave generator 5 can include a liquid jet device. In some embodiments, the liquid jet device comprises a positioning member (e.g., a guide tube) having a channel or lumen along which or through which a liquid jet can propagate. The distal end portion of the positioning member may include an impingement surface on which the liquid jet impinges and is deflected into jets or spray. The distal end portion of the positioning member may include one or more openings that permit the jet to interact with the fluid in the surrounding environment (e.g., fluid in the tooth chamber) and also permit the deflected liquid to exit the positioning member and interact with the surrounding environment and fluid 22 in the chamber 6 and/or tooth 10. The result of these interactions can be the generation of pressure waves and fluid motion in the tooth 10, which can at least partially clean the tooth 10. By generating fluid motion 24 in the tooth 10, the pressure wave generators 5 may act as fluid motion generators. In some treatment methods, the openings disposed at or near the distal end portion of the positioning member are submerged in the fluid 22 retained in the chamber 6 by the coupling member 3.

In some embodiments, the pressure wave generator 5 may include a sonic, ultrasonic, or megasonic device (e.g., a sonic, ultrasonic, or megasonic paddle, horn, or piezoelectric transducer), a mechanical stirrer (e.g., a motorized propeller or paddle or rotating/vibrating/pulsating disk or cylinder), an optical system that can provides optical energy to the chamber 6 (e.g., an optical fiber that propagates laser light into the chamber 6), or any other device that can cause sufficient rotational fluid motion and acoustic waves to be generated in the tooth or in a propagation medium in the tooth (e.g., the fluid retained in a tooth chamber).

B. Enhancing the Treatment of Teeth

The embodiments disclosed herein can advantageously remove undesirable or unhealthy materials from a tooth such that substantially all the unhealthy material is removed while inducing minimal or no discomfort and/or pain in the patient. For example, when activated by the clinician, the pressure wave generator 5 can induce various fluidic effects that interact with the unhealthy material to be removed, even when the pressure wave generator 5 is disposed at a position remote from the treatment region of the tooth, e.g., the region of the tooth that includes the unhealthy or undesirable material to be removed. The pressure wave generator 5 can impart energy to the fluid 22 that induces the relatively large-scale or bulk circulation or movement 24 of liquid in the chamber 6 and tooth 10, and that also generates pressure waves 23 that propagate through the fluid 22 and tooth 10. The generated fluid motion 24 and pressure waves 23 can magnify or enhance the properties of the fluid 22 to enhance cleaning of the tooth 10. In some embodiments, the pressure wave generator 5 can be used to obturate or fill the root canals and/or other treated regions of the tooth.

(1) Chemistry of Various Treatment Fluids

As explained above, in cleaning procedures, the fluid 22 can comprise a treatment fluid that can be introduced into the tooth 10 and the chamber 6 to assist in removing unhealthy or undesirable materials from the tooth 10. The treatment fluids can be selected based on the chemical properties of the fluids when reacting with the undesirable or unhealthy material to be removed from the tooth 10. The treatment fluids disclosed herein can include any suitable fluid, including, e.g., water, saline, etc. Various chemicals can be added to treatment fluid for various purposes, including, e.g., tissue dissolving agents (e.g., NaOCl or bleach), disinfectants (e.g., chlorhexidine), anesthesia, fluoride therapy agents, ethylenediaminetetraacetic acid (EDTA), citric acid, and any other suitable chemicals. For example, any other antibacterial, decalcifying, disinfecting, mineralizing, or whitening solutions may be used as well. The clinician can supply the various fluids to the tooth in one or more treatment cycles, and can supply different fluids sequentially or simultaneously.

During some treatment cycles, bleach-based solutions (e.g., solutions including NaOCl) can be used to dissociate diseased tissue (e.g., diseased organic matter in the root canal 13) and/or to remove bacteria from the tooth 10. One example of a treatment solution comprises water or saline with 0.3% to 6% bleach (NaOCl). In some methods, tissue dissolution and dental deposit removal in the presence of bleach may not occur when the bleach concentration is less than 1%. In some treatment methods disclosed herein, tissue dissolution and dental deposit removal can occur at smaller (or much smaller) concentrations.

During other treatment cycles, the clinician can supply an EDTA-based solution to remove undesirable or unhealthy calcified material from the tooth 10. For example, if a portion of the tooth 10 and/or root canal 13 is shaped or otherwise instrumented during the procedure, a smear layer may form on the walls of the canal 13. The smear layer can include a semi-crystalline layer of debris, which may include remnants of pulp, bacteria, dentin, and other materials. Treatment fluids that include EDTA may be used to remove part or all of the smear layer, and/or calcified deposits on the tooth 10.

During yet other cycles, for example, the clinician may supply a treatment fluid that comprises substantially water. The water can be used to assist in irrigating the tooth before, during, and/or after the treatment. For example, the water can be supplied to remove remnants of other treatment fluids (e.g., bleach or EDTA) between treatment cycles. Because bleach has a pH that tends to be a base and because EDTA is an acid, it can be important to purge the tooth 10 and chamber 6 between bleach and EDTA treatments to avoid potentially damaging chemical reactions. Furthermore, the water can be supplied with a sufficient momentum to help remove detached materials that are disrupted during the treatment. For example, the water can be used to convey waste material from the tooth 10.

Various solutions may be used in combination at the same time or sequentially at suitable concentrations. In some embodiments, chemicals and the concentrations of the chemicals can be varied throughout the procedure by the clinician and/or by the system to improve patient outcomes. For example, during an example treatment procedure, the clinician can alternate between the use of water, bleach, and EDTA, in order to achieve the advantages associated with each of these chemicals. In one example, the clinician may begin with a water cycle to clean out any initial debris, then proceed with a bleach cycle to dissociate diseased tissue and bacteria from the tooth. A water cycle may then be used to remove the bleach and any remaining detached materials from the tooth 10. The clinician may then supply EDTA to the tooth to remove calcified deposits and/or portions of a smear layer from the tooth 10. Water can then be supplied to remove the EDTA and any remaining detached material from the tooth 10 before a subsequent bleach cycle. The clinician can continually shift between cycles of treatment fluid throughout the procedure. The above example is for illustrative purposes only. It should be appreciated that the order of the cycling of treatment liquids may vary in any suitable manner and order.

Thus, the treatment fluids used in the embodiments disclosed herein can react chemically with the undesirable or unhealthy materials to dissociate the unhealthy materials from the healthy portions of the tooth 10. The treatment fluids can also be used to irrigate waste fluid and/or detached or delaminated materials out of the tooth 10. In some embodiments, as explained in more detail herein in Section VIII, the treatment solution (including any suitable composition) can be degassed, which may improve cavitation and/or reduce the presence of gas bubbles in some treatments. In some embodiments, the dissolved gas content can be less than about 1% by volume. Additional properties and characteristics of the treatment fluid 22 are presented in more detail herein in Section VII.

(2) Enhancement of Cleaning Using Pressure Waves

As explained herein, a pressure wave generator 5 can remove unhealthy materials from a tooth by propagating pressure waves 23 through a propagation medium (e.g., the treatment fluid) to the treatment region, which can include one or more teeth and/or gums. Without being limited by theory, a few potential ways that the pressure waves 23 remove undesirable materials are presented herein. Note that these principles, and the principles described above, may be generally applicable for each embodiment disclosed herein.

In some arrangements, cavitation may be induced by the generated pressure waves 23. Upon irradiation of a liquid (e.g., water or other treatment fluid) with high intensity pressure or pressure waves 23, acoustic cavitation may occur. The oscillation or the implosive collapse of small cavitation bubbles can produce localized effects, which may further enhance the cleaning process, e.g., by creating intense, small-scale localized heat, shock waves, and/or microjets and shear flows. Therefore, in some treatment methods, acoustic cavitation may be responsible for or involved in enhancing the chemical reactions, sonochemistry, sonoporation, soft tissue/cell/bacteria dissociation, delamination and breakup of biofilms.

For example, if the treatment liquid contains chemical(s) that act on a particular target material (e.g., diseased organic or inorganic matter, stains, caries, dental calculus, plaque, bacteria, biofilms, etc.), the pressure waves 23 (acoustic field) and/or the subsequent acoustic cavitation may enhance the chemical reaction via agitation and/or sonochemistry. Indeed, the pressure waves 23 can enhance the chemical effects that each composition has on the unhealthy material to be removed from the tooth. For example, with a bleach-based treatment fluid, the generated pressure waves 23 can propagate so as to dissociate tissue throughout the entire tooth 10, including in the dentinal tubules and throughout tiny cracks and crevices of the tooth 10. As another example, with an EDTA-based treatment fluid, the generated pressure waves 23 can propagate so as to remove the smear layer and/or calcified deposits from the tooth 10, including in the tubules and/or in tiny cracks and crevices formed in the tooth 10. With a water-based treatment fluid, the generated pressure waves 23 can propagate so as to flush and/or irrigate undesirable materials from the tooth, including in tubules and tiny cracks and crevices. Accordingly, the generated pressure waves 23 can enhance the removal of undesirable or unhealthy materials from the tooth 10 by magnifying the chemical effects of whatever treatment fluid composition is used during a particular treatment cycle.

Furthermore, sonoporation, which is the process of using pressure waves and/or the subsequent acoustic cavitation to modify the permeability of the bacterial cell plasma membrane, may also expedite the chemical reaction that removes the microorganisms from the tooth. It should also be appreciated that generated pressure waves, and/or the subsequent acoustic cavitation of certain frequencies, may result in cellular and bacterial rupture and death (e.g., lysis) as well as removal of decayed and weakened dentin and enamel. The cellular and bacterial rupture phenomenon may kill bacteria which might otherwise reinfect the gingival pockets and/or the oral cavity.

Generated pressure waves and/or the subsequent acoustic cavitation may also loosen the bond of the structure of the unhealthy material (e.g., diseased tissue, calculus, biofilm, caries, etc.), and/or the pressure waves may dissociate the unhealthy material from the tooth 10. In some cases, pressure waves and/or acoustic cavitation may loosen the bond between the cells and the dentin and/or delaminate the tissue from the tooth. Furthermore, the pressure waves and/or the subsequent acoustic cavitation may act on decayed hard tissue (which may be relatively weak and loosely connected) through vibrations and/or shock waves, and/or the microjets created as a result of cavitation bubble implosion, to remove decayed hard tissue from other healthy portions of the tooth.

Additional details of the acoustic effects produced by the pressure wave generators disclosed herein may be found herein in more detail in Section VII.

(3) Enhancement of Cleaning Using Large-Scale Fluid Motion

In some arrangements, bulk fluid motion 24 (e.g., fluid rotation, convection, planar flow, chaotic flow, etc.) can enhance the cleaning of unhealthy material from a diseased tooth. For example, the fluid motion 24 generated in the chamber 6 and/or tooth 10 can impart relatively large momentum to the tooth, which can help dissociate and irrigate unhealthy materials from the tooth. Furthermore, the fluid motion 24 can induce vortices 75 and/or swirl 76 in the tooth 10 that can result in negative pressures (or low positive pressures) near the apical opening 15 of the tooth 10. The resulting negative pressures at the apical opening 15 can prevent or reduce an amount of material extruded through the apical opening 15 and into the jaw of the patient. By preventing or reducing the amount of extruded material, the risk of infection can be lowered or eliminated, and patient outcomes can be substantially improved.

In addition, due to relatively short time scales of the chemical reaction processes between the fluid 22 and the unhealthy materials as compared to that of diffusion mechanisms, a faster mechanism of reactant delivery such as "macroscopic" liquid circulation may be advantageous in some of the embodiments disclosed herein. For example, liquid circulation with a time scale comparable to (and preferably faster than) that of chemical reaction may help replenish the reactants at the chemical reaction front and/or may help to remove the reaction byproducts from the reaction site. The relatively large convective time scale, which may relate to effectiveness of the convection process, can be adjusted and/or optimized depending on, e.g., the location and characteristics of the source of circulation. Furthermore, it should be appreciated that the introduction of liquid circulation or other fluid motion 24 generally does not eliminate the diffusion process, which may still remain effective within a thin microscopic layer at the chemical reaction front. Liquid circulation can also cause a strong irrigation effect at the treatment site (e.g. removing diseased tissue deep in the canal 13 and/or tubules and small spaces and cracks of the tooth 10) and may therefore result in loosening and/or removing large and small pieces of debris from the treatment site.

In some arrangements, various properties can be adjusted to enhance bulk fluid motion and/or fluid circulation, e.g., fluid motion in the chamber 6. For example, the position of the pressure wave generator 5 relative to the location of the treatment site can be adjusted. As explained herein, in some embodiments, the pressure wave generator 5 is disposed such that the pressure wave generator 5 passes a stream of liquid across the access opening 18. For example, the pressure wave generator 5 can be disposed to induce fluid motion 24 about an axis transverse to a central axis of the root canal 13, which can generate vortices 75 that propagate throughout the canal 13. In some embodiments, the fluid motion 24 can be generated about the central axis of the root canal 13, which can induce swirl motion 76 in the root canal 13. The fluid flow 24 over the access port or access opening of the tooth 10 can be varied. For example, the momentum of the fluid 24 can be varied to create the desired flow in the root canals 13. Furthermore, the angle of the fluid flow 24 relative to the access port can be varied to control the apical pressure in the canals 13, e.g., to induce apical pressures that are more positive, more negative, etc. The geometry of the space surrounding the pressure wave generator 5 and treatment site (e.g., the geometry of the coupling member 3) can also be varied. It should also be appreciated that circulation may be affected by the viscosity of the fluid 22 and/or the mechanism of action of the pressure wave generator 5. For example, the pressure wave generator 5, such as a jet of liquid ejected through an inlet opening, a stirrer such as a propeller or a vibrating object, etc., can be selected to enhance fluid motion of the treatment fluid. In some aspects, the input power of the source of liquid circulation can also be adjusted, such as the source of a pump that drives a liquid jet in some embodiments.

(4) Enhancement of Other Dental and Endodontic Procedures

In some embodiments, the pressure wave generators 5 disclosed herein can enhance other dental and endodontic procedures. For example, after cleaning a tooth (e.g., a root canal inside the tooth, a carious region on or near an exterior surface of the tooth, etc.), the treatment region can be filled with an obturation or filler material. In some embodiments, the filler material can be supplied to the treatment region as a flowable material and can be hardened to fill the treatment region (e.g., the cleaned root canal or carious region, etc.).

In some embodiments, a pressure wave generator 5 can be activated to supply the obturation material throughout the treatment region.

For example, after a root canal procedure, the pressure wave generator can supply the flowable obturation material into the tooth and root canal. The large-scale fluid movement generated by the pressure wave generator 5 can assist in propagating the obturation material throughout relatively large spaces, such as the main root canal or canals. For example, the pressure wave generator 5 may introduce sufficient momentum such that the flowable obturation material propagates throughout the canal space without introducing additional instrumentation into the tooth. For example, the bulk fluid motion of the obturation material into the canal may be such that the clinician may not need to or desire to enlarge the canals. By reducing or eliminating canal enlargement, patient outcomes and pain levels can be improved. In some arrangements, the bulk fluid motion of the flowable obturation material can be generated at relatively low frequencies produced by the pressure wave generator.

In addition to generating large-scale or bulk fluid motion of the obturation material throughout the canal, the pressure wave generators 5 disclosed herein can generate higher frequency perturbations to propagate the obturation material into smaller cracks, spaces, and crevices in the tooth. For example, higher-frequency effects, such as acoustic cavitation, can assist in propagating the filler material throughout the tooth.

Accordingly, the pressure wave generators disclosed herein can enhance the filling of a treatment region such as a root canal, carious region of the tooth, etc. For example, the obturation material can be propagated at a distance such that it flows into the treatment region from a remote pressure wave generator 5 (which may be disposed outside the tooth). Large-scale or bulk fluid motion of the obturation material can fill larger canal spaces or other treatment regions without further enlargening the treatment region. Smaller-scale and/or higher frequency agitation by the pressure wave generator 5 can propagate the obturation material into smaller cracks and spaces of the tooth. By filling substantially all the cleaned spaces of the tooth, the disclosed methods can improve patient outcomes relative to other methods by reducing the risk of infection in spaces unfilled by the obturation material.

II. Overview of Features of the Disclosed Systems

A. Pressure Wave Generators

A pressure wave generator 5 can be used in various disclosed embodiments to clean a tooth 10, e.g., from interior or exterior portions of the tooth 10 and/or gums. In other embodiments, the pressure wave generator 5 can be used to fill or obturate a cleaned root canal or other treatment region of the tooth 10. In some embodiments, the pressure wave generator 5 can comprise an elongated member having an active distal end portion 25. The active distal end portion 25 can be activated by a user to apply energy to the treatment tooth 10 to remove unhealthy or undesirable material from the tooth 10.

As explained herein, the disclosed pressure wave generators 5 can be configured to generate pressure waves 23 and fluid motion 24 with energy sufficient to clean undesirable material from a tooth 10. The pressure wave generator 5 can be a device that converts one form of energy into acoustic waves and bulk fluid motion (e.g., rotational motion) within the fluid 22. The pressure wave generator 5 can induce, among other phenomena, both pressure waves and bulk fluid dynamic motion in the fluid 22 (e.g., in the chamber 6), fluid circulation, turbulence, vortices and other conditions that can enable the cleaning of the tooth. The pressure wave generator 5 disclosed in each of the figures described herein may be any suitable type of pressure wave generator.

The pressure wave generator 5 can be used to clean the tooth 10 by creating pressure waves that propagate through the fluid 22, e.g., through treatment fluid at least partially retained in the chamber 6. In some implementations, the pressure wave generator 5 may also create cavitation, acoustic streaming, turbulence, etc. In various embodiments, the pressure wave generator 5 can generate pressure waves or acoustic energy having a broadband power spectrum (see, e.g., FIGS. 4A-4C). For example, the pressure wave generator 5 can generate pressure waves at multiple different frequencies, as opposed to only one or a few frequencies. Without being limited by theory, it is believed that the generation of power at multiple frequencies can help to remove various types of organic and/or inorganic materials that have different material or physical characteristics at various frequencies.

The pressure wave generator 5 (e.g., high-speed liquid jet, ultrasonic transducer, a laser fiber, etc.) can be placed at the desired treatment location in or on the tooth 10. The pressure wave generator 5 can create pressure waves 23 and fluid motion 24 within the fluid 22 inside a substantially-enclosed chamber 6. In general, the pressure wave generator 5 can be sufficiently strong to remove unhealthy materials such as organic and/or inorganic tissue from teeth 10. In some embodiments, the pressure wave generator 5 can be configured to avoid substantially breaking down or harming natural dentin and/or enamel.

(1) Liquid Jet Apparatus

For example, in some embodiments, the pressure wave generator 5 can comprise a liquid jet device. The liquid jet can be created by passing high pressure liquid through an orifice. The liquid jet can create pressure waves within the treatment liquid. In some embodiments, the pressure wave generator 5 comprises a coherent, collimated jet of liquid. The jet of liquid can interact with liquid in a substantially-enclosed volume (e.g., the chamber and/or the mouth of the user) and/or an impingement member to create the acoustic waves. In addition, the interaction of the jet and the treatment fluid, as well as the interaction of the spray which results from hitting the impingement member and the treatment fluid, may assist in creating cavitation and/or other acoustic effects to clean the tooth.

In various embodiments, the liquid jet device can comprise a positioning member (e.g., a guide tube) having a channel or lumen along which or through which a liquid jet can propagate. The distal end portion of the positioning member can include one or more openings that permit the deflected liquid to exit the positioning member and interact with the surrounding environment in the chamber 6 or tooth 10. In some treatment methods, the openings disposed at or near the distal end portion of the positioning member can be submerged in liquid that can be at least partially enclosed in the chamber 6 attached to or enclosing a portion of the tooth 10. In some embodiments, the liquid jet can pass through the guide tube and can impact an impingement surface. The passage of the jet through the surrounding treatment fluid and impact of the jet on the impingement surface can generate the acoustic waves in some implementations. The flow of the submerged portion of the liquid jet may generate a cavitation cloud within the treatment fluid. The creation and collapse of the cavitation cloud may, in some cases, generate a substantial hydroacoustic field in or near the tooth. Further cavitation effects may be possible, including growth, oscillation, and collapse of cavitation bubbles. In addition, as explained above, bulk fluid motion, such as rotational flow, may be induced. The induced rotational flow can enhance the cleaning process by removing detached material and replenishing reactants for the cleaning reactions. These (and/or other) effects may lead to efficient cleaning of the tooth.

Figure 3A:
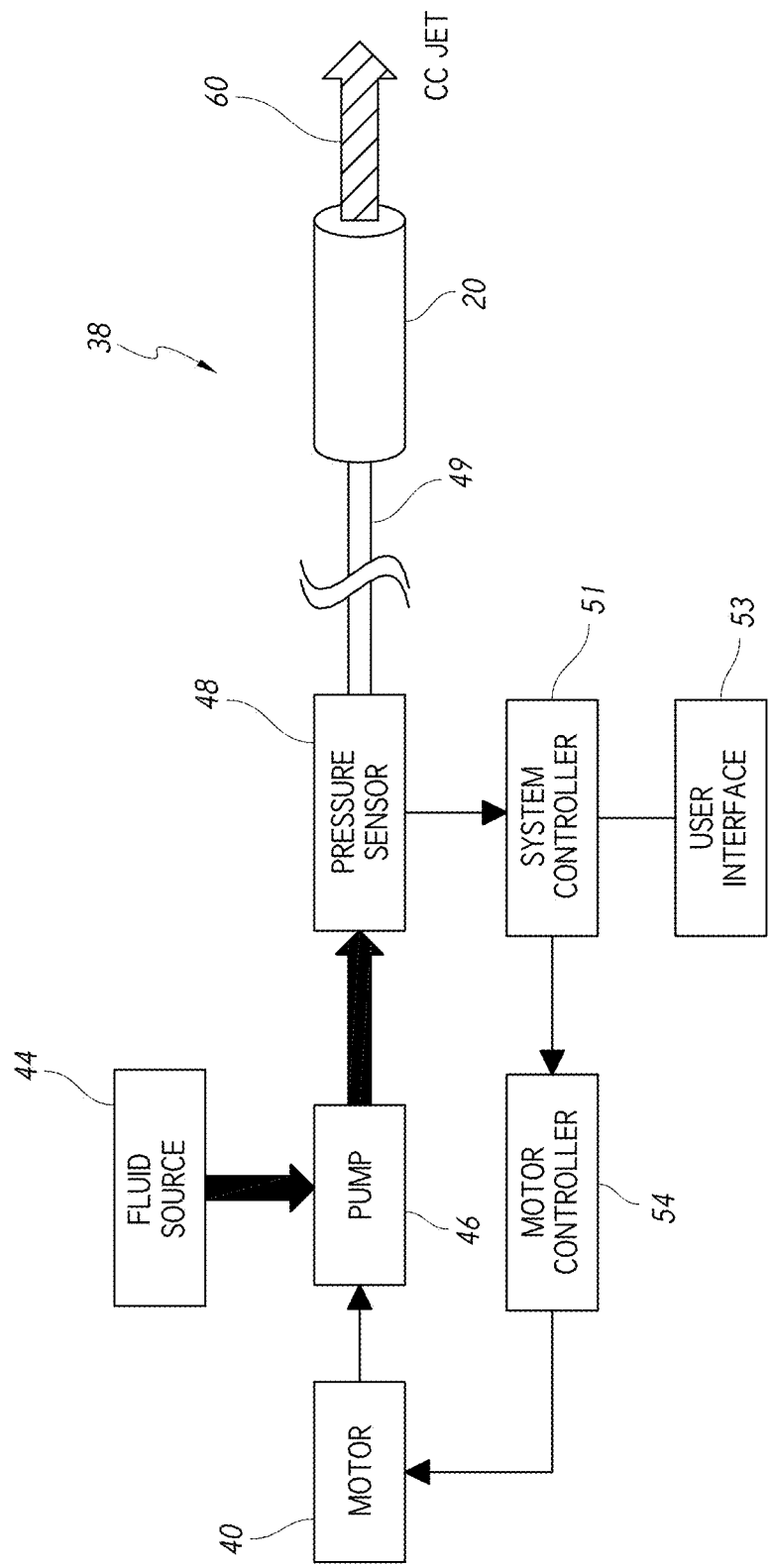
FIG. 3A is a block diagram that schematically illustrates an embodiment of a system adapted to generate a high-velocity jet of fluid for use in dental procedures.

FIG. 3A is a block diagram that schematically illustrates an embodiment of a system 38 adapted to generate a high-velocity jet 60 of fluid for use in dental procedures. The system 38 comprises a motor 40, a motor controller 54, a fluid source 44, a pump 46, a pressure sensor 48, a system controller 51, a user interface 53, and a handpiece 20 that can be operated by a dental practitioner to direct the jet 60 toward desired locations in a patient's mouth. The pump 46 can pressurize fluid received from the fluid source 44. The pump 46 may comprise a piston pump in which the piston is actuatable by the motor 40. The motor 40 can be controlled by way of the motor controller 54. The high-pressure liquid from the pump 46 can be fed to the pressure sensor 48 and then to the handpiece 20, for example, by a length of high-pressure tubing 49. The pressure sensor 48 may be used to sense the pressure of the liquid and communicate pressure information to the system controller 51. The system controller 51 can use the pressure information to make adjustments to the motor 40 and/or the pump 46 to provide a target pressure for the fluid delivered to the handpiece 20. For example, in embodiments in which the pump 46 comprises a piston pump, the system controller 51 may signal the motor 40 to drive the piston more rapidly or more slowly, depending on the pressure information from the pressure sensor 48. In some embodiments, the pressure of the liquid that can be delivered to the handpiece 20 can be adjusted within a range from about 500 psi to about 50,000 psi (1 psi is 1 pound per square inch and is about 6895 Pascal (Pa)). In certain embodiments, it has been found that a pressure range from about 2,000 psi to about 15,000 psi produces jets that are particularly effective for endodontic treatments. In some embodiments, the pressure is about 10,000 psi.

The fluid source 44 may comprise a fluid container (e.g., an intravenous bag) holding any of the treatments fluids described herein. The treatment fluid may be degassed, with a dissolved gas content less than normal (e.g., non-degassed) fluids. Examples of treatment fluids include sterile water, a medical-grade saline solution, an antiseptic or antibiotic solution (e.g., sodium hypochlorite), a solution with chemicals or medications, or any combination thereof. More than one fluid source may be used. In certain embodiments, it is advantageous for jet formation if the liquid provided by the fluid source 44 is substantially free of dissolved gases, which may reduce the effectiveness of the jet and the pressure wave generation. Therefore, in some embodiments, the fluid source 44 comprises degassed liquid such as, e.g., degassed distilled water. A bubble detector (not shown) may be disposed between the fluid source 44 and the pump 46 to detect bubbles in the liquid and/or to determine whether liquid flow from the fluid source 44 has been interrupted or the container has emptied. Also, as discussed above degassed fluids may be used. The bubble detector can be used to determine whether small air bubbles are present in the fluid that might negatively impact jet formation or acoustic wave propagation. Thus in some embodiments, a filter or de-bubbler (not shown) can be used to remove small air bubbles from the liquid. The liquid in the fluid source 44 may be at room temperature or may be heated and/or cooled to a different temperature. For example, in some embodiments, the liquid in the fluid source 44 can be chilled to reduce the temperature of the high velocity jet 60 generated by the system 38, which may reduce or control the temperature of the fluid inside a tooth 10. In some treatment methods, the liquid in the fluid source 44 can be heated, which may increase the rate of chemical reactions that may occur in the tooth 10 during treatment.

The handpiece 20 can be configured to receive the high pressure liquid and can be adapted at a distal end to generate a high-velocity beam or jet 60 of liquid for use in dental procedures. In some embodiments, the system 38 may produce a coherent, collimated jet of liquid. The handpiece 20 may be sized and shaped to be maneuverable in the mouth of a patient so that the jet 60 may be directed toward or away from various portions of the tooth 10. In some embodiments, the handpiece 20 comprises a distal housing or coupling member that can be coupled to the tooth 10.

The system controller 51 may comprise a microprocessor, a special or general purpose computer, a floating point gate array, and/or a programmable logic device. The system controller 51 may be used to control safety of the system 38, for example, by limiting system pressures to be below safety thresholds and/or by limiting the time that the jet 60 is permitted to flow from the handpiece 20. The system 38 may also include a user interface 53 that outputs relevant system data or accepts user input (e.g., a target pressure). In some embodiments, the user interface 53 comprises a touch screen graphics display. In some embodiments, the user interface 53 may include controls for a dental practitioner to operate the liquid jet apparatus. For example, the controls can include a foot switch to actuate or deactuate the jet. In some embodiments, the motor 40, motor controller 54, pump 46, fluid source 44, pressure sensor 48, system controller 51, and user interface 53 can be integrated in the console 2 illustrated schematically in FIGS. 1A-1B.

The system 38 may include additional and/or different components and may be configured differently than shown in FIG. 3A. For example, the system 38 may include an aspiration pump that is coupled to the handpiece 20 (or an aspiration cannula) to permit aspiration of organic matter from the mouth or tooth 10. In other embodiments, the system 38 may comprise other pneumatic and/or hydraulic systems adapted to generate the high-velocity beam or jet 60.

Additional details of a pressure wave generator and/or pressure wave generator that includes a liquid jet device may be found at least in ¶¶[0045]-[0050], [0054]-[0077] and various other portions of U.S. Patent Publication No. US 2011/0117517, published May 19, 2011, and in ¶¶[0136]-[0142] and various other portions of U.S. Patent Publication No. US 2012/0237893, published Sep. 20, 2012, each of which is incorporated by reference herein in its entirety and for all purposes.

As has been described, a pressure wave generator can be any physical device or phenomenon that converts one form of energy into acoustic waves within the treatment fluid and that induces rotational fluid motion in the chamber 6 and/or tooth 10. Many different types of pressure wave generators (or combinations of pressure wave generators) are usable with embodiments of the systems and methods disclosed herein.

(2) Mechanical Energy

Mechanical energy pressure wave generators can also include rotating objects, e.g. miniature propellers, eccentrically-confined rotating cylinders, a perforated rotating disk, etc. These types of pressure wave generators can also include vibrating, oscillating, or pulsating objects such as sonication devices that create pressure waves via piezoelectricity, magnetostriction, etc. In some pressure wave generators, electric energy transferred to a piezoelectric transducer can produce acoustic waves in the treatment fluid. In some cases, the piezoelectric transducer can be used to create acoustic waves having a broad band of frequencies.

(3) Electromagnetic Energy

An electromagnetic beam of radiation (e.g., a laser beam) can propagate energy into a chamber, and the electromagnetic beam energy can be transformed into acoustic waves as it enters the treatment fluid. In some embodiments, the laser beam can be directed into the chamber 6 as a collimated and coherent beam of light. The collimated laser beam can be sufficient to generate pressure waves as the laser beam delivers energy to the fluid. Furthermore, in various embodiments, the laser beam can be focused using one or more lenses or other focusing devices to concentrate the optical energy at a location in the treatment fluid. The concentrated energy can be transformed into pressure waves sufficient to clean the undesirable materials. In one embodiment, the wavelength of the laser beam or electromagnetic source can be selected to be highly absorbable by the treatment fluid in the chamber or mouth (e.g., water) and/or by the additives in the treatment fluid (e.g., nanoparticles, etc.). For example, at least some of the electromagnetic energy may be absorbed by the fluid (e.g., water) in the chamber, which can generate localized heating and pressure waves that propagate in the fluid. The pressure waves generated by the electromagnetic beam can generate photo-induced or photo-acoustic cavitation effects in the fluid. In some embodiments, the localized heating can induce rotational fluid flow in the chamber 6 and/or tooth 10 that further enhances cleaning of the tooth 10 (see, e.g., FIG. 10C). The electromagnetic radiation from a radiation source (e.g., a laser) can be propagated to the chamber by an optical waveguide (e.g., an optical fiber), and dispersed into the fluid at a distal end of the waveguide (e.g., a shaped tip of the fiber, e.g., a conically-shaped tip). In other implementations, the radiation can be directed to the chamber by a beam scanning system.

The wavelength of the electromagnetic energy may be in a range that is strongly absorbed by water molecules. The wavelength may in a range from about 300 nm to about 3000 nm. In some embodiments, the wavelength is in a range from about 400 nm to about 700 nm, about 700 nm to about 1000 nm (e.g., 790 nm, 810 nm, 940 nm, or 980 nm), in a range from about 1 micron to about 3 microns (e.g., about 2.7 microns or 2.9 microns), or in a range from about 3 microns to about 30 microns (e.g., 9.4 microns or 10.6 microns). The electromagnetic energy can be in the ultraviolet, visible, near-infrared, mid-infrared, microwave, or longer wavelengths.

The electromagnetic energy can be pulsed or modulated (e.g., via a pulsed laser), for example with a repetition rate in a range from about 1 Hz to about 500 kHz. The pulse energy can be in a range from about 1 mJ to about 1000 mJ. The pulse width can be in a range from about 1 µs to about 500 µs, about 1 ms to about 500 ms, or some other range. In some cases, nanosecond pulsed lasers can be used with pulse rates in a range from about 100 ns to about 500 ns. The foregoing are non-limiting examples of radiation parameters, and other repetition rates, pulse widths, pulse energies, etc. can be used in other embodiments.

The laser can include one or more of a diode laser, a solid state laser, a fiber laser, an Er:YAG laser, an Er:YSGG laser, an Er,Cr:YAG laser, an Er,Cr:YSGG laser, a Ho:YAG laser, a Nd:YAG laser, a CTE:YAG laser, a $CO_2$ laser, or a Ti:Sapphire laser. In other embodiments, the source of electromagnetic radiation can include one or more light emitting diodes (LEDs). The electromagnetic radiation can be used to excite nanoparticles (e.g., light-absorbing gold nanorods or nanoshells) inside the treatment fluid, which may increase the efficiency of photo-induced cavitation in the fluid. The treatment fluid can include excitable functional groups (e.g., hydroxyl functional groups) that may be susceptible to excitation by the electromagnetic radiation and which may increase the efficiency of pressure wave generation (e.g., due to increased absorption of radiation). During some treatments, radiation having a first wavelength can be used (e.g., a wavelength strongly absorbed by the liquid, for instance water) followed by radiation having a second wavelength not equal to the first wavelength (e.g., a wavelength less strongly absorbed by water) but strongly absorbed by another element, e.g. dentin, or nanoparticles added to solution. For example, in some such treatments, the first wavelength may help create bubbles in the fluid, and the second wavelength may help disrupt the tissue.

The electromagnetic energy can be applied to the chamber 6 for a treatment time that can be in a range from about one to a few seconds up to about one minute or longer. A treatment procedure can include one to ten (or more) cycles of applying electromagnetic energy to the tooth. A fluid can circulate or otherwise move in the chamber during the treatment process, which advantageously may inhibit heating of the tooth 10 (which may cause discomfort to the patient). The movement or circulation of treatment fluid (e.g., water with a tissue dissolving agent) in the chamber 6 can bring fresh treatment fluid to tissue and organic matter as well as flush out dissolved material from the treatment site. In some treatments using electromagnetic radiation, movement of the treatment fluid can increase the effectiveness of the cleaning (as compared to a treatment with little or no fluid circulation).

In some implementations, electromagnetic energy can be added to other fluid motion generation modalities. For example, electromagnetic energy can be delivered to a chamber in which another pressure wave generator (e.g., a liquid jet) is used to generate the acoustic waves.

(4) Acoustic Energy

Acoustic energy (e.g., ultrasonic, sonic, audible, and/or lower frequencies) can be generated from electric energy transferred to, e.g., an ultrasound or other transducer or an ultrasonic tip (or file or needle) that creates acoustic waves in the treatment fluid. The ultrasonic or other type of acoustic transducer can comprise a piezoelectric crystal that physically oscillates in response to an electrical signal or a magnetostrictive element that converts electromagnetic energy into mechanical energy. The transducer can be disposed in the treatment fluid, for example, in the fluid inside the chamber. As explained herein with respect to FIGS. 4A-4C, for example, ultrasonic or other acoustic devices used with the embodiments disclosed herein are preferably broadband and/or multi-frequency devices. For example, unlike the power spectra of the conventional ultrasonic transducer shown in FIG. 4B, ultrasonic or other acoustic devices used with the disclosed embodiments preferably have broadband characteristics similar to those of the power spectra of FIGS. 4A-4B (acoustic power of a liquid jet device).

(5) Further Properties of Some Pressure Wave Generators

A pressure wave generator 5 can be placed at a desired location with respect to the tooth 10. The pressure wave generator 5 creates pressure waves within the fluid 22 inside the chamber 6 (the generation of acoustic waves may or may not create or cause cavitation). The acoustic or pressure waves 23 propagate throughout the fluid 22 inside the chamber 6, with the fluid 22 in the chamber 6 serving as a propagation medium for the pressure waves 23. The pressure waves 23 can also propagate through tooth material (e.g., dentin). It is believed, although not required, that as a result of application of a sufficiently high-intensity acoustic wave, acoustic cavitation may occur. The collapse of cavitation bubbles may induce, cause, or be involved in a number of processes described herein such as, e.g., sonochemistry, tissue dissociation, tissue delamination, sonoporation, and/or removal of calcified structures. In some embodiments, the pressure wave generator can be configured such that the acoustic waves (and/or cavitation) do not substantially break down natural dentin in the tooth 110. The acoustic wave field by itself or in addition to cavitation may be involved in one or more of the abovementioned processes.

In some implementations, the pressure wave generator 5 generates primary cavitation, which creates acoustic waves, which may in turn lead to secondary cavitation. The secondary cavitation may be weaker than the primary cavitation and may be non-inertial cavitation. In other implementations, the pressure wave generator 5 generates acoustic waves directly, which may lead to secondary cavitation.

The energy source that provides the energy for the pressure wave generator 5 can be located outside the handpiece 20, inside the handpiece 20, integrated with the handpiece 20, etc.

Additional details of pressure wave generators (e.g., which may comprise a pressure wave generator) that may be suitable for use with the embodiments disclosed herein may be found, e.g., in ¶¶[0191]-[0217], and various other portions of U.S. Patent Publication No. US 2012/0237893, published Sep. 20, 2012, which is incorporated by reference herein for all purposes.

Other pressure wave generators may be suitable for use with the disclosed embodiments. For example, a fluid inlet can be disposed at a distal portion of a handpiece and/or can be coupled to a fluid platform in some arrangements. The fluid inlet can be configured to create movement of the fluid in a chamber 6, turbulence in the fluid in the chamber, fluid motion 24 of the fluid 22 in the chamber 6 and/or produce other dynamics in the fluid in the chamber 6r. For example, the fluid inlet can inject fluid into or on the tooth to be treated. In addition, mechanical stirrers and other devices can be used to enhance fluid motion and cleaning. The fluid inlet can improve the circulation of the treatment fluid in a chamber, which can enhance the removal of unhealthy materials from the tooth 10. For example, as explained herein, faster mechanisms of reactant delivery such as "macroscopic" liquid circulation may be advantageous in some of the embodiments disclosed herein.

In some embodiments, multiple pressure wave generators can be disposed in or on the chamber 6. As explained herein, each of the multiple pressure wave generators can be configured to propagate acoustic waves at a different frequency or range of frequencies. For example, different acoustic frequencies can be used to remove different types of materials. The multiple pressure wave generators can be activated simultaneously and/or sequentially in various arrangements.

B. Coupling Members

The coupling members 3 disclosed herein can be adapted to couple or orient the pressure wave generator 5 relative to the tooth 10. In some embodiments disclosed herein, the coupling member 3 can be configured to retain fluid 22 in a treatment chamber 6. In some embodiments, the coupling member 3 can be coupled to or formed with a distal portion 21 of the handpiece 20. The coupling member 3 can include or define the chamber 6 configured to retain fluid 22. Liquid can be introduced into the chamber 6 through a fluid inlet connected to, or disposed in or on, the handpiece 20. Waste treatment liquid can be removed through the coupling member 3 by way of a fluid outlet and further into the handpiece 20. In various arrangements, the coupling member 3 may be configured to cover a portion of a tooth, a whole surface of the tooth, and/or multiple teeth.

In some embodiments, the coupling member 3 can be applied to the tooth 10 with a mechanical clasp or clamp, a dental adhesive, or by pressure applied by the patient by biting on the coupling member 3. In still other embodiments, a separate cap or fluid retainer can be removably coupled to the distal portion 21 of the handpiece 20.

Additional details of coupling members 3 may be similar to those of fluid retainers, flow restrictors or caps disclosed, e.g., in ¶¶[0052]-[0053], [0115]-[0117] and various other portions of U.S. Patent Publication No. US 2011/0117517, published May 19, 2011, and in ¶¶[0040]-[0043], [0170]-[01 [0293]-[0299], [0316]-[0319] and various other portions of U.S. Patent Publication No. US 2012/0237893, published Sep. 20, 2012, each of which is incorporated by reference herein for all purposes.

The coupling member 3 can also include various components that enhance aspiration and irrigation before, during, and/or after the treatment procedure. In some embodiments, fluid 22 can enter the chamber 6 via a fluid inlet, such as a treatment liquid inflow conduit. The fluid inlet can pass through or along the handpiece 20. Under steady state operation, the amount of liquid entering the at least partially enclosed chamber 6 can be substantially the same as the amount of liquid leaving chamber 6 through the fluid outlet. In some embodiments, the fluid inlet can be driven by a pump, which can be controlled by the console 2. Furthermore, the fluid inlet can be the same as the pressure wave generator 5 in some embodiments, such as in embodiments that employ a liquid jet device. Additional details of fluid inlets that may be suitable for use with the embodiments disclosed herein may be found, e.g., in ¶¶[0075]-[0078] and various other portions of U.S. Patent Publication No. US 2012/0237893, published Sep. 20, 2012, which is incorporated by reference herein for all purposes.

As explained above, the coupling member 3 can also have a fluid outlet, e.g., an outflow conduit to transfer liquid out of the chamber 6 during the procedure. In some embodiments, waste treatment liquid may be allowed to spill directly into the patient's mouth. In other embodiments, however, waste treatment liquid (as well as removed material and byproduct gases) can be transferred through the fluid outlet, which can pass through or along the handpiece 20. The fluid outlet can be active or passive. In the case of a passive fluid outlet, the waste treatment liquid may move through the fluid outlet due to capillary forces, gravity, or because of a slight overpressure created in the enclosed chamber 6. In the case of an actively pumped fluid outlet, the waste liquid can be transferred using a pump, suction, or other device that draws liquid out through the outlet. In one example, the fluid outlet is connected to the suction system and/or vacuum lines in the clinician's office. For example, in some embodiments, the inlet and outlet can be adjusted to maintain a balanced amount of fluid in coupling member 3. Additional details of fluid outlets that may be suitable for use with the embodiments disclosed herein may be found, e.g., in ¶¶[0079]-[0081] and various other portions of U.S. Patent Publication No. US 2012/0237893, published Sep. 20, 2012, which is incorporated by reference herein for all purposes.

As explained herein, the coupling member 3 can also include one or more vents to regulate pressure of the fluid 22. The vents can be disposed in a portion of the handpiece 20 in some arrangements, such as along a waste line or fluid outlet. The vents can take the form of a permeable or semi-permeable material (e.g., a sponge), openings, pores, or holes, etc. Additional details of vents that may be suitable for use with the embodiments disclosed herein may be found, e.g., in ¶¶[0071]-[0073], [0082]-[0086], [0177]-[0194] and various other portions of U.S. Patent Publication No. US 2012/0237893, published Sep. 20, 2012, which is incorporated by reference herein for all purposes.

C. Handpiece

The systems disclosed herein can include a handpiece 20. The handpiece 20 can be configured to apply the coupling member 3 to the tooth 10 and/or to position the pressure wave generator 5 relative to the treatment site. Treatment liquids can be transferred into and out of the chamber 6 by way of the handpiece 20.

The handpiece 20 can provide the operator, user or clinician with a handheld device to hold during the procedure. For example, the handpiece 20 can include user-friendly grips and a user-friendly shape to grasp. The clinician can manipulate the handpiece 20 to accurately position the coupling member 3 and/or pressure wave generator 5 at a desired position on the tooth 10. In addition, the handpiece 20 can allow the clinician to move or rotate the coupling member 3 and pressure wave generator 5 during the procedure so as to dispose the pressure wave generator 5 at a desirable position relative to the treatment region in the tooth 10. Alternatively, the handpiece 20 can also provide a device for the operator to clamp or attach to the tooth 10 such that the handpiece 20 does not require substantial user intervention during the procedure. The handpiece 20 can be disposable (e.g., single-use), or the handpiece 20 can be reusable. In one embodiment, the handpiece 20 is disposable, but the pressure wave generator 5 is reusable. The handpiece 20 can be formed of any suitable material. In some embodiments, the handpiece 20 can be formed of a plastic material. In other embodiments, the handpiece 20 can be formed of a metal. Additional details of handpieces that may be suitable for use with the embodiments disclosed herein may be found, e.g., in ¶¶[0107], [0138]-[0142], [0156]-[0161] and various other portions of U.S. Patent Publication No. US 2012/0237893, published Sep. 20, 2012, which is incorporated by reference herein for all purposes.

Figure 3B:
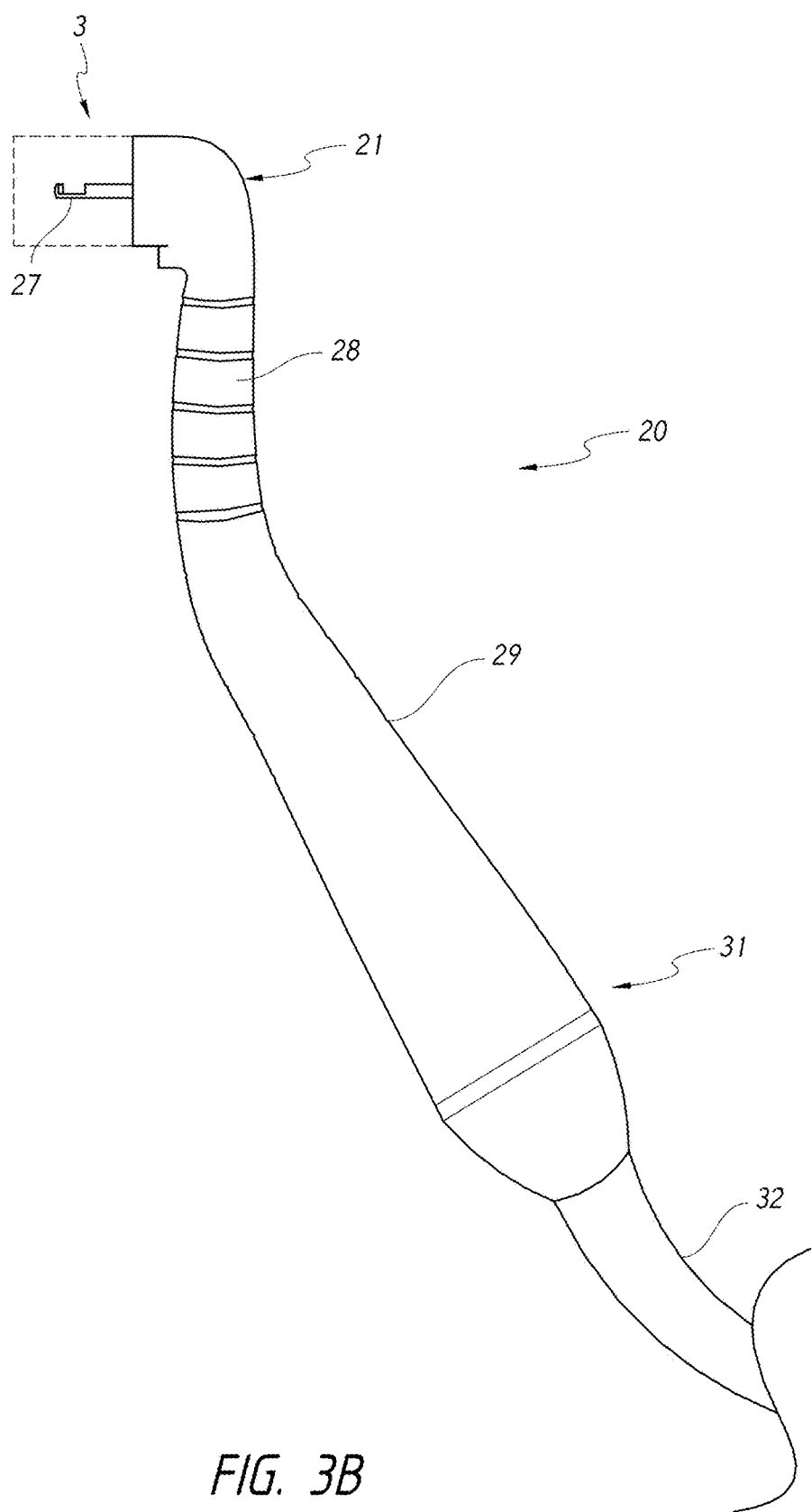
FIG. 3B is a schematic side view illustrating an embodiment of a handpiece comprising a guide tube for delivery of a liquid jet to a portion of the tooth.

For example, FIG. 3B is a schematic side view illustrating an embodiment of a handpiece 20 comprising an embodiment of a guide tube 27 for delivery of a liquid jet to a portion of a tooth 10. The handpiece 20 comprises an elongated tubular barrel 29 having a proximal end 31 that is adapted to engage tubing 32 from the system 38 and a distal end 21 adapted to be coupled or attached to the tooth 10. The barrel 29 may include features or textures 28 that enhance grasping the handpiece 20 with the fingers and thumb of the operator. The handpiece 20 can be configured to be handheld. In some cases, the handpiece 20 can be configured to be portable, movable, orientable, or maneuverable with respect to the patient. In some implementations, the handpiece 20 can be configured to be coupled to a positioning device (e.g., a maneuverable or adjustable arm). The distal end 21 of the handpiece 20 can comprise the coupling member 3 that can be coupled to the tooth 10.

The handpiece 20 may include a fluid inlet for delivering fluid 22 to the chamber 6, a fluid outlet for removing fluid from the tooth 10 (e.g., waste fluid), a pressure wave generator 5, a power line (e.g., to provide energy to a pressure wave generator), or a combination of some or all of the foregoing. The handpiece 20 may include other components such as, e.g., an irrigation line to irrigate the tooth area, a light source to illuminate the tooth area, etc. In some cases, the pressure wave generator 5 (e.g., a liquid jet) comprises the fluid inlet (e.g., the jet). The handpiece 20 can be used to apply the pressure wave generator 5 relative to the tooth 10. The handpiece 20 can be applied to the tooth 10 so as to create a substantially closed fluid circuit as the distal end 21 of the handpiece 20 engages the tooth 10, thereby enabling fluid to be delivered into and out of the chamber 6 without substantial spillage or leakage into the patient's mouth. As described herein, the handpiece 20 and/or the coupling member 3 may include a fluid retention member (e.g., sponge or vent) to reduce the likelihood of fluid leakage and/or to allow fluid to flow from the chamber 6 (e.g., to inhibit overpressurization or under-pressurization). The fluid retention member can be configured to inhibit air from entering the chamber 6 and tooth 10 (which may reduce the effectiveness of cavitation) while permitting air to enter a fluid outlet (e.g., suction line).

D. Tooth Seal and Alignment Features

A tooth seal 26 disclosed herein can be configured to temporarily secure the coupling member 3 to the tooth 10. The tooth seal 26 can be configured to flow onto or near an occlusal surface of the tooth in a flowable state. The tooth seal 26 can be configured to set and/or harden to hold its shape during treatment. In addition, the tooth seal 26 can be easily removed or pulled from the tooth 10 after use. In some arrangements, the sealing material can easily be reshaped using tools such as a dental bur, knife, etc. For example, in various embodiments, the sealing material can be shaped (e.g., planarized or curved) to support a planar coupling surface (e.g., a washer, one or more support magnets, etc.). The coupling member 3 and/or handpiece 3 can couple to the coupling surface, and the pressure wave generator 5 (e.g., a liquid jet device) can extend through the coupling surface such that a distal end portion 25 of the pressure wave generator 5 is disposed in the chamber 6 of the coupling member 3.

The tooth seal 26 can comprise any suitable sealant. For example, the tooth seal 26 can be a substantially semi-flexible material that can set or harden in less than about 30 seconds. The tooth seal 26 can be any suitable material that is able to seal the coupling member 3 to the tooth 10, but that also can easily be removed from the tooth 10. Examples of suitable sealing materials can include silicones, impression materials, bite registration materials, etc. In some embodiments, for example, the sealing materials can include 3M Imprint™ Bite, Jet Blue Bite by Colténe Whaledent®, LuxaBite bite registration material by DMG America, Alpha-Dam™ LC Gingival Dam Material or any other suitable sealant. In other embodiments, however, the tooth seal may not be used.

In some embodiments, the tooth seal 26 can comprise a permeable or semi-permeable material, such that waste fluid can flow from within the tooth 10 and/or chamber 6 through the tooth seal 6 and outside the tooth 10. In various embodiments, the tooth seal 26 can comprise a peripheral boundary shaped to secure the chamber 6 and/or coupling member 3 to the tooth seal 26. For example, in some embodiments, the tooth seal 26 can comprise a locking wall extending upwardly relative to the tooth. The locking wall can be shaped to laterally restrain the coupling member 3 during treatment. In some embodiments, a mating tube can extending outwardly from the chamber 6 and can surround an access port of the chamber 6. The mating tube can be positioned within the access opening 18 of the tooth 10 to substantially align the coupling member 3 and pressure wave generator 5 with the treatment region of the tooth 10.

In various embodiments, the tooth seal 26 can be shaped to permit the user to rotate the coupling member 3 relative to the tooth 10 to position the pressure wave generator 5 and coupling member 3 at a desired orientation relative to the treatment region of the tooth 10. For example, the tooth seal 26 can comprise a concave surface, and the distal end portion 21 of the handpiece 20 can be pressed against and/or coupled to the concave surface. The curved distal end portion 21 of the handpiece 20 can have a shape complementary to that of the curved tooth seal 26.

III. Examples of Power Generated by Pressure Wave Generators

Figure 4A:
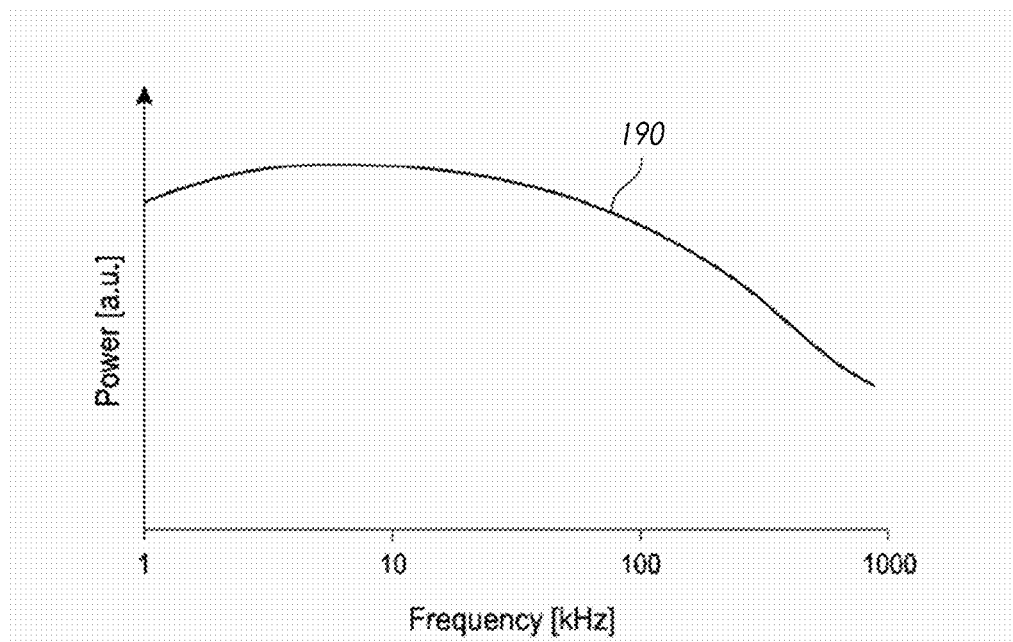
FIGS. 4A and 4B are graphs that schematically illustrate possible examples of power generated by different embodiments of the pressure wave generators disclosed herein.
Figure 4B:
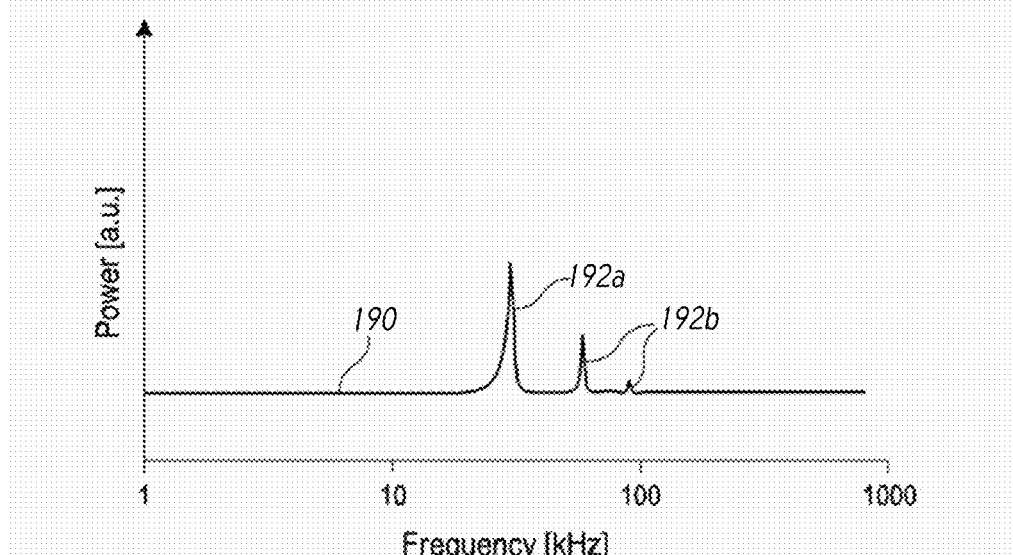

FIGS. 4A and 4B are graphs that schematically illustrate possible examples of power that can be generated by different embodiments of the pressure wave generator 5. These graphs schematically show acoustic power (in arbitrary units) on the vertical axis as a function of acoustic frequency (in kHz) on the horizontal axis. The acoustic power in the tooth may influence, cause, or increase the strength of effects including, e.g., acoustic cavitation (e.g., cavitation bubble formation and collapse, microjet formation), acoustic streaming, microerosion, fluid agitation, fluid circulation and/or rotational motion, sonoporation, sonochemistry, and so forth, which may act to dissociate organic material in or on the tooth and effectively clean the undesirable materials, e.g., undesirable organic and/or inorganic materials and deposits. In some embodiments, these effects can enhance or enable the obturation or filling of treated root canals or other treatment regions of the tooth, For example, the embodiments disclosed herein can advantageously obturate or fill substantially the entire canal(s) and/or branch structures therefrom, as explained in greater detail above. In various embodiments, the pressure wave generator can produce a pressure wave including acoustic power (at least) at frequencies above: about 1 Hz, about 0.5 kHz, about 1 kHz, about 10 kHz, about 20 kHz, about 50 kHz, about 100 kHz, or greater. The pressure wave can have acoustic power at other frequencies as well (e.g., at frequencies below the aforelisted frequencies).

The graph in FIG. 4A represents a schematic example of acoustic power generated by a liquid jet impacting a surface disposed within a chamber on or around the tooth that is substantially filled with liquid and by the interaction of the liquid jet with fluid in the chamber. This schematic example shows a broadband spectrum 190 of acoustic power with significant power extending from about 1 Hz to about 1000 kHz, including, e.g., significant power in a range of about 1 kHz to about 1000 kHz (e.g., the bandwidth can be about 1000 kHz). The bandwidth of the acoustic energy spectrum may, in some cases, be measured in terms of the 3-decibel (3-dB) bandwidth (e.g., the full-width at half-maximum or FWHM of the acoustic power spectrum). In various examples, a broadband acoustic power spectrum can include significant power in a bandwidth in a range from about 1 Hz to about 500 kHz, in a range from about 1 kHz to about 500 kHz, in a range from about 10 kHz to about 100 kHz, or some other range of frequencies. In some implementations, a broadband spectrum can include acoustic power above about 1 MHz. In some embodiments, the pressure wave generator can produce broadband acoustic power with peak power at about 10 kHz and a bandwidth of about 100 kHz. In various embodiments, the bandwidth of a broadband acoustic power spectrum is greater than about 10 kHz, greater than about 50 kHz, greater than about 100 kHz, greater than about 250 kHz, greater than about 500 kHz, greater than about 1 MHz, or some other value. In some cleaning methods, acoustic power between about 1 Hz and about 200 kHz, e.g., in a range of about 20 kHz to about 200 kHz may be particularly effective at cleaning teeth. The acoustic power can have substantial power at frequencies greater than about 1 kHz, greater than about 10 kHz, greater than about 100 kHz, or greater than about 500 kHz. Substantial power can include, for example, an amount of power that is greater than 10%, greater than 25%, greater than 35%, or greater than 50% of the total acoustic power (e.g., the acoustic power integrated over all frequencies). In some arrangements, the broadband spectrum 190 can include one or more peaks, e.g., peaks in the audible, ultrasonic, and/or megasonic frequency ranges.

The graph in FIG. 4B represents a schematic example of acoustic power generated by an ultrasonic transducer disposed in a chamber on or around the tooth that is substantially filled with liquid. This schematic example shows a relatively narrowband spectrum 192 of acoustic power with a highest peak 192a near the fundamental frequency of about 30 kHz and also shows peaks 192b near the first few harmonic frequencies. The bandwidth of the acoustic power near the peak may be about 5 to 10 kHz, and can be seen to be much narrower than the bandwidth of the acoustic power schematically illustrated in FIG. 4A. In other embodiments, the bandwidth of the acoustic power can be about 1 kHz, about 5 kHz, about 10 kHz, about 20 kHz, about 50 kHz, about 100 kHz, or some other value. The acoustic power of the example spectrum 192 has most of its power at the fundamental frequency and first few harmonics, and therefore the ultrasonic transducer of this example may provide acoustic power at a relatively narrow range of frequencies (e.g., near the fundamental and harmonic frequencies). The acoustic power of the example spectrum 190 exhibits relatively broadband power (with a relatively high bandwidth compared to the spectrum 192), and the example liquid jet can provide acoustic power at significantly more frequencies than the example ultrasonic transducer. For example, the relatively broadband power of the example spectrum 190 illustrates that the example jet device provides acoustic power at these multiple frequencies with energy sufficient to break the bonds between the decayed and healthy material so as to substantially remove the decayed material from the carious region.

It is believed, although not required, that pressure waves having broadband acoustic power (see, e.g., the example shown in FIG. 4A) can generate acoustic cavitation or other means of cleaning and disinfection that is more effective at cleaning teeth (including cleaning, e.g., unhealthy materials in or on the tooth) than cavitation generated by pressure waves having a narrowband acoustic power spectrum (see, e.g., the example shown in FIG. 4B). Further, broadband acoustic power can also generate sufficient energy at frequencies capable of obturating or filling a root canal or other treatment region (such as a treated carious region on an exterior surface of the tooth). For example, a broadband spectrum of acoustic power can produce a relatively broad range of bubble sizes in the cavitation cloud and on the surfaces on the tooth, and the implosion of these bubbles may be more effective at disrupting tissue than bubbles having a narrow size range. Relatively broadband acoustic power may also allow acoustic energy to work on a range of length scales, e.g., from the cellular scale up to the tissue scale. Accordingly, pressure wave generators that produce a broadband acoustic power spectrum (e.g., some embodiments of a liquid jet) can be more effective at tooth cleaning for some treatments than pressure wave generators that produce a narrowband acoustic power spectrum. In some embodiments, multiple narrowband pressure wave generators can be used to produce a relatively broad range of acoustic power. For example, multiple ultrasonic tips, each tuned to produce acoustic power at a different peak frequency, can be used. As used herein, broadband frequencies and broadband frequency spectrum is defined regardless of secondary effects such as harmonics of the main frequencies and regardless of any noise introduced by measurement or data processing (e.g., FFT); that is, these terms should be understood when only considering all main frequencies activated by the pressure wave generator.

Figure 4C:
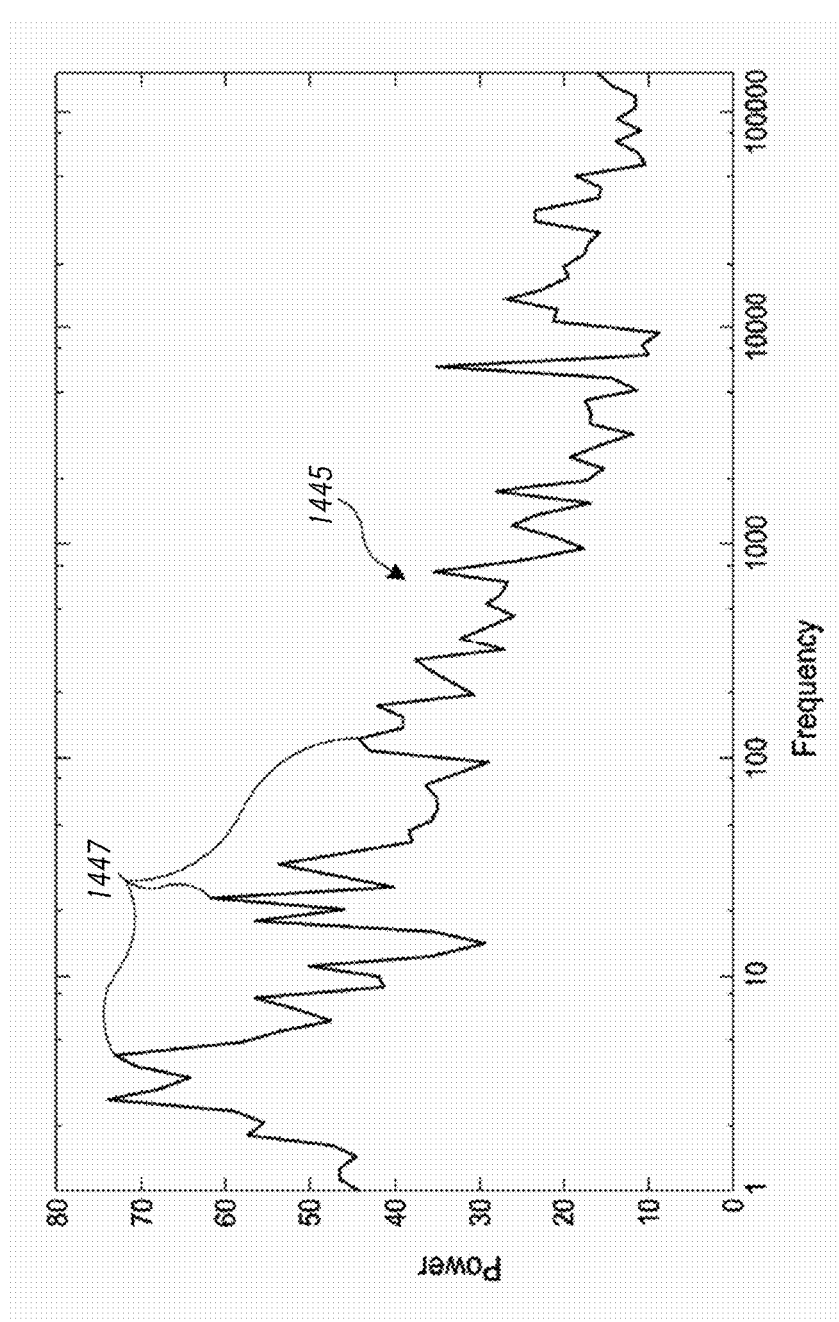
FIG. 4C is a graph of an acoustic power spectrum 1445 generated at multiple frequencies.

FIG. 4C is a graph of an acoustic power spectrum 1445 generated at multiple frequencies by the pressure wave generators disclosed herein. For example, the spectrum 1445 in FIG. 4C is an example of acoustic power generated by a liquid jet impacting a surface disposed within a chamber on, in, or around the tooth that is substantially filled with liquid and by the interaction of the liquid jet with fluid in the chamber. The spectrum 1445 of FIG. 4C represents acoustic power detected by a sensor spaced apart from the source of the acoustic energy, e.g., the pressure wave generator. The data was acquired inside an insulated water tank data when the distance between the power wave generator and the hydrophone (e.g., sensor) being about 8 inches. The vertical axis of the plot represents a measure of acoustic power: Log ($P_{acoustic}^2$), referred to herein as "power units". The units of $P_{acoustic}$ in the measurement were µPa (micro Pascal). Thus, it should be appreciated that the actual power at the source may be of a different magnitude because the sensor is spaced from the acoustic power generator. However, the general profile of the power spectrum at the source should be the same as the spectrum 1445 detected at the sensor and plotted in FIG. 4C. It should also be understood that, although the plot shows frequencies only up to 100 KHz, the power above 100 KHz was greater than zero—the data just was not plotted. It should further be noted that, as would be appreciated by one skilled in the art, the plot and the values would also depend on other parameters, such as, for example, the size and shape of the tank in which data was acquired, the insulation of the inner surface of the tank, the relative distance between the source (e.g., power wave generator), and the free water surface of the tank.

As shown in FIG. 4C, the spectrum 1445 can include acoustic power at multiple frequencies 1447, e.g., multiple discrete frequencies. In particular, the spectrum 1445 illustrated in FIG. 4C includes acoustic power at frequencies in a range of about 1 Hz to about 100 KHz. The acoustic power can be in a range of about 10 power units to about 80 power units at these frequencies. In some arrangements, the acoustic power can be in a range of about 30 power units to about 75 power units at frequencies in a range of about 1 Hz to about 10 kHz. In some arrangements, the acoustic power can be in a range of about 10 power units to about 30 power units at frequencies in a range of about 1 KHz to about 100 kHz. In some embodiments, for example, the broadband frequency range of the pressure waves generated by the pressure wave generators disclosed herein can comprise a substantially white noise distribution of frequencies (see, e.g., FIG. 11B and associated disclosure).

Pressure wave generators that generate acoustic power associated with the spectrum 1445 of FIG. 4C can advantageously and surprisingly clean undesirable materials from teeth. As explained above, the generation of power at multiple frequencies can help to remove various types of organic and/or inorganic materials that have different material or physical characteristics, and/or different bonding strengths at various frequencies. For example, some undesirable materials may be removed from the teeth and/or gums at relatively low acoustic frequencies, while other materials may be removed from the teeth at relatively high acoustic frequencies, while still other materials may be removed at intermediate frequencies between the relatively low and relatively high frequencies. As shown in FIG. 4C, lower frequency cleaning phases can be activated at higher powers, and higher frequency cleaning phases can be activated at lower powers. In other embodiments, low frequency cleaning phases may be activated at relatively low powers, and high frequency cleaning phases may be activated at relatively high powers. Pressure wave generators that generate acoustic power at multiple frequencies (e.g., multiple discrete frequencies) are capable of cleaning undesirable materials and decayed matter from interior and/or exterior portions of teeth.

In the embodiments disclosed herein, treatment procedures can be activated to generate acoustic power at various frequency ranges. For example, some treatment phases may be activated at lower frequencies, and other treatment phases may be activated at higher frequencies. The pressure wave generators disclosed herein can be adapted to controllably generate acoustic power at any suitable frequencies 1447 of the spectrum 1445. For example, the pressure wave generators disclosed herein can be adapted to generate power at multiple frequencies 1447 simultaneously, e.g., such that the delivered acoustic power in a particular treatment procedure can include a desired combination of individual frequencies. For example, in some procedures, power may be generated across the entire frequency spectrum 1445. In some treatment phases, the pressure wave generator can deliver acoustic power at only relatively low frequencies, and in other treatment phases, the pressure wave generator can deliver power at only relatively high frequencies, as explained herein. Further, depending on the desired treatment procedure, the pressure wave generator can automatically or manually transition between frequencies 1447 according to a desired pattern, or can transition between frequencies 1447 randomly. In some arrangements, relatively low frequencies can be associated with large-scale bulk fluid movement, and relatively high frequencies can be associated with small-scale, high-energy oscillations.

In some embodiments, the treatment procedure may include one or more treatment phases. In each treatment phase, energy can be applied at a different frequency or band of frequencies. For example, in one phase, energy (e.g., pressure or acoustic waves) propagating at a relatively low frequency (or band of frequencies) may be generated. The low frequency pressure waves can interact with the treatment fluid in the chamber and can induce removal of large-scale dental deposits or materials. Without being limited by theory, the low frequency pressure waves can remove a substantial portion of the unhealthy materials in the tooth. For example, the low frequency waves may have a sufficiently high energy at suitably low frequencies to remove large deposits or materials from the tooth. The acoustic power at the relatively low frequencies can include acoustic power at any suitable low-frequency band of the power spectrum of the pressure wave generator (see, e.g., FIG. 4A). For example, in some embodiments, the acoustic power in the first, low-frequency range can include one or more frequencies in a range of about 0.1 Hz to about 100 Hz, for example in a range of about 1 Hz to about 50 Hz in some arrangements.

In another phase, acoustic energy may be generated at relatively high frequencies. At higher frequencies, the pressure wave generator can be configured to remove smaller deposits and debris. For example, at higher frequencies, the pressure waves can propagate through the treatment fluid. The higher frequency waves can remove smaller portions from relatively small locations, such as crevices, cracks, spaces, and irregular surfaces of the tooth. In some embodiments, degassed liquid can be used to enhance the removal of matter from these small spaces. When the higher frequency cleaning is performed after the lower frequency cleaning, in some embodiments, the high frequency waves (and/or intermediate frequency waves) can clean the remainder of the unhealthy material left behind from the low frequency cleaning. In the relatively high frequency phases, acoustic energy can be generated in a range of about 10 kHz to about 1000 kHz, e.g., in a range of about 100 kHz to about 500 kHz.

In some embodiments, the treatment procedure can progress from the relatively low frequencies (or bands of frequencies) toward higher frequencies (or bands of frequencies). For example, the procedure can move from the relatively low frequency phase(s), through intermediate frequency phase(s), until the high frequency phase(s) are reached. Thus, in some embodiments, the treatment procedure can provide a gradual and/or substantially continuous transition between relatively low and relatively high frequencies. As the treatment progresses through the frequencies, unhealthy dental deposits or materials of varying size and type can be removed by the pressure wave generator. In other embodiments, however, the treatment procedure can transition or switch between frequencies (or bands of frequencies) or phases (e.g., between high, low and/or intermediate frequencies or bands of frequencies) at discrete levels. At various intermediate frequency ranges, acoustic energy can be generated in a range of about 100 Hz to about 10 kHz. For example, in some embodiments, the various phases of the treatment procedures described above may be activated by the user or clinician, or the pressure wave generator can be configured to automatically transition between the phases. In some embodiments, for example, the pressure wave generator can randomly switch between high, low, and intermediate frequencies.

Various treatment procedures may include any suitable number of treatment phases at various different frequencies. Furthermore, although various low- and high-frequency phases may be described above as occurring in a particular order, in other embodiments, the order of activating the low- and high-frequency phases, and/or any intermediate frequency phases, may be any suitable order. Furthermore, the treatment procedures and phases described herein can also be used to fill or obturate treatment regions of a tooth after cleaning. In obturation procedures, the embodiments disclosed herein can advantageously obturate or fill substantially the entire canal(s) and/or branch structures therefrom, as explained in greater detail herein.

IV. Examples of Coupling Members

Figure 5:
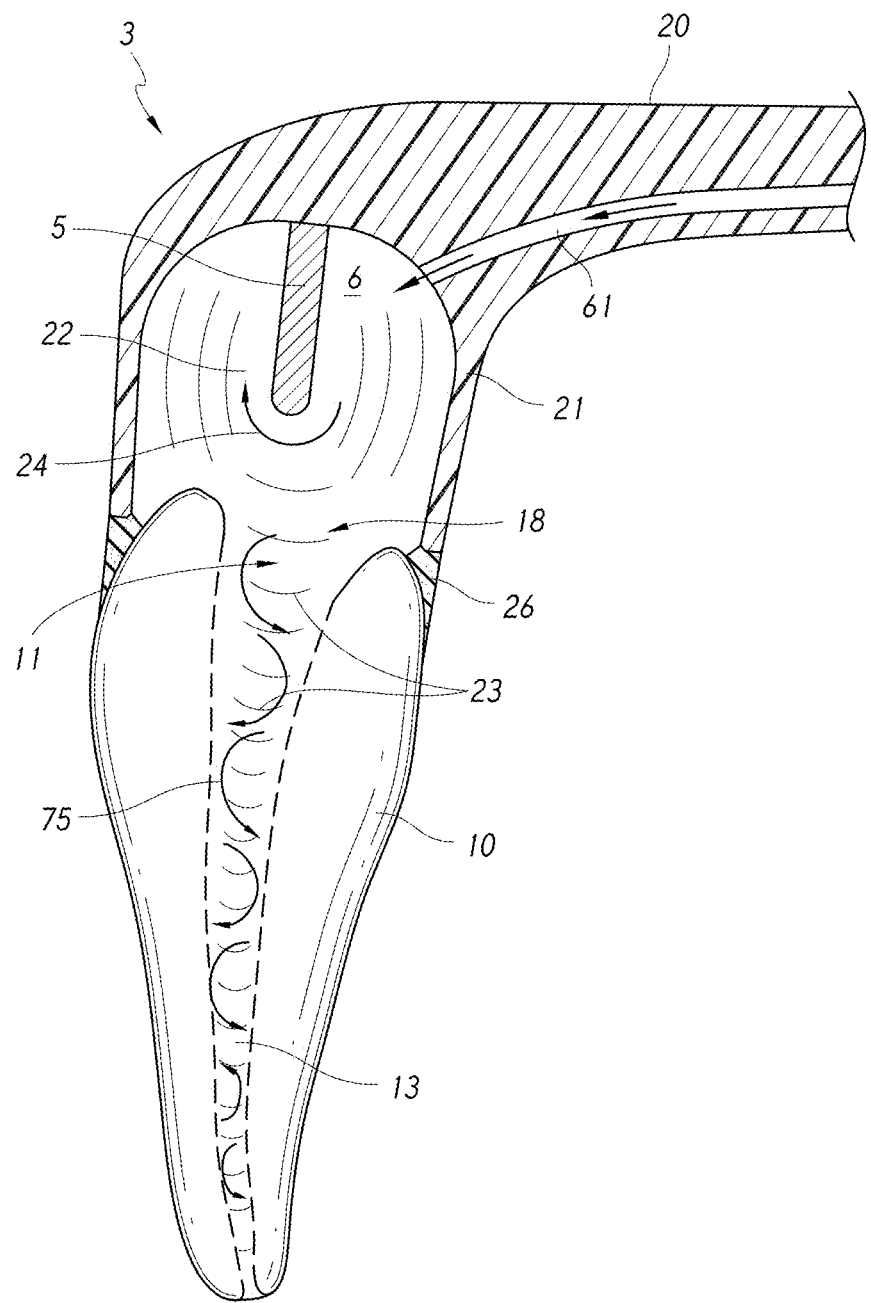
FIG. 5 is a schematic cross-sectional side view of a coupling member having a fluid inlet passing therethrough.

FIG. 5 is a schematic cross-sectional side view of a coupling member 3 having a fluid inlet 61 passing therethrough. In FIG. 5, the coupling member 3 comprises a distal portion 21 of a handpiece 20. A pressure wave generator 5 can be coupled to or integrally formed with the coupling member 3. As shown in FIG. 5, the pressure wave generator 5 can be disposed inside a chamber 6 of the coupling member 3 and outside the tooth 10. The coupling member 3 can be applied over an access opening 18 of the tooth 10. For example, a tooth seal 26 can be applied in flowable form over a top (e.g., occlusal) surface of the tooth 10 to provide a stable coupling surface to which the coupling member 3 can be secured. In some embodiments, the tooth seal 26 can be hardened to form a substantially solid material.

Once the coupling member 3 is secured to the tooth 10, the chamber 6 of the coupling member 3 can be at least partially, and in some arrangements substantially, filled with a suitable fluid 22. For example, as explained above, a treatment fluid can be used in cleaning treatments. An obturation material can be used in filling or obturation procedures. The fluid inlet 61 can comprise a hole or port in fluid communication with a fluid inlet line passing through or along the handpiece 20. Fluid 22 can be supplied actively (e.g., by way of a pump) or passively (e.g., by way of gravity or other potential flow) from the console 2 through the inlet line of the handpiece 20 and into the chamber 6. The pulp cavity 11 and/or chamber 6 of the coupling member 3 can be substantially filled with the fluid 22. For example, a controller in the console 2 can controllably direct the fluid 22 into the chamber 6 through the fluid inlet 61.

During a treatment procedure, the pressure wave generator 6 can be activated to generate sufficient fluid motion 24 and/or pressure waves 23 to clean unhealthy materials from the tooth 10, e.g., from the pulp cavity 11 and root canal 13. The fluid motion 24 can act to detach or break up the undesirable materials in the tooth 10, and can remove the materials from the tooth 10. For example, the fluid motion 24 can remove large particles or deposits of diseased tissue in some arrangements. The fluid motion 24 can also act to replenish chemical reactants supplied with the fluid 22. The pressure waves 23 can propagate through the fluid 22 and tooth to enhance the reactivity of the fluid 22 with the unhealthy materials in the tooth 10. For example, the pressure waves 23 can induce acoustic cavitation and other fluidic effects described herein that can enable the removal of unhealthy or undesirable materials from small spaces in the tooth 10, such as tubules, cracks, crevices, etc. The pressure wave generator 5 of FIG. 5 can be any suitable pressure wave generator disclosed herein, such as, a liquid jet device. In other embodiments, as explained above, the pressure wave generator 5 can also be used to fill or obturate the root canal 13. In such arrangements, the fluid 22 can comprise a flowable obturation material. The embodiments disclosed herein can advantageously obturate or fill substantially the entire canal(s) and/or branch structures therefrom, as explained in greater detail herein.

The tooth seal 26 can comprise a fluid-permeable material in the embodiment of FIG. 5. For example, the tooth seal 26 can include pores or other spaces through which waste fluid can flow. Accordingly, during a treatment procedure, fluid 22 can enter the tooth 10 and chamber 6 by way of the fluid inlet 61, and waste fluid can exit the tooth 10 and/or chamber 6 by way of the permeable tooth seal 26.

Figure 6:
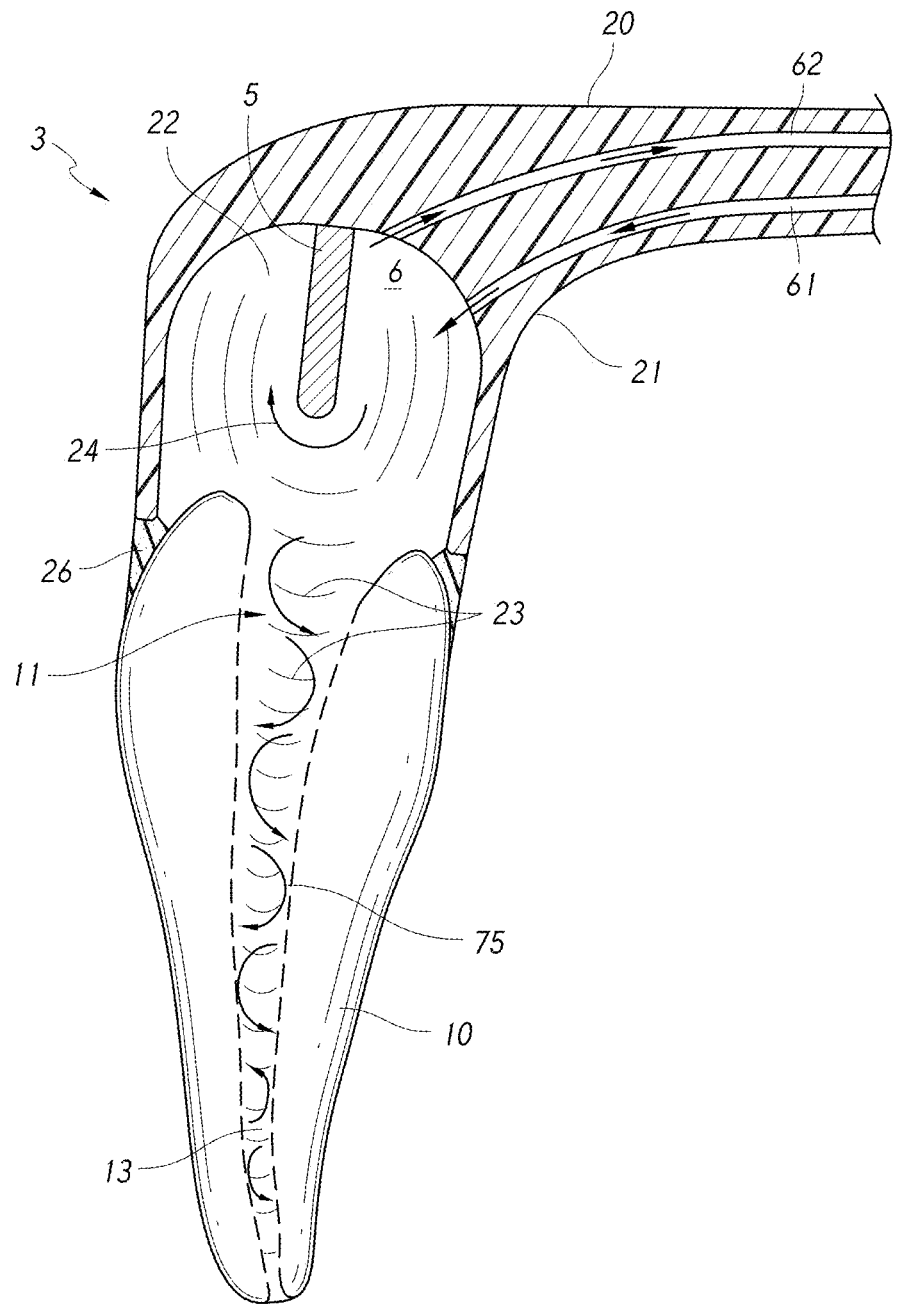
FIG. 6 is a schematic cross-sectional side view of a coupling member having a fluid inlet and a fluid outlet passing therethrough.

FIG. 6 is a schematic cross-sectional side view of a coupling member 3 having a fluid inlet 61 and a fluid outlet 62 passing therethrough. As with FIG. 5, a pressure wave generator 5 can be coupled to or integrally formed with the coupling member 3, and can be disposed in the chamber 6 of the coupling member 3. As explained herein, the pressure wave generator 5 can be used to clean and/or fill a tooth 10. Furthermore, as with the embodiment of FIG. 5, the fluid inlet 61 can be formed through the handpiece 20 and coupling member 3 to supply fluid 22 to the chamber 6 and the tooth 10. As above, the pressure wave generator 5 can be activated to induce pressure waves 23 and fluid motion 24 to clean unhealthy materials from the tooth 10. The pressure wave generator 5 of FIG. 6 can be any suitable pressure wave generator disclosed herein, such as, a liquid jet device.

In addition, a fluid outlet 62 can be disposed through the handpiece 20 to convey fluid out of the tooth 10 and chamber 6. For example, the fluid outlet 62 can act as a waste line, in which waste fluid can be expelled from the chamber 6 and tooth 10. The fluid outlet 62 can be incorporated to allow waste liquid to exit the chamber 6 into a hose which can be connected to a collection canister or a drain. The fluid outlet 62 can be an active or passive outlet. For a passive fluid outlet 62, in some cases the waste treatment liquid moves through a conduit due to capillary forces, gravity, or because of a slight overpressure created in the enclosed volume. For an actively pumped fluid outlet 62, the waste liquid can be transferred using a pump, suction, or other device that draws liquid out through an outflow conduit. In some arrangements, for example, the fluid outlet 62 can be connected to the suction system and/or vacuum lines in the clinician's office. In the embodiment of FIG. 6, the tooth seal 26 may or may not be permeable to fluid.

Accordingly, the embodiment disclosed in FIG. 6 can include both the inlet port 61 and the outlet port 62, which can balance the amount of fluid 22 in the tooth 10 at a given time. For example, the console 2 can be programmed such that the amount of fluid entering the tooth 10 and/or chamber 6 through the inlet port 61 is substantially the same as the amount of fluid exiting the tooth 10 and/or chamber 6 through the outlet port 62.

Figure 7A:
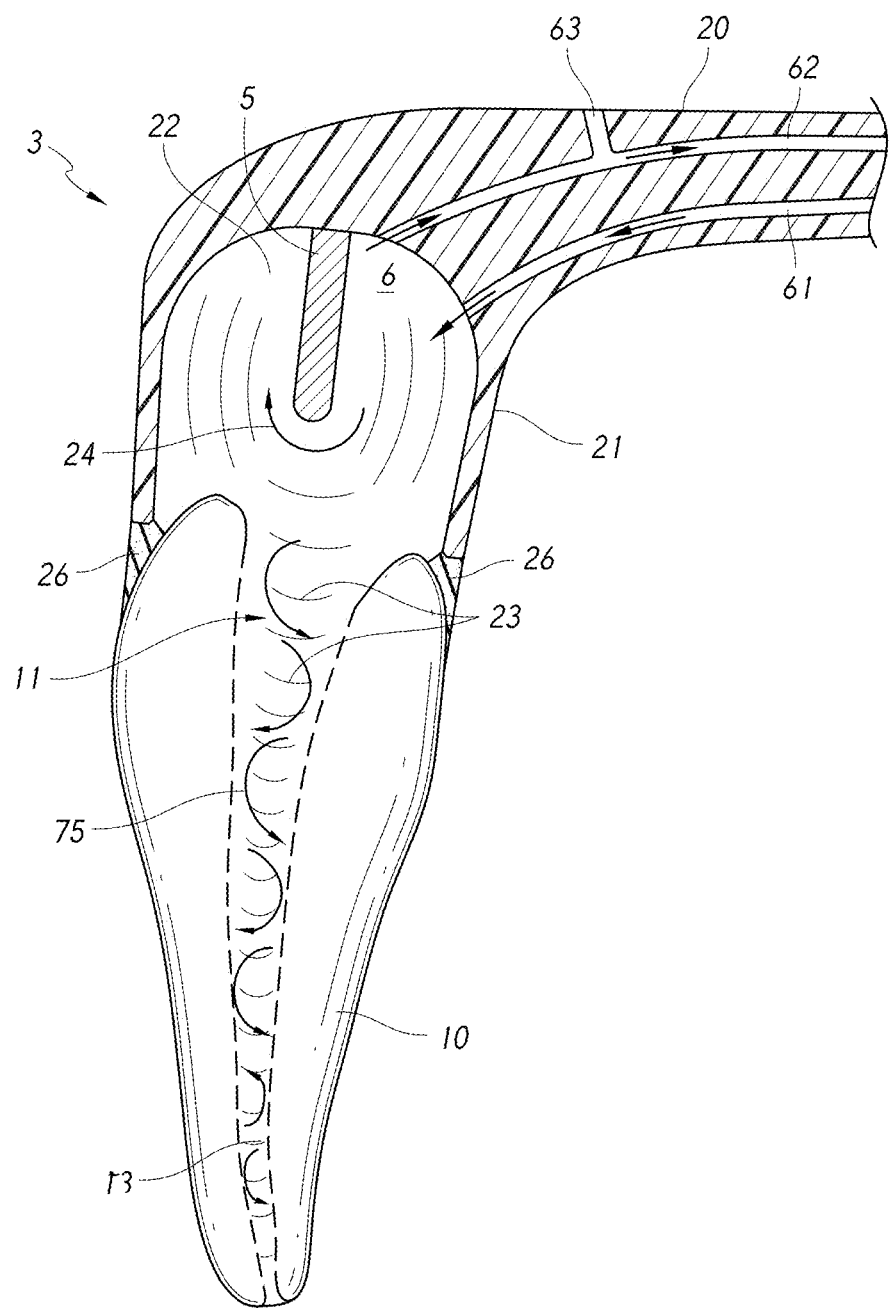
FIG. 7A is a schematic cross-sectional side view of a coupling member having a fluid inlet, a fluid outlet, and a vent configured to regulate a pressure inside the chamber and/or tooth.

FIG. 7A is a schematic cross-sectional side view of a coupling member 3 having a fluid inlet 61, a fluid outlet 62, and a vent 63 configured to regulate a pressure inside the chamber 6 and/or tooth 10. As with the embodiments of FIGS. 6A and 6B, the coupling member 3 can be coupled to or formed with a pressure wave generator 5 adapted to clean and/or fill a tooth 10. The coupling member 3 can be part of the distal end portion 21 of the handpiece 20. The coupling member 3 can couple to the tooth by way of the tooth seal 26.

The pressure wave generator 5 can be disposed inside the chamber 6 outside the tooth 10. The pressure wave generator 5 of FIG. 7A can be any suitable pressure wave generator disclosed herein, such as, a liquid jet device. Fluid 22 can be supplied to the tooth 10 and chamber 6 by way of the fluid inlet 61. For example, the fluid 22 can substantially fill the chamber 6. The pressure wave generator 5 can be activated to clean unhealthy material from the tooth 10. For example, as explained herein, the pressure wave generator 5 can generate pressure waves 23 and fluid motion 24 sufficient to clean and/or fill the tooth 10.

As shown in FIG. 7A, one or more vents 63 can be provided or formed in the coupling member 3 and/or the distal end portion 21 of the handpiece 20. The vent(s) 63 can act to at least partially regulate pressure of the fluid 22 inside the chamber 6 of the coupling member 3. For example, the vent(s) 63 can be disposed along the fluid outlet 62 (e.g., waste line). The vent 63 can fluidly communicate with the exterior environs, and air from the exterior environs can be entrained with the fluid outlet line 62.

In some vented arrangements, the inlet and outlet flow rates can be driven by independent driving forces. For example, in some implementations, the fluid inlet 61 can be in fluid communication with and driven by a pressure pump, while the fluid outlet 62 can be in fluid communication with and controlled via an evacuation system (e.g., a suction or vacuum pump). In other implementations, the fluid inlet 61 or outlet 62 can be controlled with a syringe pump. The pressures of the fluid inlet 61 and the fluid outlet 62 can be such that a negative net pressure is maintained in the chamber 6. Such a net negative pressure can assist delivering the treatment fluid into the chamber 6 from the fluid inlet 61.

In various embodiments described herein, the vents 63 can take the form of a permeable or semi-permeable material (e.g., a sponge), openings, pores, or holes, etc. The use of vents in a controlled fluid system can lead to one or more desirable advantages. For example, the evacuation system can collect waste fluid from the chamber 6, as long as there is any available. If there is a pause in treatment (e.g. the time between treatment cycles), waste fluid flow may stop, and the evacuation system may start drawing air through the one or more vents 63 to at least partially compensate for the lack of fluid supplied to the evacuation system, rather than depressurizing the chamber 6. If the evacuation system stops working for any reason, the waste fluid may flow out through the one or more vents 63 into the patient's mouth or onto a rubber dam (if used), where it can be collected by an external evacuation line. Therefore, the use of vent(s) can tend to dampen the effects of the applied pressure differential, and therefore can inhibit or prevent negative or positive pressure buildup. Also note that positive or negative pressure inside the chamber 6 can exert some amount of force on the sealing material(s), and as such a stronger seal may be required to withstand such force in some cases. Possible advantages of some vented systems include that the vent(s) help relieve pressure increases (or decreases) inside the chamber 6, reduce or eliminate the forces acting on the tooth seal 26, and therefore render the sealing more feasible and effective.

Figure 7B:
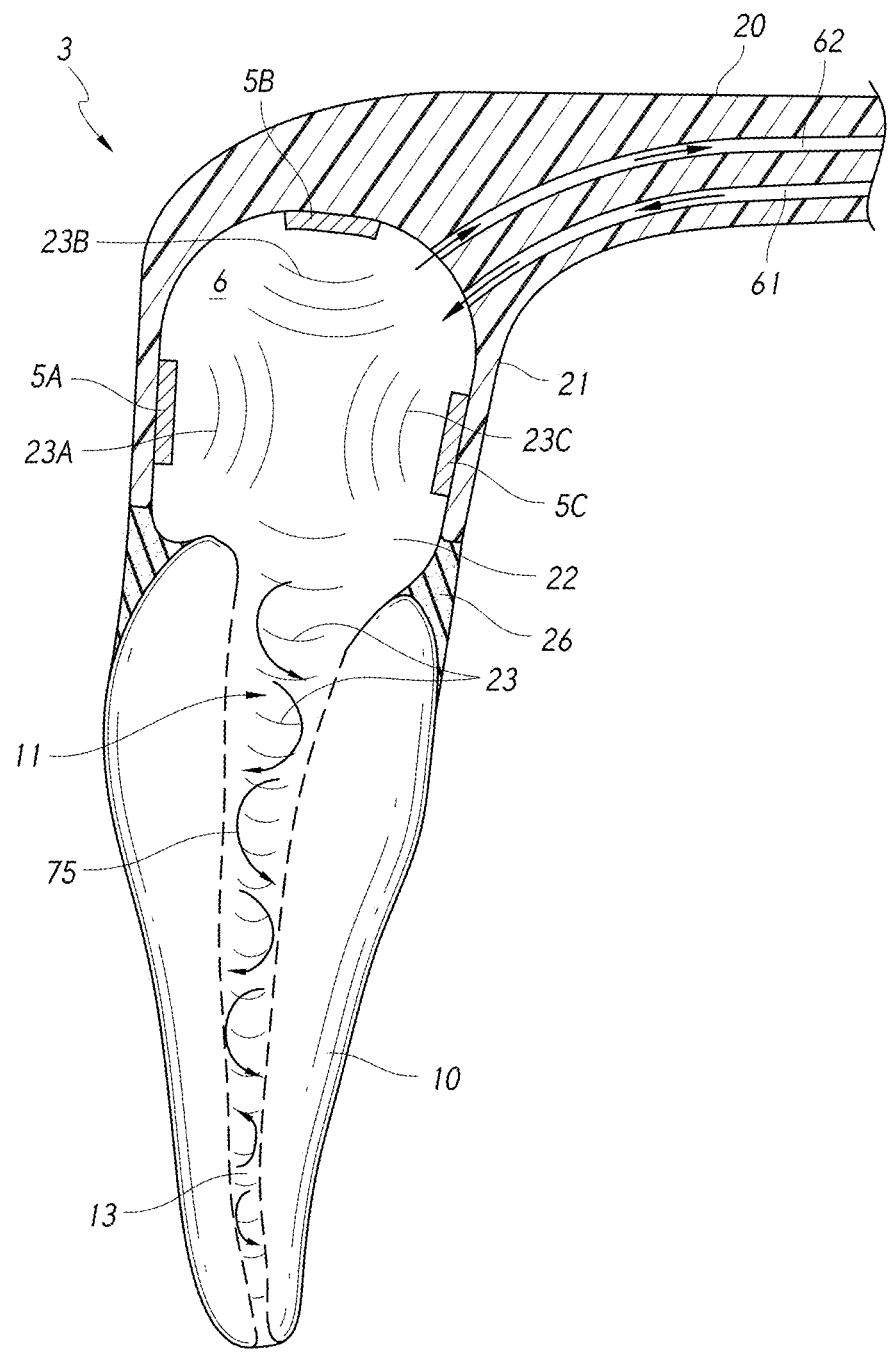
FIG. 7B is a schematic cross-sectional side view of a plurality of pressure wave generators coupled with a coupling member.

FIG. 7B is a schematic cross-sectional side view of a plurality of pressure wave generators 5A, 5B, 5C coupled with a coupling member 3. As with the embodiments of FIGS. 5-7A, the pressure wave generators 5A, 5B, 5C can be disposed in the chamber 6 of the coupling member 3 outside the tooth 10. For example, the pressure wave generators 5A, 5B, 5C can be coupled to walls of the coupling member 3. The pressure wave generators 5A, 5B, 5C of FIG. 7B can be any suitable pressure wave generator disclosed herein, such as a liquid jet device. In some embodiments, at least one of the pressure wave generators 5A, 5B, 5C can comprise an acoustic energy source. The pressure wave generators 5A, 5B, 5C can be the same type of pressure wave generator, or they can be different types of pressure wave generators. Although three pressure wave generators 5A, 5B, 5C are shown in FIG. 7B, it should be appreciated that there could be any suitable number of pressure wave generators, such as one, two, four, five, or more.

As above, the coupling member 3 can be coupled to the tooth 10 by way of the tooth seal 26. Fluid 22 can be supplied to the chamber 6 by way of the fluid inlet 61. For example, the fluid 22 can substantially fill the chamber 6. The fluid outlet 62 can convey waste fluid out of the tooth 10 and the chamber 6. Although not illustrated in FIG. 7B, one or more vents can also be provided to regulate the pressure in the chamber 6 and tooth 10.

During a treatment procedure, the pressure wave generators 5A, 5B, 5C can be activated sequentially or simultaneously. Advantageously, in some embodiments, the pressure wave generators 5A, 5B, 5C can be configured to generate corresponding pressure waves 23A, 23B, and 23C having different frequencies and/or powers. For example, the pressure wave generator 5A can generate a corresponding pressure wave 23A having a first frequency or a first range of frequencies. The pressure wave generator 5B can generate a corresponding pressure wave 23B having a second frequency or a second range of frequencies different form the first frequency or first range. The pressure wave generator 5C can generate a corresponding pressure wave 23C having a third frequency or a third range of frequencies that are different from the first and second frequencies/ranges. In some embodiments, the frequency ranges may overlap. In still other embodiments, the frequencies and ranges of frequencies can be about the same. For example, in some embodiments, each pressure wave generator 5A, 5B, 5C can generate pressure waves 23A, 23B, 23C across the full spectrum illustrated in FIG. 4A or 4C.

As explained herein, different frequencies of pressure waves may be effective at detaching or disrupting different types of tissue. For example, some frequencies may be more effective at detaching relatively large portions of unhealthy material from the tooth 10, and other frequencies may be more effective at detaching relatively small portions of unhealthy material from the tooth 10. Still other frequencies may be particularly effective at detaching intermediate sized portions from the tooth 10. In some embodiments, the acoustic frequencies that are effective at detaching material from the tooth 10 may be related to the composition of unhealthy material to be removed. For example, some frequencies may be more effective at removing diseased pulp tissue, while other frequencies may be more effective at removing calcified deposits. Still other frequencies may be effective at removing bacteria, biofilms, caries, plaque, calculus, etc.

To completely clean the tooth 10, it can be desirable to remove all types of unhealthy or undesirable materials from the tooth 10. For example, it can be desirable to remove organic and inorganic tissue from the root canal 13, in addition to bacteria, biofilms, and portions of the smear layer (if applicable). For exterior surfaces or portions of the tooth 10, it can be desirable to remove carious regions, in addition to dental deposits such as plaque, calculus, etc. Accordingly, during a treatment procedure, it can be desirable to propagate pressure waves 23A, 23B, 23C across the full range of frequencies that correspond to effective detachment of all types of unhealthy materials. In some embodiments, the full range of frequencies can be applied substantially simultaneously. For example, an acoustic signal comprising a random or noisy distribution of frequencies can be applied to the tooth 10 to clean all the unhealthy portions from the tooth 10.

In other embodiments, pressure wave generators 5A, 5B, 5C corresponding to a particular range of frequencies may be applied sequentially to sequentially remove the various types and/or sizes of unhealthy material from the tooth 10. For example, during a first treatment phase, the pressure wave generator 5A may be activated first to propagate pressure waves 23A corresponding to the first frequency or range of frequencies. During a second treatment phase, the pressure wave generator 5B may be activated next to propagate pressure waves 23B corresponding to the second frequency or range of frequencies. During a third treatment phase, the pressure wave generator 5C may be activated to propagate pressure waves 23C corresponding to the third frequency or range of frequencies. In some embodiments, the clinician can select the treatment phase as desired, e.g., to target a specific type or size of unhealthy material. In other embodiments, the system can be configured such that the treatment phases are automatically cycled in order to activate each of the plurality of pressure wave generators. In some arrangements, the system can be configured such that the treatment phases are randomly cycled.

Furthermore, the pressure wave generators 5A, 5B, 5C can act to induce bulk fluid movement, e.g., fluid motion 24 in the chamber 6, as described herein. In addition, in some embodiments, the pressure wave generators 5A, 5B, 5C can act to obturate or fill a treated tooth or treatment region. Accordingly, in the embodiment of FIG. 7B, multiple pressure wave generators 5A, 5B, 5C can be used sequentially and/or simultaneously to propagate acoustic waves in multiple frequency bands to substantially clean and/or fill the tooth 10 or a treatment region thereof.

V. Examples of Tooth Seals and Alignment Features

Figure 8A:
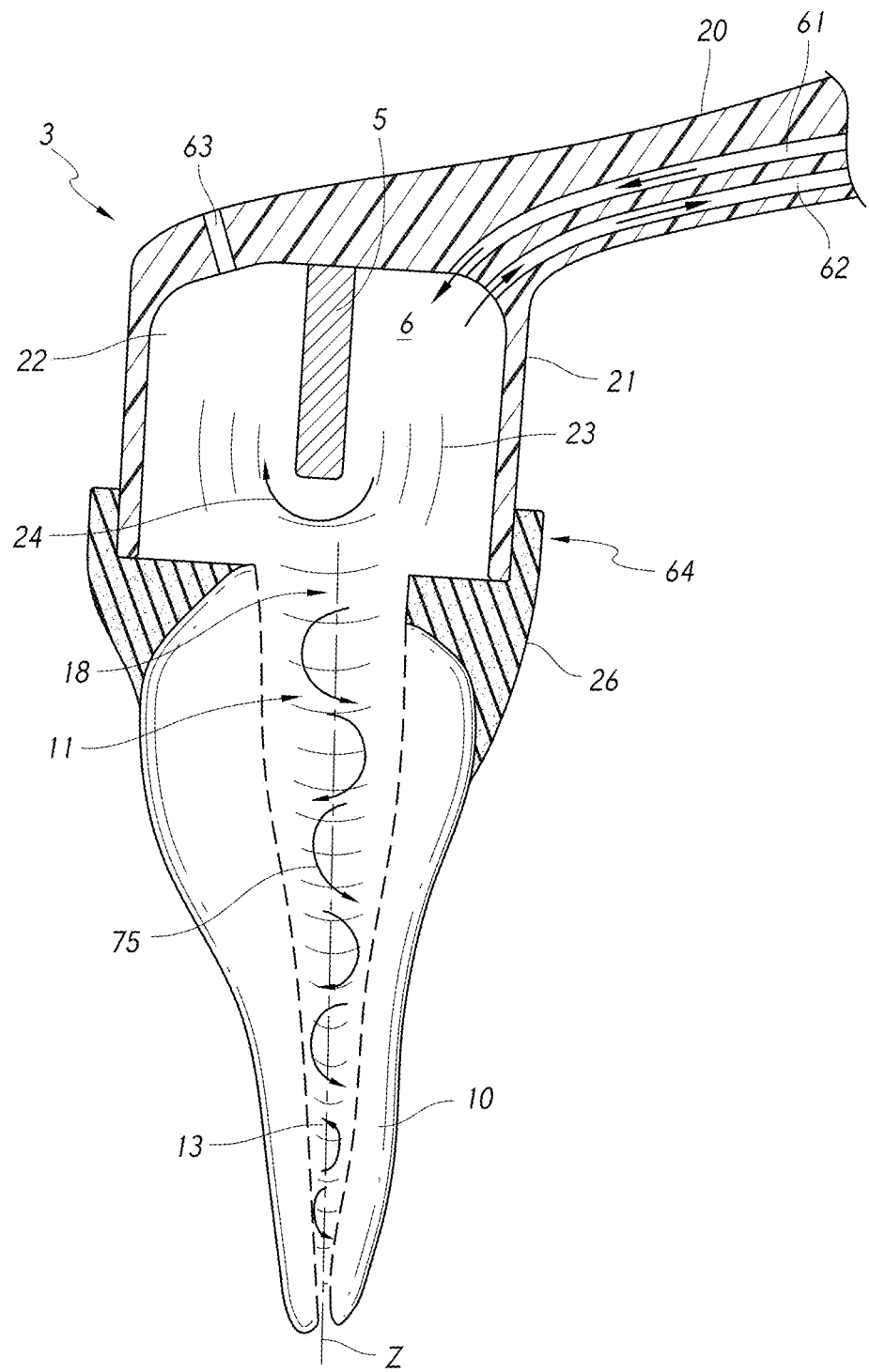
FIG. 8A is a schematic side cross-sectional view of a coupling member attached or coupled to a tooth by way of a locking tooth seal.

FIG. 8A is a schematic side cross-sectional view of a coupling member 3 attached or coupled to a tooth 10 by way of a locking tooth seal 26. It can be important to provide a stable coupling surface upon which to couple the coupling member 3. For example, if the coupling member 3 and pressure wave generator 5 are permitted to move significantly relative to the tooth 10, then the results of the procedure may be inconsistent and unsuitable.

Accordingly, the clinician can form an access opening 18 in the tooth 10. The tooth seal 26 can be applied around a perimeter of the access opening 18 such that the tooth seal 26 comprises a peripheral boundary. The chamber 6 and positioning member 3 can be positioned within the peripheral boundary of the tooth seal 26 to secure the chamber 6 and positioning member 3 to the tooth seal 26. Furthermore, it can be important to prevent or reduce lateral movement of the positioning member 3 relative to the tooth 10, e.g., movement transverse to a central axis Z of the root canal 13. For example, a locking wall 64 can be defined along the periphery of the tooth seal 26. The locking wall 64 can extend upwardly relative to the tooth 10, such that the wall 64 prevents lateral movement of the positioning member 3 and to help secure the coupling member 3 to the tooth 10. The lateral wall 64 can be defined to have a width or diameter slightly larger than a corresponding width or diameter of the coupling member 3. The lateral wall 64 can be defined to have tolerances such that a snug fit is formed between the seal 26 and the coupling member 3.

In some embodiments, the clinician can form the tooth seal 26 and locking wall 64 using a mold. The mold can be shaped to correspond to the ultimate profile of the seal 26 and locking wall 64. For example, the clinician can apply the mold about the tooth 10 and can flow the sealing material inside the mold in a flowable state. The sealing material can be cured (e.g., heated, exposed to ultraviolet light, etc.) such that the sealing material hardens into a solid or semi-solid state. In other embodiments, the clinician can manually shape the tooth seal 26 and locking wall 64 to have the desired dimensions and shape.

The clinician can apply the coupling member 3 to the seal 26 between and/or within the boundary defined by the locking wall 64. The seal 26 can comprise a substantially planar surface upon which the distal end of the coupling member 3 rests. As explained above, the locking walls 64 can prevent lateral movement of the coupling member 3. In some embodiments, the coupling member 3 can be attached to the seal 26, while in other embodiments, the clinician can press the coupling member 3 against the seal 26.

Fluid 22 can be supplied to the chamber 6 by way of the fluid inlet 61 such that the chamber 6 is at least partially or substantially filled with the fluid 22. The pressure wave generator 5 can be activated to substantially clean and/or fill the tooth 10. For example, as explained herein, the pressure wave generator 5 can induce pressure waves 23 and fluid motion 24 in the chamber 6 and/or tooth 10 that are sufficient to clean and/or fill the tooth 10. As above, the pressure wave generator 5 of FIG. 8A can be any suitable pressure wave generator, such as a liquid jet device. Waste fluid can flow out of the tooth 10 and chamber 6 by way of the fluid outlet 62 along the handpiece 20. A vent 63 can be provided to regulate the pressure in the tooth 10 and/or chamber 6. As shown in FIG. 8A, for example, the vent 63 can be formed through a wall of the coupling member 3 to provide fluid communication with the exterior environs, e.g., air.

Figure 8B:
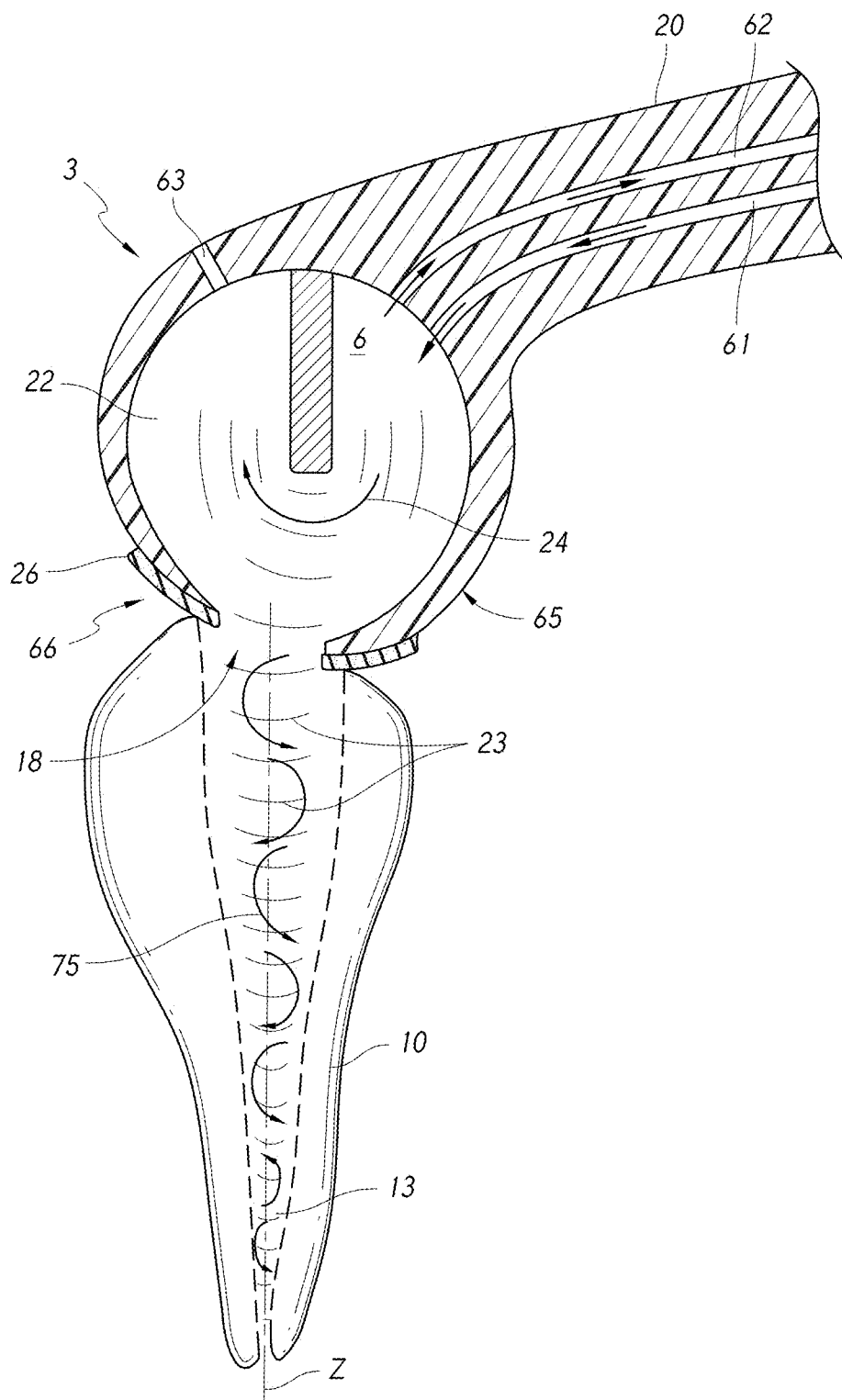
FIG. 8B is a schematic side cross-sectional view of a coupling member having a curved distal end portion shaped to mate with a curved surface of a tooth seal.

FIG. 8B is a schematic side cross-sectional view of a coupling member 3 having a curved distal end portion 65 shaped to mate with a curved surface 66 of a tooth seal 26. As shown in FIG. 8B, the coupling member 3 can be ball-shaped in some embodiments. In some procedures, it may be desirable for the clinician to rotate the coupling member 3 and pressure wave generator 5 to a desired orientation relative to the tooth 10. For example, the clinician may desire to position the pressure wave generator 5 at a particular location and/or orientation relative to the access opening 18 of the tooth 10. As explained herein, it can be advantageous in some arrangements to direct or pass fluid across the access opening 18 transverse to a central axis Z of the root canal 13.

In some embodiments, the tooth seal 26 can be applied to the tooth 10 about the access opening 18 such that the tooth seal 26 comprises a curved surface 66, e.g., a surface defining a concave portion facing the coupling member 3 and an opposing convex portion facing the tooth 10. As above, the seal 26 can be formed using a mold in some embodiments. In other embodiments, the clinician can manually shape the curved surface 66 of the tooth seal 26. The curved surface 66 of the tooth seal 26 can be defined to have a curvature (e.g., a radius of curvature) that is approximately the same as curved distal portion 65 of the coupling member 3.

After forming the tooth seal 26, the clinician can apply the curved distal portion 65 of the coupling member 3 to the corresponding curved surface 66 of the tooth seal 26 such that the curved distal portion 65 mates with the complementary curved surface 66 of the seal 26. In some embodiments, the tooth seal 26 is fixed relative to the tooth 10 and the curved distal portion 65 is rotationally free to move relative to the seal 26. In other embodiments, the curved surface 66 of the tooth seal 26 and the curved distal portion 65 are coupled together and free to rotate relative to the tooth 10 and access opening 18.

As explained above, fluid 22 is supplied to the chamber 6 and the tooth 10 by way of the fluid inlet 61. For example, the chamber 6 can be substantially filled with the fluid 22. The pressure wave generator 5 can be activated to substantially clean the tooth 10, e.g., to remove unhealthy materials from the tooth. The pressure wave generator 5 can generate pressure waves 23 and fluid motion 24 sufficient to clean the tooth 10. Waste fluid can be removed from the tooth 10 and chamber 6 by way of the fluid outlet 62. The vent 63 can be provided in the coupling member 3 to regulate the pressure in the tooth 10 and/or chamber 6.

During the treatment procedure, the clinician may want to manipulate the coupling member 3 and/or pressure wave generator 5 to orient the pressure wave generator 5 at a desired orientation and/or position. In the embodiment of FIG. 8B, for example, the clinician can manually rotate the handpiece 20, which in turn rotates the coupling member 3 and the curved distal portion 65 of the coupling member 3. The curved distal portion 65 can rotate relative to the curved surface 66 of the tooth seal 26 until the coupling member 3 and pressure wave generator 5 are oriented relative to the tooth 10 at a desired orientation. Accordingly, the tooth seal 26 and curved coupling member 3 can advantageously be used by a clinician to rotate the coupling member 3 relative to the tooth 10.

Figure 8C:
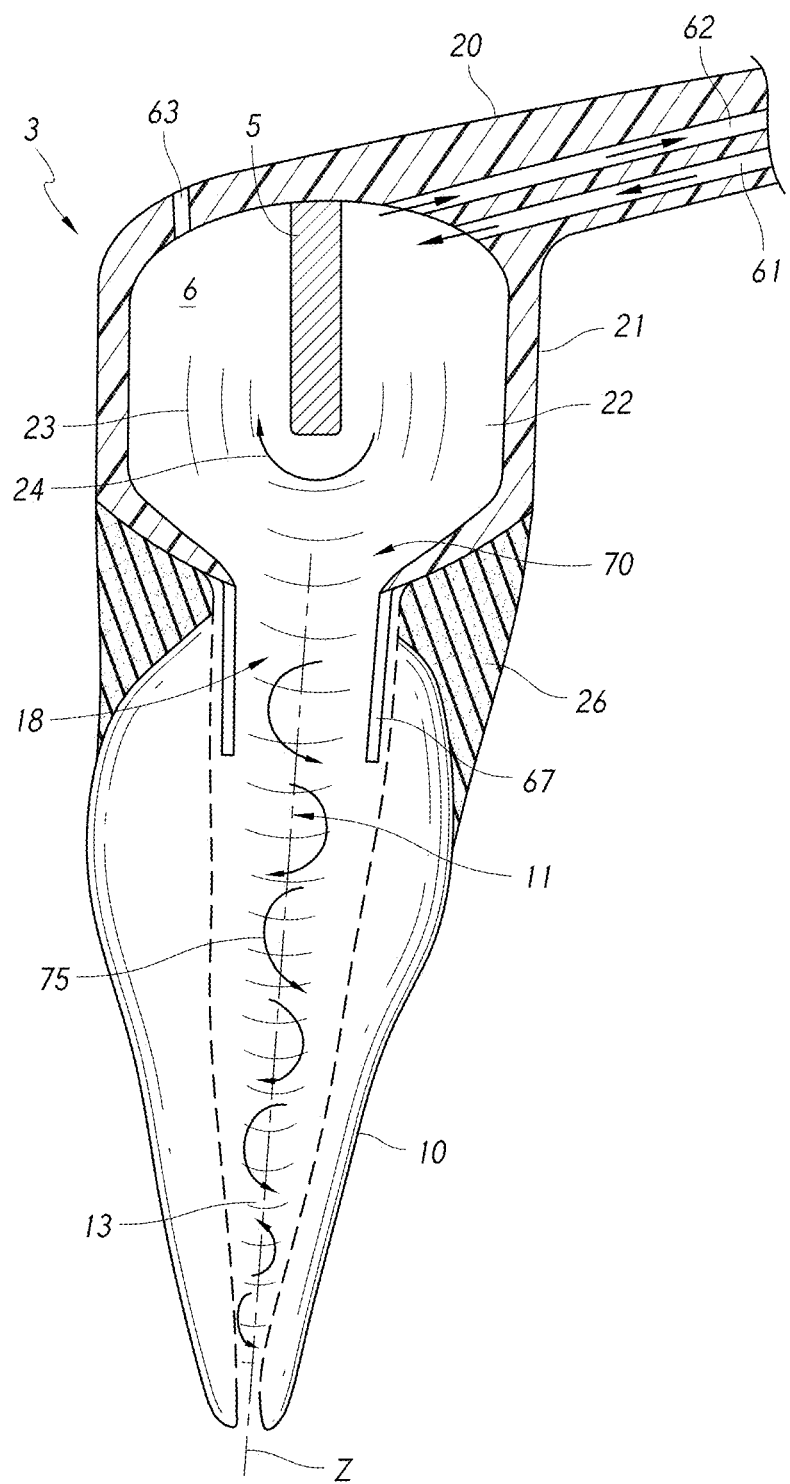
FIG. 8C is a schematic side cross-sectional view of a coupling member having an alignment feature comprising a mating tube sized and shaped to fit through an access opening formed in the tooth.

FIG. 8C is a schematic side cross-sectional view of a coupling member 3 having an alignment feature comprising a mating tube 67 sized and shaped to fit through an access opening 18 formed in the tooth 10. As shown in FIG. 8C, the coupling member 3 can comprise an access aperture 70 that defines an opening configured to provide fluid communication between the chamber 6 and the tooth 10. The mating tube 67 can surround and extend from the access aperture 70 of the coupling member 3.

In some embodiments, such as treatment procedures applied to a premolar tooth, it can be challenging to align the coupling member 3 to the access opening 18 of the tooth 10. Accordingly, in some embodiments, the clinician can form the access opening 18 and can apply the tooth seal 26 about the access opening 18 of the tooth 10. The clinician can apply the coupling member 3 to the tooth seal 26 such that the mating tube 67 is inserted through the access opening 18 and into a portion of the tooth 10. As shown in FIG. 8C, the mating tube 67 can help the clinician find the access opening 18 during treatment. Furthermore, the mating tube 67 can help laterally secure the coupling member 3 relative to the tooth 10. For example, the mating tube 67 can prevent the coupling member 3 from translating in a direction transverse to a central axis Z of the root canal 13 during treatment. The coupling member 3 can be attached to the seal 26, or the clinician can press the coupling member 3 against the tooth seal 26.

As above, the chamber 6 can be substantially filled with fluid 22 supplied by the fluid inlet 61. The pressure wave generator 5 can be activated to generate pressure waves 23 and fluid motion 24 in the chamber 6 and/or tooth 10. The pressure wave generator 5 can act to substantially clean and/or fill the tooth 10. Waste fluid can be removed by the fluid outlet 62. A vent 63 can be provided to regulate the pressure in the tooth 10 and/or chamber 6. Accordingly, the embodiment disclosed in FIG. 8C can advantageously align the coupling member 3 with the access opening 18 of the tooth 10 and can help to secure the coupling member 3 relative to the tooth 10.

VI. Examples of Pressure Wave Generators

Figure 9A:
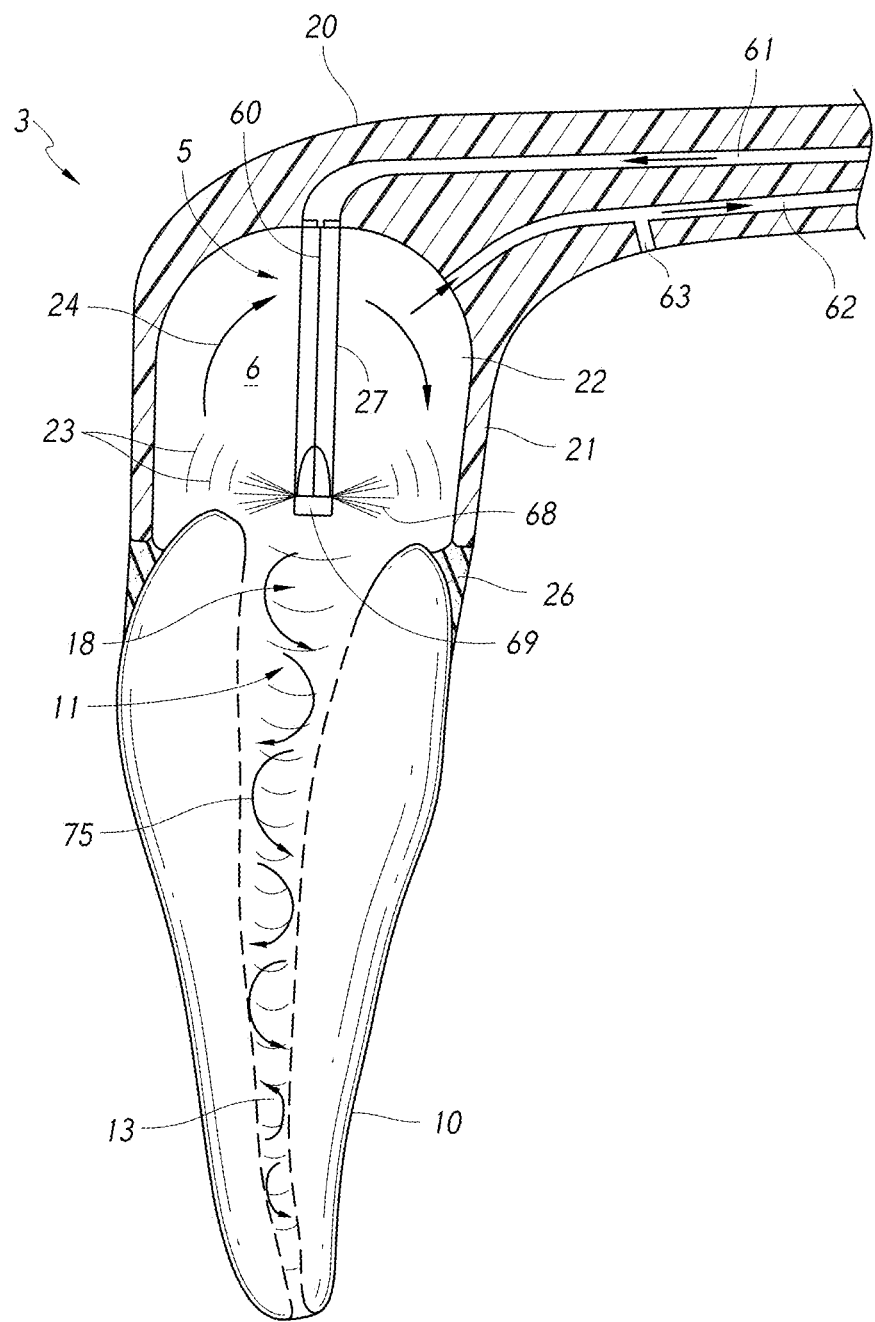
FIG. 9A is a schematic side cross-sectional view of a coupling member and a pressure wave generator comprising a liquid jet device.

FIG. 9A is a schematic side cross-sectional view of a coupling member 3 and a pressure wave generator 5 comprising a liquid jet device. As with the embodiments of FIG. 5-8C, the coupling member 3 can couple to the tooth 10 by way of a tooth seal 26. The pressure wave generator 5 can be disposed in the chamber 6 of the coupling member 3 outside the tooth 10. The fluid inlet 61 can supply fluid 22 to the tooth 10, and the pressure wave generator 5 can be activated to clean the tooth 10.

As shown in FIG. 9A, the pressure wave generator 5 comprises a liquid jet device. The liquid jet device can include a guide tube 60 and an impingement member 69 disposed at a distal end of the guide tube 60. A liquid jet 60 can be formed by a nozzle or orifice disposed in the distal end portion 21 of the handpiece. The jet 60 can propagate through a channel of the guide tube 27. One or more openings in the guide tube 27 can permit the jet 60 to interact with the fluid 22 filling the chamber 6. The jet 60 can impinge upon the impingement member 69, and can form a spray 68 of fluid that disperses through the fluid 22 in the chamber 6. Additional details of the liquid jet device disclosed in FIG. 9A can be found at least in ¶¶[0045]-[0050], [0054]-[0077] and various other portions of U.S. Patent Publication No. US 2011/0117517, published May 19, 2011, and in ¶¶[0136]-[0142] and various other portions of U.S. Patent Publication No. US 2012/0237893, published Sep. 20, 2012, each of which is incorporated by reference herein in its entirety and for all purposes.

A fluid inlet 61 can supply fluid 22 to the tooth 10. In the embodiment of FIG. 9A, the liquid jet device can comprise the fluid inlet 61. As explained herein, the interaction of the liquid jet 60 with the fluid 22 and the impingement member 69 can create pressure waves 23 and fluid motion 24 that are sufficient to clean the tooth 10 (or fill or obturate the tooth in obturation treatments). As above, waste fluid can be removed from the chamber 6 and tooth 10 by way of the fluid outlet 62. One or more vents 63 can be provided to regulate the pressure in the tooth 10 and/or chamber 6.

Figure 9B:
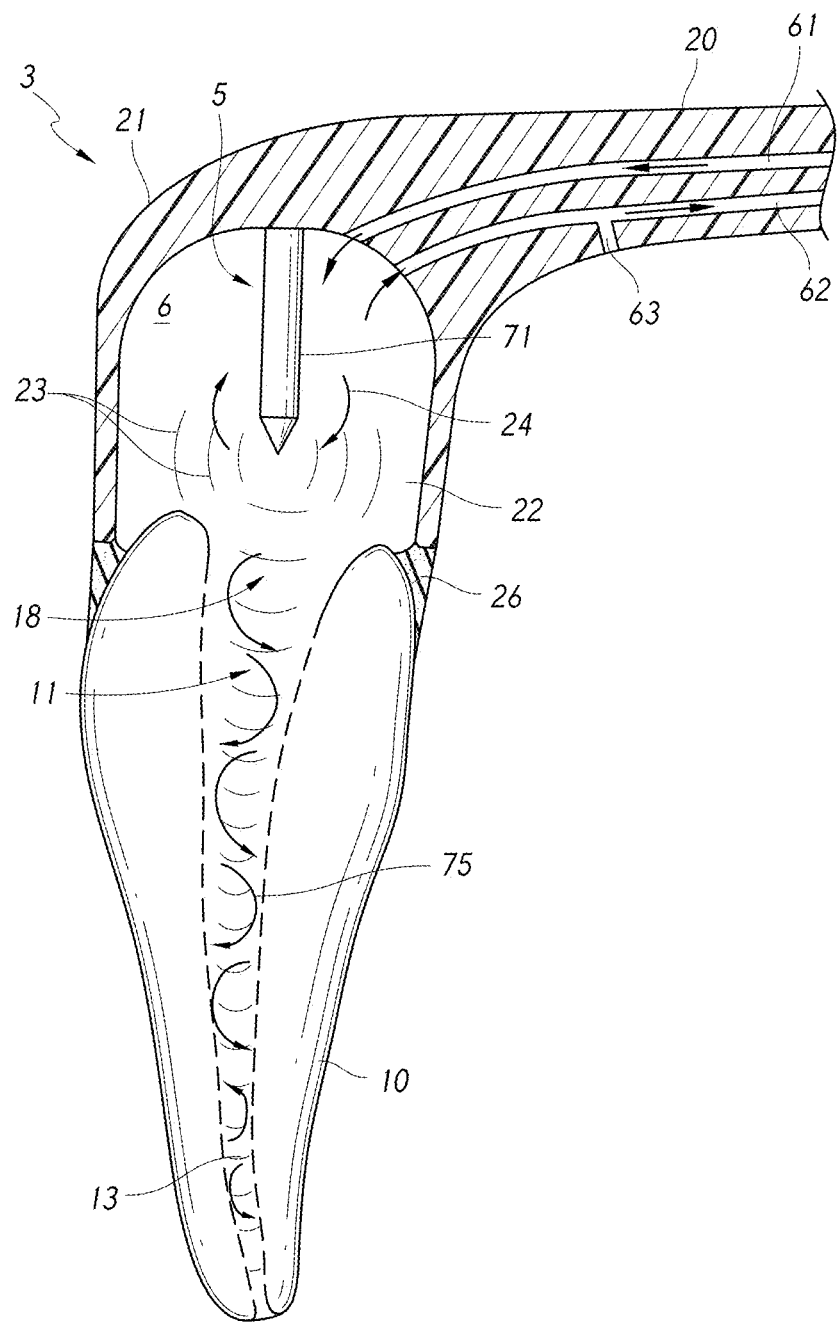
FIG. 9B is a schematic side cross-sectional view of a coupling member and a pressure wave generator comprising a light emitting element.

FIG. 9B is a schematic side cross-sectional view of a coupling member 3 and a pressure wave generator 5 comprising a light emitting element 71. Unless otherwise noted, the components illustrated in FIG. 9B are similar to or the same as similarly numbered components in FIG. 9A. The light emitting element 71 can be disposed in the chamber 6 of the coupling member 3. A laser beam or other suitable light source can propagate electromagnetic energy into the chamber 6, and the electromagnetic energy can be transformed into pressure waves 23 as it enters the fluid 22. In some embodiments, the laser beam can be directed into the chamber 6 as a collimated and coherent beam of light. The collimated laser beam can be sufficient to generate pressure waves 23 as the light delivers energy to the fluid 22. The concentrated energy can be transformed into pressure waves 23 sufficient to clean the undesirable dental matter. In some embodiments, the wavelength of the laser beam or electromagnetic source can be selected to be highly absorbable by the treatment fluid in the chamber or mouth (e.g., water) and/or by the additives in the treatment fluid (e.g., nanoparticles, etc.). For example, at least some of the electromagnetic energy may be absorbed by the fluid (e.g., water) in the chamber, which can generate localized heating and pressure waves 23 that propagate in the fluid. The acoustic waves generated by the electromagnetic beam can generate photo-induced or photo-acoustic cavitation effects in the fluid. In some embodiments, the localized heating can induce rotational fluid flow 24 in the chamber 6 and/or tooth 10 that further enhances cleaning of the tooth 10. In obturation procedures, the pressure wave generator 5 of FIG. 9B can be used to substantially fill the treated root canal 13.

Figure 9C:
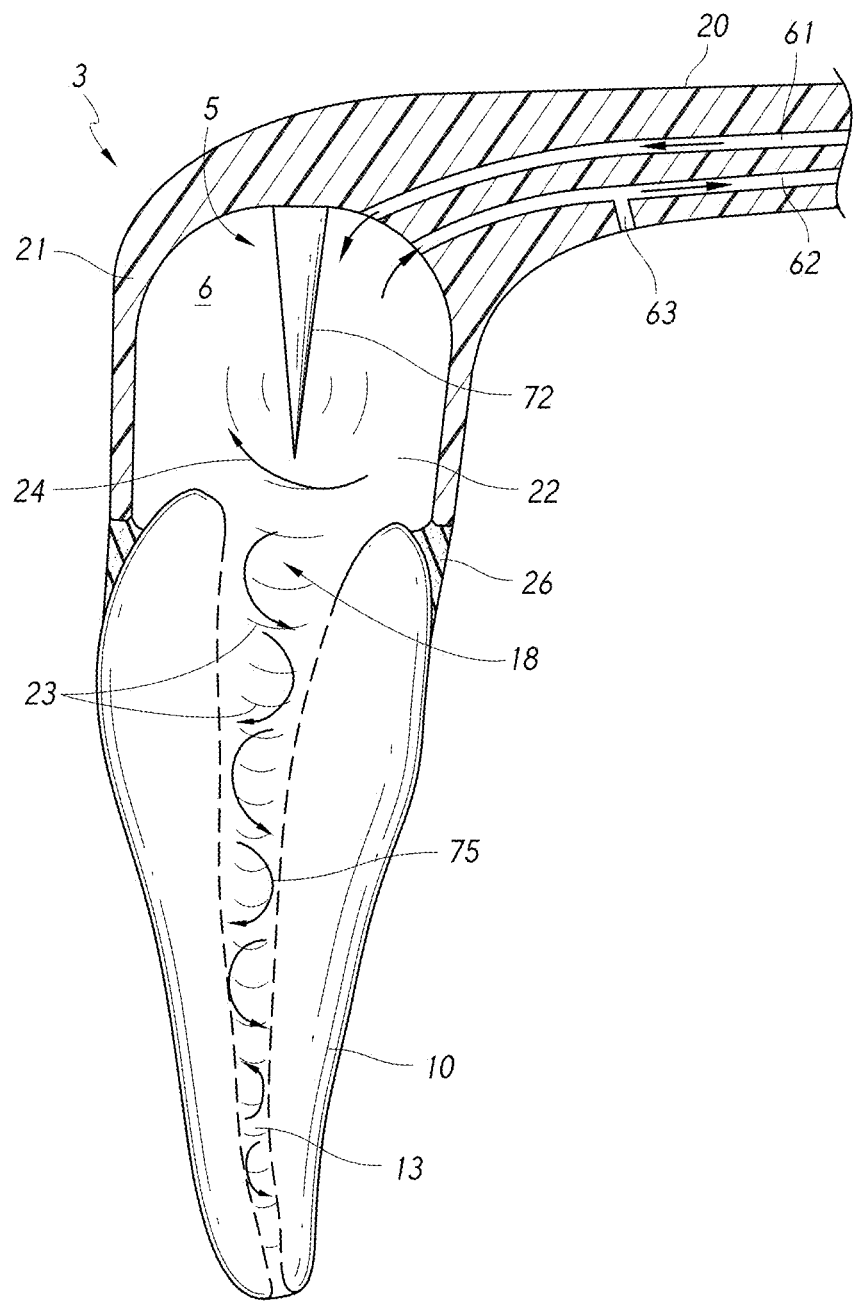
FIG. 9C is a schematic side cross-sectional view of a coupling member and a pressure wave generator comprising a vibrating mechanical element.

FIG. 9C is a schematic side cross-sectional view of a coupling member 3 and a pressure wave generator 5 comprising a vibrating mechanical element 72. Unless otherwise noted, the components illustrated in FIG. 9C are similar to or the same as similarly numbered components in FIGS. 9A-9B. The vibrating mechanical element 72 can comprise a piezoelectric element that vibrates in response to an applied electrical signal. As with the pressure wave generators 5 disclosed herein, the vibrating mechanical element 72 can be disposed in the chamber 6. When activated, the vibrating mechanical element 72 can propagate pressure waves 23 through the fluid 22 and tooth 10 and can induce fluid motion 24 in the chamber 6. The pressure wave generator 5 of FIG. 9C can therefor act to clean and/or fill the tooth 10, as explained herein.

Figure 9D:
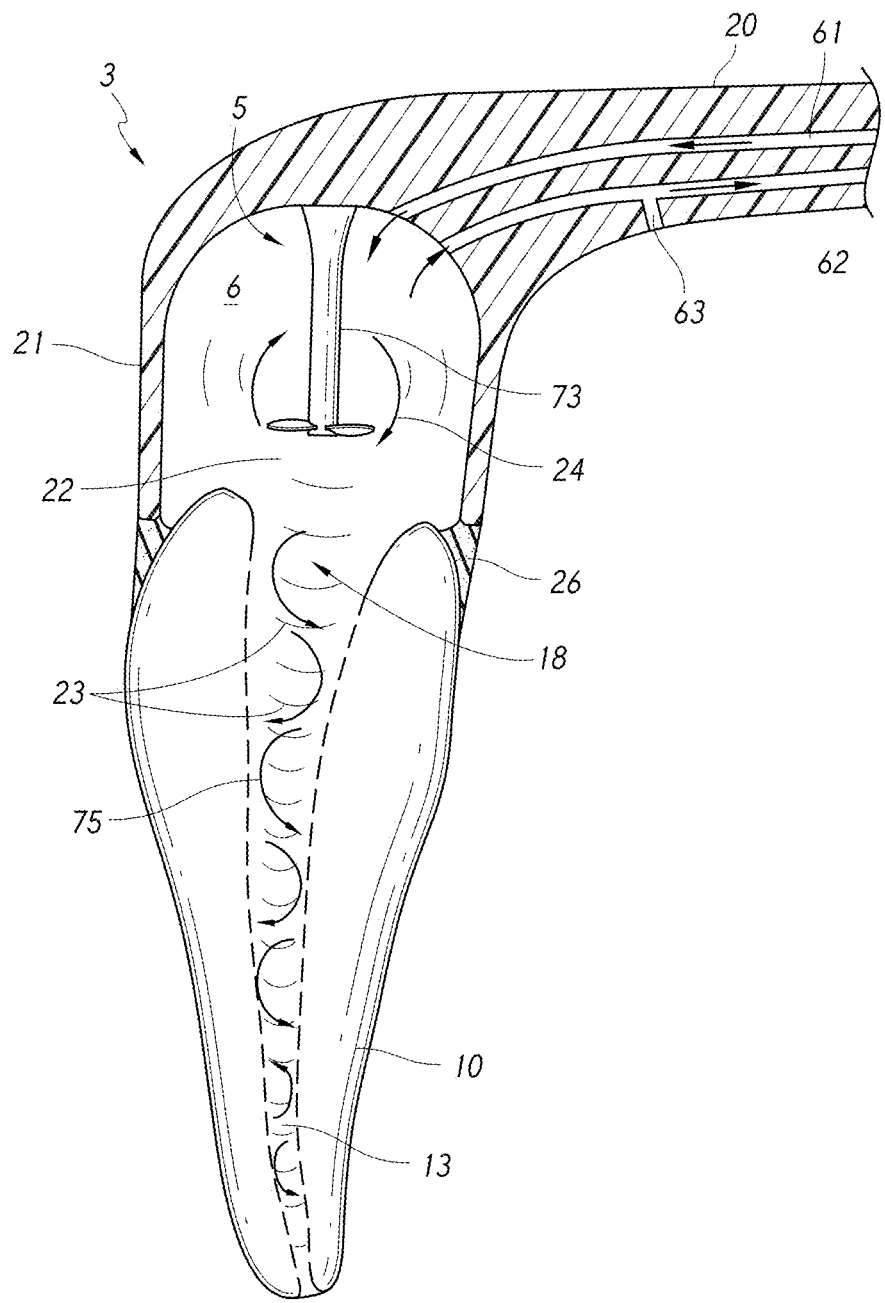
FIG. 9D is a schematic side cross-sectional view of a coupling member 3 and a pressure wave generator comprising a stifling element.

FIG. 9D is a schematic side cross-sectional view of a coupling member 3 and a pressure wave generator 5 comprising a stirring element 73. Unless otherwise noted, the components illustrated in FIG. 9D are similar to or the same as similarly numbered components in FIGS. 9A-9C. The stirring element 73 can comprise a rotational drive axis and a propeller coupled to the drive axis. When rotated, the drive axis can rotate the propeller of the stifling element 73 to generate pressure waves 23 and/or fluid motion 24 in the chamber 6 and/or tooth 10 to clean and/or fill the tooth 10.

Figure 10A:
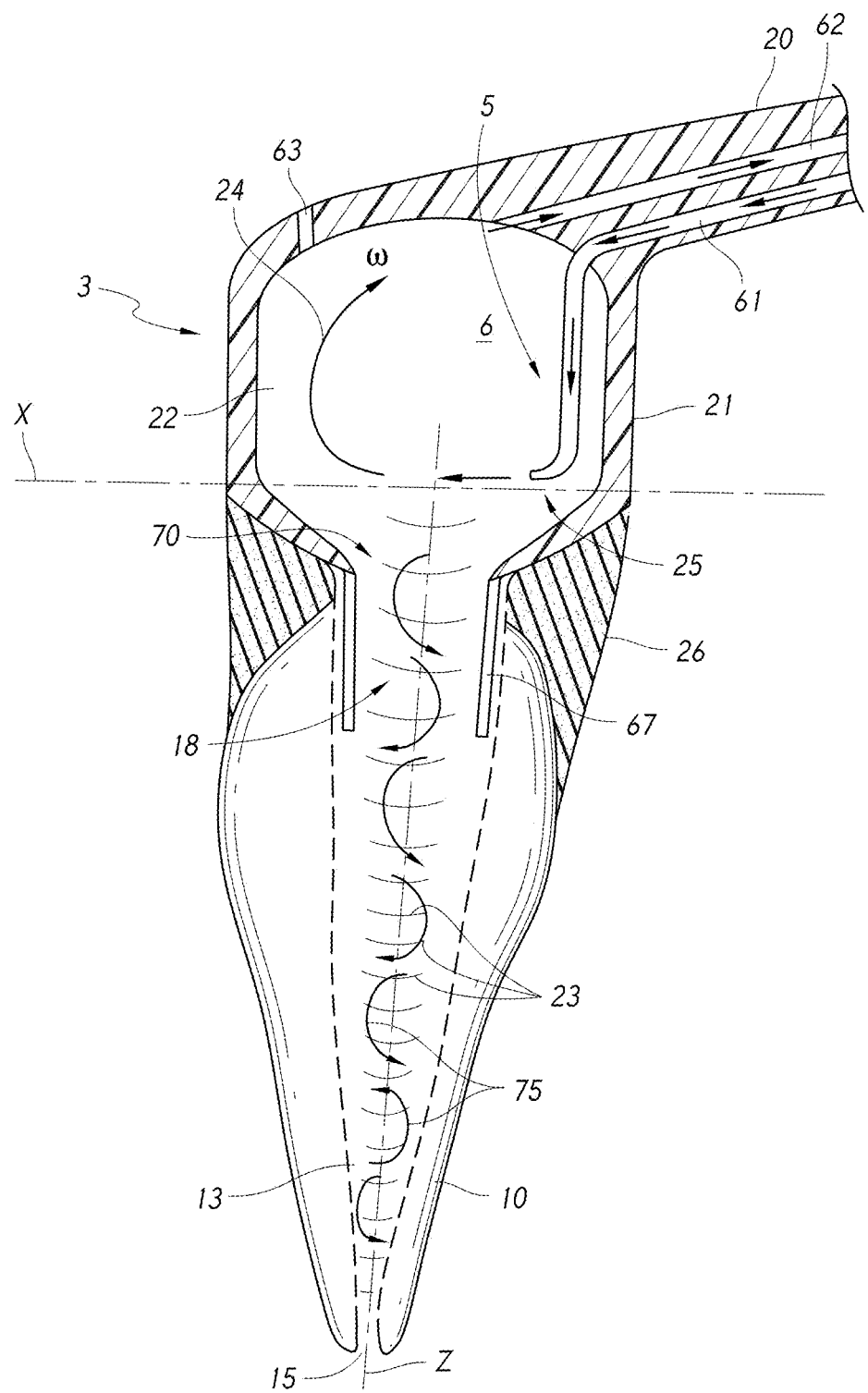
FIG. 10A is a side cross-sectional view of a coupling member having a pressure wave generator comprising a fluid inlet configured to generate a rotational fluid motion in a chamber of a coupling member.

FIG. 10A is a side cross-sectional view of a coupling member 3 having a pressure wave generator 5 configured to generate a fluid motion 24 in a chamber 6 of the coupling member 3 and/or pressure waves 23 in the fluid 22. As above, the coupling member 3 can be formed with or coupled to a distal end portion 21 of a handpiece 20. In the embodiment of FIG. 10A, the coupling member 3 is coupled to the tooth 10 by way of a tooth seal 26. A mating tube 67 can be used to align and/or secure the positioning member 3 to the tooth 10. The mating tube 67 can extend about and define an access aperture or port 70 of the coupling member 3 that provides fluid communication between the chamber 6 and the tooth 10. As shown in FIG. 10A, the root canal 13 can have a central axis Z extending along a major length or dimension of the root canal 13. The mating tube 67 can prevent the coupling member 3 from translating in a direction X transverse to the central axis Z.

In the embodiment of FIG. 10A, the pressure wave generator 5 can be disposed in the chamber 6, which can be outside the tooth 10. The pressure wave generator 5 can be positioned offset from a central region of the coupling member 3, e.g., positioned along a wall of the coupling member 3. As shown in FIG. 10A, the pressure wave generator 5 can comprise a fluid inlet 61 configured to supply a fluid 22 to the chamber 6 of the coupling member 3. For example, in some embodiments, the fluid inlet 61 can be configured to supply a treatment fluid. In embodiments using a treatment fluid, the pressure wave generator 5 can be configured to clean the tooth. As explained herein, the pressure wave generator 5 can enhance the effects of the treatment fluid to clean both larger canal spaces and smaller cracks and crevices of the tooth. The pressure wave generator 5 can be activated to generate a broad spectrum of acoustic frequencies to clean different types of material from differently-sized spaces of the tooth 10.

In other embodiments, the fluid inlet 61 can be configured to supply a flowable obturation material. As explained above, in these embodiments, the pressure wave generator can supply the flowable obturation material in a flowable state and can propagate the flowable obturation material throughout the root canal, e.g., through both the larger root canal space and smaller cracks, spaces, crevices, tubules, etc. of the tooth. By filling substantially the entire root canal system, the pressure wave generator 5 can prevent infection or other negative patient outcomes by preventing the growth of bacteria in unfilled or unobturated spaces.

The fluid inlet 61 can be in fluid communication with the console 2, and a controller can control the flow of flowable material 22 through the inlet 61. As explained herein, the controller can supply the fluid 22 (e.g., the treatment fluid or a flowable obturation material) through the inlet 61 at various frequencies during a treatment phase of the procedure. In some embodiments, the chamber 6 can be filled or substantially filled with a flowable material 22, such as a treatment fluid or an obturation material, and the pressure wave generator 5 can be activated once the chamber 6 is filled with the flowable material 22 at a desired level and/or can be activated to substantially fill the chamber 6.

As shown in FIG. 10A, the fluid inlet 61 can supply the fluid 22 into the chamber 6 to introduce fluid motion 24 in the chamber. As shown in FIG. 10A, for example, the fluid motion 24 comprises a rotational flow of fluid in the chamber 6. The fluid motion 24 can define a rotational flow path or field substantially about an axis transverse to the central axis Z of the root canal 13 (e.g. the fluid flows in a direction w about axes transverse to the central axis Z).

For example, one way to induce the fluid motion 24 illustrated in FIG. 10A is to position a distal end portion 25 of the pressure wave generator 5 adjacent to the access port 70 of the coupling member 3. As explained herein, the pressure wave generator 5 can act as a fluid motion generator to generate fluid motion 24 in the chamber 6. The distal end portion 25 of the fluid inlet 61 can direct a stream or beam of fluid across the access opening 18 of the tooth 10 (and/or across the access port 70 of the coupling member 3 and chamber 6) along an X direction transverse to the central axis Z of the root canal 13. For example, in some embodiments, the fluid inlet 61 can direct a stream of fluid 22 along a direction that is substantially perpendicular to the central axis Z of the root canal 13, e.g., in a direction that is more or less orthogonal to a major axis of the canal 13. Furthermore, the fluid (e.g., the momentum of the fluid stream) can be directed along and/or substantially parallel to a plane near the proximal-most end of the access port 70 to induce the fluid motion 24 shown in FIG. 10A. The fluid flow 24 across the access port 70 can be varied to control a desired apical pressure near the apex of the tooth 10. For example, the momentum of the fluid motion 24 can be controllably adjusted by way of the system controller 51. Further, the angle relative to the central axis Z can also be adjusted to control apical pressure. Indeed, the parameters of the pressure wave generator 5 can be adjusted to increase, decrease, and/or maintain the apical pressure to improve patient outcomes.

The motion 24 of the fluid 22 in the chamber 6 across the port 70 (which may induce flow in the rotational direction w shown in FIG. 10A) can induce vortices 75 throughout the root canal 13. For example, shear forces in the fluid 22 induced by the rotational flow 24 can generate vortices 75 that rotate or circulate in opposite directions (e.g., clockwise and counterclockwise as shown in FIG. 10A). For example, in some arrangements, stronger vortices 75 may be created near the access port 70, and weaker vortices 75 may be created nearer the apical opening 15. In some embodiments, the vortices 75 may gradually weaken along the length of the canal from a point near the access port 70 to the apical opening 15. The weaker vortices 75 nearer the apical opening 15 may help to prevent or reduce the risk of extrusion of material through the apex of the tooth, which can lead to safer treatment procedures. The vortices 75 can be adjusted by controlling the parameters of the pressure wave generator 5 and the fluid motion 24 generated by the pressure wave generator 5. In some embodiments, the vortices 75 can be steady in size, shape, and/or direction. In other embodiments, the vortices 75 can be unsteady or chaotic.

Furthermore, the alternating directions of the vortices along the root canal 13 can advantageously create a negative pressure (or low positive pressure) near the apical opening 15 of the tooth 10. For example, the vortices 75, which also rotate about axes transverse to the central axis Z of the root canal 13, may cause micro-flows upwards towards the access opening 18 such that fluid 22 tends to experience a slightly negative pressure (e.g., a slight tendency to flow upwards through the canal 13 towards the access opening 18) near the apical opening 15. As explained below with respect to FIGS. 14A-14C, the negative pressure near the apical opening 15 can prevent material in the tooth 10 from extruding out through the apical opening 15. In other treatments, for example, the pressure near the apical opening 15 can be positive such that material is pushed out, or extruded, through the apical opening 15 and into the jaw of the patient. Such extrusion can lead to undesirable patient outcomes such as infection, high levels of pain, etc.

In some embodiments, it can be advantageous to dispose the pressure wave generator 5 within the chamber 6 and to use a coupling member 3 with an access port 70 as large as possible. By increasing the diameter or major dimension of the access port 70, more energy can be directed into the tooth 10, which can enhance the tooth cleaning procedure. Increasing the diameter or major dimension can also enhance the obturation procedure when used in such embodiments. In some embodiments, for example, the mating tube 67 may not be used so as to increase the size of the access port 70 by about twice a thickness of the walls of the mating tube 67. Accordingly, in various embodiments, the access port 70 of the coupling member 3 can be at least as large as a diameter or major dimension of the access opening 18 formed in the tooth 10. In some embodiments, for example, the access port 70 can be about the same size as the access opening 18 formed in the tooth 10.

As above, the pressure wave generator 5 can also be configured to generate pressure waves 23 through the fluid 22 and the tooth 10. As explained herein, in cleaning treatments, a combination of the pressure waves 23, fluid motion 24, and chemistry of the treatment fluid can act to substantially remove unhealthy materials from the tooth 10, including in small spaces, cracks, and crevices of the tooth 10. Waste fluid and detached materials can be removed from the tooth 10 and/or the chamber 6 by way of a fluid outlet 62. As explained above, one or more vents 63 can be provided through the coupling member 3 to regulate the pressure in the chamber 6. In filling or obturation procedures, the pressure waves 23, fluid motion 24, and chemistry of the obturation material can act to substantially fill the entire root canal system.

Figure 10B:
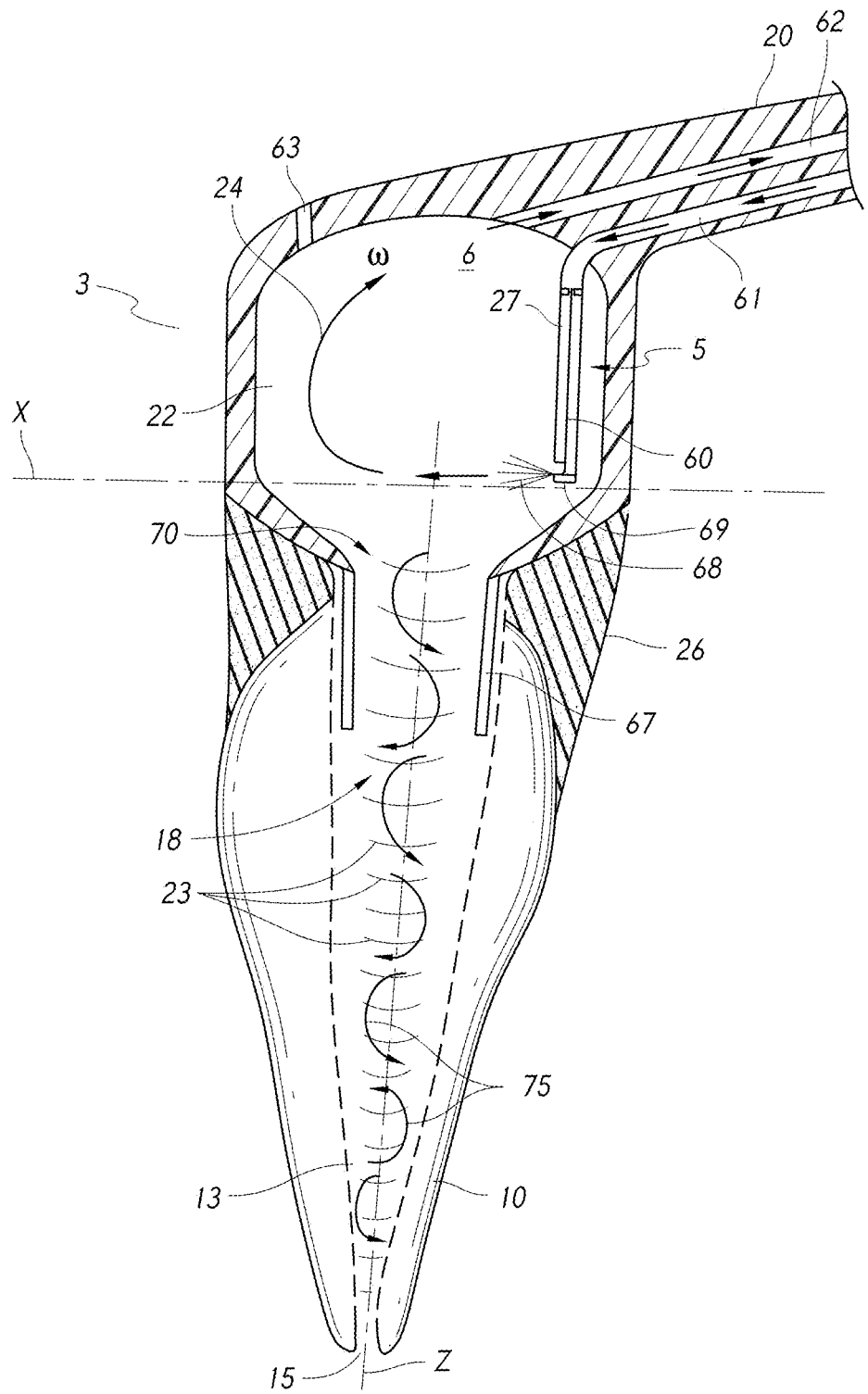
FIG. 10B is a side cross-sectional view of a coupling member having a pressure wave generator comprising a liquid jet device configured to generate a rotational fluid motion in a chamber of the coupling member.

FIG. 10B is a side cross-sectional view of a coupling member 3 having a pressure wave generator 5 comprising a liquid jet device configured to generate a fluid motion 24 in a chamber 6 of the coupling member 3. Unless otherwise noted, the components illustrated in FIG. 10B are similar to or the same as similarly numbered components in FIGS. 9A and 10A. As with the pressure wave generator 5 of FIG. 10A, the liquid jet device can be disposed along a wall of the coupling member 3. The liquid jet device can include a guide tube 27 along which the jet 60 propagates. The guide tube 27 can include one or more openings that permit fluid communication between the jet 60 and the fluid 22 in the chamber 6. In some embodiments, the fluid 22 may be supplied by an inlet other than the jet 60. In other embodiments, the jet 60 can comprise the fluid 22 and can supply the fluid 22 to the chamber 6. In some embodiments, the chamber 6 can be filled or substantially filled with the fluid 22.

The pressure wave generator 5 can be activated, and the jet 60 can impact the impingement member 69, which can deflect the jet 60 into a spray 69. For example, the spray 69 can generate fluid motion 24 across the access port 70, as explained above with respect to FIG. 10A. The liquid jet device can induce fluid motion 24 in the chamber, e.g., in a rotational direction w about an axis transverse to a central axis Z of the root canal. For example, the spray 68 can induce a stream of fluid passing across an access aperture 70 of the coupling member 3, e.g., along a direction X transverse to (e.g., substantially perpendicular to) the central axis Z of the root canal 13 and/or a central axis of the chamber. The spray 69 can induce fluid flow 24 in a direction parallel to a plane of the access port 70, e.g., a proximal-most plane of the access port that defines an opening between the chamber 6 and the tooth. The fluid flow 24 can induce opposing vortices 75 throughout the root canal 13. The fluid motion 24 induced in the tooth 10 (possibly in combination with pressure waves 23) can act to remove unhealthy materials from the tooth 10. Furthermore, as explained above with respect to FIG. 10A, the induced vortices 75 can create a negative pressure at or near the apical opening 15, which can advantageously prevent the extrusion of material through the apical opening 15. In addition, as with FIG. 10A, the diameter of the access port 70 of the coupling member 3 can be at least as large as the access opening 18 formed in the tooth 10, e.g., about the same size as the access opening 18. Furthermore, in obturation treatments, the pressure wave generator 5 of FIG. 10B can act to substantially fill the entire root canal system.

Figure 10C:
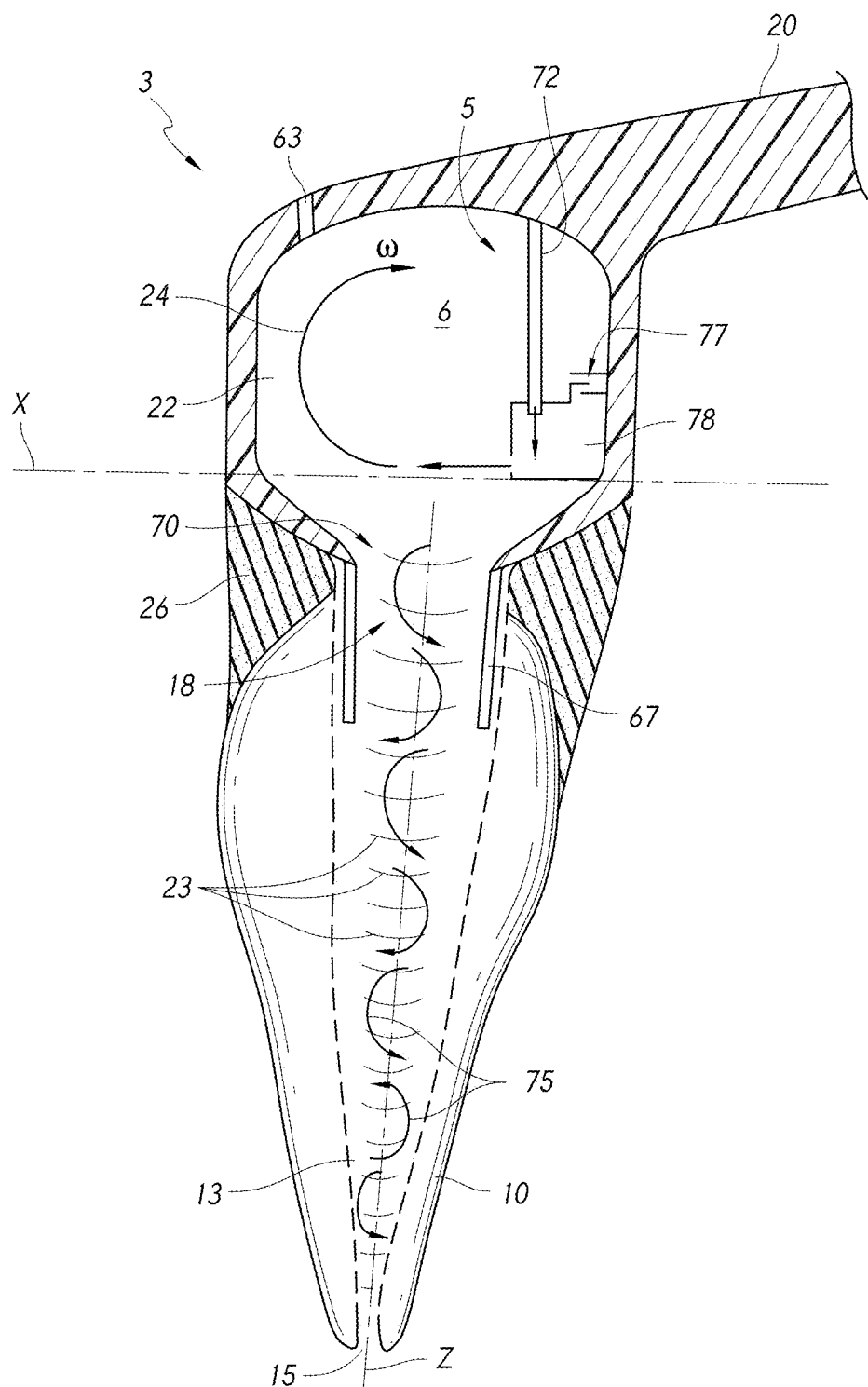
FIG. 10C is a side cross-sectional view of a coupling member having a pressure wave generator comprising a light emitting device configured to generate a rotational fluid motion in a chamber of the coupling member.

FIG. 10C is a side cross-sectional view of a coupling member 3 having a pressure wave generator 5 comprising a light emitting element 72 configured to generate a fluid motion 24 in a chamber 6 of the coupling member 3. Unless otherwise noted, the components illustrated in FIG. 10C are similar to or the same as similarly numbered components in FIGS. 9B and 10A-10B. As with the embodiment of FIG. 9B, the pressure wave generator 5 can comprise a laser or other light source. The light emitting element 72 can propagate high intensity light onto a localized reservoir 78 of fluid 22, such as a treatment fluid, an obturation material, etc. For example, a gate 77 can selectively permit fluid 22 to flow from the chamber 6 into the localized reservoir 78. The light propagating from the light emitting element 72 can impinge upon the fluid 22 in the reservoir 78 and can locally heat the fluid 22 in the reservoir 78. Heating the fluid 22 in the reservoir 78 to a sufficient degree may cause the fluid 22 to move out of the reservoir along a direction X transverse to a central axis Z of the root canal 13 of the tooth 10. For example the fluid 22 can move out of the reservoir 78 substantially perpendicular to the central axis Z of the root canal and/or in a direction substantially parallel to a proximal-most plane of the access port 70.

As with the embodiments disclosed above with respect to FIGS. 10A-10B, the flow of flowable material 22 from the reservoir 78 can induce a rotational fluid flow 24 about a rotational direction w. The rotational flow 24 can induce vortices 75 throughout the root canal 13 that can induce negative pressures at or near the apical opening 15 of the tooth 10. Furthermore, a diameter of the access port 70 can be at least as large as the access opening 18 in some embodiments. As above, in cleaning procedures, the fluid motion 24 and the pressure waves 23 can act to substantially clean the tooth 10. In obturation procedures, the pressure wave generator 5 can act to substantially fill the entire root canal system.

Figure 10D:
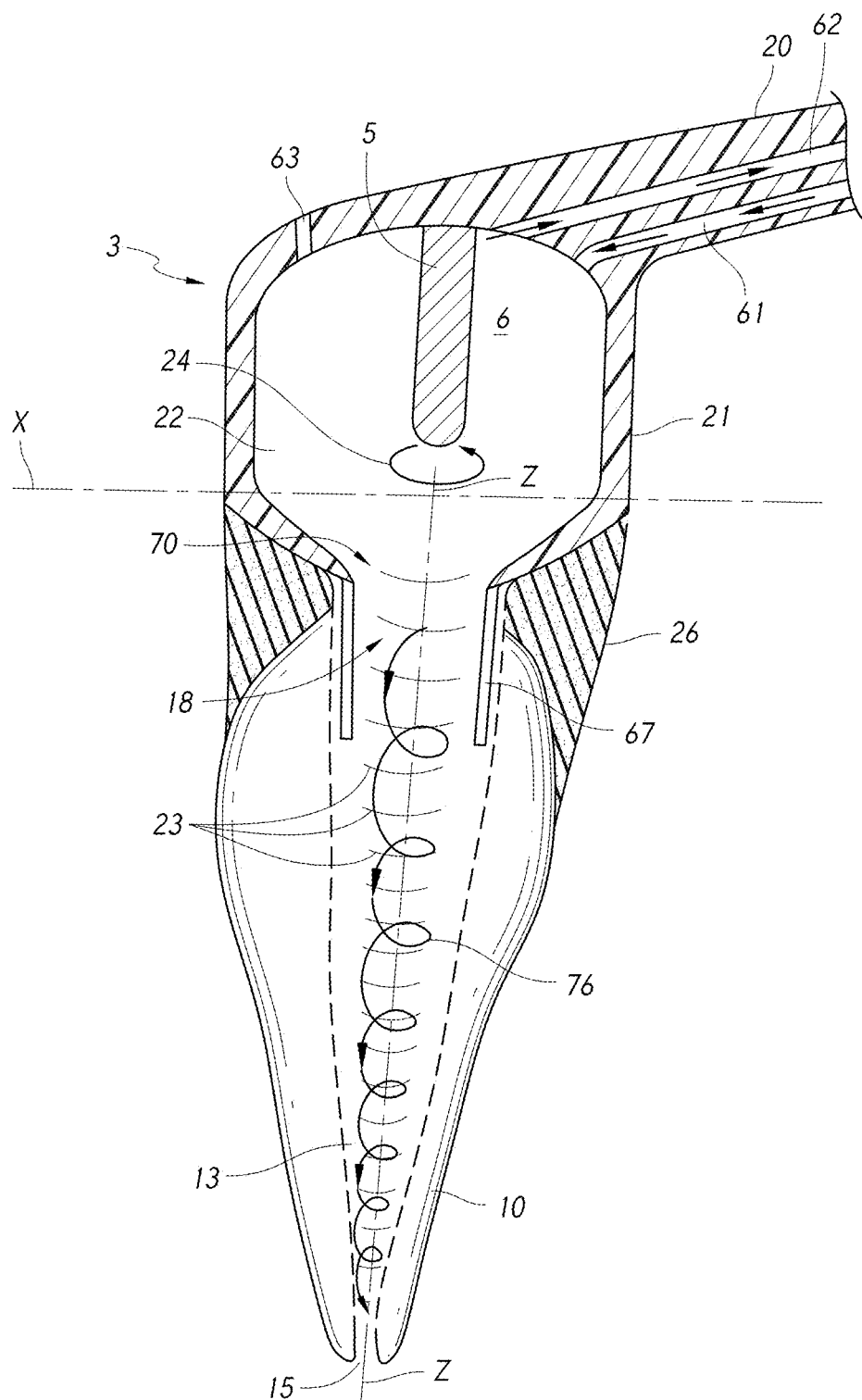
FIG. 10D is a side cross-sectional view of a coupling member having a pressure wave generator substantially aligned with a central axis Z of the root canal.

FIG. 10D is a side cross-sectional view of a coupling member 3 having a pressure wave generator 5 substantially aligned with a central axis Z of the root canal 13. The pressure wave generator 5 of FIG. 10D can be a nozzle configured to output a fluid 22 into the chamber 6, or any of the other pressure wave generators disclosed herein. Unless otherwise noted, the components illustrated in FIG. 10D are similar to or the same as similarly numbered components in FIGS. 10A-10C. The pressure wave generator 5 can be any suitable pressure wave generator disclosed herein, such as a liquid jet device, a fluid inlet, a light emitting element, etc. Unlike the embodiments of FIGS. 10A-10C, which may be offset from the Z-axis, the pressure wave generator 5 of FIG. 10D is generally aligned with the Z-axis.

Furthermore, unlike the embodiments of FIGS. 10A-10C, the pressure wave generator 5 of FIG. 10D can be configured to generate a fluid motion 24 of flowable material 22 about the Z-axis. The fluid motion 24 substantially around the Z-axis can generate a swirl 76 of fluid, which can propagate through the root canal 23. Similar to the embodiments above, the rotational power of the fluid motion 24 can be adjusted to control the amount of swirl 76 to assist with the treatment procedure. As above, in cleaning treatments, the pressure wave generator 5 can clean substantially the entire root canal 13. In obturation treatments, the pressure wave generator 5 can fill or obturate substantially the entire root canal 13, including branch structures, as explained in more detail herein.

Figure 10E:
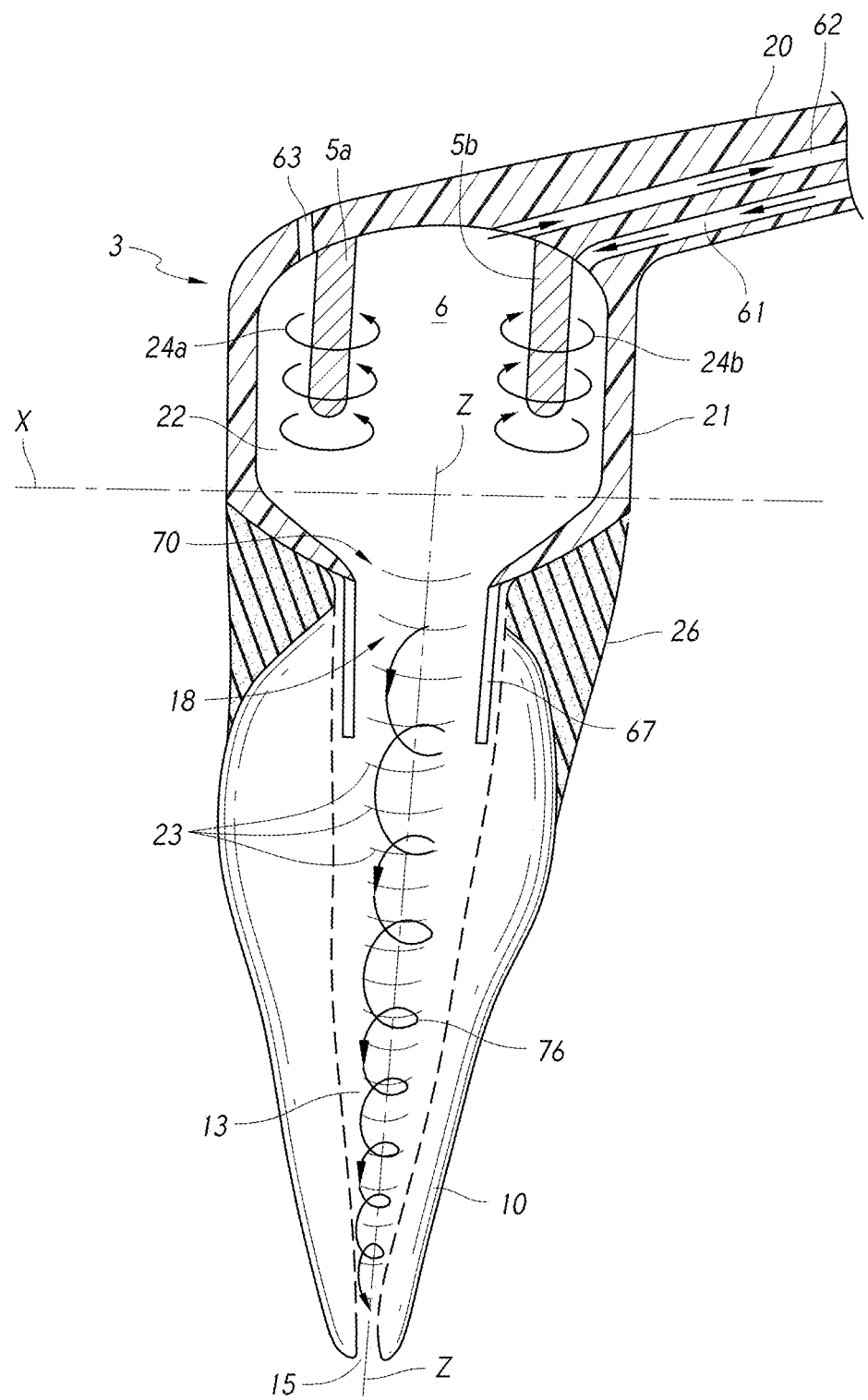
FIG. 10E is a side cross-sectional view of a coupling member having a first pressure wave generator and a second pressure wave generator.

FIG. 10E is a side cross-sectional view of a coupling member 3 having a first pressure wave generator 5a and a second pressure wave generator 5b. Unless otherwise noted, the components illustrated in FIG. 10E are similar to or the same as similarly numbered components in FIG. 10D. However, unlike the embodiment of FIG. 10D, the two pressure wave generators 5a, 5b can be disposed offset from the central axis Z. In the illustrated embodiment, the pressure wave generators 5a, 5b can be disposed eccentrically with respect to the Z-axis (e.g., a central axis of the root canal and/or a central axis of the chamber 6), e.g., the pressure wave generators 5a, 5b can be at about the same distance from the Z-axis. Like the embodiment of FIG. 10D, each pressure wave generator can generate a corresponding fluid motion 24 about the direction of the Z-axis, but the rotation is offset from the Z-axis, as shown in FIG. 10E. Furthermore, in the illustrated embodiment, the pressure wave generator 5a can generate fluid motion 24a about the Z-axis in one direction, and the pressure wave generator 5b can generate fluid motion 24b about the Z-axis direction in an opposite direction. The counter-flows induced by the two pressure wave generators 24a, 24b can cooperate to induce swirl 76 that propagate through the root canal 13. As explained above, the induced swirl 76 and pressure waves 23 can clean substantially the entire root canal 13 in cleaning treatments. In obturation treatments, the induced vortices and pressure waves 23 can fill or obturate substantially the entire root canal system.

Figure 10F:
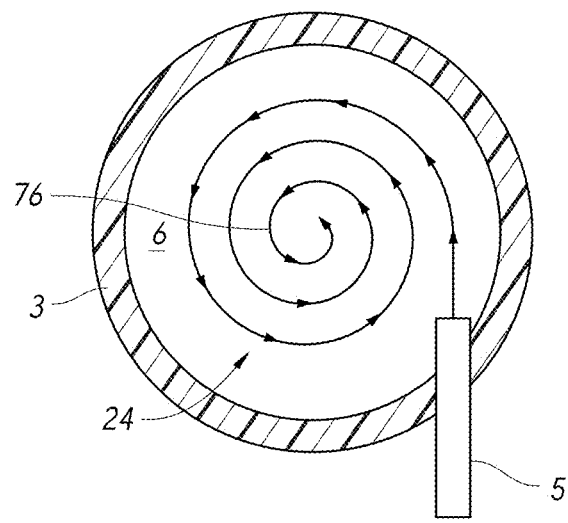
FIG. 10F is a schematic top view of a pressure wave generator at least partially disposed in a chamber and configured to generate swirl in the chamber.

FIG. 10F is a schematic top view of fluid motion generator 5 at least partially disposed in a chamber 6 and configured to generate swirl 76 in the chamber 6. The fluid motion generator 5 of FIG. 10F can comprise a nozzle or outlet configured to supply fluid 23 into the chamber 6. In the embodiment of FIG. 10F, the central Z-axis of the root canal is coming out of the page. As shown in FIG. 10F, the fluid motion generator 5 can direct fluid motion 24 in a direction transverse (e.g., substantially perpendicular to) the major axis of the root canal, e.g., across the access port 70. The fluid motion 24 can impact walls of the chamber 6 and can shear inwardly to create the swirl motion 76. As explained above, the swirl 76 can propagate through the root canal 13 to clean and/or fill the root canal 13. The fluid motion generator 5 can be disposed anywhere along the height of the chamber 6. Furthermore, as explained herein, the fluid motion generator 5 may also comprise a liquid jet, fluid inlet, etc.

Figure 10G:
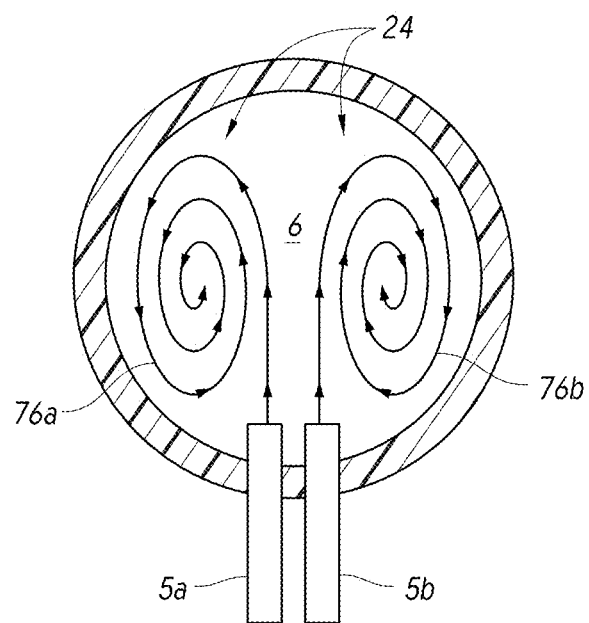
FIG. 10G is a schematic top view of multiple pressure wave generators at least partially disposed in a chamber and configured to generate counter-swirl fluid motion in the chamber.

FIG. 10G is a schematic top view of multiple fluid motion generators 5a, 5b at least partially disposed in a chamber 6 and configured to generate counter-swirl fluid motion 76a, 76b in the chamber 6. As shown in FIG. 10G, for example, the fluid motion generators can be disposed eccentrically relative to the central axis Z of the root canal and/or the central axis of the chamber 6 (e.g., out of the page). Each fluid motion generator 5a, 5b can propagate fluid motion 24 across the access port 70 in a direction transverse to (e.g., substantially perpendicular to) the central axis Z. Each counter-swirl 76a, 76b can rotate in opposing directions about the Z-axis of the root canal and can interact with one another to generate swirl 76 throughout the root canal to clean and/or fill the canals.

VII. Additional Details Regarding Enhanced Cleaning of Teeth

It is believed, although not required, that some or all of the effects described herein may be at least in part responsible for advantageous effects, benefits, or results provided by various implementations of the treatment methods and systems described herein. Accordingly, various embodiments of the systems disclosed herein can be configured to provide some or all of these effects.

In the following description, unless a different meaning is indicated, the following terms have their ordinary and customary meaning. For example, a chemical reaction front may generally refer to an interface between the tissue and the solution which contains a chemical such as a tissue dissolving agent. Tissue may refer to all types of cells existing in the tooth as well as bacteria and viruses. Calcified tissue may refer to calcified pulp, pulp stones, and tertiary dentin. Bubbles includes but is not limited to bubbles created due to a chemical reaction, dissolved gas remaining in the fluid after degassing (if used) and released as bubbles in the fluid, and any bubbles which are introduced into the tooth due to imperfect sealing.

Tissue cleaning treatments may utilize one or more of the physicochemical effects described herein to clean and remove tissue and/or calcified tissue from a tooth chamber. In some cleaning treatments, the combination of (1) acoustic or pressure waves (e.g., generation of acoustic cavitation), (2) circulation of fluid in the chamber (e.g., macroscopic eddies and flows), and (3) chemistry (e.g., use of a tissue dissolving agent, use of degassed fluids) can provide highly effective cleaning. Accordingly, certain embodiments of the systems disclosed herein utilize a pressure wave generator to generate the acoustic waves, a fluid platform (e.g., fluid retainer) to retain treatment fluid in the tooth chamber and to enable circulation of the treatment fluid, and a treatment fluid that is degassed or includes a chemical agent such as a tissue dissolving agent.

A. Pressure Waves

A pressure wave generator can be used to generate pressure waves that propagate through the fluid in the chamber 6 (and the tooth). Upon irradiation of a fluid with high intensity pressure waves (e.g., broadband frequencies), acoustic cavitation may occur. As has been described herein, the implosive collapse of the cavitation bubbles can produce intense local heating and high pressures with short lifetimes. Therefore, in some treatment methods, acoustic cavitation may be responsible for or involved in enhancing chemical reactions, sonochemistry, sonoporation, tissue dissociation, tissue delamination, as well as removing the bacteria and/or the smear layer from the root canals and tubules. The effects of enhancing chemical reaction via vibrations or sonochemistry will be described below in the section on chemistry.

Sonoporation is the process of using an acoustic field to modify the permeability of the cell plasma membrane. This process may greatly expedite the chemical reaction. It may be advantageous if the acoustic field has a relatively broad bandwidth (e.g., from hundreds to thousands of kHz). Some frequencies (e.g., low frequency ultrasound) may also result in cellular rupture and death (e.g., lysis). This phenomenon may kill bacteria which might otherwise reinfect the tooth. Acoustic waves and/or acoustic cavitation may loosen the bond between cells and/or may dissociate the cells. Acoustic waves and/or acoustic cavitation may loosen the bond between cells and dentin and/or delaminate the tissue from the dentin.

For removing calcified tissue, acoustic waves may induce sonochemistry and microscopic removal of calcified structures due to shock waves and/or microjets created as a result of cavitation bubble implosion. Pressure or acoustic waves may break microscopic calcified structures through structural vibrations. If a chemical (e.g., a chelating agent such as, e.g., EDTA) is used for this procedure, the acoustic waves may enhance the chemical reaction.

Certain properties of the system can be adjusted to enhance the effects of the acoustic waves. For example, properties of the fluid including, e.g., surface tension, boiling or vapor temperature, or saturation pressure can be adjusted. A degassed fluid with a reduced dissolved gas content can be used, which may reduce the energy loss of acoustic waves that may be generated by hydrodynamic cavitation or any other sources. The fluid can be degassed, which may help preserve the energy of the acoustic waves and may increase the efficiency of the system.

B. Fluid Circulation

Some treatment systems and methods use diffusion and/or acoustically enhanced diffusion of reactants and byproducts to and away from the chemical reaction front. However, due to the relatively short time scale of the reaction process, a faster mechanism of reactant delivery such as "macroscopic" fluid motion, circulation, convection, vorticity, or turbulence may be advantageous in some of the embodiments disclosed herein. For example, fluid inflow into the tooth chamber may induce a macroscopic circulation in the pulp cavity (see, e.g., FIGS. 1A and 10A-10C). A liquid jet device not only may create acoustic waves but may also induce circulation as the jet and/or spray enter the chamber 6. Other pressure wave generators can produce fluid circulation via their interaction with ambient fluid (e.g., via localized heating of the fluid, which may induce convection currents and circulation).

Fluid circulation with a time scale comparable to (and preferably faster than) that of chemical reaction may help replenish the reactants at a chemical reaction front and/or may help to remove reaction byproducts from the reaction site. The convective time scale, which may relate to effectiveness of the convection or circulation process, can be adjusted depending on, e.g., the location and characteristics of the source of circulation. The convective time scale is approximately the physical size of the chamber divided by the fluid speed in the chamber. Introduction of circulation generally does not eliminate the diffusion process, which may still remain effective within a thin microscopic layer at the chemical reaction front. Fluid circulation may create flow-induced pressure oscillations inside the root canal which may assist in delaminating, loosening, and/or removing larger pieces tissue from the root canal.

For removing calcified tissue, fluid circulation may create flow-induced pressure oscillations inside the root canal which may assist in removing larger pieces of calcified structures from the root canal.

Certain properties of the system can be adjusted to enhance the effects of the circulation in the tooth. For example, the location of the source of circulation inside the tooth, the source flow characteristics such as shape (e.g. planar vs. circular jets) or velocity and/or direction of a fluid stream, and the fluid kinematic viscosity may be adjusted. The circulation may also be effected by the anatomy of the tooth or the canal orifice or root canal size. For example, a narrow root canal with constrictions may have a lower solution replenishment rate than a wide canal with no constrictions. If the source of convection/circulation is placed near the pulp chamber floor, a tooth with a smaller pulp chamber may have stronger circulation than one with a larger pulp chamber. Convection-induced pressure exerted at the periapical region of the tooth may be controlled to reduce or avoid extrusion of the treatment fluid into the periapical tissues. Large magnitude vacuum or low pressure in the tooth may cause discomfort in some patients. Thus, the properties of the coupling member 3 (e.g., vents, sponges, flow restrictors, etc.) can be adjusted to provide a desired operating pressure range in the chamber 6 and/or tooth 10.

C. Chemistry

As explained herein, various reaction chemistries can be adjusted or designed to improve the cleaning process. For example, to enhance the dissolution of organic tissue, a tissue dissolving agent (e.g., a mineralization therapy agent, EDTA, sodium hypochlorite—NaOCl) can be added to the treatment liquid. The agent may react with various components at the treatment site. In some cases, tissue dissolution may be a multi-step process. The agent may dissolve, weaken, delaminate or dissociate organic and/or inorganic matter, which may result in better patient outcomes. The chemical reaction can modify the physical characteristics of the treatment solution locally (e.g., reducing the local surface tension via saponification), which may assist in the penetration of the treatment liquid into gaps and small spaces in the treatment sites or to remove bubbles formed during the chemical reaction. A tissue dissolving agent (e.g., sodium hypochlorite or bleach) may be added to the treatment fluid to react with tissue. Tissue dissolution may be a multi-step and complex process. Dissolution of sodium hypochlorite in water can include a number of reactions such as, e.g., the sodium hypochlorite (bleach) reaction, a saponification reaction with triglycerides, an amino acid neutralization reaction, and/or a chloramination reaction to produce chloramine. Sodium hypochlorite and its by-products may act as dissolving agents (e.g. solvents) of organics, fats, and proteins; thereby, degrading organic tissue in some treatments.

Sodium hypochlorite may exhibit a reversible chemical equilibrium based on the bleach reaction. Chemical reactions may occur between organic tissue and sodium hypochlorite. For example, sodium hydroxide can be generated from the sodium hypochlorite reaction and can react with organic and fat (triglycerides) molecules to produce soap (fatty acid salts) and glycerol (alcohol) in the saponification reaction. This may reduce the surface tension of the remaining solution. Sodium hydroxide can neutralize amino acids forming amino acid salts and water in the amino acid neutralization reaction. Consumption of sodium hydroxide can reduce the pH of the remaining solution. Hypochlorous acid, a substance that can be present in sodium hypochlorite solution, can release chlorine that can react with amino groups of proteins and amino acids to produce various chloramines derivatives. For example, hypochlorous acid can react with free amino acids in tissue to form N-chloro amino acids which can act as strong oxidizing agents that may have higher antiseptic activity than hypochlorite.

Chemical(s) in the fluid, depending on their type, may affect the surface tension of the solution, which in turn may modify the cavitation phenomenon. For example, solution of an inorganic chemical such as, e.g., sodium hypochlorite in water, may increase the ion concentration in the solution which may increase the surface tension of the solution, which may result in stronger cavitation. In some cases, the magnitude of a cavitation inception threshold may increase with increasing surface tension, and the cavitation inducing mechanism (e.g., a pressure wave generator) may be sufficiently intense to pass the threshold in order to provide inception of cavitation bubbles. It is believed, but not required, that once the cavitation threshold is passed, increased surface tension may result in stronger cavitation. Reducing the dissolved gas content of a fluid (e.g., via degassing) can increase the surface tension of the fluid and also may result in stronger cavitation. Addition of chemicals, agents, or substances (e.g., hydroxyl functional groups, nanoparticles, etc.) to the treatment may increase the efficiency of conversion of a pressure wave into cavitation, and such chemoacoustic effects may be desirable in some treatment procedures.

In some methods, a chemical, such as sodium hypochlorite, may cause saponification. The removal of bubbles created or trapped inside the root canals (or tubules) may be accelerated due to local reduction of surface tension at the chemical reaction front as a result of saponification. Although in some methods it may be desirable to have a relatively high surface tension at the pressure wave source (e.g. inside the pulp chamber), inside the canals it may be beneficial to have locally reduced surface tension to accelerate bubble removal. This phenomenon may happen as tissue dissolving agent(s) react with the tissue. For example, sodium hypochlorite can act as a solvent degrading fatty acids, transforming them into fatty acid salts (soap) and glycerol (alcohol) that can reduce the surface tension of the remaining solution at the chemical reaction front.

A number of variables or factors may be adjusted to provide effective cleaning. For example, each chemical reaction has a reaction rate determining the speed of reaction. The reaction rate may be dependent on several parameters including temperature. The concentration of reactants can be a factor and may affect the time for the reaction to complete. For instance, a 5% sodium hypochlorite solution generally may be more aggressive than a 0.5% sodium hypochlorite solution and may tend to dissolve tissue faster.

The refreshment rate of reactants may be affected by some or all of the following. Bubbles may form and stay at the chemical reaction front (e.g., due to surface tension forces) and may act as barriers at the chemical reaction front impeding or preventing fresh reactants from reaching the reaction front. Accordingly, circulation of the treatment fluid can help remove the bubbles and the reaction byproducts, and may replace them with fresh treatment fluid and fresh reactants. Thus, use of an embodiment of the fluid platform that can provide fluid circulation in the tooth chamber advantageously may improve the cleaning process.

Heat may increase the chemical reaction rate and may be introduced through a variety of sources. For example, the treatment solution may be preheated before delivery to the tooth chamber. Cavitation, exothermic chemical reactions, or other internal or external dissipative sources may produce heat in the fluid, which may enhance, sustain, or increase reaction rates.

Sonication of the fluid may increase chemical reaction rates or effectiveness. For example, upon irradiation of a fluid (e.g., water) with high intensity pressure waves (including, e.g., sonic or ultrasonic waves, or broad spectrum acoustic power produced by a liquid jet) acoustic cavitation may occur. The implosive collapse of the cavitation bubbles can produce intense local heating and high pressures with short lifetimes. Experimental results have shown that at the site of the bubble collapse, the temperature and pressure may reach around 5000 K and 1000 atm, respectively. This phenomenon, known as sonochemistry, can create extreme physical and chemical conditions in otherwise cold liquids. Sonochemistry, in some cases, has been reported to enhance chemical reactivity by as much as a million fold. In cases where acoustic cavitation does not occur (or occurs at a relatively low amplitude), the vibration of reactants, due to the pressure waves, may enhance the chemical reaction as it assists in replacing the byproducts by fresh reactants.

For removing calcified tissue, a decalcifying agent (e.g., an acid such as, e.g., EDTA or citric acid) may be added to the treatment fluid. The decalcifying agent may remove calcium or calcium compounds from the tooth dentin. The substances remaining after treatment with the decalcifying agent may be relatively softer (e.g., gummy) than prior to treatment and more easily removable by the fluid circulation and acoustic waves.

VIII. Degassed Treatment Fluids

As will be described below, the treatment fluid (and/or any of solutions added to the treatment fluid) can be degassed compared to normal liquids used in dental offices. For example, degassed distilled water can be used (with or without the addition of chemical agents or solutes).

A. Examples of Possible Effects of Dissolved Gases in the Treatment Fluid

In some procedures, the treatment fluid can include dissolved gases (e.g., air). For example, the fluids used in dental offices generally have a normal dissolved gas content (e.g., determined from the temperature and pressure of the fluid based on Henry's law). During cleaning procedures using a pressure wave generator, the acoustic field of the pressure wave generator and/or the flow or circulation of fluids in the chamber can cause some of the dissolved gas to come out of solution and form bubbles.

The bubbles can block small passageways or cracks or surface irregularities in the tooth, and such blockages can act as if there were a "vapor lock" in the small passageways. In some such procedures, the presence of bubbles may at least partially block, impede, or redirect propagation of acoustic waves past the bubbles and may at least partially inhibit or prevent cleaning action from reaching, for example, unhealthy dental materials in tubules and small spaces of the tooth 10. The bubbles may block fluid flow or circulation from reaching these difficult-to-reach, or otherwise small, regions, which may prevent or inhibit a treatment solution from reaching these areas of the tooth.

In certain procedures, cavitation is believed to play a role in cleaning the tooth. Without wishing to be bound by any particular theory, the physical process of cavitation inception may be, in some ways, similar to boiling. One possible difference between cavitation and boiling is the thermodynamic paths that precede the formation of the vapor in the fluid. Boiling can occur when the local vapor pressure of the liquid rises above the local ambient pressure in the liquid, and sufficient energy is present to cause the phase change from liquid to a gas. It is believed that cavitation inception can occur when the local ambient pressure in the liquid decreases sufficiently below the saturated vapor pressure, which has a value given in part by the tensile strength of the liquid at the local temperature. Therefore, it is believed, although not required, that cavitation inception is not determined by the vapor pressure, but instead by the pressure of the largest nuclei, or by the difference between the vapor pressure and the pressure of the largest nuclei. As such, it is believed that subjecting a fluid to a pressure slightly lower than the vapor pressure generally does not cause cavitation inception. However, the solubility of a gas in a liquid is proportional to pressure; therefore lowering the pressure may tend to cause some of the dissolved gas inside the fluid to be released in the form of gas bubbles that are relatively large compared to the size of bubbles formed at cavitation inception. These relatively large gas bubbles may be misinterpreted as being vapor cavitation bubbles, and their presence in a fluid may have been mistakenly described in certain reports in the literature as being caused by cavitation, when cavitation may not have been present.

In the last stage of collapse of vapor cavitation bubbles, the velocity of the bubble wall may even exceed the speed of sound and create strong shock waves inside the fluid. The vapor cavitation bubble may also contain some amount of gas, which may act as a buffer and slow down the rate of collapse and reduce the intensity of the shockwaves. Therefore, in certain procedures that utilize cavitation bubbles for tooth cleaning, it may be advantageous to reduce the amount of the dissolved air in the fluid to prevent such losses.

The presence of bubbles that have come out of solution from the treatment fluid may lead to other disadvantages during certain procedures. For example, if the pressure wave generator produces cavitation, the agitation (e.g. pressure drop) used to induce the cavitation may cause the release of the dissolved air content before the water molecules have a chance to form a cavitation bubble. The already-formed gas bubble may act as a nucleation site for the water molecules during the phase change (which was intended to form a cavitation bubble). When the agitation is over, the cavitation bubble is expected to collapse and create pressure waves. However, cavitation bubble collapse might happen with reduced efficiency, because the gas-filled bubble may not collapse and may instead remain as a bubble. Thus, the presence of gas in the treatment fluid may reduce the effectiveness of the cavitation process as many of the cavitation bubbles may be wasted by merging with gas-filled bubbles. Additionally, bubbles in the fluid may act as a cushion to damp pressure waves propagating in the region of the fluid comprising the bubbles, which may disrupt effective propagation of the pressure waves past the bubbles. Some bubbles may either form on or between tooth surfaces, or be transferred there by the flow or circulation of fluid in the tooth. The bubbles may be hard to remove due to relatively high surface tension forces. This may result in blocking the transfer of chemicals and/or pressure waves into the irregular surfaces and small spaces in and between teeth, and therefore may disrupt or reduce the efficacy of the treatment.

B. Examples of Degassed Treatment Fluids

Accordingly, it may be advantageous in some systems and methods to use a degassed fluid, which can inhibit, reduce, or prevent bubbles from coming out of solution during treatments as compared to systems and methods that use normal (e.g., non-degassed) fluids. In dental procedures in which the treatment fluid has a reduced gas content (compared with the normal fluids) tooth surfaces or tiny spaces in the tooth may be free of bubbles that have come out of solution. Acoustic waves generated by the pressure wave generator can propagate through the degassed fluid to reach and clean the surfaces, cracks, and tooth spaces and cavities. In some procedures, the degassed fluid can be able to penetrate spaces as small as about 500 microns, 200 microns, 100 microns, 10 microns, 5 microns, 1 micron, or smaller, because the degassed fluid is sufficiently gas-free that bubbles are inhibited from coming out of solution and blocking these spaces (as compared to use of fluids with normal dissolved gas content).

For example, in some systems and methods, the degassed fluid can have a dissolved gas content that is reduced when compared to the "normal" gas content of water. For example, according to Henry's law, the "normal" amount of dissolved air in water (at 25 C and 1 atmosphere) is about 23 mg/L, which includes about 9 mg/L of dissolved oxygen and about 14 mg/L of dissolved nitrogen. In some embodiments, the degassed fluid has a dissolved gas content that is reduced to approximately 10%-40% of its "normal" amount as delivered from a source of fluid (e.g., before degassing). In other embodiments, the dissolved gas content of the degassed fluid can be reduced to approximately 5%-50% or 1%-70% of the normal gas content of the fluid. In some treatments, the dissolved gas content can be less than about 70%, less than about 50%, less than about 40%, less than about 30%, less than about 20%, less than about 10%, less than about 5%, or less than about 1% of the normal gas amount.

In some embodiments, the amount of dissolved gas in the degassed fluid can be measured in terms of the amount of dissolved oxygen (rather than the amount of dissolved air), because the amount of dissolved oxygen can be more readily measured (e.g., via titration or optical or electrochemical sensors) than the amount of dissolved air in the fluid. Thus, a measurement of dissolved oxygen in the fluid can serve as a proxy for the amount of dissolved air in the fluid. In some such embodiments, the amount of dissolved oxygen in the degassed fluid can be in a range from about 1 mg/L to about 3 mg/L, in a range from about 0.5 mg/L to about 7 mg/L, or some other range. The amount of dissolved oxygen in the degassed fluid can be less than about 7 mg/L, less than about 6 mg/L, less than about 5 mg/L, less than about 4 mg/L, less than about 3 mg/L, less than about 2 mg/L, or less than about 1 mg/L.

In some embodiments, the amount of dissolved gas in the degassed fluid can be in a range from about 2 mg/L to about 20 mg/L, in a range from about 1 mg/L to about 12 mg/L, or some other range. The amount of dissolved gas in the degassed fluid can be less than about 20 mg/L, less than about 18 mg/L, less than about 15 mg/L, less than about 12 mg/L, less than about 10 mg/L, less than about 8 mg/L, less than about 6 mg/L, less than about 4 mg/L, or less than about 2 mg/L.

In other embodiments, the amount of dissolved gas can be measured in terms of air or oxygen percentage per unit volume. For example, the amount of dissolved oxygen (or dissolved air) can be less than about 5% by volume, less than about 1% by volume, less than about 0.5% by volume, or less than about 0.1% by volume.

The amount of dissolved gas in a liquid can be measured in terms of a physical property such as, e.g., fluid viscosity or surface tension. For example, degassing water tends to increase its surface tension. The surface tension of non-degassed water is about 72 mN/m at 20° C. In some embodiments, the surface tension of degassed water can be about 1%, 5%, or 10% greater than non-degassed water.

In some treatment methods, one or more secondary fluids can be added to a primary degassed fluid (e.g., an antiseptic solution can be added to degassed distilled water). In some such methods, the secondary solution(s) can be degassed before being added to the primary degassed fluid. In other applications, the primary degassed fluid can be sufficiently degassed such that inclusion of the secondary fluids (which can have normal dissolved gas content) does not increase the gas content of the combined fluids above what is desired for a particular dental treatment.

In various implementations, the treatment fluid can be provided as degassed liquid inside sealed bags or containers. The fluid can be degassed in a separate setup in the operatory before being added to a fluid reservoir. In an example of an "in-line" implementation, the fluid can be degassed as it flows through the system, for example, by passing the fluid through a degassing unit attached along a fluid line (e.g., the fluid inlet). Examples of degassing units that can be used in various embodiments include: a Liqui-Cel® MiniModule® Membrane Contactor (e.g., models 1.7×5.5 or 1.7×8.75) available from Membrana-Charlotte (Charlotte, N.C.); a PermSelect® silicone membrane module (e.g., model PDM-SXA-2500) available from MedArray, Inc. (Ann Arbor, Mich.); and a FiberFlo® hollow fiber cartridge filter (0.03 micron absolute) available from Mar Cor Purification (Skippack, Pa.). The degassing can be done using any of the following degassing techniques or combinations of thereof: heating, helium sparging, vacuum degassing, filtering, freeze-pump-thawing, and sonication.

In some embodiments, degassing the fluid can include de-bubbling the fluid to remove any small gas bubbles that form or may be present in the fluid. De-bubbling can be provided by filtering the fluid. In some embodiments, the fluid may not be degassed (e.g., removing gas dissolved at the molecular level), but can be passed through a de-bubbler to remove the small gas bubbles from the fluid.

In some embodiments, a degassing system can include a dissolved gas sensor to determine whether the treatment fluid is sufficiently degassed for a particular treatment. A dissolved gas sensor can be disposed downstream of a mixing system and used to determine whether mixing of solutes has increased the dissolved gas content of the treatment fluid after addition of solutes, if any. A solute source can include a dissolved gas sensor. For example, a dissolved gas sensor can measure the amount of dissolved oxygen in the fluid as a proxy for the total amount of dissolved gas in the fluid, since dissolved oxygen can be measured more readily than dissolved gas (e.g., nitrogen or helium). Dissolved gas content can be inferred from dissolved oxygen content based at least partly on the ratio of oxygen to total gas in air (e.g., oxygen is about 21% of air by volume). Dissolved gas sensors can include electrochemical sensors, optical sensors, or sensors that perform a dissolved gas analysis. Examples of dissolved gas sensors that can be used with embodiments of various systems disclosed herein include a Pro-Oceanus GTD-Pro or HGTD dissolved gas sensor available from Pro-Oceanus Systems Inc. (Nova Scotia, Canada) and a D-Opto dissolved oxygen sensor available from Zebra-Tech Ltd. (Nelson, New Zealand). In some implementations, a sample of the treatment can be obtained and gases in the sample can be extracted using a vacuum unit. The extracted gases can be analyzed using a gas chromatograph to determine dissolved gas content of the fluid (and composition of the gases in some cases).

Accordingly, fluid delivered to the tooth from a fluid inlet and/or the fluid used to generate the jet in a liquid jet device can comprise a degassed fluid that has a dissolved gas content less than normal fluid. The degassed fluid can be used, for example, to generate the high-velocity liquid beam for generating acoustic waves, to substantially fill or irrigate a chamber, to provide a propagation medium for acoustic waves, to inhibit formation of air (or gas) bubbles in the chamber, and/or to provide flow of the degassed fluid into small spaces in the tooth (e.g., cracks, irregular surfaces, tubules, etc.). In embodiments utilizing a liquid jet, use of a degassed fluid can inhibit bubbles from forming in the jet due to the pressure drop at a nozzle orifice where the liquid jet is formed.

Thus, examples of methods for dental and/or endodontic treatment comprise flowing a degassed fluid onto a tooth or tooth surface or into a chamber. The degassed fluid can comprise a tissue dissolving agent and/or a decalcifying agent. The degassed fluid can have a dissolved oxygen content less than about 9 mg/L, less than about 7 mg/L, less than about 5 mg/L, less than about 3 mg/L, less than about 1 mg/L, or some other value. A fluid for treatment can comprise a degassed fluid with a dissolved oxygen content less than about 9 mg/L, less than about 7 mg/L, less than about 5 mg/L, less than about 3 mg/L, less than about 1 mg/L, or some other value. The fluid can comprise a tissue dissolving agent and/or a decalcifying agent. For example, the degassed fluid can comprise an aqueous solution of less than about 6% by volume of a tissue dissolving agent and/or less than about 20% by volume of a decalcifying agent.

IX. Various Performance Characteristics of the Disclosed Systems and Methods

The disclosed methods, compositions, and systems (e.g., the disclosed pressure wave generators, treatment fluids, etc.) may clean outer and inner surfaces of teeth better than other systems, and may do so more safely than the other systems.

Figure 11A:
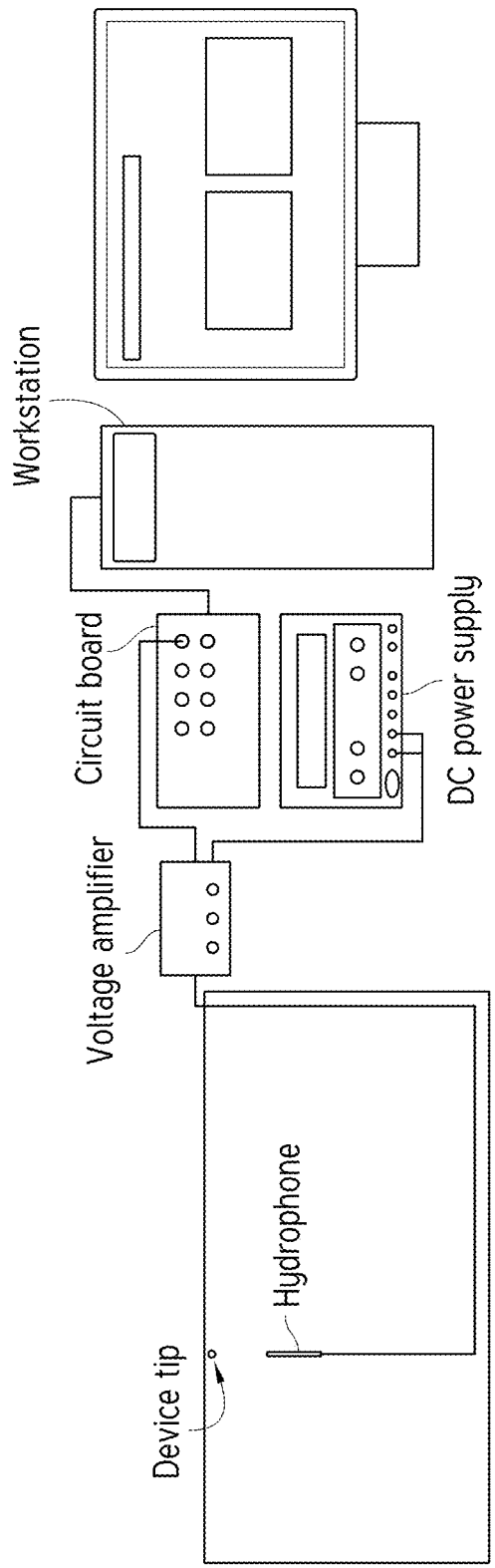
FIG. 11A is a schematic diagram of an experimental setup designed to measure the power output of various tooth cleaning devices.

FIG. 11A is a schematic diagram of an experimental setup designed to measure the power output of various tooth cleaning devices. As shown in FIG. 11A, a tank was filled with a liquid (e.g., water), and a tip of the device to be tested was placed underneath the surface of the liquid. A hydrophone was placed in the tank to measure the output of each device under operating conditions. A voltage amplifier, circuit board, a DC power supply, and a workstation were used to measure the voltage output from the hydrophone for each measurement.

Figure 11B:
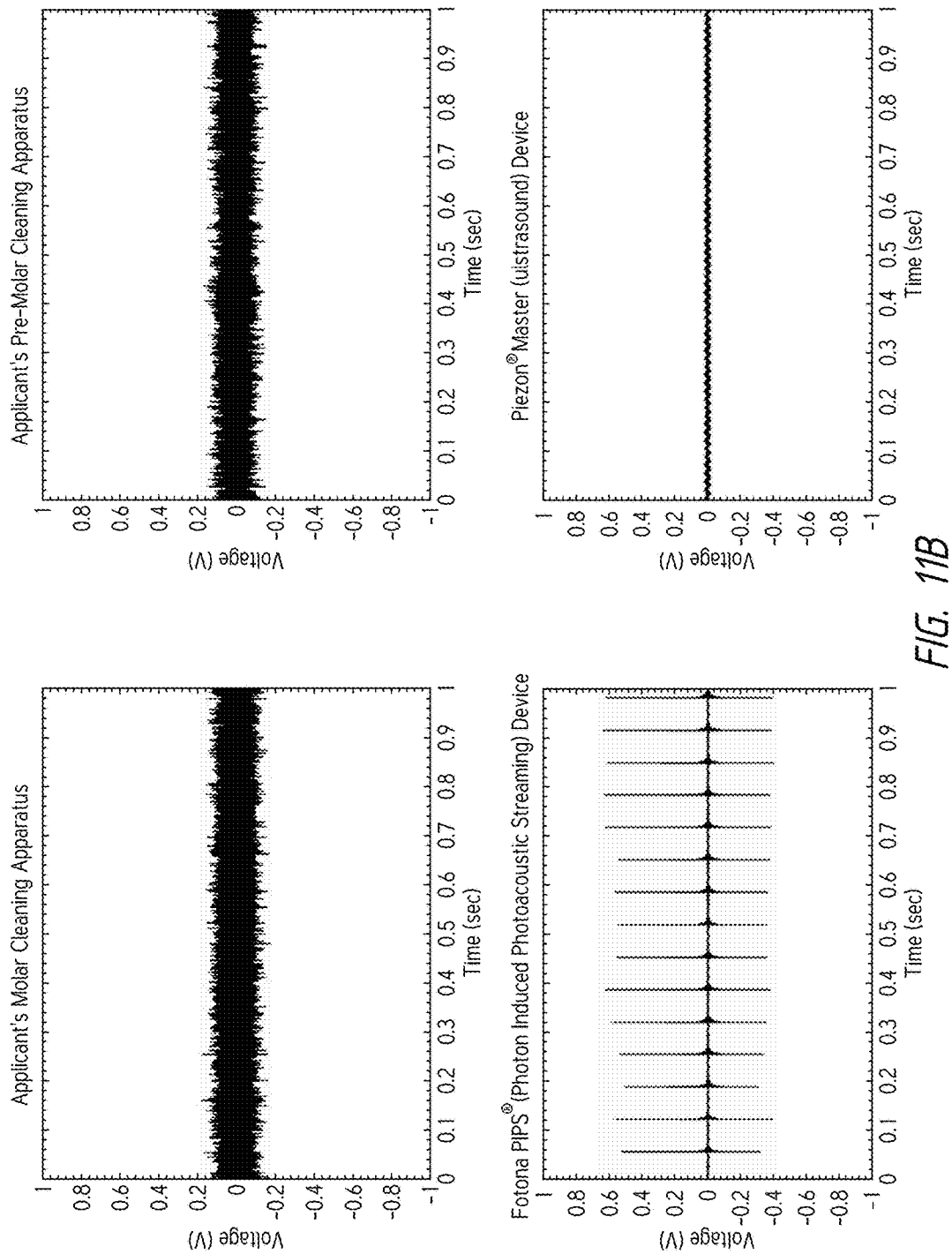
FIG. 11B is a plot of the voltage (in volts) output by the hydrophone over time (in seconds) for each device tested.

FIG. 11B is a plot of the voltage (in volts) output by the hydrophone over time (in seconds) for each device. Measurements for four experiments are shown in FIG. 11B. In particular, the plot in the upper left corner is a measure of voltage output over time for systems disclosed in this Application that are adapted to clean a molar tooth (referred to herein as "Applicant's Molar Cleaning Apparatus"). In particular, Applicant's Molar Cleaning Apparatus used in the experimental setup of FIG. 11A is generally similar to the handpiece 50 described in relation to FIGS. 15A-15C of U.S. Patent Publication No. 2012/0237893, which is incorporated by reference herein. An impingement member having a concave impingement surface similar to the impingement members 110 described in relation to FIGS. 12A-12C of U.S. Patent Publication No. 2011/0117517, which is also incorporated by reference herein, can be disposed at a distal portion of the guide tube. Furthermore, Applicant's Molar Cleaning Apparatus can include a jet device configured to form a liquid jet beam at a pressure of about 9000 psi, +/− about 1000 psi. The jet can be formed by passing pressurized liquid through a nozzle having a diameter of about 63 microns, +/− about 5 microns. In general, the parameters for the nozzle and guide tube can be similar to those described in U.S. Patent Publication No. 2012/0237893 and U.S. Patent Publication No. 2011/0117517 such that a coherent, collimated jet with a length of at least about 1 mm is produced. The plot in the upper right corner is a measure of voltage output over time for systems disclosed in this Application that are adapted to clean a pre-molar tooth (referred to herein as "Applicant's Pre-Molar Cleaning Apparatus"). In Applicant's Pre-Molar Cleaning Apparatus, a jet similar to the one described for the Molar Cleaning Apparatus can be used. The jet device for the Pre-Molar Cleaning Apparatus can be used in conjunction with a pre-molar handpiece such as the one illustrated in FIG. 10B. The plot in the lower left corner is a measure of voltage output over time for a Fotona photon induced photoacoustic streaming (PIPS®)) device. The plot in the lower right corner is a measure of voltage output over time for a Piezon® Master ultrasonic device.

As shown in FIG. 11B, Applicant's Molar and Pre-Molar Cleaning Apparatuses generate a voltage output (representative of power) over time that includes multiple frequencies. Indeed, as shown in FIG. 11B, Applicant's Molar and Pre-Molar Cleaning Apparatuses can generate a signal including a significant amount of noise. For example, the frequencies in the signal may include multiple, substantially random frequencies (e.g., approximating white noise in some arrangements). By contrast, the signal produced by the PIPS device includes pulses generated at substantially regular intervals, and the signal produced by the ultrasonic device can include a substantially periodic signal, e.g., one frequency, or only a few frequencies. As explained herein, the broadband signals generated by Applicant's Molar and Pre-Molar Apparatuses can advantageously clean different types of materials from the tooth and can do so quickly and effectively. For example, different frequencies may clean different types and/or sizes of materials effectively.

Figure 12A:
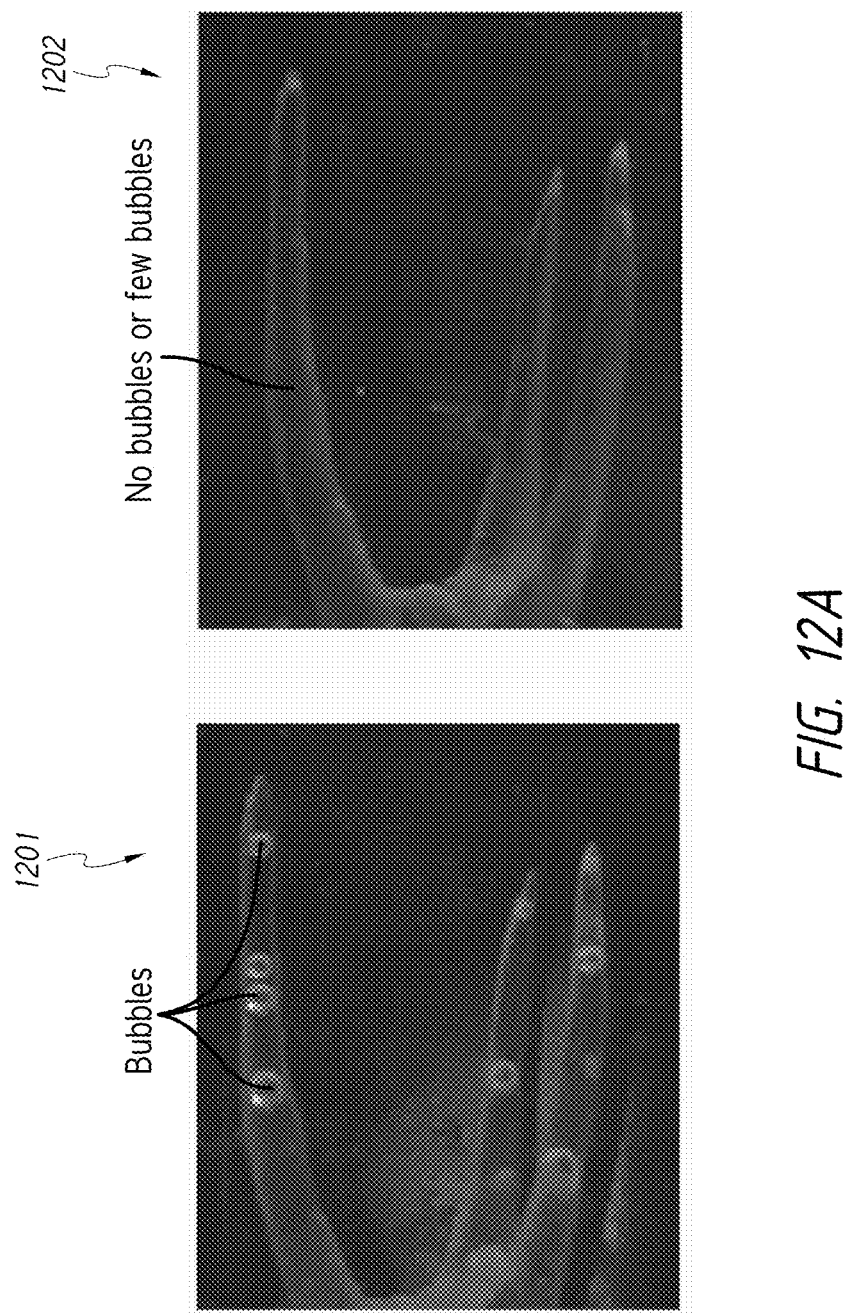
FIG. 12A illustrates images of root canals that compare the use of non-degassed liquid and degassed liquid in the disclosed pressure wave generators.
Figure 12B:
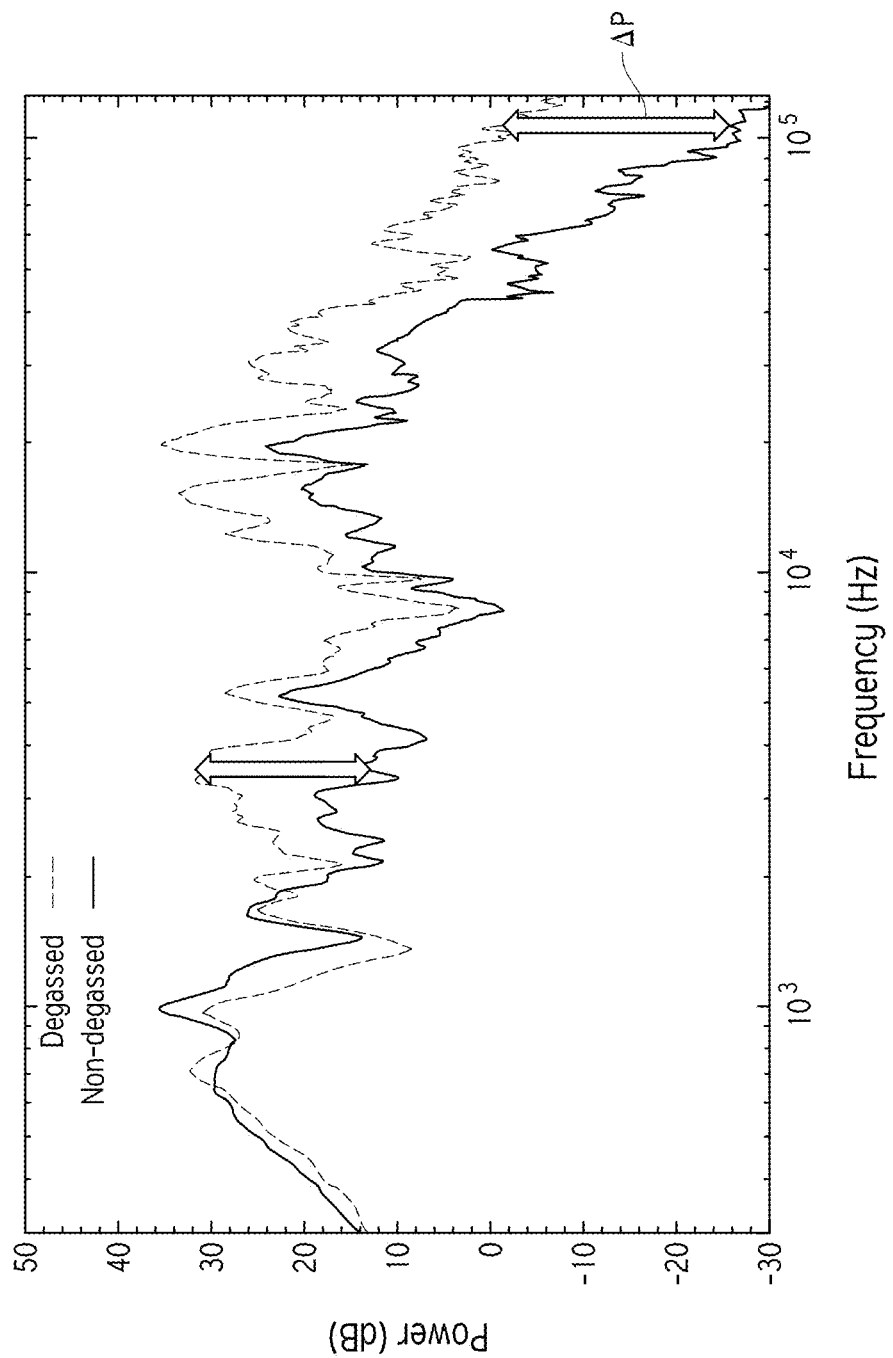
FIG. 12B is a plot comparing the power output for techniques using non-degassed and degassed liquids.

FIG. 12A illustrates images of root canals that compare the use of non-degassed liquid and degassed liquid in the disclosed pressure wave generators. As shown in image 1201 on the left side of FIG. 12A, the use of non-degassed liquid may cause bubbles to form in the canals, which may inhibit the propagation of energy in some arrangements. As shown in image 1202 on the right side of FIG. 12A, the use of degassed liquid may substantially prevent the formation of bubbles in the root canals when exposed to broadband acoustic or pressure waves. FIG. 12B is a plot comparing the power output for techniques using non-degassed and degassed liquids. The power outputs plotted in FIG. 12B are measured based on the liquid jet device described above with respect to Applicant's Molar Cleaning Apparatus. As shown in FIG. 12B, at higher acoustic frequencies, the use of degassed liquid in the disclosed systems can generate significantly more power than in techniques using non-degassed liquid. As illustrated in FIG. 12B, for example, at high acoustic frequencies, the difference between power generated by degassed and non-degassed liquids can be given by $\Delta P$, which can be in a range of about 5 dB to about 25 dB for frequencies in a range of about 20 kHz to about 200 kHz. For example, for frequencies in a range of about 70 kHz to about 200 kHz, $\Delta P$ can be in a range of about 10 dB to about 25 dB. At lower frequencies, the differences in power generated by degassed and non-degassed techniques may not be noticeable. At lower frequencies, relatively high powers may be generated even with non-degassed liquid because low frequency, large-scale fluid motion may produce substantial momentum that contributes to the cleaning of the tooth.

Figure 13:
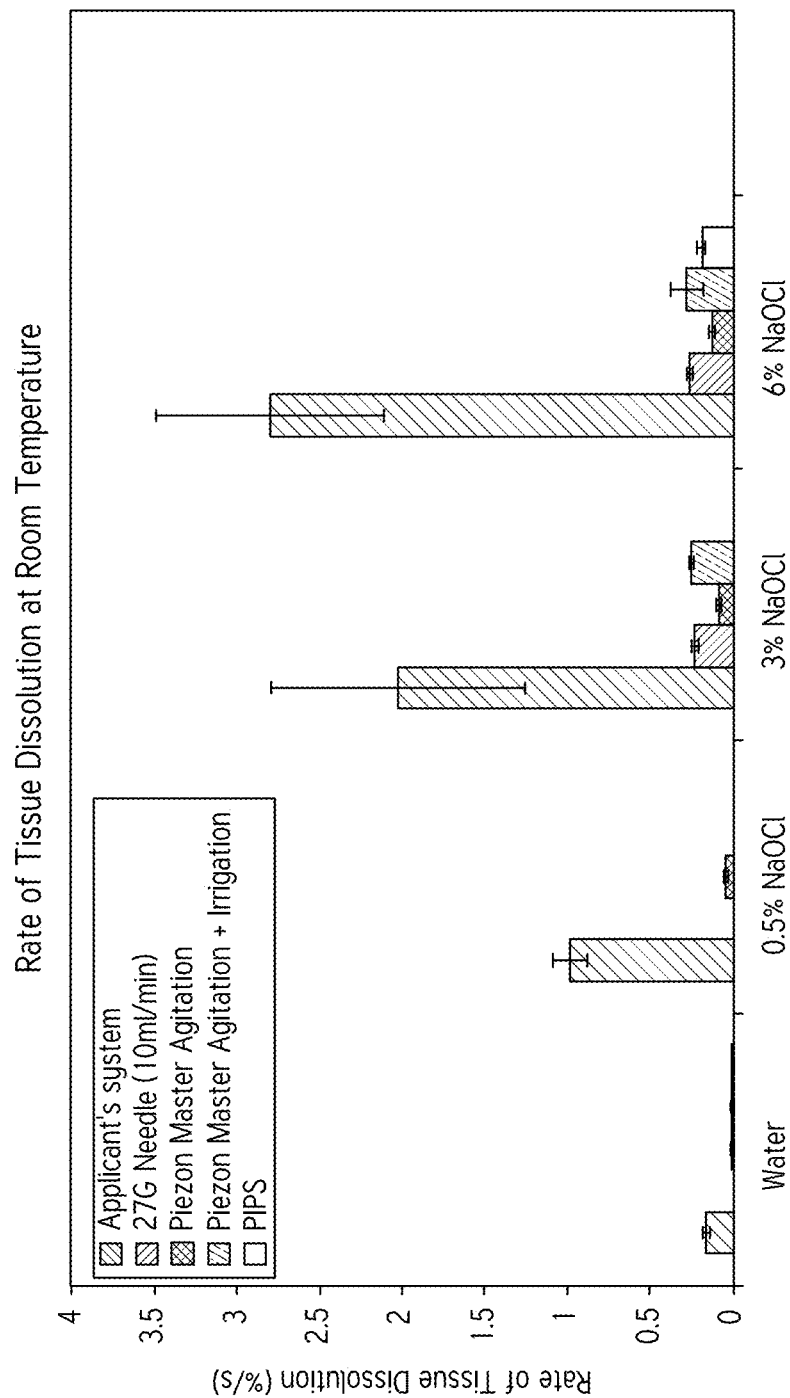
FIG. 13 is a plot comparing the rates of tissue dissolution (in units of % per second) for Applicant's device versus other devices, for different treatment fluids and compositions.

FIG. 13 is a plot comparing the rates of tissue dissolution (in units of % per second) for Applicant's device versus other devices, for different treatment fluids and compositions. As used herein, the data labeled "Applicant's system" was obtained from a system similar to that described above in relation to Applicant's Molar Cleaning Apparatus. In FIG. 13, the plot compares tissue dissolution rates for pure water, 0.5% NaOCl, 3% NaOCl, and 6% NaOCl. For example, FIG. 13 compares tissue dissolution rates at room temperature for Applicant's device, a 27G irrigation needle supplying irrigation fluid at a rate of 10 mL/min, an activated Piezon Master device, an activated Piezon Master Agitation in addition to some fluid irrigation, and an activated PIPS device. As shown in FIG. 13, for each treatment fluid and concentration, Applicant's system cleans at substantially higher rates than the other tested devices. For example, tissue dissolution rates for each treatment solution using Applicant's system may be at least 8-10 times the dissolution rates for the other tested devices.

Figure 14A:
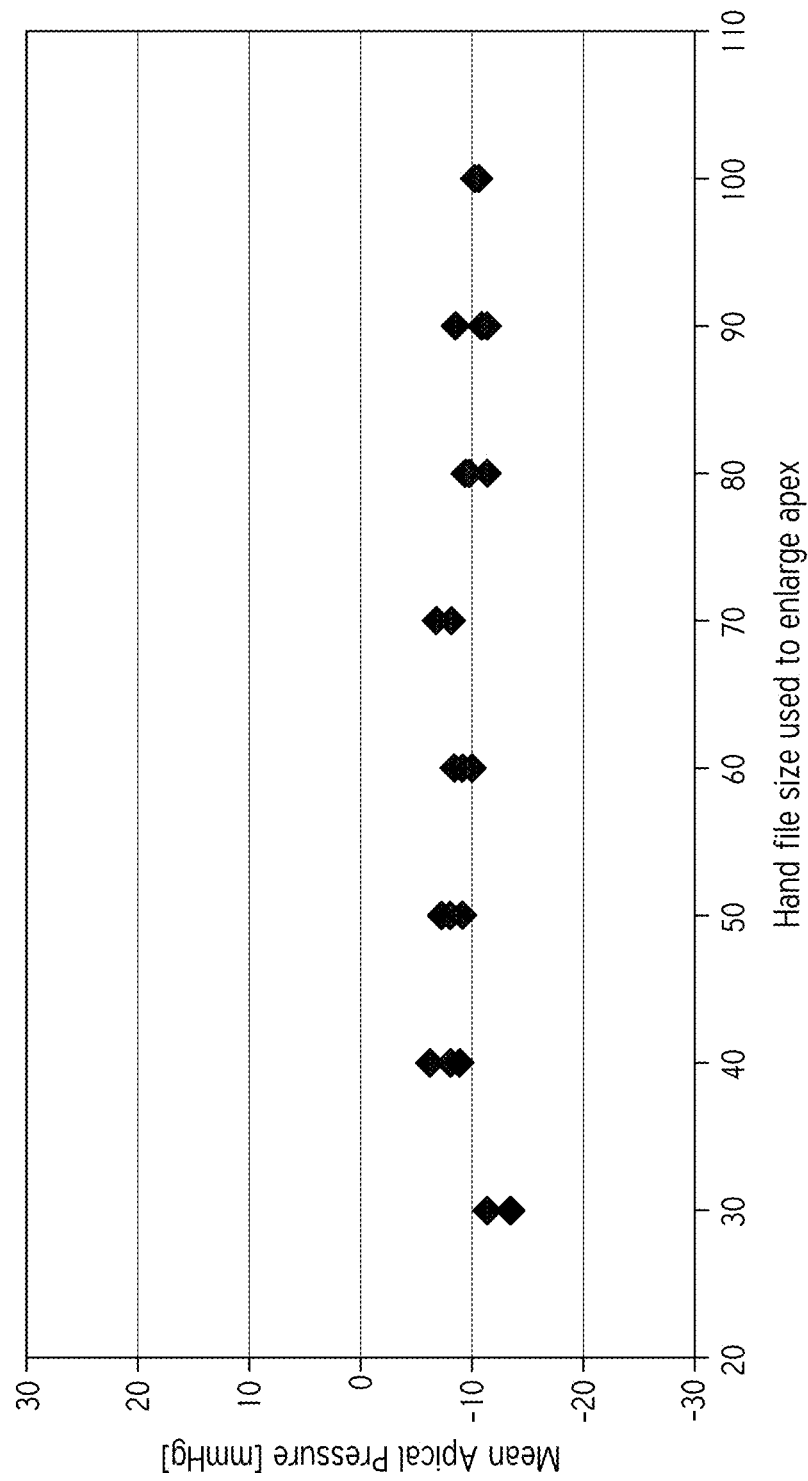
FIGS. 14A-14B are plots relating to the pressure measured at or near the apical opening of the root canal during treatment.
Figure 14B:
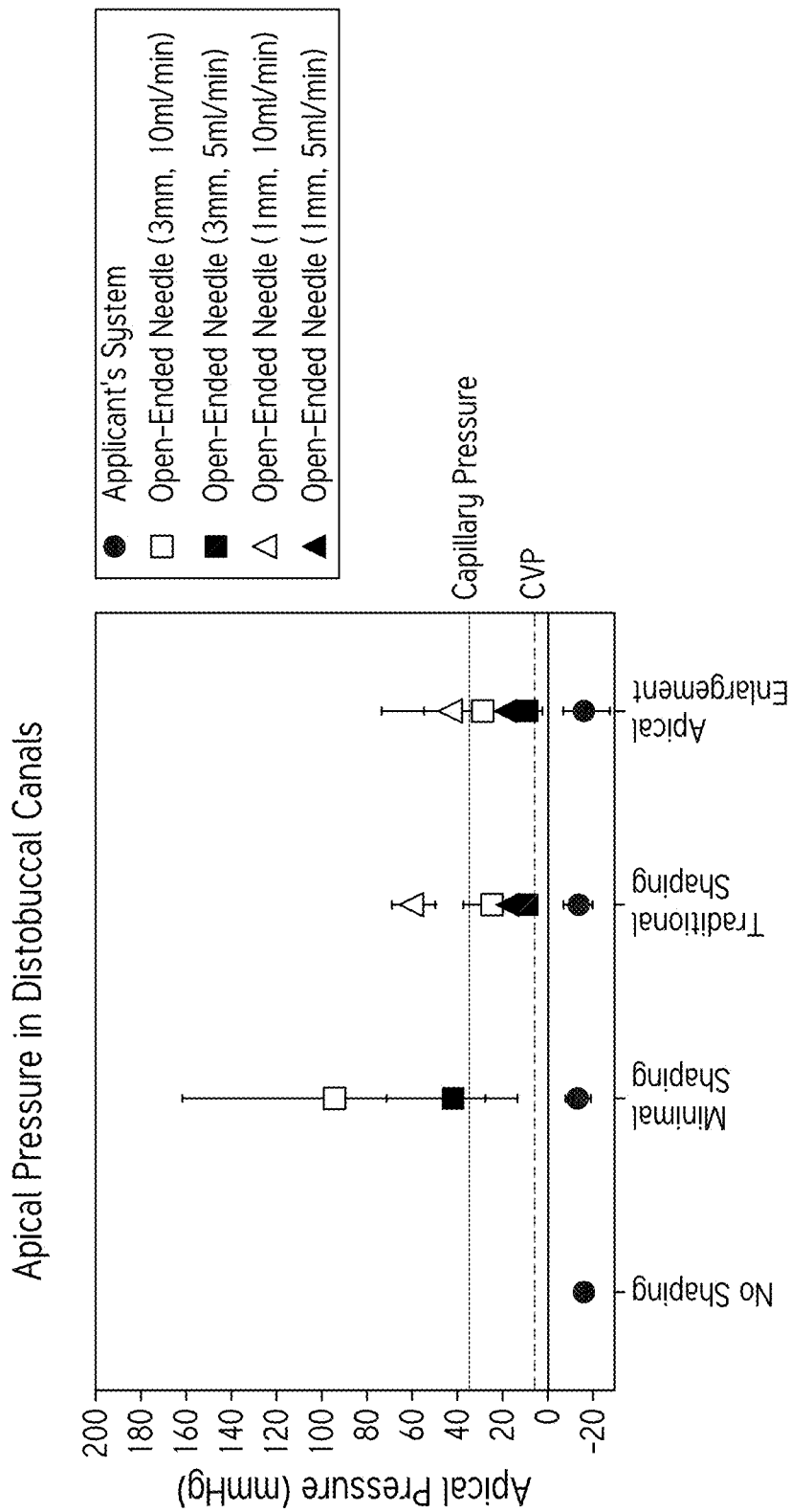

FIGS. 14A-14B are plots relating to the pressure measured at or near the apical opening of the root canal during treatment. As used herein, the data labeled "Applicant's system" was obtained from a system similar to that described above in relation to Applicant's Molar Cleaning Apparatus. As explained herein, it should be appreciated that high apical pressures can harm the patient. For example, high apical pressures can cause fluid or other material to extrude through the apex and into the patient's jaw. Extrusion through the apex can cause the patient substantial pain and can cause various health problems. Accordingly, it can be desirable for endodontic treatments to have low or negative apical pressures. FIG. 14A is a plot of mean apical pressure versus the hand file size used to enlarge the apex. As shown in FIG. 14A, Applicant's system generates negative pressures for each file size. Such negative pressures can advantageously prevent extrusion through the apex. For example, as explained above, the induced vortices can cause the pressures at or near the apical opening to be slightly negative. For example, the mean apical pressures can be in a range of about −5 mmHG to about −15 mmHg.

FIG. 14B is a plot comparing the apical pressures during treatments using Applicant's system and various other devices, such as various sizes of and flow rates dispensed from open-vented needles. The plot of FIG. 14B includes data for a distobuccal canal, and the plot compares the pressures for different amounts of canal shaping (e.g., no shaping, minimal shaping, traditional shaping, apical enlargement). As shown in FIG. 14B, Applicant's techniques and systems produce negative apical pressures, as compared to the high, positive apical pressures generated by the other plotted devices.

Figure 14C:
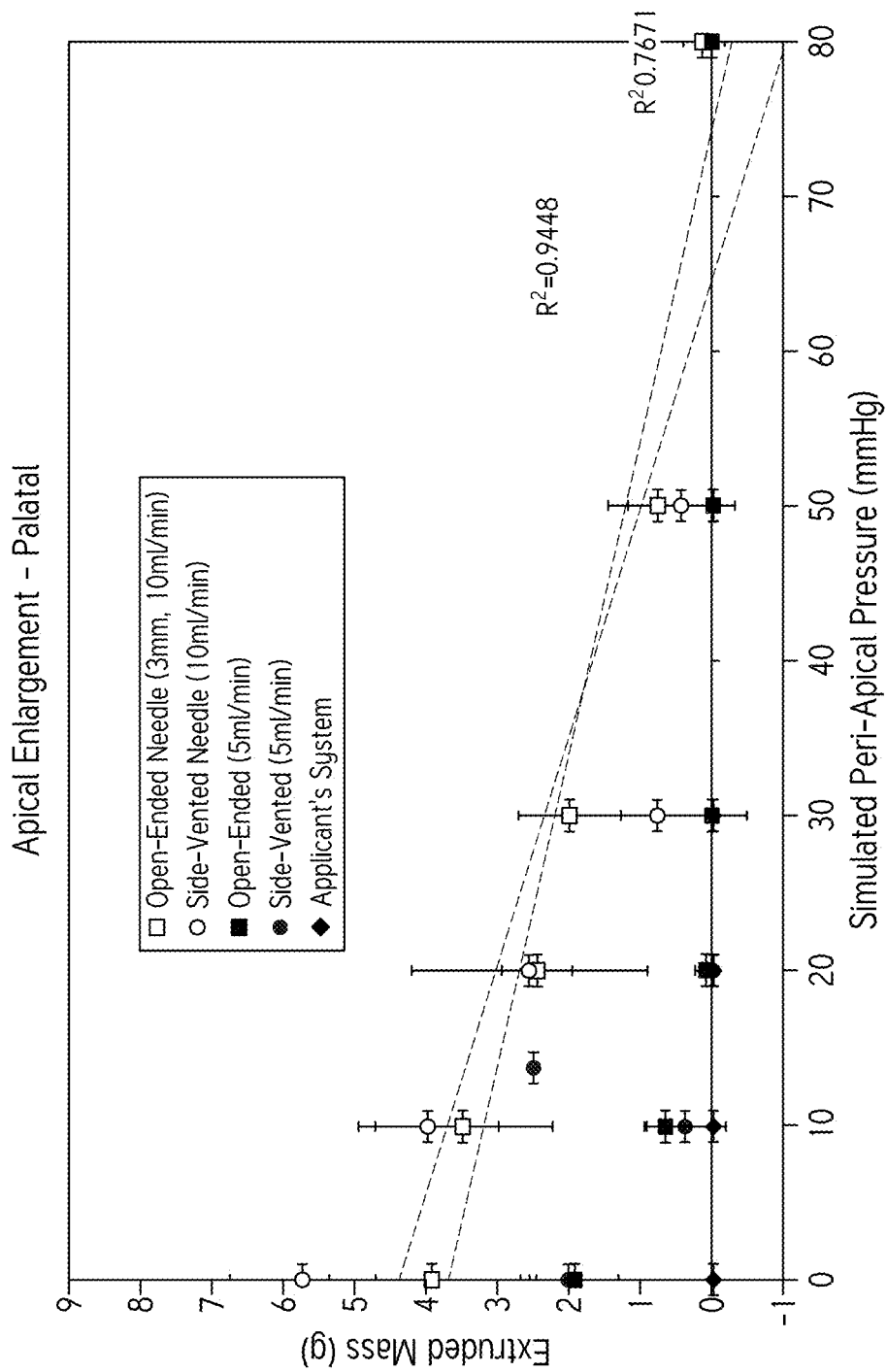
FIG. 14C is a plot of the mass of material extruded through the apex for various simulated peri-apical pressures for Applicant's system and for various needles.

The negative apical pressures generated by Applicant's systems can advantageously improve patient outcomes by preventing and/or reducing extrusion of materials through the apex. FIG. 14C is a plot of the mass of material extruded through the apex for various simulated peri-apical pressures for Applicant's system and for various needles. As used herein, the data labeled "Applicant's system" was obtained from simulations of a system similar to that described above in relation to Applicant's Molar Cleaning Apparatus. As shown in FIG. 14C, the mass of material extruded when Applicant's system and methods are used to clean canals is less than that of other devices. Indeed, the disclosed systems and methods can clean root canals with minimal or no material extruded through the apex.

X. Additional Examples of Fluid Motion Generators

Figure 15:
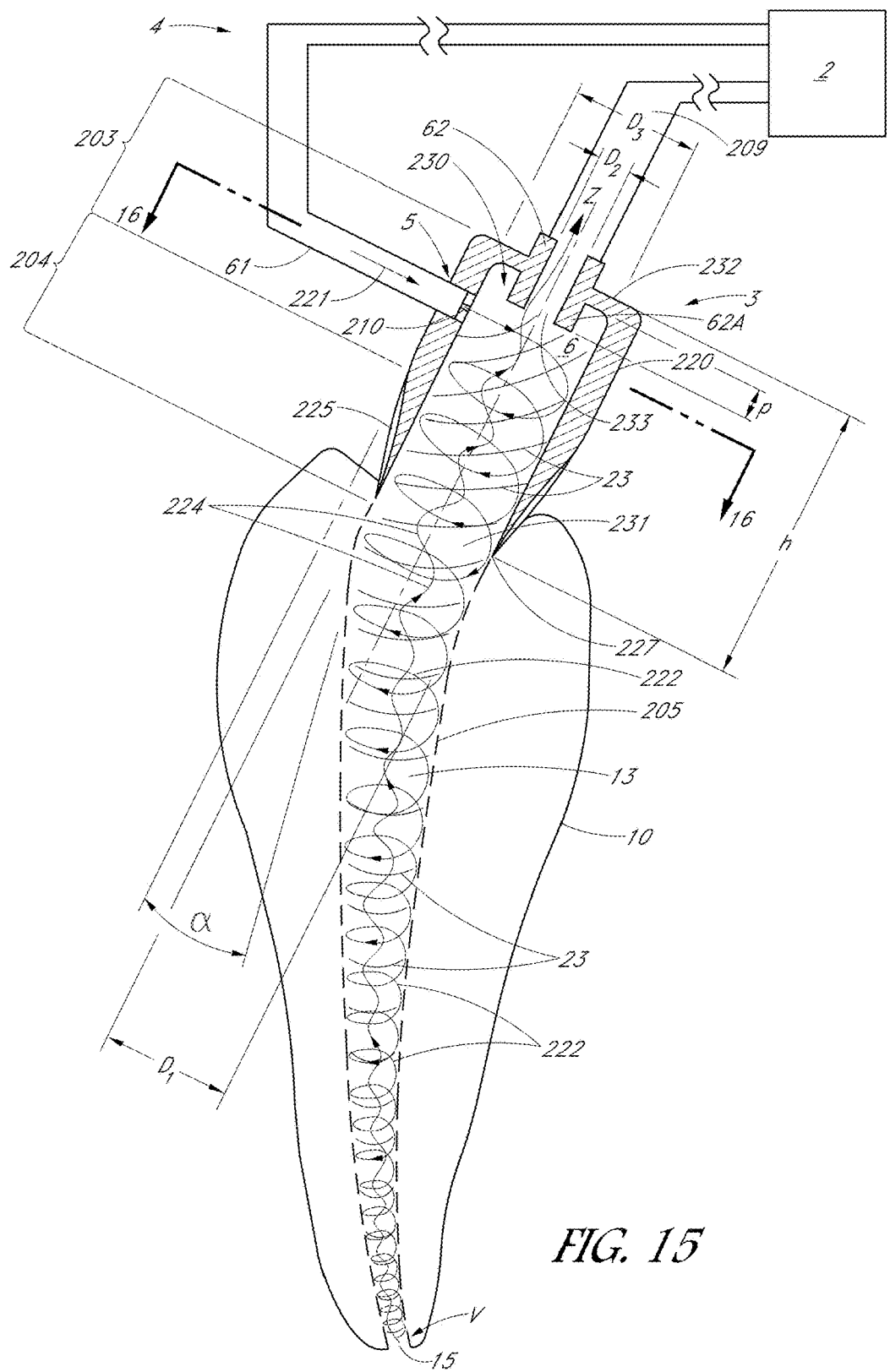
FIG. 15 is a schematic side sectional view of a dental treatment system, according to one embodiment.
Figure 16:
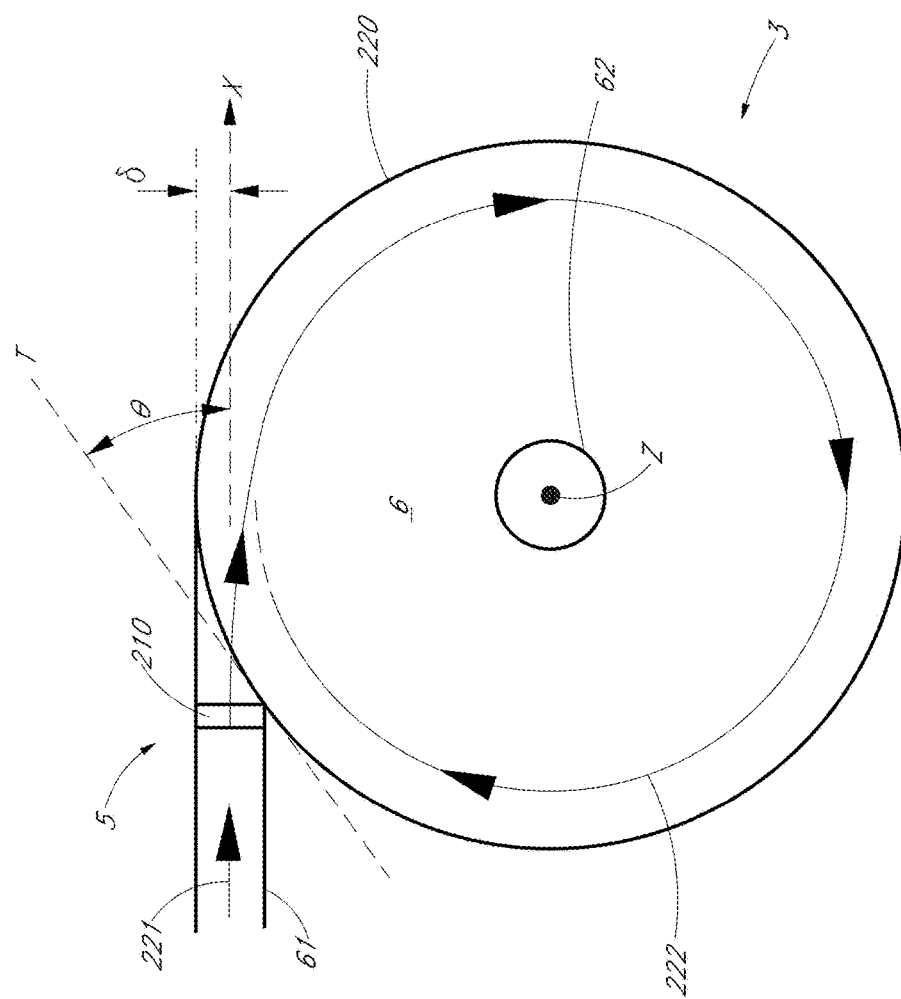
FIG. 16 is a schematic top sectional view of the system shown in FIG. 15.

FIGS. 15-24C illustrate additional examples of systems for treating teeth and root canals. FIG. 15 is a schematic side sectional view of a system 1, according to one embodiment. FIG. 16 is a schematic top sectional view of the system 1 shown in FIG. 15. As explained above, a tooth coupler 3 can be configured to be applied to (e.g., pressed against or attached to) a treatment region of the tooth 10. A fluid motion generator 5 (which may be a pressure wave generator) can be activated to clean (or fill) the treatment region. The system 1 can include a console 2 (similar to the console 2 described in the above embodiments) configured to control the operation of the system 1 and one or more conduits 4 that provide fluid communication (and/or electrical or wireless/electronic communication) between the tooth coupler 3 and the console 2. The console 2 can include one or more fluid pumps and reservoirs that can supply treatment liquids to the treatment region of the tooth 10. The console 2 can also comprise a fluid removal system including a suction pump and a waste reservoir for removing liquids and waste materials from the tooth 10 by way of the conduit(s) 4. The console 2 can also include one or more processors that are configured to electronically control the operation of the evacuation and/or delivery pumps to control and the delivery of liquid to the tooth and the removal of liquid from the tooth.

The system 1 shown in FIG. 15 can include a tooth coupler 3 that is sized and shaped to couple to a treatment region of the tooth 10. For example, as explained above, the tooth coupler 3 can comprise a distal portion of a handpiece that is manually pressed against the tooth by the clinician. In various embodiments, the tooth coupler 3 can be attached to the tooth 10 for the treatment procedure. The tooth coupler 3 in FIG. 15 is shown in connection with a root canal treatment procedure; however, it should be appreciated that the tooth coupler 3 can also be used with other treatment procedures, such as the caries treatment procedure described in FIG. 1B. The tooth coupler 3 can comprise a chamber 6 defined at least in part by an upper wall 232 and a side wall 220 that extends transversely from the upper wall 232. When coupled to the tooth 10 (e.g., pressed against the tooth or attached to the tooth), the chamber 6 can retain liquid and other materials during a treatment procedure. The upper wall 232 and side wall 220 may be integrally formed as a single component in some embodiments; in other embodiments the upper wall 232 and side wall 220 may comprise separate components that are connected or joined together. The side wall 220 can extend annularly relative to the upper wall 232 to at least partially define the chamber 6. It should be appreciated that the upper wall 232, as used herein, refers to the wall near the proximal end of the chamber 6; thus, during some treatments (such as those of upper teeth), the upper wall 232 may be disposed in a downward orientation.

In addition, the tooth coupler 3 or chamber 6 can include a distal portion 227 configured to contact the treatment region of the tooth (or a portion thereof). The distal portion 227 can define an access port 231 that provides fluid communication between the chamber 6 and the treatment region of the tooth 10 (e.g., the root canal 13). In various arrangements, the distal portion 227 can taper radially inwardly towards a central axis Z of the tooth coupler 3 and/or chamber 6. The central axis Z can be perpendicular to and comprise a central axis of the access port 231. For example, the side wall 220 can comprise a substantially conical taper that continuously and substantially linearly tapers inwardly and distally. Thus, as shown in FIG. 15, a proximal portion of the chamber 6 can have an inner diameter $D_3$ (or other major dimension) and the access port 231 of the distal portion 227 can have an inner diameter $D_1$ (or other major dimension) that is smaller than $D_3$. The chamber 6 may also have a height h. The height h of the chamber 6 can be less than about 5 cm in various embodiments, e.g., less than about 2 cm. Moreover, although not illustrated in FIG. 15, a sealing member (which can be the same as or similar to the sealing member 105 shown in FIG. 21A) can be disposed about the chamber 6 and tooth coupler 3. The sealing member can comprise a compressive material (such as a foam) that can seal the treatment region when pressed against the tooth by the clinician. When pressed against the tooth, the tooth coupler 3 can be urged into the tooth such that the sealing member is proximal the distal end of the tooth coupler 3.

For root canal treatments, as shown in FIG. 15, the distal portion 227 can be inserted into or onto an access opening of the tooth 10 to provide fluid communication with the root canal 13. A sealing material 225 may be applied between the distal portion 227 and the tooth 10 to create or enhance a fluid seal such that liquid, air, and/or debris does not escape to or from the chamber 6 and/or the tooth 10. As shown in FIG. 15, the distal portion 227 can be tapered such that the taper extends from an intermediate or proximal portion of the tooth coupler 3 to the distal-most end of the tooth coupler 3. For example, as shown in FIG. 15, the side wall 220 of the tooth coupler 3 can comprise a generally straight or cylindrical portion 203 (along which the diameter $D_3$ remains substantially constant) and a tapered or conical portion 204 that tapers inwardly and distally from the straight portion 203 such that the inner diameter $D_1$ decreases along the distal direction (e.g., towards the tooth 10 in FIG. 15). The tapered portion 204 can be disposed distal the straight portion 203 and can include the distal portion 227 and the distal-most end of the tooth coupler 3. Tapering the tooth coupler 3 as shown in FIG. 15 can advantageously enable the clinician to conduct treatment procedures on teeth of any size, including very small teeth or teeth that have very small root canal spaces, e.g., the smallest human tooth that would be treated by the system 1. For example, the distal portion 227 can be sized to treat teeth with endodontic access openings having sizes (e.g., diameters or other major dimension) in a range of about 0.5 mm to about 5 mm.

The inner diameter $D_1$ of the access port 231 may be smaller than the access opening of the tooth (e.g., the opening that the clinician forms to access the interior of the tooth), larger than the access opening, or the same size as the access opening. In some embodiments, advantageously, the outer diameter (and the inner diameter $D_1$) of the access port 231 may be smaller than the access opening so as to enable the distal portion 227 to be inserted into the access opening. In other embodiments, the outer diameter of the distal portion 227 may be the same size as or larger than the access opening. Accordingly, the distal portion 227 of the tooth coupler 3 may be inserted into the endodontic access opening such that the access port 231 and the access opening are substantially aligned and/or overlapping.

The inner diameter $D_1$ of the opening defined by the distal portion 227 can be in a range of about 0.3 mm (+/−0.05 mm) to about 5 mm (+/−1 mm), e.g., in a range of about 0.5 mm (+/−0.1 mm) to about 3 mm (+/−0.5 mm), or in a range of about 1 mm (+/−0.1 mm) to about 2 mm (+/−0.1 mm). The distal portion 227 of the tooth coupler 3 may have a wall thickness in a range of about 0.001 mm (+/−0.0001 mm) to about 5 mm (+/−1 mm), e.g., in a range of about 0.01 mm (+/−0.001 mm) to about 1 mm (+/−0.1 mm). Further, the outer diameter of the distal portion 227 (e.g., the inner diameter $D_1$ plus twice the wall thickness of the distal portion 227) may be in a range of about 0.5 mm (+/−0.1 mm) to about 5 mm (+/−1 mm), e.g., in a range of about 1 mm (+/−0.1 mm) to about 2 mm (+/−0.1 mm). The inner diameter $D_3$ of the proximal portion of the chamber 6 may be less than about 5 cm (+/−1 cm), e.g., less than about 1 cm (+/−0.1 cm). For example, the inner diameter $D_3$ may be in a range of about 0.5 cm (+/−0.1 cm) to about 1.5 cm (+/−0.3 cm), or in a range of about 0.7 cm (+/−0.1 cm) to about 1 cm (+/−0.1 cm). Moreover, as shown in FIG. 15, the conical shape of the tooth coupler 3 can have a tapering angle α that defines the amount by which an outside surface of the side wall 220 tapers inwardly and distally to the distal-most end of the tooth coupler 3. In FIG. 15, an inner surface of the side wall 220 may not taper inwardly. However, in other embodiments, the inner surface of the side wall 220 may taper inwardly, similar to the embodiment shown in FIG. 23. The tapering angle α can be in a range of about 0° (+/−1°) to about 45° (+/−1°), or more particularly, in a range of about 0.5° (+/−0.1°) to about 45° (+/−1°), e.g., in a range of about 0.5° (+/−0.1°) to about 20° (+/−1°). In some embodiments, the tapering angle α can be in a range of about 1° (+/−0.1°) to about 15° (+/−1°), or in a range of about 1° (+/−0.1°) to about 10° (+/−1°).

The fluid motion generator 5 (which may also be a pressure wave generator, as described above) can be disposed on and/or through the side wall 220 of the tooth coupler 3. The fluid motion generator 5 can supply liquid 221 to the chamber 6 so as to generate rotational liquid motion in the chamber 6. The supplied liquid 221 can comprise a degassed liquid as explained herein. The supplied liquid 221 can be any suitable type of treatment fluid, including, e.g., water, EDTA, bleach, obturation material (for filling procedures), etc. For example, a fluid inlet 61 can supply pressurized liquid 221 to the chamber 6. In FIG. 15, the pressurized liquid 221 can be passed through a nozzle 210 at a location in the side wall 220 of the tooth coupler 3 (e.g., a sealing cap) at a location near the top wall 232. As shown in the top sectional view of FIG. 16, the fluid motion generator 5 may be off-center or asymmetric relative to the tooth coupler 3 or sealing cap. For example, the fluid inlet 61 and the nozzle 210 can be offset relative to the central axis Z of the tooth coupler 3. In FIG. 16, the fluid motion generator can be radially offset relative to the central axis Z and can be directed in a direction X transverse to the central axis Z. As shown in FIG. 15, the central axis Z can pass distally along the height h of the tooth coupler 3 through the center of the access port 231, e.g., the central axis Z can be transverse to the access port 231 at or near the center of the access port 231. The central axis Z can also define the central longitudinal axis of the conical shape of the tooth coupler 3, e.g., transverse to the radial direction of the conical shape.

The pressurized liquid 221 supplied by the fluid motion generator 5 can induce liquid circulation in the chamber 6 of the tooth coupler 3. For example, the fluid motion generator 5 (e.g., the inlet 61 and/or nozzle 210) can generate a swirling, rotational motion of influent liquid 222 about the central axis Z of the chamber, which can be transverse to (e.g., substantially perpendicular to in some arrangements) the X axis along which the liquid is introduced into the tooth coupler 3. In some arrangements, rotational or circulatory motion can also be induced about other directions, e.g., about axis parallel to the direction of fluid introduction. As shown in FIG. 15, the influent liquid 222 can introduce rotational flow near and/or along walls 205 of the canal spaces 13 as the rotating liquid 222 enters the canal spaces 13.

In some embodiments, the pressurized liquid 221 can pass through the nozzle 210 and can emerge as a coherent, collimated liquid jet, which can act as a fluid motion generator and/or pressure wave generator, as explained above. In various embodiments of the nozzle 210, an orifice or opening in the nozzle may have a diameter $d_1$ at an inlet or a diameter $d_2$ at an outlet that may be in a range from about 5 microns to about 1000 microns. Other diameter ranges are possible. In various embodiments, one or both of the diameters $d_1$ or $d_2$ of the nozzle opening may be in a range from about 10 microns to about 100 microns, a range from about 100 microns to about 500 microns, or range from about 500 microns to about 1000 microns. In various other embodiments, one or both of the orifice diameters $d_1$ or $d_2$ may be in a range of about 40-80 microns, a range of about 45-70 microns, or a range of about 45-65 microns. In one embodiment, the orifice diameter $d_1$ is about 60 microns. The ratio of axial length $L_1$ to diameter $d_1$, the ratio of axial length $L_2$ to diameter $d_2$, or the ratio of total axial length $L_1+L_2$ to diameter $d_1$, $d_2$, or average diameter $(d_1+d_2)/2$ may, in various embodiments, be about 50:1, about 20:1, about 10:1, about 5:1, about 1:1, or less. In one embodiment, the axial length $L_1$ is about 500 microns. Additional examples of nozzles may be found in U.S. Patent Publication No. US 2011/0117517, which is incorporated by reference herein.

In some embodiments, the liquid 221 may comprise a stream of liquid that is not a jet, or that is not a circular jet. After entering the chamber 6, the liquid 221 can impact the side wall 220 of the tooth coupler 3. In some arrangements, the jet may impact an impingement surface before entering the chamber, e.g., a surface in the inlet path leading to chamber 6. The angle of the jet at the impact may be adjusted such that the impact leads to minimal loss of momentum. The fluid motion generator 5 can be angled such that, upon impingement of the liquid 221 against the wall 220, a rotating sheet of influent liquid 222 is generated in which the sheet of influent liquid 222 rotates in a swirling motion about the central axis Z and travels distally along the side wall 220 in the chamber 6 towards the opening 227 in the tooth coupler. The rotating sheet of influent liquid 222 can continue downward along the inner walls 205 of the root canal(s) 13 towards the apical opening 15 of the tooth 10. The rotating liquid 222 can effectively and efficiently clean the entire root canal space 13. For example, the rapid, bulk fluid motion of the influent liquid 222 can interact with diseased matter in the root canal 13 and can dislodge or otherwise remove the diseased matter from the root canal 13.

As shown in FIG. 16, it can be advantageous to orient the fluid motion generator 5 such that sufficient rotational influent flow 222 is provided in the chamber 6 and treatment region. For example, the inlet 61 and nozzle 210 can be directed along the X-direction, which can be transverse to (e.g., perpendicular to) the central axis Z. The X-direction along which liquid is directed can be oriented at an angle between 80° and 100°, or more particularly, between 85° and 95°, relative to the central axis Z. The X-direction can be generally tangent to the outer edge of the side wall 220. The X-direction may be slightly angled relative to the tangent T of the side wall 220 at the location at which the inlet 221 and nozzle 210 intersect the wall 220 of the chamber 6. For example, the X-axis along which the ingoing liquid 222 is directed may be at an inlet angle θ relative to the tangent T. The inlet angle θ can be at or close to zero. For example, θ can be in a range of about 0° to about 15°, or in a range of about 0° to about 10°. In some embodiments, the angle θ can be in a range of about 1° to about 10°, or in a range of about 1° to about 5°. The fluid motion generator 5 can also be disposed such that the center of the influent stream 222 enters the chamber 6 at a distance δ, from the outermost edge of the wall 220. The distance δ can be relatively small, e.g., in a range of about 5 μm to about 2 mm, or in a range of about 15 μm to about 40 μm. As shown in FIGS. 15-16, the fluid motion generator 5 can be oriented such that the X-axis is directed perpendicular to the central axis Z such that the X-axis is substantially horizontal relative to the chamber 6. In some embodiments, the X-axis can be directed distally or proximally to assist in generating downward or upward rotating influent flow 222 into the treatment region. In some cases, the angle of impact θ, the angle of distal/proximal bias, and/or the shape of the impact region on the surface can be adjusted to adjust the flow properties that may affect efficacy of the procedure. The flow entering the chamber 6 may comprise one or more of the following: a jet impacting a surface of the chamber 6 which turns into a rotating sheet of fluid, a sheet of fluid (planar flow) as a result of impact of the jet onto a surface before entering the chamber, a planar flow generated via flowing a fluid through a slit, and/or any other suitable technique for generating a sheet of fluid Furthermore, in the embodiment shown in FIG. 15, when the liquid jet emerges from the nozzle 210, the jet can interact with treatment liquid in an interaction zone 230 near the interface between the nozzle 210 and the chamber 6. As explained herein, the liquid jet can pass through the liquid and can generate pressure waves 23 that propagate through the liquid in the chamber 6 and root canal 13 of the tooth 10. As shown in FIG. 15, and as explained above, the pressure waves 23 can propagate from the interaction zone 230 distally into the canal 13 of the tooth 10. The pressure waves 23 can comprise multiple frequencies that can cause liquid to flow into small spaces, cracks, and tubules of the tooth 10 to substantially clean the tooth 10. In some arrangements, the bulk flow of influent liquid 222 or large scale fluid motion may act to remove larger amounts of diseased material from relatively large spaces of the tooth, and the pressure waves 23 can flow into smaller spaces that may not be exposed to the bulk flow of liquid 222 or large scale fluid motion. The combination of rotating influent liquid 222 and pressure waves 23 can act to substantially clean the tooth, including large and small spaces of the tooth that may include different types and sizes of organic and inorganic matter.

It can be important to enable the influent liquid 222 to be removed from the treatment region to ensure that waste materials (e.g. dislodged debris, etc.) are irrigated from the tooth 10 and/or to enhance the fluid rotation at the treatment region. Accordingly, a fluid outlet 62 can be provided in and/or through the top wall 232 of the tooth coupler 3. The fluid outlet 62 can comprise a suction port 233 defining an opening between the chamber 6 and an outlet passage 209 (which may be one of the conduit(s) 4 described above) that conveys outgoing fluid to the waste system by way of a suction pump. The suction pump can apply suction to the outlet passage 209 and outlet 62 to draw fluids out of the chamber 6 and towards a reservoir outside the tooth coupler 3.

The fluid outlet 62 may have an inner diameter $D_2$ that is equal to or smaller than the inner diameter $D_1$ of the distal portion 227 of the chamber 6 of the tooth coupler 3. In other embodiments, the fluid outlet 62 may have an inner diameter $D_2$ that is larger than the inner diameter $D_1$ of the distal portion 227. The relative size of $D_2$ and $D_1$ may be selected base on the desired type and rate of fluid flow. In FIG. 15, the inner diameter $D_2$ is smaller than $D_1$. The inner diameter $D_2$ may influence the depth at which the flow stagnates and changes direction (e.g., the return location V), from a spiraling downward motion next to the walls of the root canal to the spiraling upward motion through the interior of the influent flow 222. For example, in some embodiments, the inner diameter $D_2$ of the suction port 233 may in a range of about 0.1 mm to about 5 mm, e.g., in a range of about 0.1 mm to about 2 mm. The fluid outlet 62 can be disposed at or near the center of the top wall 232 of the tooth coupler 3. As shown in FIG. 15, the central axis Z of the tooth coupler 3 and access port 231 can pass through both the access port 231 of the distal portion 227 and the suction port 233 of the outlet 62. The central axis Z can be perpendicular, or substantially perpendicular, to the suction port 233. For example, the central axis Z can be disposed at about a 90° angle (between 70° and 110°, or more particularly between 80° and 100°, or more particularly between 85° and 95°) relative to the suction port 233. For example, in some embodiments, the access port 231 can define a plane that is transverse to (e.g., perpendicular to) the central axis Z, and the central axis Z can pass through the center of the access port 231 and through at least a portion of the suction port 233. In some embodiments, the suction port 233 can define a plane that is transverse to (e.g., perpendicular to) the central axis Z, and the central axis Z can pass through the center of the suction port 233 and through at least a portion of the 231 access port 231. In some embodiments, the access port 231 and the suction port 233 define respective planes that are both transverse to (e.g., perpendicular to) the central axis Z, and the central axis Z can pass through both the access port 231 and the suction port 233. In some embodiments, the central axis Z can pass through the center of both the access port 231 and the suction port 233. The suction port 233 can be symmetric about the central axis Z in some embodiments. In some embodiments, a center of the suction port 233 can lie on the central axis Z. In some embodiments, a flange 62A of the outlet 62 can extend partially into the chamber 6 by a length p. The length p can be adjusted to improve the fluid outflow and/or fluid rotation in the chamber 6 and/or tooth 10. The length p of the flange 62A may also influence the depth of the return location V, e.g., the depth at which the flow stagnates and changes direction from spiral downward motion next to the walls to the spiral upward motion through the center. For example, the length p of the flange 62A may be in a range of about 0.1 mm to about 10 mm. In some embodiments, the length p may be about the same as the height h of the chamber 6, such that the flange 62A extends downwardly to near the access port 231.

The outlet 62 and chamber 6 can be configured such that the influent liquid 222 turns back proximally at a return location V to be drawn out of the chamber 6. At the return location V (which may be at or near the apical opening 15), the treatment liquid can turn back towards the tooth coupler 3 in an outgoing fluid path 224. The outgoing fluid path 224 may be different from the flow path or pattern of the influent liquid 222. For example, the returning or outgoing flow 224 path can comprise rotational (or semi-planar) flow near the center of the canal spaces and/or within the swirling influent flow path 222. In some embodiments, the outgoing flow 224 can comprise a spiral flow path that passes inside the rotating influent liquid 222. The induced outward flow 224 can be carried outside the treatment region to carry waste and other matter away from the treatment region (e.g., outside the canal 13 and tooth 10). Moreover, the suction provided by the outlet 62 and/or the rotating influent liquid 222 can provide a negative pressure at the apical opening 15 in which treatment liquid and/or waste is prevented from passing through the apical opening 15, which can reduce the risk of infection and/or pain to the patient. The outgoing liquid 224 can pass through the suction port 233 and can be drawn to the waste reservoir through the outlet line 209 by the suction pump. In addition, although not illustrated in FIG. 15, a vent assembly can be provided to enhance the removal of waste fluids from the system. For example, one or more vents can be provided through the tooth coupler 3 downstream of the suction port 233. In addition, in some embodiments, an auxiliary port can be provided on the tooth coupler 3. The auxiliary port can include a one way valve, such as a duckbill valve. If the pressure inside the chamber 6 increases, for example, due to a clog in the outlet passage 209, the rising pressure inside the chamber 6 may exceed the cracking pressure of the safety valve so that the valve can relieve pressure. The auxiliary safety valve may be disposed anywhere on the tooth coupler 3 with at least one opening to the chamber 6. Examples of vent assemblies can be found in, e.g., U.S. Patent Publication No. 2012/0237893, which is incorporated by reference herein in its entirety.

Figure 16A:
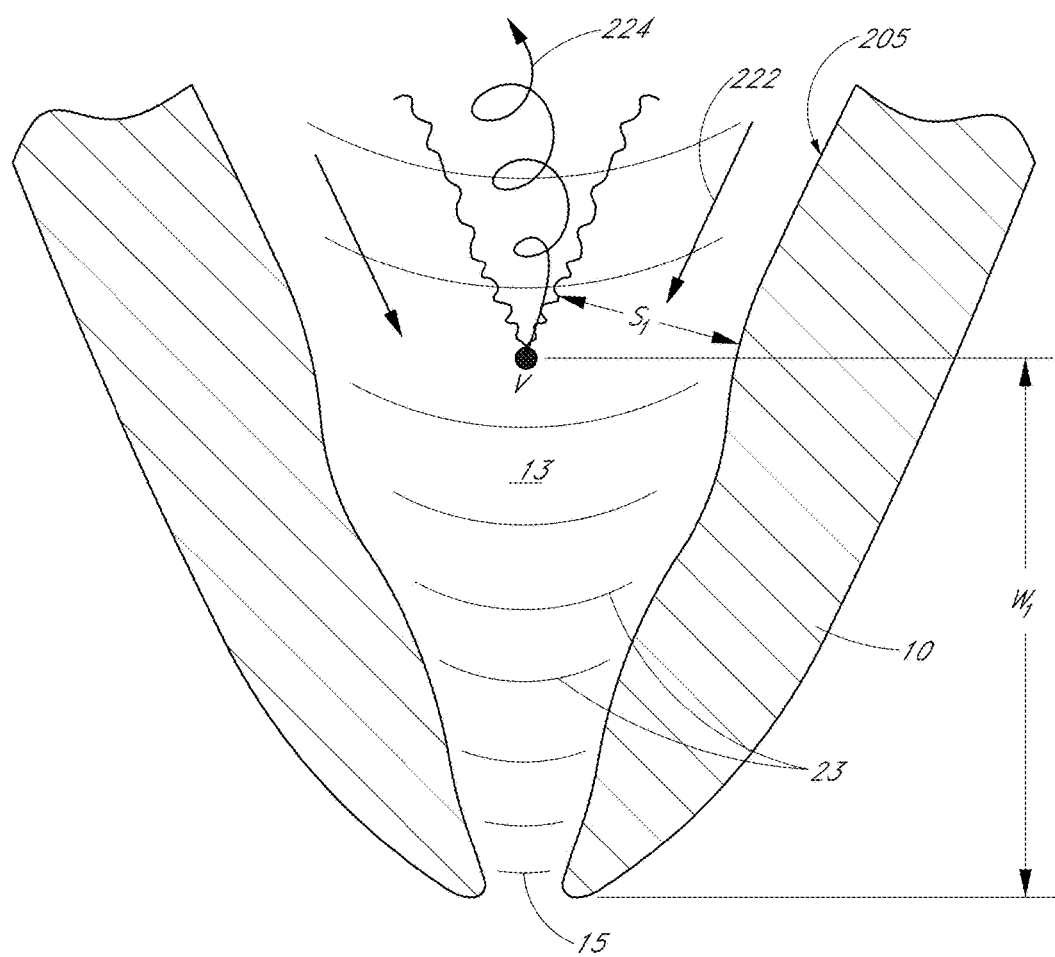
FIGS. 16A and 16B are enlarged side cross-sections of the tooth shown in FIG. 15 that illustrates influent and outgoing fluid flow paths.
Figure 16B:
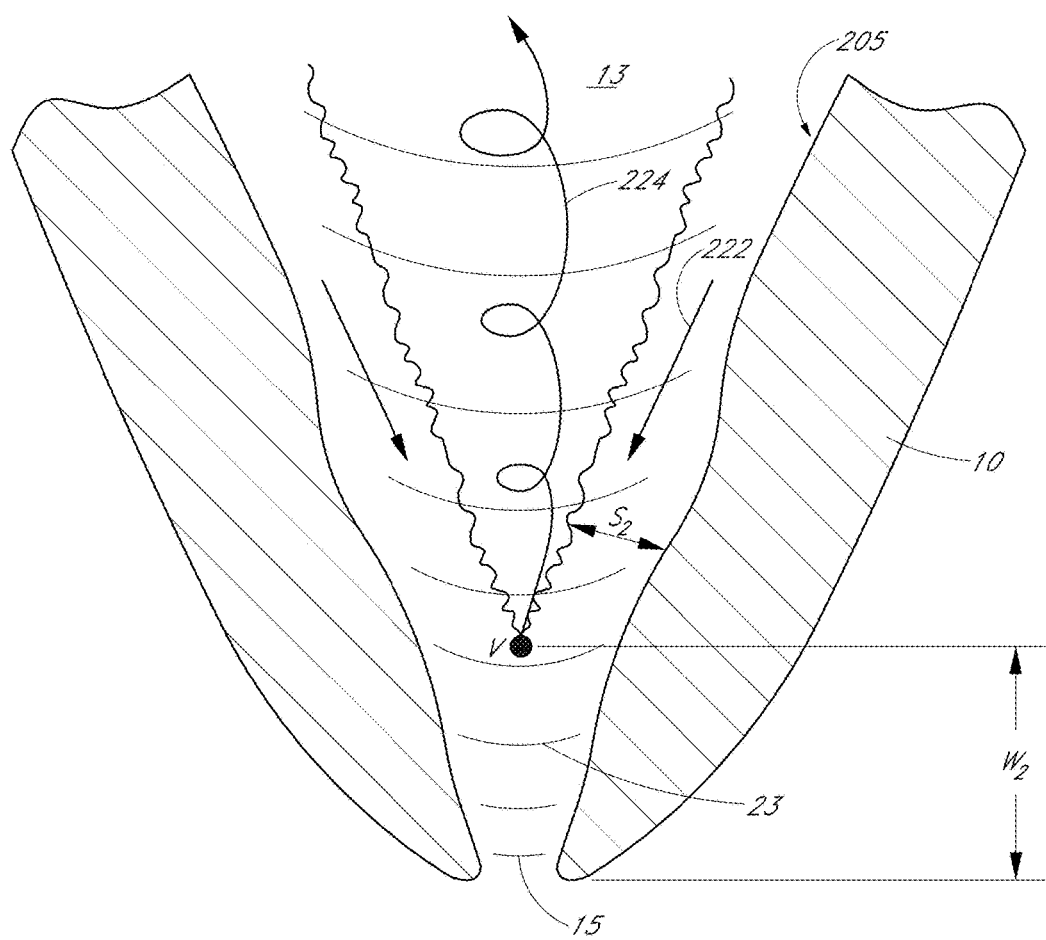

FIGS. 16A and 16B are enlarged side cross-sections of the tooth 10 shown in FIG. 15 that illustrates the influent and outgoing fluid flow paths 222, 224. FIGS. 16A and 16B illustrate the flow patterns that can be generated by the embodiments of FIGS. 15 and 17-24C. As explained herein, it can be important to configure the fluid motion generator 5, the shape of the chamber 6, and/or the outlet 62 such that the influent rotating flow 222 effectively cleans a large volume of the root canal 13 or other treatment region. For example, it can be important to generate influent rotational flow 222 that comprises a thin sheet of treatment liquid that flows distally into the tooth 10. In FIG. 16A, the sheet of influent liquid 222 has a sheet thickness $S_1$ relative to the wall 205 of the canal 13. As shown in FIG. 16A, the sheet of liquid 222 along the wall 205 can converge at the return location V.

Upon converging at the return location V, the liquid turns back proximally and the outgoing liquid 224 returns towards the tooth coupler 3. As shown in FIG. 16A, the outgoing liquid 224 can comprise rotational fluid flow that passes within or inside the rotating influent flow 222 as it flows towards the outlet 62. With the sheet thickness $S_1$, the return location V may be at a distance $w_1$ from the apical opening 15 of the tooth 10. The distance $w_1$ may be as small as zero, resulting in the rotating influent flow 222 reaching the apical opening of the tooth and turning at the apical opening. Because the rotating sheet of influent liquid 222 converges at location V, the effectiveness of the bulk fluid motion of the influent liquid 222 may be reduced for locations that are below or distal the location V. However, as shown in FIG. 16A, the pressure waves 23 may propagate through the liquid past the return location V to clean the regions of the tooth 10 that are below or distal the return location 222.

In FIG. 16B, the fluid motion generator 5, the chamber 6, and/or the outlet 62 are configured to generate a sheet of rotating influent liquid 222 that has a sheet thickness $S_2$ that is smaller than the sheet thickness $S_1$ shown in FIG. 16A. The reduced thickness $S_2$ may cause the return location V to be positioned further along the root canal 13 than in the example shown in FIG. 16A. For example, the influent liquid 222 can converge at the location V that is at a distance $w_2$ that is closer to the apical opening 15 than the return location V in FIG. 16A. By having the return location V nearer the apical opening 15, the bulk fluid motion of the influent liquid 222 can clean deeper into the canal 13. In addition, as explained above, the pressure waves 23 can clean the smaller spaces and cracks of the tooth 10 that may not be exposed to the bulk motion of the influent liquid 222. Other phenomena that may help clean the region distal to return location V can include mass transfer via diffusion and/or via the fluid displacement due to the transport of bubbles generated through tissue dissolution from the apical region of the tooth towards the coronal region of the tooth.

Various parameters can enhance the influent and outgoing flow patterns 222, 224 shown in FIGS. 15-16B. For example, the centrally-located outlet 62 along the upper wall 232 can advantageously pull the outgoing fluid 224 out of the chamber 6 and tooth 10 in a flow pattern that causes the fluid 224 to pass within the rotating influent liquid 222. Such flow patterns can enable effective cleaning and irrigation of the treatment region. Furthermore, providing a suction port 233 with an inner diameter $D_2$ that is smaller than the inner diameter $D_1$ of the distal access port 231 can also help enable the central outgoing liquid flow path 224. For example, the larger distal access port 231 can enable the rotating influent liquid 222 to flow distally along the wall 220 of the chamber 6 and the canal walls 205, and the smaller suction port can draw the outgoing liquid 224 proximally within the rotating influent flow 222. As explained herein, an evacuation apparatus (e.g., vacuum pump) can apply a suction force to the suction port to draw the outgoing liquid 224 out of the suction port 233 within rotating (e.g., swirling) influent liquid 222. In addition, the inner diameter $D_2$ of the suction port 233 may be selected to create desired rotational and outflow profiles. For example, the suction port 233 may be sufficiently narrow such that the return location V is sufficiently deep in the canal space 13 to provide deeper penetration of the rotational influent liquid 222, yet wide enough to prevent over-pressurization at the outlet 62.

In addition, the characteristics of the inlet fluid 221 (such as speed, flow rate, cross-sectional shape of inlet stream, angle of inlet stream relative to chamber and wall, etc.) may be selected so as to improve the influent and outgoing flow 222, 224 through the canal spaces 13. For example, to at least partially enable a thin sheet of influent liquid 222, the jet may have a relatively small diameter so as to provide a relatively small flow rate. In some embodiments, the operating pressure of the system may be between 1000 psi and 20000 psi, e.g. in a range of 5000 psi and 15000 psi, e.g. about 9000 psi (+/−1000 psi). In some embodiments, for example, the diameter (or other major dimension) of the jet may be in a range of about 30 µm to about 90 µm, e.g., in a range of about 45 µm to about 70 µm, e.g., about 55 µm. Other jet (e.g., nozzle) diameters may be used depending on the operating pressure of the system. The operating flow rate may be in a range of 10 cc/min to 150 cc/min, e.g. in a range of 30 cc/min to 70 cc/min, e.g. about 40 cc/min (+/−5 cc/min). The pressure and the flow rate may be constant during procedure or may vary. Furthermore, the shape and dimensions of the chamber 6 defined by the tooth coupler 3 can be selected to enhance circulation. For example, a height of the cylindrical portion 203 of the tooth coupler 3 or sealing cap, a height of the conical portion 204, the major dimensions (e.g., diameters) of the chamber, surface quality, tapering of the conical portion 204 (e.g., the angle α), and other parameters may be configured to improve cleaning. In some embodiments, an interface between the access port 231 of the chamber 6 and the access opening of the tooth may be a substantially water-proof and/or air-tight seal. Providing a fluid seal at the interface between the access opening and the distal or bottom portion of the sealing cap (which may be part of a handpiece) can enhance the fluid dynamic and pressure wave effects of the embodiments disclosed herein. The vents and waste collection systems can also be configured to enhance removal of waste materials. For example, the size of the suction port 233 on the chamber 6 can be configured to enhance material removal. Advantageously, the embodiments disclosed herein can enable a reduction in the volume of fluid used and a reduction in cost of manufacturing. Further, the shear stress exerted on the root canal walls 205 may be stronger, and the outflow 224 of fluid through the outlets can be enhanced without impairing the amount of influent, fresh treatment fluids 222. Further, it should be appreciated that, although the side cross-section of FIG. 15 shows the inlet 61 and outlet 62 as being co-planar for ease of illustration, the inlet 61 is instead offset relative to the outlet 62 and the central axis Z as shown in the top cross-section of FIG. 16.

The tooth coupler 3 shown in FIG. 15 comprises a conical shape, but in other embodiments, the tooth coupler 3 can have other suitable shapes. For example, the tooth coupler 3 may be straight, may comprise a straight section and a conical section extending from the straight section (or vice versa), or may comprise a straight section, a conical section and a straight section. The conical section may have a single tapering angle or multiple tapering angles. In various embodiments, the tooth coupler 3 may have a single wall thickness or multiple wall thicknesses. In the embodiment of FIG. 15, the tooth coupler 3 may be axisymmetric about the central axis Z, but in other embodiments, the tooth coupler 3 may be asymmetric, which can assist in controlling sealing with the tooth 10. The internal surface of the chamber may have a smooth finish to minimize momentum loss and maintain the influent flow substantially laminar and undisturbed. The inner surface of the wall 220 may be smooth or rough, or may have both a smooth portion and a rough portion. The inner surface of the wall 220 may also include channels to help direct the rotational flow. For example, the channels can have a predetermined pitch. The channels can have a depth in a range of about 0.001 mm to about 10 mm deep, e.g., a depth in a range of about 0.01 mm to about 1 mm. The channels may have a width in a range of about 0.001 mm to about 10 mm, e.g., a width in a range of about 0.01 mm to about 1 mm.

The system 1 shown in FIG. 15 may be configured to treat teeth with various anatomical and/or morphological features. For example, the system 1 can be used to treat premolar teeth, anterior teeth, molar teeth, teeth with various occlusal anatomies (e.g., various number of cusps, decayed or not, slanted or not), teeth with circular endodontic access openings, teeth with oval endodontic access openings, teeth with irregular endodontic openings, teeth with straight endodontic access, teeth with curved endodontic access, teeth with an endodontic access opening having an axis not aligned with the axis of root canals, teeth with multiple roots, teeth with a single root, teeth with curved roots (e.g., teeth with curvatures up to about 90 degrees), teeth with various lengths of roots (e.g., lengths in a range of about 5 mm to about 30 mm), teeth with canals with circular and/or large cross-sectional aspect ratios, teeth with canal constrictions, teeth with canal contractions, teeth with auxiliary canals, teeth with multiple islands, teeth with a single island, teeth with bifurcations, teeth with trifurcations, teeth with multiple furcations, teeth with apical deltas, and/or teeth with multiple apical terminations.

Although the rotational influent flow 222 may be generated as described above with respect to FIGS. 15-16B, the influent rotational flow may be generated by a rotating chamber, a partially rotating chamber, a rotating chamber upper wall 232, and/or a rotating side wall 220. The rotating components of the chamber 6 may be smooth or rough, and may comprise features that improve fluid entrainment (such as teeth, blades, etc.). Rotational flow may also be generated by a rotating evacuation feature, e.g., a rotating outlet 62. The rotating evacuation feature may be smooth or rough, and the rotating evacuation feature may have features improving fluid entrainment (e.g. teeth, blades, etc.).

In the embodiment of FIG. 15, the rotational fluid flow (e.g., influent flow 222) may be generated by injection of liquid into the chamber 6. There may be a single inlet 61 or multiple inlets. The fluid may be injected with an impingement angle between 0 deg and +90 deg. The fluid may be injected with a latitude angle between −45° and +45°, e.g., a latitude angle between −10° and +10° is preferred. The fluid may be injected from near the top of the chamber 6 as shown in FIG. 15. The incoming liquid 221 can be injected by a bulk flow or a jet (which may be cylindrical or planar). The fluid inlet 61 may be any suitable cross-sectional shape, including rectangular, oval, square, circular, etc. The inner diameter of the inlet 61 may be less than or equal to about half the diameter $D_3$ of the chamber 6.

The rotational influent flow 222 may comprise a sheet that swirls or rotates about the wall 220 of the chamber 6. Downward rotational flow may be induced in the outer layer of the fluid inside the chamber 6. In other embodiments, the downward flow may be induced on the inner axis of the fluid chamber. The influent flow 222 can rotate at a speed in a range of about 0.1 to about 100,000 revolutions per second, e.g., in a range of about 1 to 50,000 revolutions per minute. The incoming liquid 221 may be injected into the chamber 6 through the inlet 61 at flow rates in a range of about 0.1 mL/min to about 100 mL/min.

The treatment fluid supplied to the chamber 6 may comprise any suitable treatment fluid, such as a cleaning liquid or an obturation material. For example, in cleaning procedures, the supplied cleaning liquid can rotate as shown in FIGS. 16A and 16B, and can interact with diseased matter to clean the tooth. In obturation procedures, the supplied obturation material can similarly rotate as shown in FIGS. 16A and 16B, and can substantially fill the treatment region (e.g., a treated root canal, a treated carious region, etc.). In addition, although not shown in FIG. 15, the tooth coupler 3 can have one or more additional openings that can supply obturation material to the treatment region.

Figures 17, 17A:
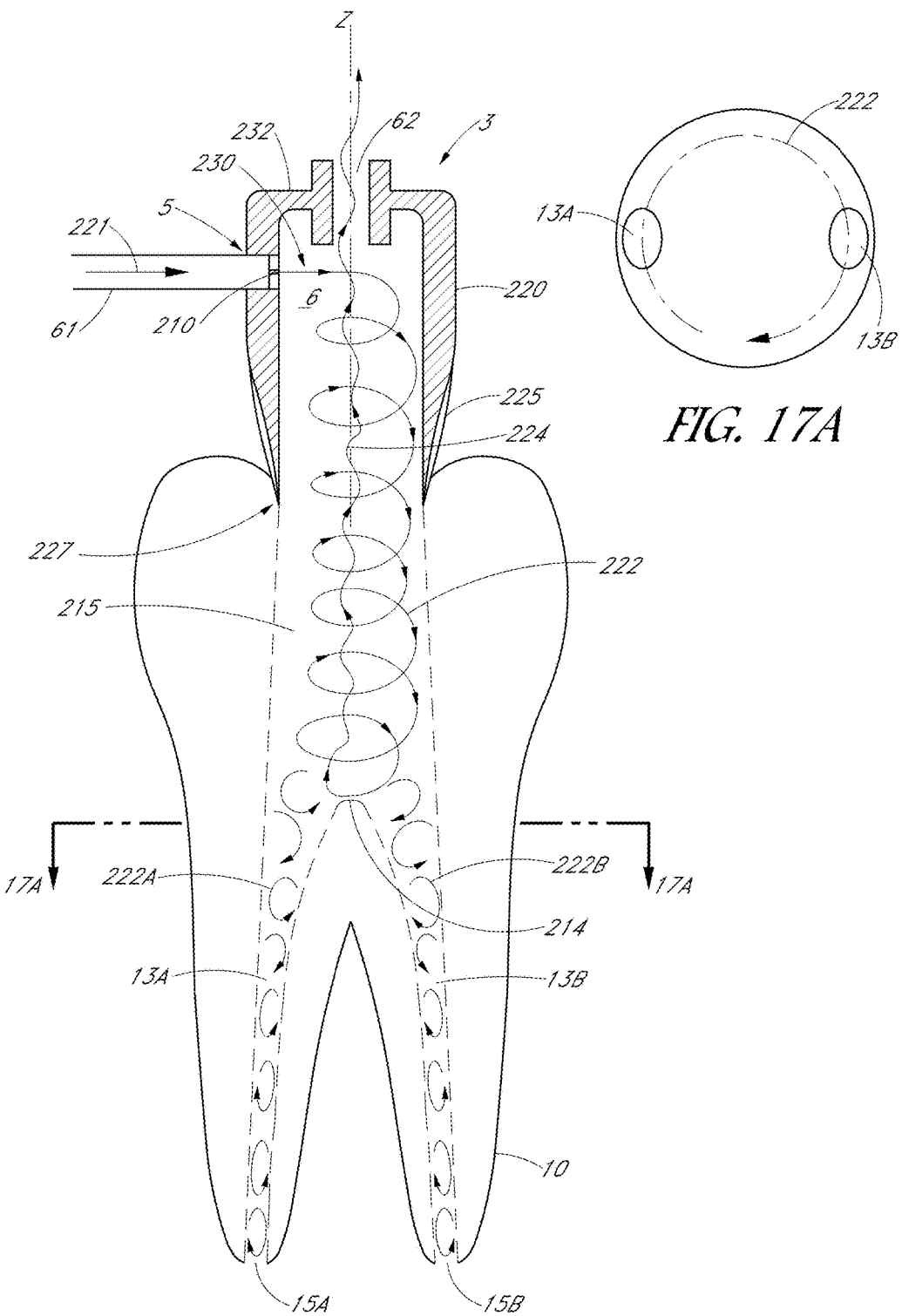
FIGS. 17 and 18 are schematic side sectional views of a tooth coupler configured to treat a tooth having multiple canals.
FIGS. 17A and 18A are top sectional views of the tooth couplers shown in FIGS. 17 and 18, respectively.
Figures 18, 18A:
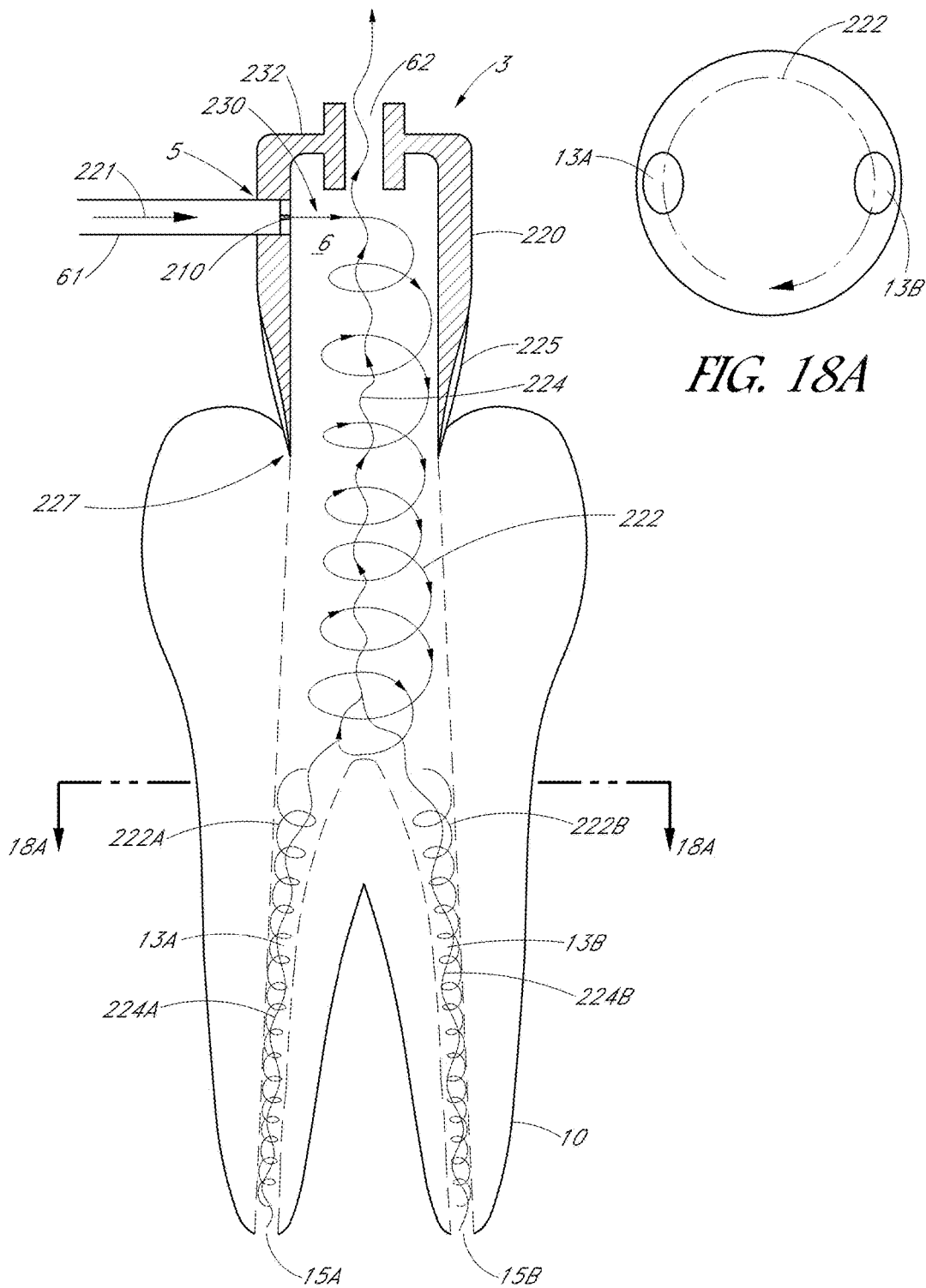

FIGS. 17 and 18 are schematic side sectional views of a tooth coupler 3 configured to treat a tooth 10 having multiple canals 13A, 13B (e.g., a molar tooth in some arrangements). FIGS. 17A and 18A are top sectional views of the arrangements shown in FIGS. 17 and 18, respectively. Unless otherwise noted, the tooth coupler 3 is the same as or substantially similar to the tooth coupler 3 illustrated and described above in connection with FIGS. 15-16B. The arrangements shown in FIGS. 17-18 illustrate that the tooth coupler 3 may be used to treat teeth that have various internal geometries, e.g., teeth with different number and shapes of root canals. As shown in FIG. 17, the tooth coupler 3 can be configured such that the rotating influent liquid 222 splits into the two canals 13A, 13B to clean each canal. The influent liquid 222 may rotate in a swirling path (e.g., about the central axes of the canals 13A, 13B) and/or may include rotation components about axes transverse to the central canal axes. The outgoing or return liquid 224 can return through the outlet 62 (which may include a venting system) near the center of the main canal after reaching a floor 214 of the pulp chamber 215. Thus, in FIG. 17, the liquid can turn around at the floor 214 of the pulp chamber 215 rather than within the canals 13A, 13B. As shown in FIG. 18, the system can be configured such that the outgoing or return liquid 224 returns through the outlet 62 by way of a central return path 224 and multiple return paths 224A, 224B in each of the canals 13A, 13B. As explained above, various parameters of the inlet fluid, the outlet, the shape of the chamber, etc., may be selected to achieve the flow patterns of FIGS. 17 and 18. Thus, depending on the geometry of the particular treatment tooth, the fluid flow paths may vary, but the tooth coupler 3 can still provide sufficient cleaning and irrigation of the treatment region. It should be appreciated that, although the pressure waves 23 are not illustrated in FIGS. 17-18, pressure waves still may be generated by interaction of the liquid jet with liquid in the chamber 6, as in the embodiment of FIGS. 15-16B.

Figure 19:
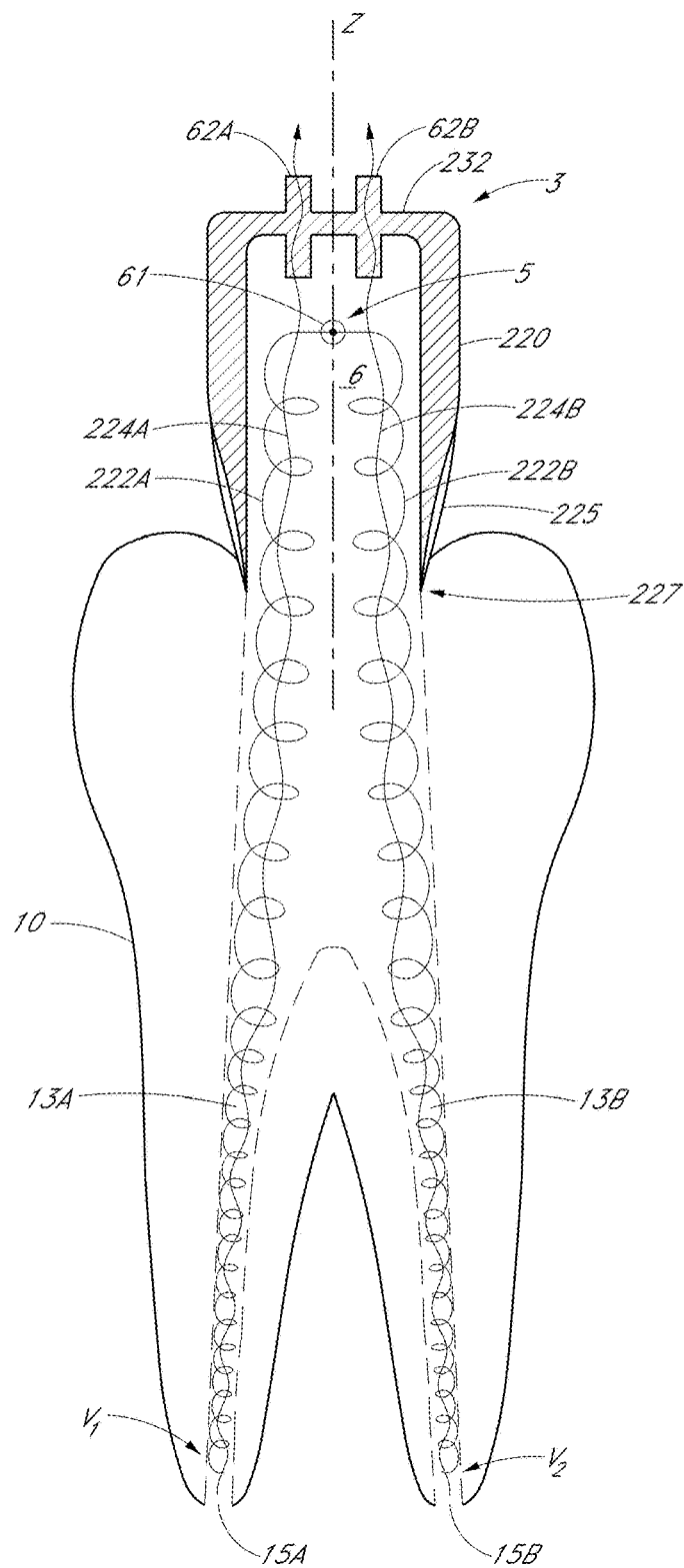
FIG. 19 is a schematic side sectional view of a tooth coupler configured to treat a tooth, according to another embodiment.
Figure 20:
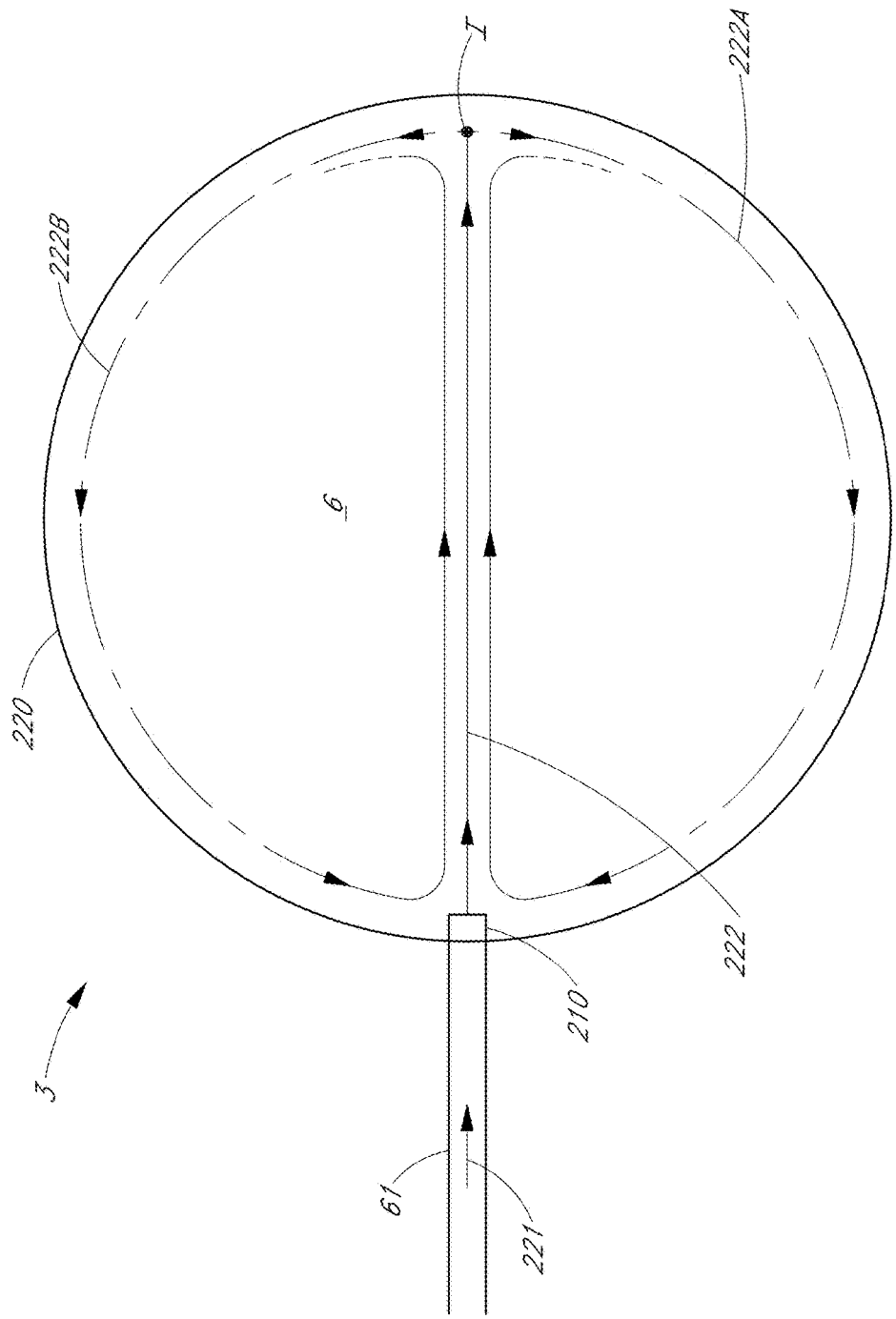
FIG. 20 is a schematic top sectional view of the tooth coupler shown in FIG. 19 that illustrates pressurized liquid entering a chamber through a nozzle.

FIG. 19 is a schematic side sectional view of a tooth coupler 3 configured to treat a tooth 10. FIG. 20 is a schematic top sectional view of the tooth coupler 3 shown in FIG. 19 that illustrates pressurized liquid 221 entering a chamber 6 through a nozzle 210. Unless otherwise noted, the tooth coupler 3 shown in FIGS. 19-20 is substantially similar to the tooth coupler 3 described above in connection with FIGS. 15-16B. For example, the tooth coupler 3 can include a side wall 220 and a top wall 232 that at least partially define a chamber 6. The tooth coupler 3 can comprise a fluid motion generator 5 that supplies liquid 221 to the chamber 6 by way of an inlet 61. The nozzle 210 can convert the liquid 221 to a jet which can generate fluid motion and/or pressure waves in the chamber 6 and tooth 10. The dimensions and other characteristics of the tooth coupler 3 may be substantially the same as those described above in connection with FIGS. 15-16B, except where denoted herein.

As shown in FIG. 19, the incoming fluid 221 (shown coming into the page in FIG. 19) can generate two influent rotational flow paths 222A, 222B passing through the chamber 6 of the tooth coupler 3, the pulp chamber, and into corresponding canal spaces 13A, 13B. Unlike in the embodiment of FIGS. 15-16B, however, the fluid motion generator 5 and inlet 61 may pass transverse to and through the central axis Z of the chamber 6. As shown in FIG. 20, the liquid 222 can pass through a central portion of the chamber and can impinge on an opposing surface at a location I on the wall 220 in or on the chamber 6. The impingement can induce bifurcated flow, which can cause two co-existing, influent rotational flows 222A, 222B in the chamber 6. The two rotational flows can act to clean multiple (e.g., two) root canal spaces 13A, 13B of a tooth 10. The two influent rotational flow paths 222A, 222B can pass through the root canal spaces 13A, 13B and, upon reaching respective return locations $V_1$, $V_2$ (which may be at or near the apical openings 15A, 15B), can return along respective central paths 224A, 224B near the center of the root canal spaces 13A, 13B and within the influent flow paths 222A, 222B. The outgoing or exiting fluid 224A, 224B can exit through one or more corresponding outlets. As shown in FIG. 19, for example, the tooth coupler 3 can include two outlets 62A, 62B that can draw the outgoing liquid 224A, 224B towards a waste reservoir. The central axis Z can be disposed between the outlets 62A, 62B. The rotational fluid flow disclosed herein can act to effectively treat (e.g., clean) a tooth 10.

Figures 21A, 21B:
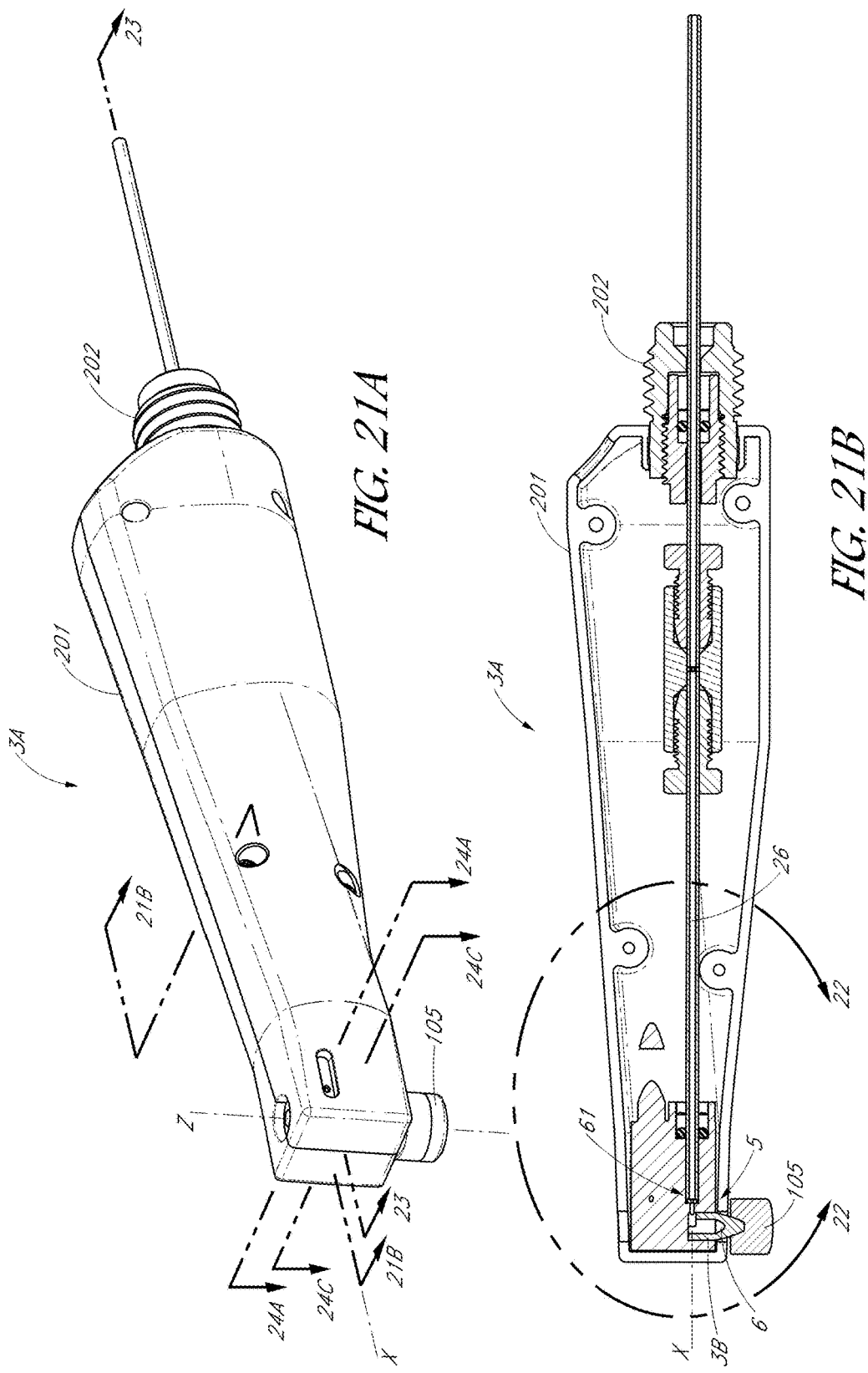
FIG. 21A is a schematic perspective view of a handpiece configured to clean a treatment region of a tooth.
FIG. 21B is a schematic side cross-sectional view of the handpiece shown in FIG. 21A taken along section 21B-21B.
Figure 22:
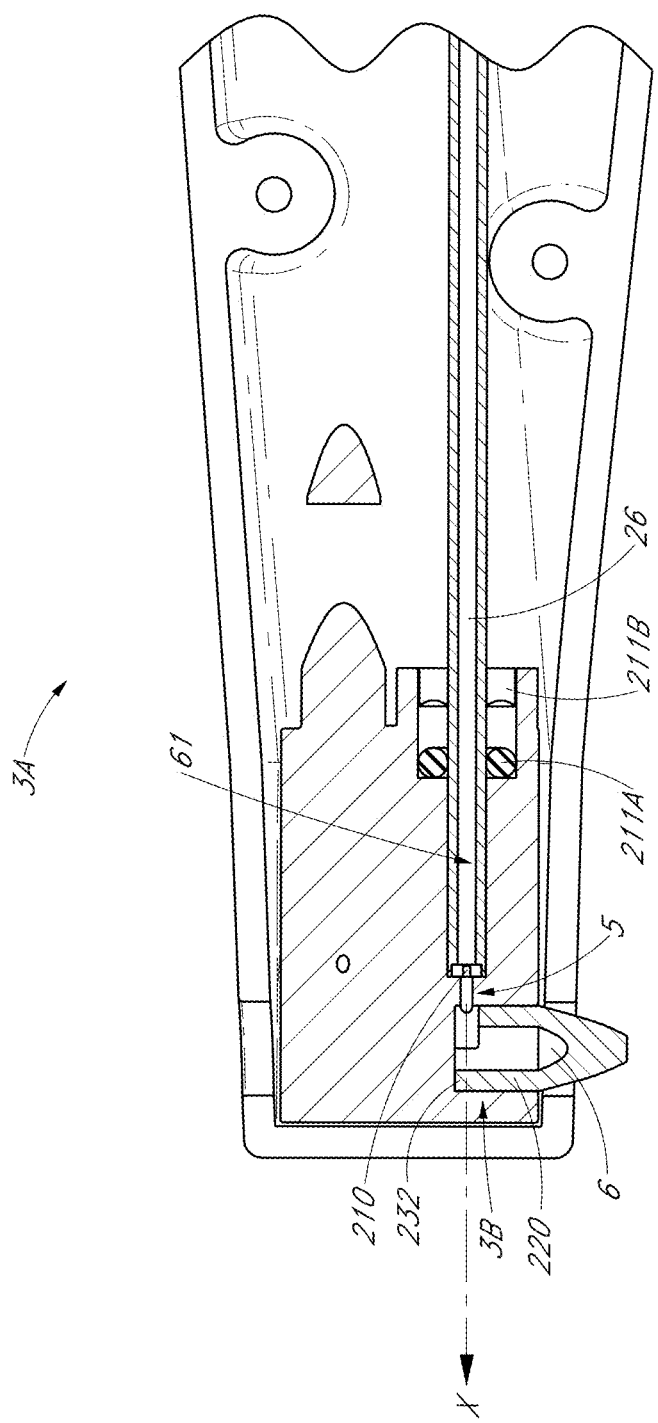
FIG. 22 is a magnified side cross-sectional view of FIG. 21B.
Figure 23:
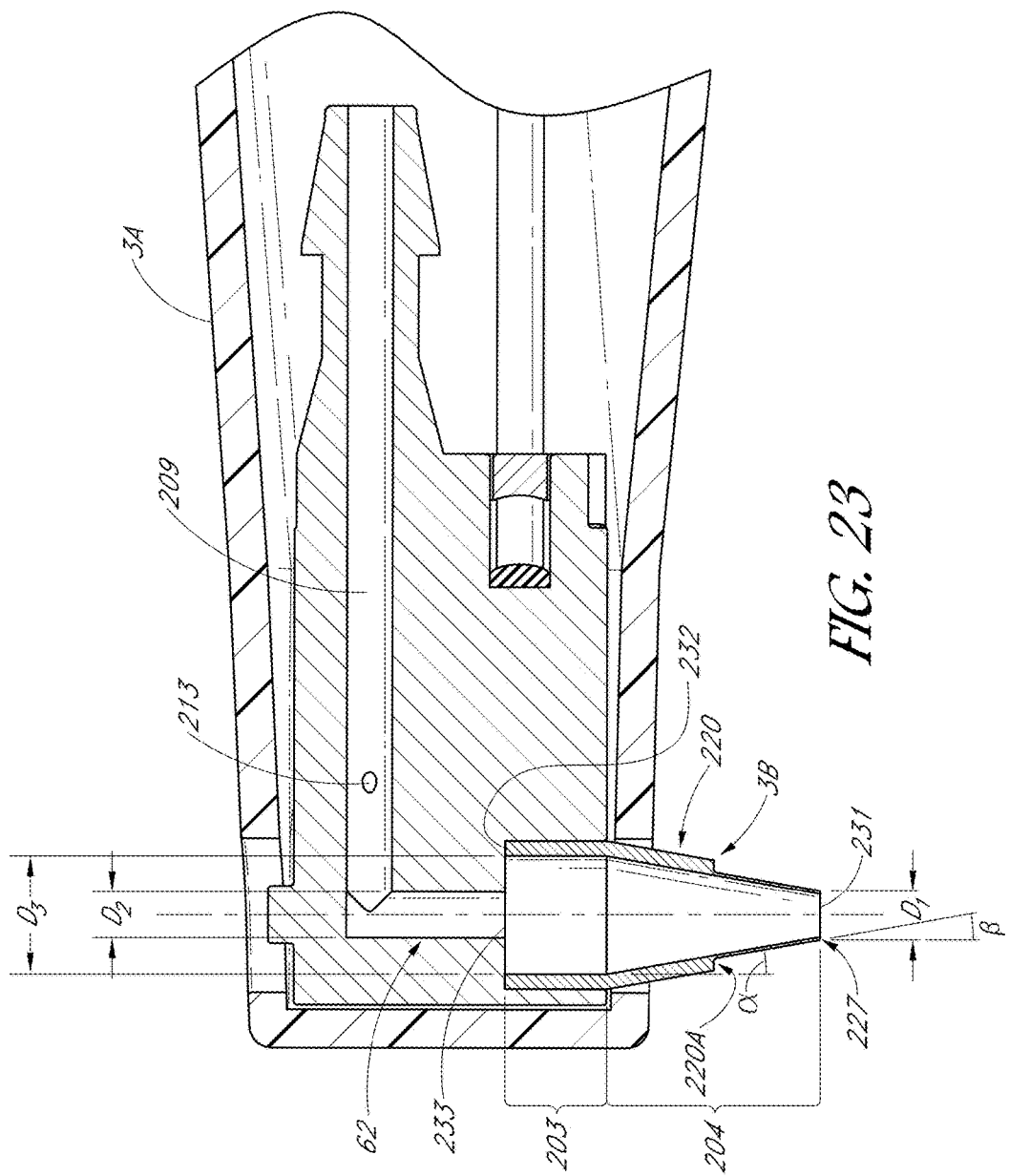
FIG. 23 is a schematic side-cross-sectional view of the handpiece of FIG. 21A taken along section 23-23.
Figure 24B:
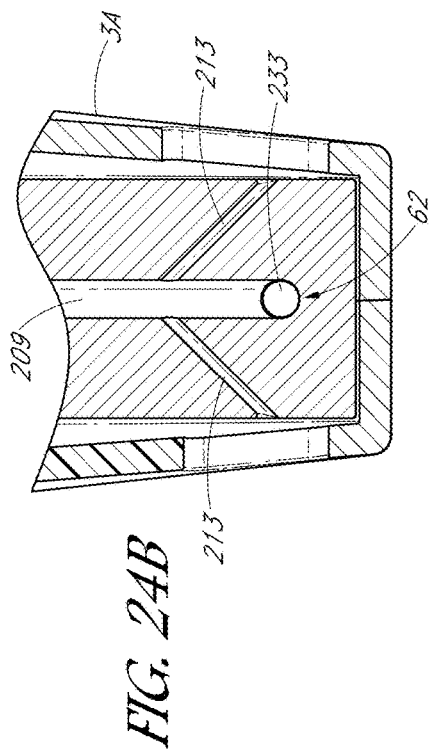
FIG. 24B is a top plan view of the section shown in FIG. 24A.
Figure 24C:
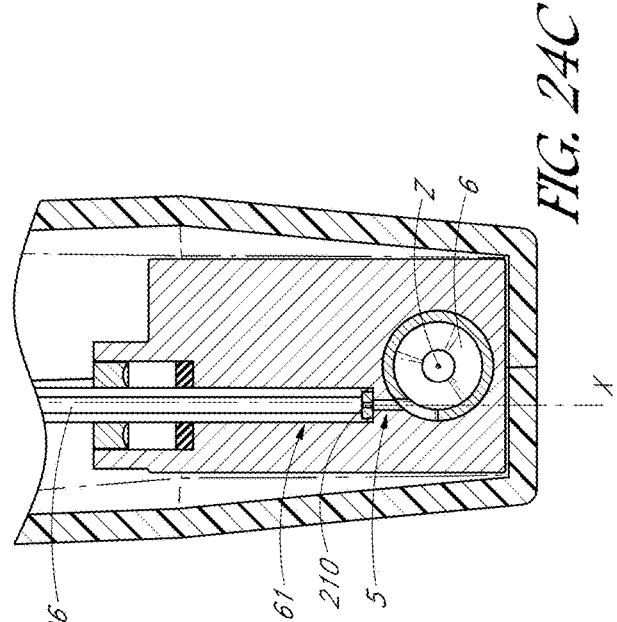
FIG. 24C is a top sectional view of a portion of the handpiece shown in FIG. 21A, taken along section 24C-24C.

FIGS. 21A-24C illustrate another embodiment of a system configured to clean a tooth. The embodiment of FIGS. 21A-24C may be similar to those described above in connection with FIGS. 15-16B. FIG. 21A is a schematic perspective view of a handpiece 3A configured to clean a treatment region (e.g., a root canal) of a tooth. FIG. 21B is a schematic side cross-sectional view of the handpiece 3A shown in FIG. 21A taken along section 21B-21B. FIG. 22 is a magnified side cross-sectional view of FIG. 21B. FIG. 23 is a schematic side-cross-sectional view of the handpiece 3A of FIG. 21A taken along section 23-23. FIG. 24A is a schematic, perspective top sectional view of a portion of the handpiece 3A shown in FIG. 21A, taken along section 24A-24A. FIG. 24B is a top plan view of the section shown in FIG. 24A. FIG. 24C is a top sectional view of a portion of the handpiece 3A shown in FIG. 21A, taken along section 24C-24C. The handpiece 3A shown in FIGS. 21A-24C may be configured to clean a root canal of a tooth, similar to the embodiment described above in connection with FIGS. 15-16B.

The handpiece 3A can include a body portion 201 and an interface member 202. During a treatment procedure, the clinician can hold the body portion 201 in his or her hand, and can press a sealing member 105 against the tooth to substantially seal the treatment region. In other embodiments, the clinician can attach the sealing member 105 to the tooth for the treatment procedure. The sealing member 105 may comprise a compressible material, such as foam, that can deform when applied to the tooth. The sealing cap 105 can be disposed about chamber 6. When the clinician presses the handpiece 3A against the tooth, the sealing cap 105 can be compressed to create a substantially sealed environment within the chamber 6 and/or tooth. The interface member 202 can removably engage fluid conduit(s) that extend from the console (not shown), e.g., including a high pressure supply line that supplies treatment liquid to the handpiece 3A. Additional details of the handpiece 3A (including the interface member 202) may be similar to those described in U.S. Patent Publication No. US 2015/0010882, the contents of which are incorporated by reference herein in their entirety and for all purposes.

As shown in FIGS. 21B-23, a sealing cap 3B (which may be the same as or similar to the tooth coupler 3 described in connection with FIGS. 15-16B) may be coupled with a distal portion of the handpiece 3A. As with the tooth coupler 3 of FIGS. 15-16B, the sealing cap 3B can include a tapered portion that tapers inwardly and distally. The distal-most end of the sealing cap 3B can be inserted into an access opening of a root canal. For example, when the clinician presses the sealing member 105 against the tooth, the sealing cap 3B can be urged into the access opening. When the distal portion 227 of the sealing cap 3B is disposed in the tooth, the distal end of the sealing member 105 is disposed proximal the distal end of the cap 3B. Further, a central axis Z can pass vertically through the center of the sealing cap 3B, as well as through the center of the distal portion of the handpiece 3A. In particular, the central axis Z lies on the plane at which the cross-section of FIG. 23 is taken. As with the embodiment of FIGS. 15-16B, liquid can be supplied to a chamber 6 along the X-direction, which can be generally transverse to (e.g., perpendicular to) and offset from the central axis Z. The X-direction along which liquid is directed can be oriented at an angle between 80° and 100°, or more particularly, between 85° and 95°, relative to the central axis Z. The X-axis or direction can lie on the plane at which the cross-section of FIG. 21B is taken.

The sealing cap 3B can comprise the chamber 6 that is defined at least in part by an upper wall 232 and a side wall 220 that extends transversely from the upper wall 232. When coupled to the tooth (e.g., pressed against the tooth or attached to the tooth), the chamber 6 can retain liquid and other materials during a treatment procedure. The upper wall 232 and side wall 220 may be integrally formed as a single component in some embodiments; in other embodiments the upper wall 232 and side wall 220 may comprise separate components that are connected or joined together. The side wall 220 can extend annularly (e.g., in a conical shape) relative to the upper wall 232 to at least partially define the chamber 6. It should be appreciated that the upper wall 232, as used herein, refers to the wall near the proximal end of the chamber 6; thus, during some treatments (such as those of upper teeth), the upper wall 232 may be disposed in a downward orientation In addition, as shown in FIG. 23, the sealing cap 3B or chamber 6 can include a distal portion 227 configured to contact the treatment region of the tooth (or a portion thereof). The distal portion 227 can define an access port 231 that provides fluid communication between the chamber 6 and the treatment region of the tooth (e.g., the root canal). In various arrangements, the distal portion 227 can taper radially inwardly towards the central axis Z of the sealing cap 3B and/or chamber 6. The central axis Z can be perpendicular to and comprise a central axis of the access port 231. For example, the side wall 220 can comprise a substantially conical taper that continuously and substantially linearly tapers inwardly and distally. Moreover, in some embodiments, the side wall 220 can comprise a shoulder portion 220A that defines a transition from a thick wall portion to a thin wall portion distal the thick wall portion. Thus, as shown in FIG. 23, a proximal portion of the chamber 6 can have an inner diameter $D_3$ (or other major dimension) and the access port 231 of the distal portion 227 can have an inner diameter $D_1$ (or other major dimension) that is smaller than $D_3$. The chamber 6 may also have a height h (see FIG. 15). The height h of the chamber 6 can be less than about 5 cm in various embodiments, e.g., less than about 2 cm.

For root canal treatments, the distal portion 227 can be inserted into an access opening of the tooth to provide fluid communication with the root canal. A sealing material may be applied between the distal portion 227 and the tooth to create or enhance a fluid seal such that liquid and/or debris does not escape from the chamber 6 and/or the tooth. As shown in FIG. 23, the distal portion 27 can be tapered such that the taper extends from an intermediate or proximal portion of the sealing cap 3B to the distal-most end of the cap 3B. For example, as shown in FIG. 23, the side wall 220 of the sealing cap 3B can comprise a generally straight or cylindrical portion 203 (along which the diameter $D_3$ remains substantially constant) and a tapered or conical portion 204 that tapers inwardly and distally from the straight portion 203 such that the inner diameter $D_1$ decreases along the distal direction. The tapered portion 204 can be disposed distal the straight portion 203 and can include the distal portion 227 and the distal-most end of the sealing cap 3B. Tapering the sealing cap 3B as shown in FIG. 23 can advantageously enable the clinician to conduct treatment procedures on teeth of any size, including very small teeth or teeth that have very small root canal spaces, e.g., the smallest human tooth that would be treated by the system. For example, the distal portion 227 can be sized to treat teeth with endodontic access openings having sizes (e.g., diameters or other major dimension) in a range of about 0.5 mm to about 5 mm. In some embodiments, an extension portion can be attached to and can extend distally from the distal portion 227 illustrated in FIG. 23. The extension portion can be further tapered (e.g., so as to fit within smaller teeth) in some arrangements. In other arrangements, the extension portion can be straight or cylindrical (without a taper) to be used for teeth that have a small chamber opening or for those that are recessed compared to adjacent teeth.

The inner diameter $D_1$ of the access port 231 may be smaller than the access opening of the tooth (e.g., the opening that the clinician forms to access the interior of the tooth), larger than the access opening, or the same size as the access opening. In some embodiments, advantageously, the outer diameter (and the inner diameter $D_1$) of the access port 231 may be smaller than the access opening so as to enable the distal portion 227 to be inserted into the access opening. In other embodiments, the outer diameter of the distal portion 227 may be the same size as or larger than the access opening. Accordingly, the distal portion 227 of the tooth coupler 3 may be inserted into the endodontic access opening such that the access port 231 and the access opening are substantially aligned and/or overlapping.

The inner diameter $D_1$ of the access port 231 defined by the distal portion 227 can be in a range of about 0.3 mm (+/−0.05 mm) to about 5 mm (+/−1 mm), e.g., in a range of about 0.5 mm (+/−0.1 mm) to about 3 mm (+/−0.5 mm), or in a range of about 1 mm (+/−0.1 mm) to about 2 mm (+/−0.1 mm). The distal portion 227 of the sealing cap 3B may have a wall thickness in a range of about 0.001 mm (+/−0.0001 mm) to about 5 mm (+/−1 mm), e.g., in a range of about 0.01 mm (+/−0.001 mm) to about 1 mm (+/−0.1 mm). Further, the outer diameter of the distal portion 227 (e.g., the inner diameter $D_1$ plus twice the wall thickness of the distal portion 227) may be in a range of about 0.5 mm (+/−0.1 mm) to about 5 mm (+/−1 mm), or in a range of about 0.5 mm (+/−0.1 mm) to about 3 mm (+/−0.5 mm) e.g., in a range of about 1 mm (+/−0.1 mm) to about 2 mm (+/−0.1 mm). The inner diameter $D_3$ of the proximal portion of the chamber 6 may be less than about 5 cm (+/−1 cm), e.g., less than about 1 cm (+/−0.1 cm). For example, the inner diameter $D_3$ may be in a range of about 0.5 cm (+/−0.1 cm) to about 1.5 cm (+/−0.3 cm), or in a range of about 0.7 cm (+/−0.1 cm) to about 1 cm (+/−0.1 cm).

Moreover, as shown in FIG. 23, the conical shape of the sealing cap 3B can have a tapering angle α that defines the amount by which an outside surface of the side wall 220 tapers inwardly and distally to the distal-most end of the tooth coupler 3. The outside surface tapering angle α can be in a range of about 0.5° (+/−0.1°) to about 65° (+/−1°), e.g., in a range of about 0.5° (+/−0.1°) to about 20° (+/−1°). In some embodiments, the outside tapering angle α can be in a range of about 1° (+/−0.1°) to about 15° (+/−1°), or in a range of about 1° (+/−0.1°) to about 10° (+/−1°). The outside tapering angle α can advantageously allow the sealing cap 3B to fit within the smallest access opening. For example, the clinician can insert the tapered distal portion 227 within the access opening until the tapered outer surface contacts the walls of the root canal. In addition, the conical shape of the sealing cap 3B can have an inner tapering angle β that defines the angle by which an inner surface of the wall 220 tapers. Advantageously, the inner tapering angle β can enable the access opening 231 (with inner diameter $D_1$) to be smaller than the inner diameter of the proximal portion of the chamber (e.g., $D_3$). Such a smaller opening can result in a smooth transition of flow from the proximal portion of the chamber 6 (e.g., portion 203) to the distal portion 227. For example, the increased space at the proximal portion of the chamber can give the influent flow 222 more room to smooth out before entering the tooth, and can prevent or reduce interference between the influent flow 222 and the outgoing flow 224. The inner surface tapering angle β can be in a range of about 0.5° (+/−0.1°) to about 65° (+/−1°), e.g., in a range of about 0.5° (+/−0.1°) to about 20° (+/−1°). In some embodiments, the inner tapering angle β can be in a range of about 1° (+/−0.1°) to about 15° (+/−1°), or in a range of about 1° (+/−0.1°) to about 10° (+/−1°).

As shown in FIGS. 21B-22, the handpiece 3A can comprise a fluid inlet 61 that includes a high pressure supply line 26 configured to convey a pressurized treatment fluid to the treatment area. A fluid motion generator 5 (which can also be a pressure wave generator) can be disposed near a distal portion of the handpiece 3A and in fluid communication with the supply line 26. The fluid motion generator 5 can comprise a nozzle 210 configured to convert the pressurized fluid to a liquid jet, e.g., a coherent, collimated jet, or a planar jet. The chamber 6 can be disposed distal the fluid motion generator 5. A pumping system (e.g., in the console) can be configured to drive treatment fluid along the supply line 26 to the fluid motion generator 5. In addition, a first fluid seal 211A and a second fluid seal 211B can be disposed about the high pressure supply line 26 proximal the nozzle 210. The seals 211A, 211B can prevent air from being entrained in the liquid that forms the jet and/or can prevent liquids from leaking from the handpiece.

The fluid motion generator 5 (which may also be a pressure wave generator, as described above) can be disposed on and/or through the side wall 220 of the sealing cap 3B. The fluid motion generator 5 can supply liquid to the chamber 6 so as to generate rotational liquid motion in the chamber 6. The supplied liquid can comprise a degassed liquid as explained herein. The supplied liquid can be any suitable type of treatment fluid, including, e.g., water, EDTA, bleach, obturation material (for filling procedures), etc. For example, the fluid inlet 61 can supply pressurized liquid to the chamber 6. As with the embodiment of FIG. 15, the pressurized liquid can be passed through the nozzle 210 to generate a coherent, collimated liquid jet. In various embodiments of the nozzle 210, an orifice or opening in the nozzle may have a diameter $d_1$ at an inlet or a diameter $d_2$ at an outlet that may be in a range from about 5 microns to about 1000 microns. Other diameter ranges are possible. In various embodiments, one or both of the diameters $d_1$ or $d_2$ of the nozzle opening may be in a range from about 10 microns to about 100 microns, a range from about 100 microns to about 500 microns, or range from about 500 microns to about 1000 microns. In various other embodiments, one or both of the orifice diameters $d_1$ or $d_2$ may be in a range of about 40-80 microns, a range of about 45-70 microns, or a range of about 45-65 microns. In one embodiment, the orifice diameter $d_1$ is about 60 microns. The ratio of axial length $L_1$ to diameter $d_1$, the ratio of axial length $L_2$ to diameter $d_2$, or the ratio of total axial length $L_1+L_2$ to diameter $d_1$, $d_2$, or average diameter $(d_1+d_2)/2$ may, in various embodiments, be about 50:1, about 20:1, about 10:1, about 5:1, about 1:1, or less. In one embodiment, the axial length $L_1$ is about 500 microns. Additional examples of nozzles may be found in U.S. Patent Publication No. US 2011/0117517, which is incorporated by reference herein.

As shown in the top sectional view of FIG. 24C, the fluid motion generator 5 may be off-center or asymmetric relative to the sealing cap 3B. For example, the fluid inlet 61 and the nozzle 210 can be offset relative to the central axis Z of the tooth coupler 3. In FIG. 24C, the fluid motion generator 5 can be radially offset relative to the central axis Z and can be directed in a direction X transverse to the central axis Z. As shown in FIG. 23, the central axis Z can pass distally along the height of the sealing cap 3B through the center of the access port 231, e.g., the central axis Z can be transverse to the access port 231 at or near the center of the access port 231. The central axis Z can also define the central longitudinal axis of the conical shape of the sealing cap 3B, e.g., transverse to the radial direction of the conical shape.

The pressurized liquid supplied by the fluid motion generator 5 can induce liquid circulation in the chamber 6 of the sealing cap 3B. For example, as with the embodiment of FIGS. 15-16B, the fluid motion generator 5 (e.g., the inlet 61 and/or nozzle 210) can generate a swirling, rotational motion of influent liquid 222 about the central axis Z of the chamber, which can be transverse to (e.g., substantially perpendicular to in some arrangements) the X axis along which the liquid is introduced into the sealing cap 3B. In some arrangements, rotational or circulatory motion can also be induced about other directions, e.g., about axis parallel to the direction of fluid introduction. As with the embodiment of FIGS. 15-16B, the influent liquid can introduce rotational flow near and/or along walls of the canal spaces as the rotating liquid enters the canal spaces.

As with the embodiment of FIGS. 15-16B, in some embodiments, the pressurized liquid can pass through the nozzle 210 and can emerge as a coherent, collimated liquid jet, which can act as a fluid motion generator and/or pressure wave generator, as explained herein. In some embodiments, the supplied liquid may comprise a stream of liquid that is not a jet. After entering the chamber 6, the liquid can impact and/or slide along the side wall 220 of the sealing cap 3B. The fluid motion generator 5 can be angled such that, upon impingement of the liquid against the wall 220, a rotating sheet of influent liquid is generated in which the sheet of influent liquid rotates in a swirling motion about the central axis Z and travels distally along the side wall 220 in the chamber 6 towards the opening 227 in the sealing cap 3B. The rotating sheet of influent liquid can continue downward along the inner walls of the root canal(s) towards the apical opening of the tooth. The rotating liquid can effectively and efficiently clean the entire root canal space. For example, the rapid, bulk fluid motion of the influent liquid can interact with diseased matter in the root canal and can dislodge or otherwise remove the diseased matter from the root canal.

As shown in FIGS. 16 and 23, it can be advantageous to orient the fluid motion generator 5 such that sufficient rotational influent flow 222 (see FIGS. 15 and 16) is provided in the chamber 6 and treatment region. For example, the inlet 61 and nozzle 210 can be directed along the X-direction, which can be transverse to (e.g., perpendicular to) the central axis Z. The X-direction can be generally tangent to the outer edge of the side wall 220. The X-direction may be slightly angled relative to the tangent T of the side wall 220 at the location at which the inlet 221 and nozzle 210 intersect the wall 220 of the chamber 6 (see FIG. 16). For example, the X-axis along which the ingoing liquid 222 is directed may be at an inlet angle θ relative to the tangent T (see FIG. 16). The inlet angle θ can be at or close to zero. For example, θ can be in a range of about 0° to about 15°, or in a range of about 0° to about 10°. In some embodiments, the angle θ can be in a range of about 1° to about 10°, or in a range of about 1° to about 5°. The fluid motion generator 5 can also be disposed such that the center of the influent stream 222 enters the chamber 6 at a distance δ, from the outermost edge of the wall 220 (see FIGS. 15 and 16, and the description thereof). The distance δ can be relatively small, e.g., in a range of about 5 μm to about 2 mm, or in a range of about 15 μm to about 40 μm. As shown in FIGS. 15-16, 23, and 24C, the fluid motion generator 5 can be oriented such that the X-axis is directed perpendicular to the central axis Z such that the X-axis is substantially horizontal relative to the chamber 6. In some embodiments, the X-axis can be directed distally to assist in generating downward or distal rotating influent flow into the treatment region.

Furthermore, as with the embodiment shown in FIG. 15, in the embodiment of FIGS. 21A-14C, when the liquid jet emerges from the nozzle 210, the jet can interact with treatment liquid in an interaction zone near the interface between the nozzle 210 and the chamber 6. As explained herein, the liquid jet can pass through the liquid and can generate pressure waves (see FIGS. 15-16B) that propagate through the liquid in the chamber 6 and root canal of the tooth. The pressure waves can propagate from the interaction zone distally into the canal of the tooth. The pressure waves can comprise multiple frequencies that can cause liquid to flow and deliver energy into small spaces, cracks, and tubules of the tooth to substantially clean the tooth. In some arrangements, the bulk flow of influent liquid may act to remove larger amounts of diseased material from relatively large spaces of the tooth, and the pressure waves can flow into smaller spaces that may not be exposed to the bulk flow of liquid. The combination of rotating influent liquid and pressure waves can act to substantially clean the tooth, including large and small spaces of the tooth that may include different types and sizes of organic and inorganic matter. During an obturation or filling procedure, the rotational flow and/or pressure waves can act to substantially fill the treatment region.

FIG. 23 illustrates a sectional view of the outlet 62 which extends along the central axis Z of the sealing cap 3B and chamber 6. As with the embodiment of FIGS. 15-16B, it can be important to enable the influent liquid to be removed from the treatment region to ensure that waste materials (e.g. dislodged debris, etc.) are irrigated from the tooth and/or to enhance the fluid rotation at the treatment region. Accordingly, the fluid outlet 62 can be disposed in and/or through the top wall 232 of the sealing cap 3B. The fluid outlet 62 can comprise a suction port 233 defining an opening between the chamber 6 and an outlet passage 209 (which may be one of the conduit(s) 4 described above) that conveys outgoing fluid to the waste system by way of a suction pump. The suction pump can apply suction to the outlet passage 209 and outlet 62 to draw fluids out of the chamber 6 and towards a reservoir outside the sealing cap 3B.

The fluid outlet 62 or suction port 233 may have an inner diameter $D_2$ (or other major dimension) that is equal to or smaller than the inner diameter $D_1$ of the distal portion 227 of the sealing cap 3B. In FIG. 23, the inner diameter $D_2$ is smaller than $D_1$.

For example, in some embodiments, the inner diameter $D_2$ of the suction port 233 may in a range of about 0.1 mm to about 5 mm, 0 e.g., in a range of about 0.1 mm to about 2 mm. The fluid outlet 62 can be disposed at or near the center of the top wall 232 of the sealing cap 3B. As shown in FIG. 23, the central axis Z of the sealing cap 3B and access port 231 can pass through both the access port 231 of the distal portion 227 and the suction port 233 of the outlet 62. The central axis Z can be perpendicular, or substantially perpendicular, to the suction port 233. For example, the central axis Z can be disposed at about a 90° angle (between 70° and 110°, or more particularly between 80° and 100°, or more particularly between 85° and 95°) relative to the suction port 233. For example, in some embodiments, the access port 231 can define a plane that is transverse to (e.g., perpendicular to) the central axis Z, and the central axis Z can pass through the center of the access port 231 and through at least a portion of the suction port 233. In some embodiments, the suction port 233 can define a plane that is transverse to (e.g., perpendicular to) the central axis Z, and the central axis Z can pass through the center of the suction port 233 and through at least a portion of the access port 231. In some embodiments, the access port 231 and the suction port 233 define respective planes that are both transverse to (e.g., perpendicular to) the central axis Z, and the central axis Z can pass through both the access port 231 and the suction port 233. In some embodiments, the central axis Z can pass through the center of both the access port 231 and the suction port 233. The suction port 233 can be symmetric about the central axis Z in some embodiments. A center of the suction port 233 can lie on the central axis Z.

The outlet 62 and chamber 6 can be configured such that the influent liquid turns back proximally at a return location to be drawn out of the chamber 6, as explained above in connection with FIGS. 16A-16B. At the return location V (which may be at or near the apical opening), the treatment liquid can turn back towards the sealing cap 3B in an outgoing fluid path. The outgoing fluid path may be different from the flow path or pattern of the influent liquid. For example, the returning or outgoing flow path can comprise rotational (or semi-planar) flow near the center of the canal spaces and/or within the swirling influent flow path. In some embodiments, the outgoing flow can comprise a spiral flow path that passes inside the rotating influent liquid. The induced outward flow can be carried outside the treatment region to carry waste and other matter away from the treatment region (e.g., outside the canal and tooth). Moreover, the suction provided by the outlet 62 and/or the rotating influent liquid can provide a negative pressure at the apical opening in which treatment liquid and/or waste is prevented from passing through the apical opening, which can reduce the risk of infection and/or pain to the patient. The outgoing liquid can pass through the suction port 233 and can be drawn to the waste reservoir through the outlet line 209 by the suction pump.

Figure 24A:
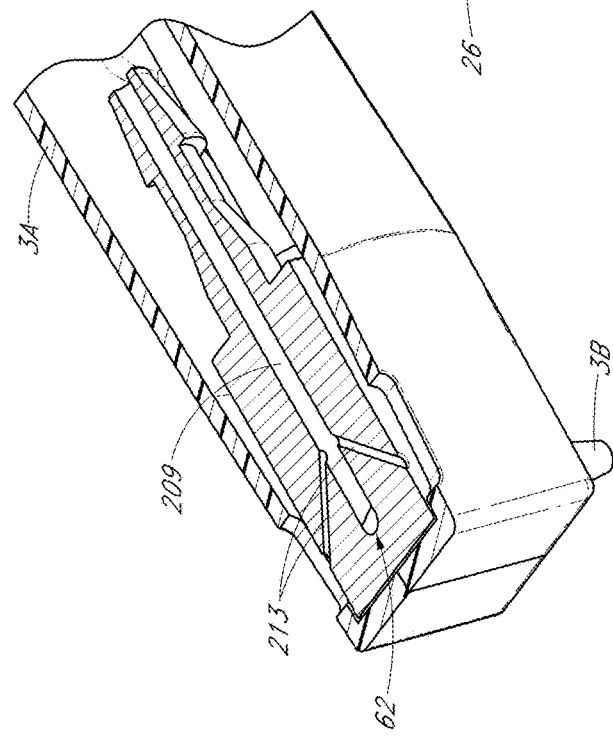
FIG. 24A is a schematic, perspective top sectional view of a portion of the handpiece shown in FIG. 21A, taken along section 24A-24A.

In addition, as shown in the side sectional view of FIG. 23 and in the top sectional views of FIGS. 24A and 24B, the handpiece 3A can include one or more vents 213. The vent 213 can be configured to permit fluid from the chamber 6 to flow out of the vent 213, for example, if the fluid pressure becomes too large in the chamber 6. The vent 213 can also act as a relief valve to inhibit over-pressurization of the chamber 6. the vent 73 may be configured to permit air to enter the fluid outlet 72 and be entrained with fluid removed from the tooth chamber 65. For example, as shown in FIGS. 24A-24B, the vents 213 may be positioned and oriented such that ambient air flows into the fluid outlet 62 in the direction of the fluid flow in the outlet 62. In such embodiments, the flow in the fluid outlet 72 includes both fluid from the chamber 6 and ambient air. In some implementations, the vent 213 is disposed near the entry point of fluid into the outlet 62, e.g., within a few millimeters, which may make it easier for fluid to flow from the chamber 6 if the pressure therein rises too high. In various embodiments, a plurality of vents 213 may be used such as, two, three, four, or more vents. The vents 213 may be sized, shaped, positioned, and/or oriented to allow fluid to flow from the chamber 6 while inhibiting air from entering the chamber 6. Additional examples of vent assemblies that can be used in conjunction with the handpiece 3A of FIGS. 21A-24C can be similar to the vents 73 described in, e.g., U.S. Patent Publication No. 2012/0237893, which is incorporated by reference herein in its entirety and for all purposes.

In the embodiment illustrated in FIGS. 24A-24B, two vents 213 are illustrated. The vents 213 are angled towards the direction of flow in the outlet passage 209 such that air is directed in the outward flow of fluid rather than towards the chamber 6. The vents 213 can be positioned downstream of the suction port 233 such that the suction port 233 is between the chamber 6 and the vents 213. Moreover, as shown in FIG. 24A-24B, the vents 213 can comprise a channel or lumen that extends from an outer surface of the handpiece 3A to the outlet passage 209. The vents 213 can be symmetric with respect to outlet passage 209 or can be distributed alongside the outlet passage 209. The number of vents can be combination of even or odd numbers (e.g., 2, 3, 4, etc.). The angle between vent axes and the outlet passage 209 can vary between 0.1 to 90 degrees (perpendicular), or between 0.1 to 179.1 degrees.

Figure 24D:
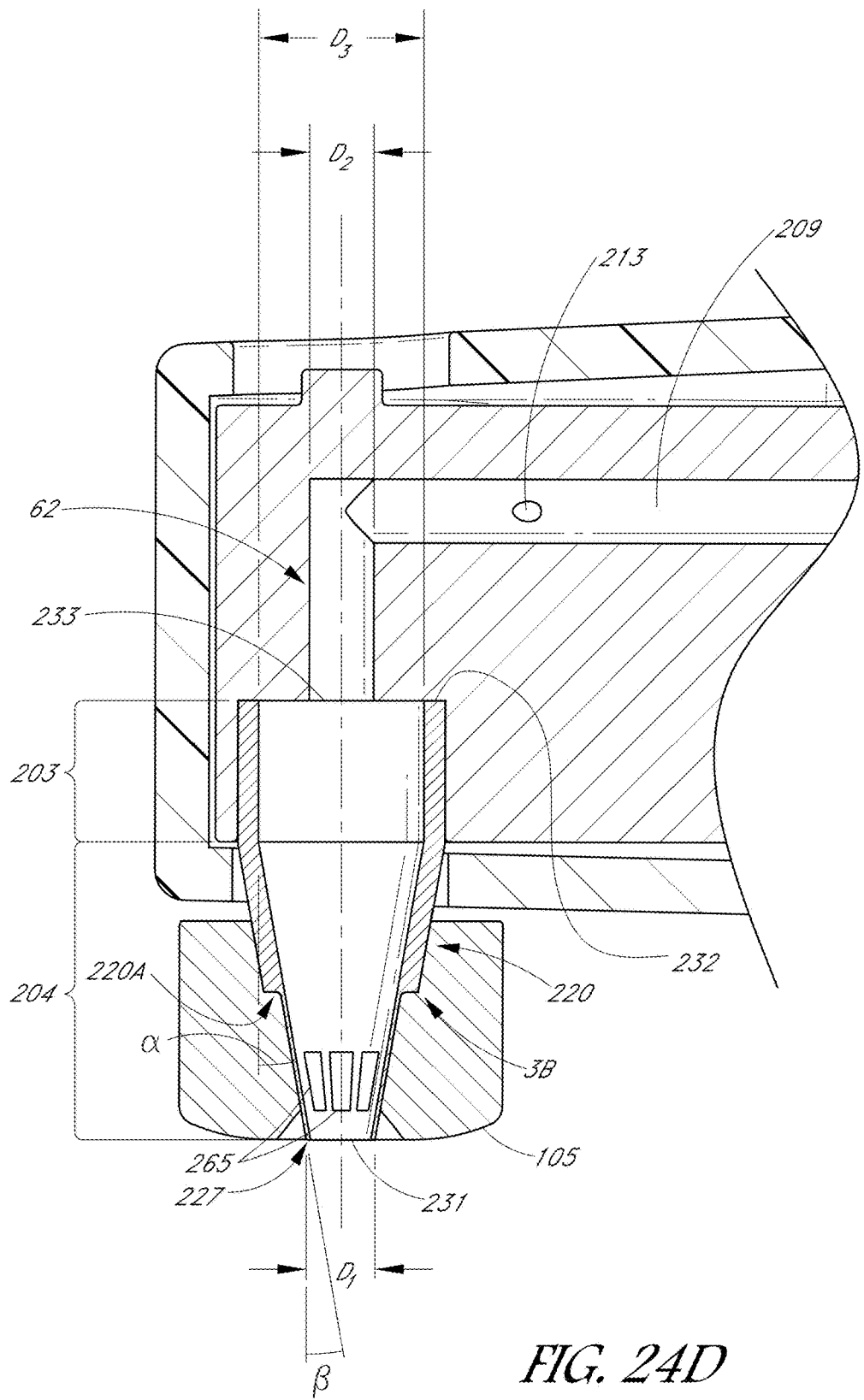
FIG. 24D is a side sectional view of the handpiece shown in FIGS. 21A-24C, in accordance with another embodiment.

FIG. 24D is a side sectional view of the handpiece 3A shown in FIGS. 21A-24C, in accordance with another embodiment. The handpiece 3A can be the same as that shown and described in connection with FIGS. 21A-24C, except in FIG. 24D, one or more wall openings 265 are provided in the side wall 220 of the tooth coupler 3. As shown, the wall openings 265 can be disposed at or near the distal portion 227. During a treatment procedure, some treatment fluid can leave the chamber 6 through the wall openings 265 to flow along the walls of the root canal, while the rest of the fluid passes from the chamber 6 to the treatment region by way of the access port 231. By dispensing fluid to the treatment region through the wall openings 265 in addition to the access port 231, the effectiveness of a cleaning procedure can be improved. For example, the portion of the tooth adjacent the wall 220 of the chamber can be cleaned by the fluid that passes through the openings 265. In addition, the openings 265 can also be provided on the distal portion 227 of the tooth coupler 3 described and illustrated in connection with FIG. 15.

Thus, in various embodiments disclosed herein, high momentum fluid can be introduced at the top of the fluid chamber 6 by way of a high velocity treatment fluid stream, which can be formed by the nozzle 210. The stream of liquid can pass in a direction transverse (e.g., almost or substantially perpendicular) to the central axis of the chamber 6, e.g., the axis that is directed towards the tooth during treatment. The stream may be transverse the longitudinal axis of the chamber 6 and may also be offset relative to the center of the chamber 6 such that the stream eccentrically flows relative to the chamber 6. The high momentum, thin treatment fluid stream can then travel downward towards the tooth while rotating inside the chamber 6. The chamber 6 may be straight or slightly converge to reduce the diameter of the chamber 6. For example, the chamber 6 can be tapered in various arrangements. The rotational high momentum fluid exits the chamber 6 through a bottom access port 231 that is large enough to ensure efficient delivery of the high momentum fluid into the tooth and allow for the exhaust path, yet small enough to ensure adequate interaction and sealing on all potential anatomies and geometries that the teeth may have. An interface mechanism (e.g., the sealing member 105) can allow the sealing cap 3B and chamber 6 to be applied onto the tooth in such a way that it allows the rotational fluid to enter the tooth with minimum interruption or loss and maintain the safety and efficacy of treatment. The sealing member 105 provides a seal both to prevent air from entering the tooth and chamber 6 and to minimize the amount of liquid leaking out or chamber and tooth. After exiting the fluid chamber 6, the high momentum treatment fluid generates a high shear stress rotational flow inside the root canal cavity or treatment region. The high shear stresses generated on the pulp tissue and the dentin walls contribute to efficient cleaning of the root canal. The momentum carried by the fluid introduced into the tooth can be selected to ensure deep penetration into the root canal system, while ensuring a safe delivery. At the point of deepest penetration, the rotational flow may converge to the centerline of rotation, and flow reversal occurs at the return point V which allows for evacuation of debris and waste fluid through the center of the influent rotational flow. An inner vortex may be formed that flows through the evacuation opening located at the center of the top of the chamber 6. The evacuation opening can be connected to an external vacuum that is used in the collection of waste fluid. The evacuation vacuum can also combined with a set of vents 213 that are sized in order to maintain a safe pressure inside the fluid chamber 6 and consequently the treatment tooth.

In addition to the high momentum, high shear stress fluid being supplied to the tooth, wide spectrum (broadband) pressure waves can be generated through the interactions of the high velocity liquid jet. The treatment fluid may be degassed and contain chemicals to accelerate the rate of cleaning. The mechanism can also be used for obturation or filling of the treatment region.

The treatment fluid supplied to the chamber 6 in FIGS. 21A-24D may comprise any suitable treatment fluid, such as a cleaning liquid or an obturation material. For example, in cleaning procedures, the supplied cleaning liquid can rotate as shown in FIGS. 16A and 16B, and can interact with diseased matter to clean the tooth. In obturation procedures, the supplied obturation material can similarly rotate as shown in FIGS. 16A and 16B, and can substantially fill the treatment region (e.g., a treated root canal, a treated carious region, etc.). In addition, although not shown in FIGS. 21A-24D, the chamber 6 or sealing cap 3B can have one or more additional openings that can supply obturation material (or a component of an obturation material) to the treatment region. The additional openings can be used to fill the treatment region.

Figure 25A:
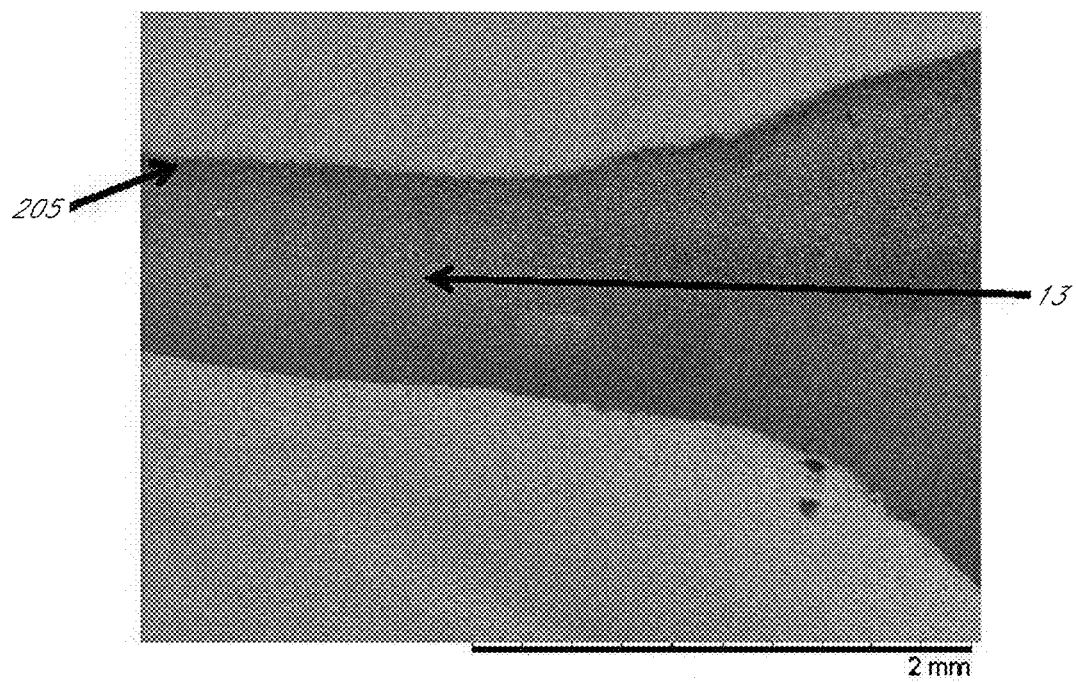
FIGS. 25A-25B are scanning electron microscope (SEM) images of a tooth after completion of a treatment procedure using the handpiece shown in FIGS. 21A-24C.
Figure 25B:
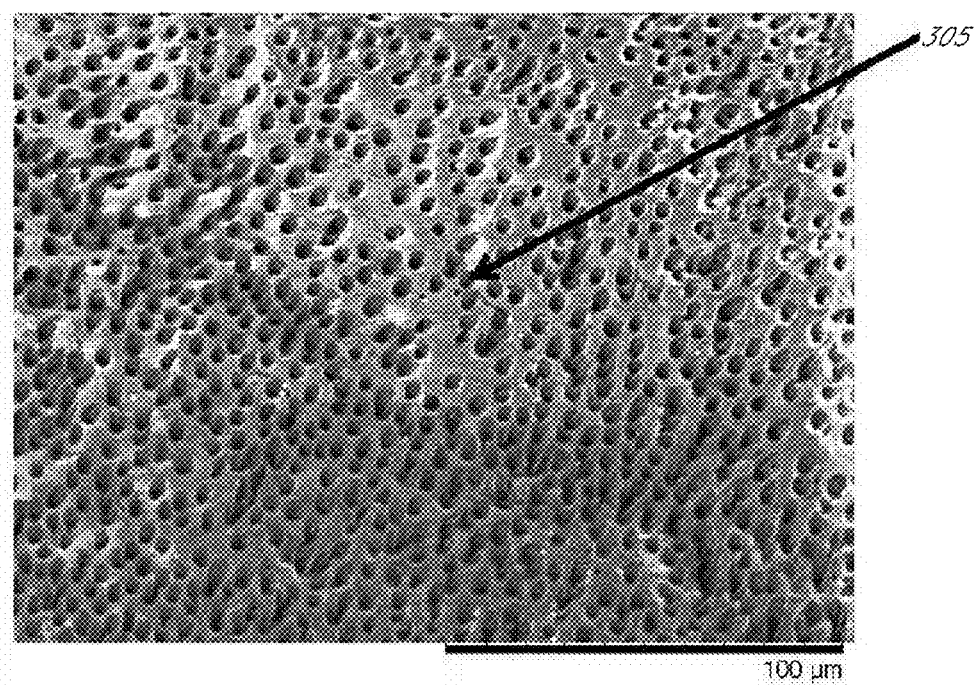

FIGS. 25A-25B are scanning electron microscope (SEM) images of a tooth after completion of a treatment procedure using the handpiece 3A shown in FIGS. 21A-24C. As shown in FIG. 25A, for example, the handpiece 3A has substantially cleaned the root canal 13 of diseased materials. In FIG. 25B, tubules 305 are also shown to be substantially clean. As explained herein, the combination of rotational fluid motion and pressure waves can substantially clean the entire treatment region.

XI. Examples of Various Embodiments.

In one embodiment, an apparatus for treating a tooth is disclosed. The apparatus can include a chamber having an access port which places the chamber in fluid communication with a treatment region of the tooth when the chamber is coupled to the tooth, the access port having a central axis. The apparatus can include a fluid motion generator being arranged to generate rotational fluid motion in the chamber. The apparatus can include a suction port communicating with the chamber on a side of the chamber opposite of the access port, and being disposed relative to the access port such that the central axis of the access port passes through the suction port. In some embodiments, the suction port can be disposed at or near a center of a top wall of the chamber. The suction port can be symmetric about the central axis. A center of the suction port can lie on the central axis. The fluid motion generator can generate a swirling influent fluid path around the central axis. The apparatus can be configured to draw outgoing fluid from the treatment region to the suction port in a path that flows inside the swirling influent fluid path with a suction force applied to the suction port. The central axis can lie substantially perpendicular to the suction port. The suction port can have a major dimension that is not greater than a major dimension of the access port. The suction port can be smaller than the access port. The fluid motion generator can be disposed on a side wall of the chamber and can be oriented to direct liquid in a flow direction that lies generally transverse to the central axis of the access port. The flow direction may not intersect the central axis. The fluid direction can be generally tangent to a wall of the chamber. The suction port can be disposed on a top wall of the chamber that opposes the access port. The chamber can comprise a distal portion that defines the access port, the distal portion being sized and shaped to be inserted into an access opening of the tooth, and tapering distally towards the central axis. An inner surface of the distal portion can taper distally towards the central axis. An outer surface of the distal portion can taper distally towards the central axis. The chamber can comprise a cylindrical portion coupled to or formed with the distal portion, the cylindrical portion being disposed between the distal portion and the suction port. The distal portion can taper at an angle in a range of about 0.5° to about 20°. The distal portion can taper at an angle in a range of about 1° to about 10°. The fluid motion generator can comprise a liquid jet device. The liquid jet device can comprise an inlet to receive pressurized liquid and a nozzle being configured to convert the pressurized liquid to a coherent, collimated liquid jet. At least one vent can be disposed downstream of the suction port such that the suction port lies between the chamber and the vent along an outlet passage that extends from the suction port. At least one additional vent that communications with the outlet passage can be downstream of the suction port. Each vent can be disposed along the outlet passage and can be angled towards the direction of fluid outflow in the outlet passage. A handpiece and a tooth coupler can be at a distal portion of the handpiece, the chamber being disposed within the tooth coupler. A sealing member can extend from the tooth coupler, the sealing member being configured to seal the treatment region. A console can be in fluid communication with the chamber, the console comprising one or more pumps to drive fluid to and aspirate fluid from the chamber. The fluid motion generator can be a pressure wave generator configured to propagate pressure waves through the treatment region to substantially clean the treatment region. An outer diameter or major dimension of the access port can be in a range of about 0.5 mm to about 5 mm. The outer diameter or major dimension of the access port can be in a range of about 0.5 mm to about 3 mm. The outer diameter or major dimension of the access port can be in a range of about 1 mm to about 2 mm. An inner diameter or major dimension of the access port can be in a range of about 0.3 mm to about 5 mm. The inner diameter or major dimension of the access port can be in a range of about 0.5 mm to about 3 mm. The inner diameter or major dimension of the access port can be in a range of about 1 mm to about 2 mm. A diameter or major dimension of the suction port can be in a range of about 0.1 mm to about 5 mm. The diameter or major dimension of the suction port can be in a range of about 0.1 mm to about 2 mm. A flange can extend from the suction port into the chamber. A distal portion of the chamber can comprise one or more side openings in a side wall of the chamber to provide fluid communication with the treatment region.

In another embodiment, an apparatus for treating a tooth is disclosed. The apparatus can comprise a chamber having a distal portion defining an access port that places the chamber in fluid communication with a treatment region of the tooth when the chamber is coupled to the tooth, the access port having a central axis. The apparatus can comprise a fluid motion generator coupled to the chamber, the fluid motion generator configured to generate rotational fluid motion in the chamber. The distal portion can be sized and shaped to be inserted into an access opening of the tooth, the distal portion tapering distally towards the central axis. In some embodiments, a suction port can be disposed at or near a center of a top wall of the chamber. The suction port can be symmetric about the central axis. A center of the suction port can lie on the central axis. The fluid motion generator can generate a swirling influent fluid path around the central axis. The apparatus can be configured to draw outgoing fluid from the treatment region to the suction port in a path that flows inside the swirling influent fluid path with a suction force applied to the suction port. The central axis can lie substantially perpendicular to the suction port. The suction port can have a major dimension that is not greater than a major dimension of the access port. The suction port can be smaller than the access port. The fluid motion generator can be disposed on a side wall of the chamber and can be oriented to direct liquid in a flow direction that lies generally transverse to the central axis of the access port. The flow direction may not intersect the central axis. The fluid direction can be generally tangent to a wall of the chamber. The suction port can be disposed on a top wall of the chamber that opposes the access port. An inner surface of the distal portion can taper distally towards the central axis. An outer surface of the distal portion can taper distally towards the central axis. The chamber can comprise a cylindrical portion coupled to or formed with the distal portion, the cylindrical portion being disposed between the distal portion and the suction port. The distal portion can taper at an angle in a range of about 0.5° to about 20°. The distal portion can taper at an angle in a range of about 1° to about 10°. The fluid motion generator can comprise a liquid jet device. The liquid jet device can comprise an inlet to receive pressurized liquid and a nozzle being configured to convert the pressurized liquid to a coherent, collimated liquid jet. At least one vent can be disposed downstream of the suction port such that the suction port lies between the chamber and the vent along an outlet passage that extends from the suction port. At least one additional vent that communications with the outlet passage can be downstream of the suction port. Each vent can be disposed along the outlet passage and can be angled towards the direction of fluid outflow in the outlet passage. A handpiece and a tooth coupler can be at a distal portion of the handpiece, the chamber being disposed within the tooth coupler. A sealing member can extend from the tooth coupler, the sealing member being configured to seal the treatment region. A console can be in fluid communication with the chamber, the console comprising one or more pumps to drive fluid to and aspirate fluid from the chamber. The fluid motion generator can be a pressure wave generator configured to propagate pressure waves through the treatment region to substantially clean the treatment region. An outer diameter or major dimension of the access port can be in a range of about 0.5 mm to about 5 mm. The outer diameter or major dimension of the access port can be in a range of about 0.5 mm to about 3 mm. The outer diameter or major dimension of the access port can be in a range of about 1 mm to about 2 mm. An inner diameter or major dimension of the access port can be in a range of about 0.3 mm to about 5 mm. The inner diameter or major dimension of the access port can be in a range of about 0.5 mm to about 3 mm. The inner diameter or major dimension of the access port can be in a range of about 1 mm to about 2 mm. A diameter or major dimension of the suction port can be in a range of about 0.1 mm to about 5 mm. The diameter or major dimension of the suction port can be in a range of about 0.1 mm to about 2 mm. A flange can extend from the suction port into the chamber. A distal portion of the chamber can comprise one or more side openings in a side wall of the chamber to provide fluid communication with the treatment region.

In another embodiment, an apparatus for treating a tooth is disclosed. The apparatus can include a chamber having an access port which places the chamber in fluid communication with a treatment region of the tooth when the chamber is coupled to tooth, the access port comprising a central axis. The apparatus can include a fluid motion generator coupled to the chamber, the fluid motion generator configured to generate a swirling influent fluid path around the central axis. The apparatus can include a suction port configured to remove fluid from the treatment region and the chamber. The apparatus can be configured to draw outgoing fluid from the treatment region to the suction port in a path that flows inside the swirling influent fluid path with a suction force applied to the suction port. In some embodiments, a suction port can be disposed at or near a center of a top wall of the chamber. The suction port can be symmetric about the central axis. A center of the suction port can lie on the central axis. The fluid motion generator can generate a swirling influent fluid path around the central axis. The central axis can lie substantially perpendicular to the suction port. The suction port can have a major dimension that is not greater than a major dimension of the access port. The suction port can be smaller than the access port. The fluid motion generator can be disposed on a side wall of the chamber and can be oriented to direct liquid in a flow direction that lies generally transverse to the central axis of the access port. The flow direction may not intersect the central axis. The fluid direction can be generally tangent to a wall of the chamber. The suction port can be disposed on a top wall of the chamber that opposes the access port. An inner surface of the distal portion can taper distally towards the central axis. An outer surface of the distal portion can taper distally towards the central axis. The chamber can comprise a cylindrical portion coupled to or formed with the distal portion, the cylindrical portion being disposed between the distal portion and the suction port. The distal portion can taper at an angle in a range of about 0.5° to about 20°. The distal portion can taper at an angle in a range of about 1° to about 10°. The fluid motion generator can comprise a liquid jet device. The liquid jet device can comprise an inlet to receive pressurized liquid and a nozzle being configured to convert the pressurized liquid to a coherent, collimated liquid jet. At least one vent can be disposed downstream of the suction port such that the suction port lies between the chamber and the vent along an outlet passage that extends from the suction port. At least one additional vent that communications with the outlet passage can be downstream of the suction port. Each vent can be disposed along the outlet passage and can be angled towards the direction of fluid outflow in the outlet passage. A handpiece and a tooth coupler can be at a distal portion of the handpiece, the chamber being disposed within the tooth coupler. A sealing member can extend from the tooth coupler, the sealing member being configured to seal the treatment region. A console can be in fluid communication with the chamber, the console comprising one or more pumps to drive fluid to and aspirate fluid from the chamber. The fluid motion generator can be a pressure wave generator configured to propagate pressure waves through the treatment region to substantially clean the treatment region. An outer diameter or major dimension of the access port can be in a range of about 0.5 mm to about 5 mm. The outer diameter or major dimension of the access port can be in a range of about 0.5 mm to about 3 mm. The outer diameter or major dimension of the access port can be in a range of about 1 mm to about 2 mm. An inner diameter or major dimension of the access port can be in a range of about 0.3 mm to about 5 mm. The inner diameter or major dimension of the access port can be in a range of about 0.5 mm to about 3 mm. The inner diameter or major dimension of the access port can be in a range of about 1 mm to about 2 mm. A diameter or major dimension of the suction port can be in a range of about 0.1 mm to about 5 mm. The diameter or major dimension of the suction port can be in a range of about 0.1 mm to about 2 mm. A flange can extend from the suction port into the chamber. A distal portion of the chamber can comprise one or more side openings in a side wall of the chamber to provide fluid communication with the treatment region.

In yet another embodiment, a method of treating a tooth is disclosed. The method can include applying a chamber to a treatment region of the tooth, the chamber having an access port which places the chamber in fluid communication with the treatment region, the access port comprising a central axis. The method can include swirling influent fluid along a fluid path around the central axis. The method can include drawing outgoing fluid from the treatment region to a suction port in a path that flows inside the swirling influent fluid path. In some embodiments, swirling the influent fluid can comprise activating a fluid motion generator. Activating the fluid motion generator can comprise activating the fluid motion generator with a console in fluid communication with the chamber. Drawing outgoing fluid can comprise activating a vacuum pump in fluid communication with the suction port by way of an outlet passage. Swirling influent fluid can comprise directing liquid along an axis transverse to the central axis. Directing the liquid can comprise directing the liquid along the transverse axis that is offset from the central axis. Activating the fluid motion generator can comprise activating a liquid jet device. The chamber can comprise a distal portion that defines the access port, the distal portion tapering distally and inwardly towards the central axis, wherein applying the chamber can comprise inserting the tapered distal portion into an access opening of the tooth. Applying the chamber can comprise pressing the chamber against the tooth. Applying the chamber can comprise attaching the chamber to the tooth. The method can include supplying substantially degassed liquid to the tooth. The method can include generating pressure waves in the treatment region. Generating pressure waves can comprise generating multiple acoustic frequencies.

Although the tooth schematically depicted in some of the figures is a pre-molar, the procedures can be performed on any type of tooth such as an incisor, a canine, a bicuspid, a pre-molar, or a molar. Further, although the tooth may be depicted as a lower (mandibular) tooth in the figures, this is for purposes of illustration, and is not limiting. The systems, methods, and compositions can be applied to lower (mandibular) teeth or upper (maxillary) teeth. Also, the disclosed apparatus and methods are capable of any portions of a tooth, including interior spaces such as root canals, pulp cavity, etc., and/or exterior surfaces of the tooth. Moreover, the disclosed apparatus, methods, and compositions can be applied to human teeth (including juvenile teeth) and/or to animal teeth.

Reference throughout this specification to "some embodiments" or "an embodiment" means that a particular feature, structure, element, act, or characteristic described in connection with the embodiment is included in at least one embodiment. Thus, appearances of the phrases "in some embodiments" or "in an embodiment" in various places throughout this specification are not necessarily all referring to the same embodiment and may refer to one or more of the same or different embodiments. Furthermore, the particular features, structures, elements, acts, or characteristics may be combined in any suitable manner (including differently than shown or described) in other embodiments. Further, in various embodiments, features, structures, elements, acts, or characteristics can be combined, merged, rearranged, reordered, or left out altogether. Thus, no single feature, structure, element, act, or characteristic or group of features, structures, elements, acts, or characteristics is necessary or required for each embodiment. All possible combinations and subcombinations are intended to fall within the scope of this disclosure.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

The foregoing description sets forth various example embodiments and other illustrative, but non-limiting, embodiments of the inventions disclosed herein. The description provides details regarding combinations, modes, and uses of the disclosed inventions. Other variations, combinations, modifications, equivalents, modes, uses, implementations, and/or applications of the disclosed features and aspects of the embodiments are also within the scope of this disclosure, including those that become apparent to those of skill in the art upon reading this specification. Additionally, certain objects and advantages of the inventions are described herein. It is to be understood that not necessarily all such objects or advantages may be achieved in any particular embodiment. Thus, for example, those skilled in the art will recognize that the inventions may be embodied or carried out in a manner that achieves or optimizes one advantage or group of advantages as taught herein without necessarily achieving other objects or advantages as may be taught or suggested herein. Also, in any method or process disclosed herein, the acts or operations making up the method or process may be performed in any suitable sequence and are not necessarily limited to any particular disclosed sequence.

What is claimed is:

1. An apparatus for treating a tooth, the apparatus comprising:
   a chamber having an access port which places the chamber in fluid communication with a treatment region of the tooth when the chamber is coupled to the tooth, the access port having a central axis;
   a fluid motion generator being arranged to generate rotational fluid motion in the chamber; and
   a suction port having a distal-most plane exposed to the chamber on a side of the chamber opposite of the access port, and being disposed relative to the access port such that the central axis of the access port passes through the suction port.

2. The apparatus of claim 1, wherein the suction port is symmetric about the central axis.

3. The apparatus of claim 1, wherein a center of the suction port lies on the central axis.

4. The apparatus of claim 1, wherein the fluid motion generator generates a swirling influent fluid path around the central axis.

5. The apparatus of claim 4, wherein the apparatus is configured to draw outgoing fluid from the treatment region to the suction port in a path that flows inside the swirling influent fluid path with a suction force applied to the suction port.

6. The apparatus of claim 1, wherein the suction port is smaller than the access port.

7. The apparatus of claim 1, wherein the fluid motion generator is disposed on a side wall of the chamber and is oriented to direct liquid in a flow direction that lies generally transverse to the central axis of the access port.

8. The apparatus of claim 7, wherein the flow direction is generally tangent to a wall of the chamber.

9. The apparatus of claim 1, wherein the suction port is disposed on a top wall of the chamber that opposes the access port.

10. The apparatus of claim 1, wherein the chamber comprises a distal portion that defines the access port, the distal portion being sized and shaped to be inserted into an access opening of the tooth, and tapering distally towards the central axis.

11. The apparatus of claim 1, wherein the fluid motion generator comprises a liquid jet device.

12. The apparatus of claim 1, further comprising at least one vent disposed downstream of the suction port such that the suction port lies between the chamber and the vent along an outlet passage that extends from the suction port.

13. The apparatus of claim 12, wherein each vent is disposed along the outlet passage and is angled towards the direction of fluid outflow in the outlet passage.

14. The apparatus of claim 1, further comprising a handpiece and a tooth coupler at a distal portion of the handpiece, the chamber being disposed within the tooth coupler.

15. The apparatus of claim 14, further comprising a sealing member extending from the tooth coupler, the sealing member being configured to seal the treatment region.

16. The apparatus of claim 1, further comprising a console to be in fluid communication with the chamber, the console comprising one or more pumps to drive fluid to and aspirate fluid from the chamber.

17. The apparatus of claim 1, wherein an outer diameter or major dimension of the access port is in a range of about 0.5 mm to about 5 mm.

18. An apparatus for treating a tooth, the apparatus comprising:
   a chamber having a distal portion defining an access port that places the chamber in fluid communication with a treatment region of the tooth when the chamber is coupled to the tooth, the access port having a central axis;
   a fluid motion generator coupled to the chamber, the fluid motion generator configured to generate rotational fluid motion in the chamber; and
   a suction port having a distal-most plane exposed to the chamber and communicating with the chamber to remove fluid from the chamber and the treatment region,
   wherein the distal portion is sized and shaped to be inserted into an access opening of the tooth, the distal portion tapering distally towards the central axis.

19. The apparatus of claim 18, wherein an inner surface of the distal portion tapers distally towards the central axis.

20. An apparatus for treating a tooth, the apparatus comprising:
   a chamber having an access port which places the chamber in fluid communication with a treatment region of the tooth when the chamber is coupled to tooth, the access port comprising a central axis;
   a fluid motion generator coupled to the chamber, the fluid motion generator configured to generate a swirling influent fluid path around the central axis; and
   a suction port having a distal-most plane exposed to the chamber and configured to remove fluid from the treatment region and the chamber,
   wherein the apparatus is configured to draw outgoing fluid from the treatment region to the suction port in a path that flows inside the swirling influent fluid path with a suction force applied to the suction port.

21. The apparatus of claim 20, wherein the central axis of the access port passes through the suction port.

22. The apparatus of claim 20, wherein the suction port is symmetric about the central axis.

23. The apparatus of claim 20, wherein the suction port is disposed at or near a center of a top wall of the chamber.

24. The apparatus of claim 20, wherein the central axis lies generally perpendicular to the suction port.

25. The apparatus of claim 20, wherein the suction port is smaller than the access port.

26. The apparatus of claim 20, wherein the fluid motion generator is disposed on a side wall of the chamber and is oriented to direct liquid in a flow direction that lies generally transverse to the central axis of the access port.

27. The apparatus of claim 20, wherein the fluid motion generator comprises a liquid jet device.

28. The apparatus of claim 20, further comprising at least one vent disposed downstream of the suction port such that the suction port lies between the chamber and the vent along an outlet passage that extends from the suction port.

* * * * *